US007057017B2

(12) United States Patent
McCarthy

(10) Patent No.: US 7,057,017 B2
(45) Date of Patent: Jun. 6, 2006

(54) HUMAN DICKKOPF-RELATED PROTEIN AND NUCLEIC ACID MOLECULES AND USES THEREFOR

(75) Inventor: Sean A. McCarthy, San Diego, CA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 324 days.

(21) Appl. No.: 09/972,473

(22) Filed: Oct. 4, 2001

(65) Prior Publication Data

Related U.S. Application Data

(63) Continuation of application No. 09/263,022, filed on Mar. 5, 1999, now abandoned, which is a continuation-in-part of application No. PCT/US98/07894, filed on Apr. 16, 1998, which is a continuation-in-part of application No. 09/009,802, filed on Jan. 20, 1998.

(60) Provisional application No. 60/071,589, filed on Jan. 15, 1998.

(51) Int. Cl.
C07K 14/47 (2006.01)
C07K 14/475 (2006.01)
C07K 19/00 (2006.01)

(52) U.S. Cl. .............. 530/350; 530/300; 530/324; 530/866

(58) Field of Classification Search ............... 530/350, 530/387.3, 300, 324, 866; 536/23.5
See application file for complete search history.

(56) References Cited

U.S. PATENT DOCUMENTS

| 5,168,050 | A | 12/1992 | Hammonds, Jr. et al. ... 435/69.1 |
| 5,525,486 | A | 6/1996 | Honjo et al. ............... 435/69.1 |
| 6,844,422 | B1 | 1/2005 | Niehrs et al. |
| 2005/0069915 | A1 | 3/2005 | McCarthy |
| 2005/0079173 | A1 | 4/2005 | Niehrs et al. |

FOREIGN PATENT DOCUMENTS

| WO | WO 98/27932 | 7/1998 |
| WO | WO 98/46755 | 10/1998 |
| WO | WO 99/14328 | 1/1999 |
| WO | WO 99/06549 | 2/1999 |
| WO | WO 99/03990 | 3/1999 |
| WO | WO 99/22000 | 5/1999 |
| WO | WO 99/31236 | 6/1999 |
| WO | WO 99/46281 A2 | 9/1999 |
| WO | WO 00/12708 | 3/2000 |
| WO | WO 00/18194 | 3/2000 |
| WO | WO 00/18914 | 4/2000 |
| WO | WO 00/53756 | 9/2000 |
| WO | WO 00/78961 A1 | 12/2000 |
| WO | WO 01/04311 A1 | 1/2001 |
| WO | WO 01/16318 A2 | 3/2001 |
| WO | WO 01/38528 A1 | 5/2001 |
| WO | WO 01/40466 A2 | 6/2001 |
| WO | WO 01/54477 A2 | 8/2001 |
| WO | WO 01/57188 A2 | 8/2001 |
| WO | WO 01/57190 A2 | 8/2001 |
| WO | WO 01/68848 A2 | 9/2001 |

OTHER PUBLICATIONS

Aravind, L. and E.V. Koonin, "A colipase fold in the carboxy-terminal domain of the Wnt antagonists—the Dickkopfs", *Curr. Biol.* 8(14):R477-8 (1998).

Austin, T.W. et al., "A role for the Wnt gene family in hematopoiesis: Expansion of multilineage progenitor cells", *Blood* 89(10):3624-3635 (1997).

Barton, "Protein sequence alignment and database scanning" in *Protein Structure Prediction, A Practical Approach* (IRL Press, Oxford University Press, Oxford, UK, Jan. 1997) pp. 31-63.

Bowie et al. "Deciphering the message in protein sequences: tolerance to amino acid substitutions" *Science* 247(4948):1306-10 (Mar. 16, 1990).

Cadigan, K.M et al., "Wnt signaling: A common theme in animal development", *Genes & Development* 11:3286-3305 (1997).

Fedi, P. et al., "Isolation and biochemical characterization of the human Dkk-1 homologue, a novel inhibitor of mammalian Wnt signaling", *J. Biol. Chem.* 274(27):19465-19472 (1999).

Finch, Paul W. et al. "Purification and molecular cloning of a screted, Frizzled-related antagonist of Wnt action" *Proc. Natl. Acad. Sci. USA* 94(13):6770-75 (Jun. 1997).

GenBank™ Accession No. 2724106 for RIG-like 7-1 [*Homo sapiens*][Dec. 4, 1997].

GenBank™ Accession No. 2736292 for mdkkk-1 [*Mus musculus*][Feb. 10, 1998].

GenBank™ Accession No. 2736294 for Xdkk-1 [*Xenopus laevis*][Feb. 10, 1999].

GenBank™ Accession No. 3660556 for hdkk-4 [*Homo sapiens*][Oct. 3, 1998].

GenBank™ Accession No. 3688630 for hdkk-4 [*Homo sapiens*][Oct. 3, 1998].

(Continued)

*Primary Examiner*—David Romeo
(74) *Attorney, Agent, or Firm*—Scott L. Ausenhus; Mario Cloutier; Robert H. Underwood

(57) ABSTRACT

Novel Dkk and Dkk-related polypeptides, proteins, and nucleic acid molecules are disclosed. In addition to isolated, full-length Dkk and Dkk-related proteins, the invention further provides isolated fusion proteins, antigenic peptides and antibodies. The invention also provides Dkk and Dkk-related nucleic acid molecules, recombinant expression vectors containing a nucleic acid molecule of the invention, host cells into which the expression vectors have been introduced and non-human transgenic animals in which a Dkk and Dkk-related gene has been introduced or disrupted. Diagnostic, screening and therapeutic methods utilizing compositions of the invention are also provided.

20 Claims, 29 Drawing Sheets

OTHER PUBLICATIONS

GenBank™ Accession No. A39976 for Sequence 9 from Patent WO942179 [Mar. 5, 1997].

GenBank™ Accession No. AA018255 for Soares retina N2b4HR *Homo sapiens* cDNA clone 361535 5', mRNA sequence [Nov. 29, 1996].

GenBank™ Accession No. AA031969 for Soares_pregnant_uterus_NbHPU *Homo sapiens* cDNA clone 470646 3', mRNA sequence [Aug. 21, 1996].

GenBank™ Accession No. AA032060 for Soares_pregnant_uterus_NbHPU *Homo sapiens* cDNA clone IMAGE:470646 5', mRNA sequence [Aug. 21, 1996].

GenBank™ Accession No. AA035345 for Soares_pregnant_uterus_NbHPU *Homo sapiens* cDNA clone IMAGE:471479 3', mRNA sequence [May 10, 1997].

GenBank™ Accession No. AA035443 for Soares_pregnant_uterus_NbHPU *Homo sapiens* cDNA clone IMAGE;471724 3', mRNA sequence [May 10, 1997].

GenBank™ Accession No. AA035583 for Soares_pregnant_uterus_NbHPU *Homo sapiens* clone IMAGE:471724 5', mRNA sequence [May 10, 1997].

GenBank™ Accession No. AA037322 for Soares_senescent_fibroblasts_NbHSF *Homo sapiens* cCNA clone 325915 5', mRNA sequence [Nov. 25, 1996].

GenBank™ Accession No. AA041360 for Soares_fetal_heart_NbHH19W *Homo sapiens* cDNA clone 376472 3', mRNA sequence [Feb. 1, 1997].

GenBank™ Accession No. AA042806 for Soares_pregnant_uterus_NbHPU *Homo sapiens* cDNA clone IMAGE:486515 3', mRNA sequence [Sep. 4, 1996].

GenBank™ Accession No. AA043027 for Soares_pregnant_uterus_NbHPU *Homo sapiens* cDNA clone IMAGE:486515 5', mRNA sequence [Sep. 4, 1996].

GenBank™ Accession No. AA063859 for Stratagene mouse testis (#937309) *Mus musculus* cDNA clone 514640 5' similar to TR:G517093 G517093 Hypothetical 39.2 KD Protein; mRNA sequence [Feb. 3, 1997].

GenBank™ Accession No. AA065307 for Testis 5 *Homo sapiens* cDNA clone a03500 5' end, mRNA sequence [Dec. 31, 1996].

GenBank™ Accession No. AA073904 for Stratagene mouse heart (#937316) *Mus musculus* cDNA clone 536577 5', mRNA sequence [Feb. 15, 1997].

GenBank™ Accession No. AA88618 for Soares_pregnant_uterus_NbHPU *Homo sapiens* cDNA clone IMAGE:487642 5', mRNA sequence [Oct. 24, 1996].

GenBank™ Accession No. AA107210 for Stratagene mouse testic (#937308) *Mus musculus* cDNA clone IMAGE:516168 5' similar to TR:G517093 G517093 HYPOTHETICAL 39.2 kd protein; mRNA sequence [Feb. 3, 1997].

GenBank™ Accession No. AA115249 for Soares_pregnant_uterus_NbHPU *Homo sapiens* cDNA clone IMAGE:501425 3', mRNA sequence [May. 14, 1997].

GenBank™ Accession No. AA115337 for Soares_pregnant_uterus_NbHPU *Homo sapiens* cDNA clone 501425 5', mRNA sequence [May 14, 1997].

GenBank™ Accession No. AA129488 for Stratagene lung carcinoma 937218 *Homo sapiens* cDNA clone IMAGE:564360 3', mRNA sequence [May 19, 1997].

GenBank™ Accession No. AA136192 for Soares_pregnant_uterus_NbHPU *Homo sapiens* cDNA clone IMAGE:490113 5', mRNA sequence [Nov. 30, 1996].

GenBank™ Accession No. AA137219 for Soares_pregnant_uterus_NbHPU *Homo sapiens* cDNA clone IMAGE:490113 3', mRNA sequence [Nov. 30, 1996].

GenBank™ Accession No. AA143670 for Stratagene pancreas (#937208) *Homo sapiens* cDNA clone IMAGE:591770 5', mRNA sequence [Dec. 4, 1996].

GenBank™ Accession No. AA155928 for Stratagene endothelial cell 937223 *Homo sapiens* cDNA clone 590026 5', mRNA sequence [Dec. 11, 1996].

GenBank™ Accession No. AA207078 for NCI_CGAP_GCB1 *Homo sapiens* cDNA clone IMAGE:682716 5', mRNA sequence [Aug. 13, 1997].

GenBank™ Accession No. AA209468 for Stratagene hNT neuron (#937233) *Homo sapiens* cDNA clone 648310 3', mRNA sequence [Mar. 12, 1998].

GenBank™ Accession No. AA220766 for Soares mouse 3NME 12 5 *Mus musculus* cDNA clone IMAGE:660068 5', mRNA sequence [Feb. 10, 1997].

GenBank™ Accession No. AA237194 for Soares mouse NML *Mus musculus* cDNA clone IMAGE:678567 5' similar to gb:U11248 *Mus musculus* C57BL/6J ribosomal protein S28 mRNA, complete (MOUSE), mRNA sequence [Mar. 3, 1997].

GenBank™ Accession No. AA253446 for Soares_NhHMPu_S1 *Homo sapiens* cDNA clone IMAGE:669375 5', mRNA sequence [Mar. 12, 1997].

GenBank™ Accession No. AA253464 for Soares_NhHMPu_S1 *Homo sapiens* cDNA clone 669375 3', mRNA sequence [Mar. 12, 1997].

GenBank™ Accession No. AA259742 for Soares mouse 3NME 12 5 *Mus musculus* cDNA clone IMAGE:734543 5' similar to gb:U11248 *Mus musculus* C57BL/6J ribosomal protein S28 mRNA, complete (MOUSE), mRNA sequence [Mar. 18, 1997].

GenBank™ Accession No. AA265561 for Soares mouse lymph node NbMLN *Mus musculus* cDNA clone 718668 5' similar to TR:G517093 G517093 Hypothetical 39.2 KL Protein mRNA sequence [Mar. 20, 1997].

GenBank™ Accession No. AA269333 for Soares mouse 3NME 12 5 *Mus musculus* cDNA clone IMAGE:733911 5', mRNA sequence [Mar. 26, 1997].

GenBank™ Accession No. AA273430 for Soares mouse lymph node NBMLN *Mus musculus* cDNA clone IMAGE:764999 5, mRNA sequence [Mar. 28, 1997].

GenBank™ Accession No. AA292828 for Soares_testis_NHT *Homo sapiens* cDNA clone IMAGE:727099 5', mRNA sequence [Aug. 12, 1997].

GenBank™ Accession No. AA304984 for Colon carcinoma (Caco-2) cell line II *Homo sapiens* cDNA 5' end, mRNA sequence [Apr. 18, 1997].

GenBank™ Accession No. AA336797 for Enbdometrial tumor *Homo sapiens* cDNA 5' end, mRNA sequence [Apr. 21, 1997].

GenBank™ Accession No. AA351624 for infant brain *Homo sapiens* cDNA 5' end similar to RIG, mRNA sequence [Apr. 21, 1997].

GenBank™ Accession No. AA371363 for Prostate gland I *Homo sapiens* cDNA 5' end, mRNA sequence [Apr. 21, 1997].

GenBank™ Accession No. AA393069 Soares_testis_NHT *Homo sapiens* cDMA clone IMAGE:727624 5', mRNA sequence [Aug. 12, 1997].

GenBank™ Accession No. AA397836 for Soares_testis_NHT *Homo sapiens* cDNA clone 728407 5' similar to TR:G517093 G517093 Hypothetical 39.2 KD Protein; mRNA sequence [May 16, 1997].

GenBank™ Accession No. AA402127 Soares_testis_NHT *Homo sapiens* cDNA clone IMAGE:727430 5', mRNA sequence [Aug. 12, 1997].
GenBank™ Accession No. AA405079 Soares_testis_NHT *Homo sapiens* cDNA clone IMAGE:731664 5', mRNA sequence [Aug. 12, 1997].
GenBank™ Accession No. AA425947 for Soares_total_fetus_Nb2HF8_9w *Homo sapiens* cDNA clone 760299 3', mRNA sequence [Oct. 16, 1997].
GenBank™ Accession No. AA426107 Soares_testis_NHT *Homo sapiens* cDNA clone IMAGE:743011 5', mRNA sequence [Oct. 16, 1997].
GenBank™ Accession No. AA431512 Soares_testis_NHT *Homo sapiens* cDNA clone IMAGE:782156 5', mRNA sequence [May 22, 1997].
GenBank™ Accession No. AA497850 for Stratagene mouse testis (#937308) *Mus musculus* cDNA clone 917486 5' similar to TR:G517093 G517093 Hypothetical 39.2 KD Protein; mRNA sequence [Jul. 1, 1997].
GenBank™ Accession No. AA497886 for Stratagene mouse testis (#937308) *Mus musculus* cDNSA clone 917858 5' similar to TR:G517093 G517093 Hypothetical 39.2 KD Protein mRNA sequence [Jul. 1, 1997].
GenBank™ Accession No. AA522097 for Barstead mouse proximal colon MPLRB6 *Mus musculus* cDNA clone IMAGE:903996 5' similar to gb:U11248 *Mus musculus* C57BL/6J ribosomal protein S28 mRNA, complete (MOUSE), mRNA sequence [Jul. 17, 1997].
GenBank™ Accession No. AA528575 for NCI_CGAP_Kid1 *Homo sapiens* cDNA clone IMAGE:912545 similar to SW:RL37_Human PO2403 6OS Ribosomal Protein L37, mRNA sequence [Aug. 20, 1997].
GenBank™ Accession No. AA538551 for Knowles Solter mouse blastocyst B1 *Mus musculus* cDNA clone IMAGE:932825 5' similar to gb:U11248 *Mus musculus* C57BL/6J ribosomal protein S28 mRNA, complete (MOUSE), mRNA sequence [Jul. 29, 1997].
GenBank™ Accession No. AA565546 for NCI_CGAP_GC2 *Homo sapiens* cDNA clone IMAGE:1016173 3', mRNA sequence [Sep. 8, 1997].
GenBank™ Accession No. AA616966 for Barstead mouse proximal colon MPLRB6 *Mus musculus* cDNA clone IMAGE:904368 5', mRNA sequence [Oct. 7, 1997].
GenBank™ Accession No. AA619642 Knowles Solter mouse blastocyst B1 *Mus musculus* cDNA clone IMAGE:962896 5' similar to TR:G517093 G517093 Hypothetical 39.2 KD Protein, mRNA sequence [Oct. 9, 1997].
GenBank™ Accession No. AA628979 for Soares Testis NHT *Homo sapiens* cDNA clone 743604 3' similar to TR:G517093 G517093 Hypothetical 39.2 KD Protein; mRNA sequence [Oct. 16, 1997].
GenBank™ Accession No. AA641247 for NCI_CGAP_Pr24 *Homo sapiens* cDNA clone IMAGE: 1173698 3',mRNA sequence [Oct. 27, 1997].
GenBank™ Accession No. AA653979 for NCI_CGAP_Pr25 *Homo sapiens* cDNA clone IMAGE:1198589 3', mRNA sequence [Nov. 13, 1997].
GenBank™ Accession No. AA689611 for Barstead mouse irradiated colon MPLRB7 *Mus musculus* cDNA clone IMAGE: 1137654 5',mRNA sequence [Dec. 16, 1997].
GenBank™ Accession No. AA691908 for Barstead mouse myotubes MPLRB5 *Mus musculus* cDNA clone 1163091 5' similar to gb:U11248 *Mus musculus* C57BL/6J ribosomal protein S28 mRNA, complete (MOUSE) [Dec. 16, 1997].
GenBank™ Accession No. AA692959 for Knowles Solter mouse 2 cell *Mus musculus* cDNA clone 1125007 5', mRNA sequence [Dec. 16, 1997].
GenBank™ Accession No. AA693679 for Soares_fetal_liver_spleen_1NFLS_S1 *Homo sapiens* cDNA clone IMAGE:434242 3', mRNA sequence [Dec. 16, 1997].
GenBank™ Accession No. AA710868 for Barstead mouse irradiated colon MPLRB7 *Mus musculus* cDNA clone IMAGE:1166873 5', mRNA sequence [Dec. 24, 1997].
GenBank™ Accession No. AA731642 for NCI_CGAP_GCB1 *Homo sapiens* cDNA clone IMAGE:1251357 3', mRNA sequence [Jan. 27, 1998].
GenBank™ Accession No. AA741294 for NCI_CGAP_GCB1 *Homo sapiens* cDNA clone IMAGE:1286515 3' similar to SW:ANP2_AUSBR P12101 Antifreeze Peptide AB2 [1] mRNA sequence [Feb. 7, 1998].
GenBank™ Accession No. AA765298 for NCI_CGAP_GCB1 *Homo sapiens* cDNA clone IMAGE:1303697 3', mRNA sequence [Feb. 8, 1998].
GenBank™ Accession No. AA770231 Soares_testis_NHT *Homo sapiens* cDNA clone 1322151 3', mRNA sequence [Jan. 28, 1998].
GenBank™ Accession No. AA774161 for Stratagene hNT neuron (#937233) *Homo sapiens* cDNA clone IMAGE:858573 3',mRNA sequence [Jan. 29, 1998].
GenBank™ Accession No. AA815342 Soares_testis_NHT *Homo sapiens* cDNA clone 1375447 3', mRNA sequence [Feb. 13, 1998].
GenBank™ Accession No. AA826797 for NCI_CGAP_Pr24 *Homo sapiens* cDNA clone IMAGE:1174528 3', mRNA sequence [Mar. 5, 1998].
GenBank™ Accession No. AA854987 Soares_testis_NHT *Homo sapiens* cDNA clone IMAGE: 1394074 3', mRNA sequence [Mar. 6, 1998].
GenBank™ Accession No. AA868111 Soares_testis_NHT *Homo sapiens* cDNA clone IMAGE: 1407610 3' similar to contain element MSR1 repetitive element, mRNA sequence [Mar. 16, 1998].
GenBank™ Accession No. AA991644 for NCI_CGAP_GC2 *Homo sapiens* cDNA clone IMAGE:1612003 3', mRNA sequence [Jun. 3, 1998].
GenBank™ Accession No. AAB92664 for RIG-like 7-1 [Dec. 28, 1997].
GenBank™ Accession No. AAC02426 for mdkk-1 [Feb. 10, 1998].
GenBank™ Accession No. AAC02427 for Xdkk-1 [Feb. 10, 1998].
GenBank™ Accession No. AAD21087 for Sk/Dkk-1 protein precursor [Jun. 29, 1999].
GenBank™ Accession No. AAD22461 for dickkopf-1[Mar. 31, 1999].
GenBank™ Accession No. AAF02674 for dickkopf-1 [Oct. 16, 1999].
GenBank™ Accession No. AAF02675 for dickkopf-2 [Oct. 16, 1999].
GenBank™ Accession No. AAF02676 for dickkoff-3 [Oct. 16, 1999].
GenBank™ Accession No. AAF02677 for dickkopf-4 [Oct. 16, 1999].
GenBank™ Accession No. AAF026778 for soggy-1 protein [Oct. 16, 1999].
GenBank™ Accession No. AAF02679 for soggy-1 protein [Oct. 16, 1999].

GenBank™ Accession No. AAF02680 for Dkk-3 protein [Oct. 16, 1999].

GenBank™ Accession No. AB003095 for Fruitfly strain S1259 mitochondrial DNA, A+T-rich region, partial sequence [Sep. 17, 1997].

GenBank™ Accession No. AB003097 for Fruitfly strain g20 mitochondrial DNA, A+T-rich region, partial sequence [Sep. 17, 1997].

GenBank™ Accession No. AB005216 for *Homo sapiens* mRNA for Nck, Ash and phospholipase C gamma- binding protein NAP4, partial cds [Nov. 14, 1997].

GenBank™ Accession No. AB017788 for *Homo sapiens* hdkk-4 mRNA, complete cds. [Oct. 3, 1998].

GenBank™ Accession No. AB018003 for *Homo sapiens* hdkk-4 gene, exon-1, partial sequence [Oct. 3, 1998].

GenBank™ Accession No. AB018004 *Homo sapiens* hdkk-4 gene, exon-2 [Oct. 3, 1998].

GenBank™ Accession No. AB018005 for *Homo sapiens* hdkk-4 gene, exon-3, exon-4 and complete cds. [Oct. 3, 1998].

GenBank™ Accession No. AB020314 for *Homo sapiens* Dickkopf-1 (hdkk-1-gene, exons, $1^{st}$ and $2^{nd}$ coding region [Nov. 23, 1999].

GenBank™ Accession No. AB020315 for *Homo sapiens* Dickkopf-1 (hdkk-1) gene, $3^{rd}$, $4^{th}$ coding region and complete cds [Nov. 23, 1999].

GenBank™ Accession No. AB033208 for *Homo sapiens* dickkopf-2 mRNA, complete cds. [Oct. 20, 1999].

GenBank™ Accession No. AB033421 for *Homo sapiens* dickkopf-3 mRNA, complete cds. [Oct. 20, 1999].

GenBank™ Accession No. AB035180 for *Homo sapiens* Dickkopf-2 gene, exon [Nov. 27, 1999].

GenBank™ Accession No. AB035181 for *Homo sapiens* Dickkopf-2 gene. exon and partial cds. [Nov. 27, 1999].

GenBank™ Accession No. AB035182 for *Homo sapiens* Dickkopf-3 gene, partial cds. [Nov. 27, 1999].

GenBank™ Accession No. AC000127 for Human Cosmid g1572c198, complete sequence [Feb. 3, 1997].

GenBank™ Accession No. AC001235 for Human Chromosome 11 pac pDJ360p17; HTGS phase 1, 44 unordered pieces [Apr. 18, 1997].

GenBank™ Accession No. AC003099 for *Homo sapiens* chromosome 4q25, BAC clone B284B3, complete sequence [Nov. 13, 1997].

GenBank™ Accession No. AF009075 for Hepatitis C virus genomic RNA, 3' nonstranslated region, partial sequence. clone #16, [Aug. 9, 1997].

GenBank™ Accession No. AF021106 for *Homo sapiens* trinucleotide repeat CTG-11 sequence tagged site [Apr. 4, 1998].

GenBank™ Accession No. AF030155 for *Drosophila melanogaster* translation initiation factor eIF4G mRNA, complete cds [Apr. 17, 1998].

GenBank™ Accession No. AF030433 for *Mus musculus* Dickkopf-1 (mdkk-1) mRNA, complete cds [Feb. 11, 1998].

GenBank™ Accession No. AF030434 for *Xenopus laevis* Dickkopf-1 (Xdkk-1) mRNA, complete cds [Feb. 11, 1998].

GenBank™ Accession No. AF034208 for *Homo sapiens* RIG-like 7-1 mRNA, complete cds [Dec. 29, 1997].

GenBank™ Accession No. AF052685 for *Homo sapiens* protocadherin 43 gene, exon 3, exon 4, and complete cds. [Mar. 29, 1998].

GenBank™ Accession No. AF116852 for *Danio rerio* dickkopf-1 (dkk1) mRNA, complete cds. [Mar. 31, 1999].

GenBank™ Accession No. AF127563 for *Homo sapiens* Sk/Dkk-1 protein precursor, mRNA, complete cds. [Jun. 29, 1999].

GenBank™ Accession No. AF177394 for *Homo sapiens* dickkopf-1 (DKK-1) mRNA; complete cds. [Oct. 16, 1999].

GenBank™ Accession No. AF177395 for *Homo sapiens* dickkopf-2 (DKK-2) mRNA, complete cds. [Oct. 16, 1999].

GenBank™ Accession No. AF177396 for *Homo sapiens* dickkopf-3 (DKK-3) mRNA, complete cds. [Oct. 16, 1999].

GenBank™ Accession No. AF177397 for *Homo sapiens* dickkopf-4 (DKK-4); mRNA, complete cds. [Oct. 16, 1999].

GenBank™ Accession No. AF177398 for *Homo sapiens* soggy-1 protein (SG-1) mRNA, complete cds. [Oct. 16, 1999].

GenBank™ Accession No. AF177399 for *Mus musculus* soggy-1 protein (Sgy-1) mRNA, complete cds. [Oct. 16, 1999].

GenBank™ Accession No. AF177400 for *Mus musculus* Dkk-3 protein (Dkk-3) mRNA, complete cds. [Oct. 16, 1999].

GenBank™ Accession No. AI004529 Soares_testis_NHT *Homo sapiens* cDNA clone IMAGE: 1620926 3', mRNA sequence [Aug. 27, 1998].

GenBank™ Accession No. AI028601 Soares_testis_NHT *Homo sapiens* cDNA clone IMAGE: 1644098 3', mRNA sequence [Aug. 27, 1998].

GenBank™ Accession No. AI037464 Soares mouse mammary gland NbMMG *Mus musculus* cDNA clone IMAGE: 1381445 5' similar to SW:LFE4_Chick Q90839 Unknown Lens Fiber Protein Clefest4 Precursor, mRNA sequence [Jun. 26, 1998].

GenBank™ Accession No. AI066004 Stratagene mouse testis (#937308) *Mus musculus* cDNA clone IMAGE:515718 5' similar to TR:G517093 G517093 G517093 Hypothetical 39.2 kd protein, mRNA sequence [Feb. 3, 1997].

GenBank™ Accession No. AI074879 for Soares_senescent_fibroblasts NbHSF *Homo sapiens* cDNA clone IMGAE: 1667074 3', mRNA sequence [Sep. 24, 1998].

GenBank™ Accession No. AI085115 for Soares_senescent_fibroblasts NbHSF *Homo sapiens* cDNA clone IMAGE: 1665669 3', mRNA sequence [Sep. 24, 1998].

GenBank™ Accession No. AI093106 for Soares_fetal_heart_NbHH19W *Homo sapiens* cDNA clone IMAGE: 1694687 3', mRNA sequence [Aug. 18, 1998].

GenBank™ Accession No. AI095783 for Soares_pregnant_uterus_NbHPU *Homo sapiens* cDNA clone IMAGE: 1696830 3', mRNA sequence [Oct. 5, 1998].

GenBank™ Accession No. AI107210 Stratagene mouse testis (#937308) *Mus musculus* cDNA clone IMAGE:516168 5' similar to TR:G517093 G517093 Hypothetical 39.2 kd protein, mRNA sequence [Nov. 24, 1998].

GenBank™ Accession No. AI120461 for Soares mouse mammary gland NMLMG *Mus musculus* cDNA clone IMAGE: 1383114 5' similar to gb:U11248 *Mus musculus* C57BL/6J ribosomal protein S28 mRNA, complete (MOUSE); mRNA sequence [*Mus musculus*] [Sep. 2, 1998].

GenBank™ Accession No. AI128249 for Soares_pregnant_uterus NbHPU *Homo sapiens* cDNA clone IMAGE: 1711454 3"; mRNA sequence [*Homo sapiens*] [Oct. 27, 1998].

GenBank™ Accession No. AI129651 for Soares_pregnant_uterus_NbHPU *Homo sapiens* cDNA clone IMAGE: 1712938 3', mRNA sequence [*Homo sapiens*][Oct. 27, 1998].

GenBank™ Accession No. AI129657 for Soares_pregnant_iteris_NbPU *Homo sapiens* cDNA clone IMAGE: 1712950 3', mRNA sequence [*Homo sapiens*][Oct. 27, 1998].

GenBank™ Accession No. AI136880 for UI-R-C2p-of-f-01-0-UI.s1 UI-R-C2p *Rattus norvegicus* cDNA clone UI-R-C2p-of-f-01-0-UI e', mRNA sequeance [*Rattus norvegicus*][Sep. 18, 1998].

GenBank™ Accession No. AI138943 Soares_testis_NHT *Homo sapiens* cDNA clone IMAGE: 1735666 3', mRNA sequence [Oct. 28, 1998].

GenBank™ Accession No. AI139919 Soares_testis_NHT *Homo sapiens* cDNA clone IMAGE:1737911 3' similar to SW:LFE4_Chick Q90839 Unknown Lens Fiber Protein Clefest4 Precursor, mRNA sequence [Oct. 29, 1998].

GenBank™ Accession No. AI146900 for Soares_senescent_fibroblasts_NbHSF *Homo sapiens* cDNA clone IMAGE:1666722 3', mRNA sequence [*Homo sapiens*][Oct. 23, 1998].

GenBank™ Accession No. AI150592 Soares_testis_NHT *Homo sapiens* cDNA clone IMAGE:1752164 3', mRNA sequence [Nov. 10, 1998].

GenBank™ Accession No. AI200822 Soares_testis_NHT *Homo sapiens* cDNA clone IMAGE:1755100 3', mRNA sequence [Oct. 14, 1998].

GenBank™ Accession No. AIl200868 Soares_testis_NHT *Homo sapiens* cDNA clone IMAGE:1754662 3', mRNA sequence [Oct. 14, 1998].

GenBank™ Accession No. AI201865 for NCI_CGAP_Pr28 *Homo sapiens* cDNA clone IMAGE:1944264 3', mRNA sequence [*Homo sapiens*][Dec. 2, 1998].

GenBank™ Accession No. AJ006866 for *Orthochirus scrobiculosus* mRNA for insecticidal toxin, partial [Jun. 27, 1998].

GenBank™ Accession No. AJ243963 for *Mus musculus* mRNA for dickkopf-2 (dkk-2 gene) [Nov. 4, 1999].

GenBank™ Accession No. AJ243964 for *Mus musculus* mRNA for dickkop-3 (dkk-3 gene) [Nov. 4, 1999].

GenBank™ Accession No. AU007007 *Schizosaccharomyces pombe* late log phase cDNA *Schizosaccharomyces pombe* cDNA clone spc01322, mRNA sequence [Jul. 31, 1998].

GenBank™ Accession No. AU007010 *Schizosaccharomyces pombe* late log phase cDNA *Schizosaccharomyces pombe* cDNA clone spc04811, mRNA sequence [Jul. 31, 1998].

GenBank™ Accession No. AU009349 *Schizosaccharomyces pombe* late log phase cDNA *Schizosaccharomyces pombe* cDNA clone spc01322, mRNA sequence [Jul. 31, 1998].

GenBank™ Accession No. B24434 for *Arabidopsis thalia* genomic clone F20C17, genomic survey sequence [Oct. 9, 1997].

GenBank™ Accession No. B39066 for Human Genomic Sperm Library C *Homo sapiens* genomic clone Plate=CT 771 Col=13 Row=C, genomic survey sequence [Oct. 17, 1997].

GenBank™ Accession No. BAA33475 for hdkk-4 [Nov. 23, 1999].

GenBank™ Accession No. BAA34651 for homologue of mouse dkk- gene:ACC# AF030433 [Nov. 23, 1999].

GenBank™ Accession No. BAA85465 for Dickkopf-2 [Oct. 20, 1999].

GenBank™ Accession No. BAA85488 for Dickkopf-3 [Oct. 20, 1999].

GenBank™ Accession No. BAA87044 for Dickkopf-3 [Nov. 27, 1999].

GenBank™ Accession No. BAA87056 for Dickkopf-2 [Nov. 27, 1999].

GenBank™ Accession No. C89869 for *Dictyostelium discoideum* SS (H.Urushihara) *Dictyostelium discoideum discoideum* cDNA clone SSG557, mRNA sequence [Apr. 20, 1998].

DDBJ™ (DNA Database of Japan) Accession No. C94299 for *Dictyostelium discoideum* SS (H. Urushihara) *Dictyostelium discoideum* cDNA clone SSK759, mRNA sequence [Jun. 15, 1998].

GenBank™ Accession No. CAB60110 dickkopf-2 [Nov. 4, 1999].

GenBank™ Accession No. CAB60111 for dickkopf-3 [Nov. 4, 1999].

GenBank™ Accession No. D26311 for Chicken mRNA for unknown protein. complete cds [Dec. 12, 1996].

DDBJ™ (DNA Database of Japan)™ Accession No. D63286 for Clontech human placenta polyA+ mRNA (#6572) *Homo sapiens* cDNA clone 5' GEN-517H04 5', mRNA sequence [Aug. 29, 1995].

GenBank™ Accession No. D67096 for Hepatitis C virus genome, 3'terminus [Aug. 14, 1996].

GenBank™ Accession No. D85016 for Non-A non-B hepatitis virus genomic RNA for 3'UTR [Oct. 8, 1996].

GenBank™ Accession No. D85017 for Non-A non-B hepatitis virus gennomic RNA for 3' UTR [Oct. 8, 1996].

GenBank™ Accession No. D85020 for Non-A non-B hepatitis virus genomic RNA for 3' UTR [Oct. 8, 1996].

GenBank™ Accession No. D85021 for Non-A non-B hepatitis virus genomic RNA for 3' UTR [Oct. 8, 1996].

GenBank™ Accession No. D85022 for Non-A non-B hepatitis virus genomic RNA for 3' UTR [Oct. 8, 1996].

GenBank™ Accession No. D85024 for Non-A non-B hepatitis virus genomic RNA for 3' UTR [Oct. 8, 1996].

GenBank™ Accession No. D85025 for Non-A non-B hepatitis virus genomic RNA for 3' UTR [Oct. 8, 1996].

GenBank™ Accession No. F06027 Normalized infant brain cDNA *Homo sapiens* cDNA clone c-0ud06, mRNA sequence [Feb. 19, 1995].

GenBank™ Accession No. F08729 Normalized infant brain cDNA *Homo sapiens* cDNA clone c-15d12, mRNA sequence [Feb. 20, 1995].

GenBank™ Accession No. G05905 human STS WI-6501 [Oct. 19, 1995].

GenBank™ Accession No. H71273 for Soares fetal liver spleen 1NFLS *Homo sapiens* cDNA clone 229921 5', mRNA sequence [Oct. 26, 1995].

GenBank™ Accession No. H83446 for Soares melanocyte 2NBHM *Homo sapiens* cDNA clone IMAGE:249345 3', mRNA sequence [Nov. 13, 1995].

GenBank™ Accession No. H83554 for Soares melanocyte 2NbHM *Homo sapiens* cDNA clone IMAGE:249345 5'; mRNA sequence [Nov. 13, 1995].

GenBank™ Accession No. H99266 for Soares melanocyte 2NbHM *Homo sapiens* cDNA clone 260362 3', mRNA sequence [Dec. 15, 1995].

GenBank™ Accession No. I80064 for Sequence 37 from patent US 5708157 [Mar. 20, 1998].

GenBank™ Accession No. L17318 for *Rattus norvegicus* proline-rich proteoglycan (PRG2) mRNA, complete cds [Oct. 27, 1993].

GenBank™ Accession No. L47975 *Equus caballus* TATA-box binding protein (TBP) gene, partial cds [Apr. 1, 1996].

GenBank™ Accession No. L49359 *Homo sapiens* huntingtin gene, partial exon [Jan. 19, 1996].

GenBank™ Accession No. M29111 for D.discoideum actin A-2-sub-2 gene, 5' flank [Mar. 15, 1990].

GenBank™ Accession No. M29121 for D.discoideum actin A-11 gene, 5' flank [Mar. 15, 1990].

GenBank™ Accession No. M32514 Rat simple sequence DNA, clone 5 [Sep. 15, 1990].

GenBank™ Accession No. M32515 Rat simple sequence DNA, clone 8 [Sep. 15, 1990].

GenBank™ Accession No. M36626 Rat simple sequence DNA, clone 5 [Sep. 15, 1990].

GenBank™ Accession No. M64793 M36414 for Rat salivary proline-rich protein (RP 15) gene, complete cds [May 9, 1991].

GenBank™ Accession No. M95930 for *Manihot esculenta* (clone rubssr37) ribulose-1,5 bisphosphate caraboxylase/oxygenase small subunit EC 4.1.1.39 (rbc S) mRNA sequence [Jun. 26, 1992].

GenBank™ Accession No. M98807 for *Xenopus laevis* noggin mRNA, complete cds [Oct. 14, 1992].

GenBank™ Accession No. N26884 for Soares melanocyte 2NbHM *Homo sapiens* cDNA clone IMAGE:269713 3', mRNA sequence [Dec. 29, 1995].

GenBank™ Accession No. N94525 for Soares_senescent_fibroblasts_NbHSF *Homo sapiens* cDNA clone 309678 3', mRNA sequence [Aug. 20, 1996].

GenBank™ Accession No. P18563 for integrin subunit Beta 6 [*Cavia porcellus*][Jul. 15, 1999].

GenBank™ Accession No. Q90839 Unknown lens fiber protein CLFEST4 precursor [Nov. 1, 1997].

GenBank™ Accession No. R14945 for Soares infant brain 1NIB *Homo sapiens* cDNA clone IMAGE:30231 5', mRNA sequence [Apr. 13, 1995].

GenBank™ Accession No. R27865 for Soares placenta Nb2HP *Homo sapiens* cDNA clone IMAGE:133741 5', mRNA sequence [Apr. 25, 1995].

GenBank™ Accession No. R32328 for Soares placenta Nb2HP *Homo sapiens* cDNA clone IMAGE:134911 3' similar to gb:X70218 Protein Phosphatase PP-X (Human); contains L1 repetitive element, mRNA sequence [Apr. 28, 1995].

GenBank™ Accession No. R52311 for Soares infant brain 1NIB *Homo sapiens* cDNA clone IMAGE:39710 5', mRNA sequence [May 18, 1995].

GenBank™ Accession No. R54473 for Soares infant brain 1NIB *Homo sapiens* cDNA clone IMAGE:39710 3', mRNA sequence [May 18, 1995].

GenBank™ Accession No. T02494 for Debopam Chakrabarti Plasmodium falciparum cDNA clone PF0093C, mRNA sequence [*Plasmodium falciparum*] [May 26, 1995].

GenBank™ Accession No. U32331 for *Homo sapiens* RIG mRNA, complete cds [Sep. 17, 1998].

GenBank™ Accession No. U38801 for *Rattus norvegicus* high molecular weight DNA polymerase beta (rnpolb) mRNA, complete cds [May 21, 1996].

GenBank™ Accession No. U83980 for Oncorhynchus mykiss cytochrome c oxidase subunit VIa mRNA, complete cds. [May 31, 1997].

GenBank™ Accession No. V00185 J01268 for Slime mold (D. discoideum) gene for actin 2 sub2 [Jul. 6, 1989].

GenBank™ Accession No. W10587 Soares mouse p3NMF 19.5 *Mus musculus* cDNA clone IMAGE:313054 5', mRNA sequence [Oct. 1, 1997].

GenBank™ Accession No. W30750 for Soares_senescent_fibroblasts_NbHSF *Homo sapiens* cDNA clone IMAGE:309678 5', mRNA sequence [Aug. 20, 1996].

GenBank™ Accession No. W39572 for Soares_senescent_fibroblasts NbHSF *Homo sapiens* cDNA clone 322829 5', mRNA sequence [Oct. 10, 1996].

GenBank™ Accession No. W39690 for Soares_senescent_fibroblasts NbHSF *Homo sapiens* cDNA clone IMAGE:322977 5', mRNA sequence [Oct. 10, 1996].

GenBank™ Accession No. W45045 for Soares_senescent_fibroblasts_NbHSF *Homo sapiens* cDNA IMAGE:clone 322981 3', mRNA sequence [Oct. 10, 1996].

GenBank™ Accession No. W45126 for Soares_senescent_fibroblasts_NbHSF *Homo sapiens* cDNA clone 322864 3', mRNA sequence [Oct. 10, 1996].

GenBank™ Accession No. W46824 for Soares_senescent_fibroblasts_NbHSF *Homo sapiens* cDNA clone IMAGE:324601 3', mRNA sequence [May 23, 1996].

GenBank™ Accession No. W46873 for Soares_senescent_fibroblasts_NbHSF *Homo sapiens* cDNA clone IMAGE:324601 5', mRNA sequence [May 23, 1996].

GenBank™ Accession No. W51876 for Soares_senescent_fibroblasts_NbHSF *Homo sapiens* cDNA clone 324400 3', mRNA sequence [Nov. 25, 1996].

GenBank™ Accession No. W55979 for Soares_senescent_fibroblasts_NBhh 19w *Homo sapiens* cDNA clone 340680 5', mRNA sequence [Oct. 15, 1996].

GenBank™ Accession No. W61032 for Soares_senescent_fibroblasts_NBHSF *Homo sapiens* cDNA clone 326135 5' similar to contains element MER22 repetitive element; mRNA sequence [Oct. 11, 1996].

GenBank™ Accession No. W61716 for Soares mouse embryo NbME13.5 14.5 *Mus musculus* cDNA clone IMAGE:372542 5' similar to gb:U01317_cds4 Hemoglobin Delta Chain (Human); gb:V00722 Mouse gene for beta-1-globin (Mouse) [Jun. 7, 1996].

GenBank™ Accession No. W72126 for Soares_fetal_heart_NbHH19W *Homo sapiens* cDNA clone 345970 3', mRNA sequence [Oct. 17, 1996].

GenBank™ Accession No. W79975 for Soares mouse embryo NbME13.5 14.5 *Mus musculus* cDNA clone 402616 5'. mRNA sequence [Jun. 25, 1996].

GenBank™ Accession No. X78612 for G.gallus genomic DNA repeat region, clone 12F6 [Apr. 6, 1994].

GenBank™ Accession No. Z31224 Mouse testis t-ZAP *Mus musculus* cDNA, mRNA sequence [Jan. 24, 1995].

GenSeq™ Accession No. V38798 for *Homo sapiens* cerebellum and embryo specific protein [Nov. 9, 1998].

GenSeq™ Accession No. X22249 for Human secreted protein gene 39 clone HPMBZ15 [May 18, 1999].

GenSeq™ Accession No. X51459 for Human secreted protein 5' EST Seq ID No.: 38 [Jun. 21, 1999].

GenSeq™ Accession No. X52255 for Protein PRO295 cDNA clone DNA38268-1188 [Jun. 25, 1999].

GenSeq™ Accession No. X56830 for Human phdkk-2 cDNA [Jul. 14, 1999].

GenSeq™ Accession No. X97746 for Extended human secreted protein coding sequence, Seq ID No.: 311 [Sep. 13, 1999].

George et al. "Current methods in sequence comparison and analysis" in *Macromolecular Sequencing and Synthesis Selected Methods and Applications* (D.H. Schlesinger, ed., Alan R. Liss, Inc., New York, NY, Mar. 1988) pp. 127-149.

Glinka, Andrei et al. "Dickkopf-1 is a member of a new family of secreted roteins and functions in head induction" *Nature* 391(6665):357-62 (Jan. 22, 1998).

Grotewold, L. et al. "Expression pattern of *Dkk*-1 during mouse limb development" *Mech. Dev.* 89:151-153 (1999).

Klein R.D. et al. "Selection for genes encoding secreted proteins and receptors" *Pro. Natl. Acad. Sci. USA* 93:7108-7113 (1996).

Krupnick, Valery E. et al. "Functional and structural diversity of the human Dickkopf gene family" *Gene* 238(2):301-13 (Oct. 1, 1999).

Lennon et al. "The I.M.A.G.E. Consortium: an integrated molecular analysis of genomes and their expression" *Genomics* 33(1): 151-52 (Apr. 1, 1996).

Ligon, A.H. et al. "Identification of a novel gene product, *RIG*, that is down-regulated in human glioblastoma" *Oncogene* 14(9):1075-1081 (1997).

Lodish et al. Molecular Cell Biology, 3rd Edition (W.H. Freeman & Co., Mar. 1995), p. 266.

Monaghan, A.P. et al. "Dickkopf genes are co-ordinately expressed in mesodermal lineages", *Mech. Dev.* 87(1-2):45-56 (1999).

Ngo et al. The Protein Folding Problem and Tertiary Structure Prediction (Merz & Le Grand Eds., Springer Derlag, 1994) pp. 433, 492-495.

Nusse, R. et al. "Wnt genes" *Cell*, 69:1073-1087 (1992).

Parr, B.A. et al. "Wnt genes and vertebrate development" *Current Opinion in Genetics and Development* 4:523-528 (1994).

Results of BLASTN Search of GenBank™ Non-Redundant EST Database (dbEST) using human CRSP-2 Nucleic Acid Sequence.

Results of BLASTN Search of GenBank™ Non-Redundant Nucleic Acid Database (nuc) using human CRSP-2 Nucleic Acid Sequence.

Results of BLASTX Search of GenBank™ Non-Redundant Protein Database (prot) using human CRSP-2 Nucleic Acid Sequence.

Results of BLASTN Search of GenBank™ Non-Redundant EST Database (dbEST) using human CRSP-3 Nucleic Acid Sequence.

Results of BLASTN Search of GenBank™ Non-Redundant Nucleic Acid Database (nuc) using human CRSP-3 Nucleic Acid Sequence.

Results of BLASTX Search of GenBank™ Non-Redundant Protein Database (prot) using human CRSP-3 Nucleic Acid Sequence.

Results of BLASTN Search of GenBank™ Non-Redundant EST Database (dbEST) using human CRSP-N Nucleic Acid Sequence.

Results of BLASTN Search of GenBank™ Non-Redundant Nucleic Acid Database (nuc) using human CRSP-N Nucleic Acid Sequence.

Results of BLASTX Search of GenBank™ Non-Redundant Protein Database (prot) using human CRSP-N Nucleic Acid Sequence.

Results of BLASTN Search of GenBank™ Non-Redundant EST Database (dbEST) using human CRSP-4 Nucleic Acid Sequence.

Results of BLASTN Search of GenBank™ Non-Redundant Nucleic Acid Database (nuc) using human CRSP-4 Nucleic Acid Sequence.

Results of BLASTX Search of GenBank™ Non-Redundant Protein Database (prot) using human CRSP-4 Nucleic Acid Sequence.

Sambrook et al. *Molecular Cloning: A Laboratory Manual*, Second Edition, vol. 1, 2 & 3 (Cold Spring Harbor Laboratory Press, Cold Spring Harbor, New York, Nov. 1989) p. 9.5.

Sawada, K. et al. "Characterization of termanally differentiated cell state by categorizing cDNA clones derived from chicken lens fibers" *Intl. J. Dev. Biol.* 40:531-535 (1996).

Tate, G. and T. Mitsuya, "Human Dickkopf as well as DAN Family Members, Cerbeus and Gremlin, are preferentially expressed in epithelial malignant cell lines" *J. Biochem. Mol. Biol. & Biophys.* 3:239-242 (1999).

Van Tilbeurgh, H. et al. "Colipase: structure and interaction with pancreatic lipase" *Biochim. Biophys. Acta* 1441:173-184 (1999).

U.S. Appl. No. 11/069,137, filed Feb. 28, 2005, Sean A. McCarthy.

U.S. Appl. No. 09/009,802, filed Jan. 20, 1998, Sean A. McCarthy.

Daniel, C. et al., "Mapping of linear antigenic sites on the S glycoprotein of a neurotropic murine coronavirus with synthetic peptides: A combination of nine prediction algorithms fails to identify relevant epitopes and peptide immunogenicity is drastically influenced by the nature of the protein carrier," *Virology*, 202: 540-549, 1994.

Mao, B. et al., "Kremen2 modulates Dickkopf2 activity during Wnt/LRP6 signaling," *Gene 302*:179-183, 2003.

Tian, E. et al., "The role of the Wnt-signaling antagonist DKK1 in the development of osteolytic lesions in multiple myeloma," *New England Journal of Medicine 349*(26): 2483-2494, 2003.

FIG. 1A

```
                                                                                                        10
GGCACGAGGGGCGGCGGCTGCGGGCCGCAGAGCGGAG                                                                   67
                                     M   Q   R   L   G   A   T   L   L   C
                                     ATG CAG CGG CTT GGG GCC ACC CTG TGC

L   L   L   A   A   A   V   P   T   A   P   A   P   A   P   T   A   T   S   A             30
CTG CTG CTG GCA GCG GCG GTC CCG ACG GCC CCC GCG CCG GCT GCG CCG ACG TCG GCT                 127

P   V   K   P   G   P   A   L   S   Y   P   Q   E   E   A   E   L   N   E   M             50
CCA GTC AAG CCC GGC CCG GCT CTC AGC TAC CCG CAG GAG GAG GCC GAG CTC AAT GAG ATG             187

F   R   E   V   E   E   L   M   E   D   T   Q   H   L   R   S   A   V   E             70
TTC CGC GAG GTT GAG GAA CTG ATG GAG GAC ACG CAG CAC CTG CGC AGC GCG GTG GAA            247

E   M   E   A   E   A   A   K   A   S   E   V   N   L   A   N   L             90
GAG ATG GAG GCA GAA GAA GCT GCT AAA GCA TCA GAA GTG AAC CTG GCA AAC TTA            307

P   P   S   Y   H   N   E   T   N   T   T   K   V   G   N   T   I   H             110
CCT CCC AGC TAT CAC AAT GAG ACC AAC ACA ACG AAG GTT GGA AAT ACC ATC CAT            367

V   H   R   E   I   H   K   I   T   N   N   Q   M   V   F   S   E             130
GTG CAC CGA GAA ATT CAC AAG ATA ACC AAC AAC CAG ATG GTC TTT TCA GAG            427

T   V   I   T   S   V   G   D   E   G   R   R   S   H   E   C   I   D             150
ACA GTT ATC ACA TCT GTG GGA GAC GAA GGA AGG AGC CAC GAG TGC ATC ATC GAC            487

E   D   C   G   P   S   M   Y   Q   F   A   S   F   Q   Y   T   C   Q   P             170
GAG GAC TGT GGG CCC AGC ATG TAC CAG TTT GCC AGC TTC CAG TAC ACC TGC CAG CCA            547

C   R   G   Q   R   M   L   C   T   F   R   D   S   E   C   G   L   C             190
TGC CGG GGC CAG AGG ATG CTC TGC ACC TGC CGG GAC AGT GAG TGT GGA GAC CAG CTG TGT            607
```

FIG. 1B

```
      V   W   G   H   C   T   K   M   A   T   R   G   S   N   G   T   I   C   D   N     210
     GTC TGG GGT CAC TGC ACC AAA ATG GCC ACC AGG GGC AGC AAT GGG ACC ATC TGT GAC AAC     667

Q   R   D   C   Q   P   G   L   C   A   F   Q   R   G   L   F   P   V            230
     CAG AGG GAC TGC CAG CCG GGG CTG TGC GCC TTC CAG AGA GGC TTC CTG CTG CCT GTG         727

C   T   P   L   P   V   E   G   E   L   C   H   D   P   A   S   R   L   L   D     250
     TGC ACA CCC CTG CCC GTG GAG GGC GAG CTT TGC CAT GAC CCC GCC AGC CGG CTT CTG GAC     787

L   I   T   W   E   L   E   P   D   G   A   L   G   V   Y   C   P   C   A   G     270
     CTC ATC ACC TGG GAG CTA GAG CCT GAT GGA GCC TTG GGT GTG TAT TGC CCT TGT GCC AGT GGC  847

L   C   Q   P   H   S   I   L   P   L   E   D   V   C   K   P   T   F   V   G     290
     CTC TGC CAG CCC CAC AGC ATC CTG CCC CTG GAG GAT GTG TGC AAG CCG ACC TTC GTG GGG     907

S   R   D   Q   M   E   G   E   V   R   Q   L   E   D   E   A   Y   E   V         310
     AGC CGT GAC CAA GAT GGG GAG GTG CGC CAG CTG GAG GAC GAG GAG TAT GAG GTC             967

G   S   F   M   L   G   E   P   L   A   A   A   A   A   L   G   S   L   T   E     330
     GGC AGC TTC ATG CTG GGG GAG CCT CTG GCC GCT GCA GCG GCT GCC AGC CTG ACT GAA         1027

E   M   A   L   G   E   L   L   G   E   I                                         350
     GAG ATG GCG CTG GGG GAG CTG CTG GGA GGG GAA ATT                                     1087

*                                                                                 351
     TAG                                                                                 1090
```

FIG. 1C

```
ATCTGGACCAGGCTGTGGGTAGATGTGCAATAGAAATAGCTAATTTATTCCCCANGTGTGTGCTTTAAGCGTGGGCTG    1169
ACCAGGCTTCTTCCTACATCTTCTTCCCAGTAAGTTTCCCCTCTGGCTTGACAGCATGAGGTGTTGTGCATTGTTCAG    1248
CTCCCCCAGGCTGTTCTCCAGCTTCACAGTCTGGTGCTTGGGAGAGTCAGGCAGGGTTAAACTGCAGGAGCAGTTTGC    1327
CACCCCTGTCCAGATTATTGGCTGCTTTGCCTCTACCAGTTGGGCAGACAGCCGTTTGTTCTACATGGCTTTGATAATTG   1406
TTTGAGGGGAGGAGATGGAAACAATGTGGAGTCTCCCTCTGATTGGTTTTGGGGAAATGTGGAGAAGAGTGCCCTGCTT   1485
TGCAAACATCAACCTGGCCAAAAATGCAACAAATGAATTTTCCACGCCAGTTCTTTCCATGGGCATAGGTAAGCTGTGCCT   1564
TCAGCTGTTGCAGATGAAATGTTCGTTCACCCTGCATTACATGTGTTTATTCATCCAGCAGTGTTGCTCAGCTCCTAC    1643
CTCTGTGCCAGGGCAGCATTTCATATCCAAGATCAATTCCCTCTCTCAGCACACAGCCTGGGGAGGGGTCATTGTTCTC   1722
CTCGTCCATCAGGGATTTCAGAGGCTCTAAGCTCAGTGCTCTCTCCAGTCACACAGCTAGTGAAGACCAGAGCAG        1801
TTTCATCTGGTTGTGACTCTAAGCTCAGTGCTCTCTCCACTACCCCACACCAGCCTTGGTGCCACCAAAAGTGCTCCCC   1880
AAAAGGAAGGAGAATGGGATTTTTCTTTTGAGGCATGCACATCTGGAATTAAGGTCAAACTAATTCTCACATCCCCTA    1959
AAAGTAAACTACTGTTAGGAACAGCAGTGTTCTCACAGTGTGGGGCAGCCGTCCTTCTAATGAAGACAATGATATTGAC    2038
ACTGTCCCTCTTTGGCAGTTGCATTAGTAACTTTGAAAGGTATATGACTGAGCGTAGCATACAGGTTAACCTGCAGAAA   2117
CAGTACTTAGGTAATTGTAGGGCGAGGATTATAAATGAAATTTGCAAAATCACTTAGCAGCAACTGAAGACAATTATCA   2196
```

FIG. 1D

```
ACCACGTGGAGAAATCAAACCGAGCAGGGCTGTGTGTGAAACATGGTTGTAATATGCGACTGCGAACACTGAACTCTACG   2275

CCACTCCACAAATGATGTTTCAGGTGTCATGGACTGTTGCCACCATGTATTCATCCAGAGTTCTTAAAGTTTAAAGTT   2354

GCACATGATTGTATAAGCATGCTTTCTTTGAGTTTTAAATTATGTATAAACATAAGTTGCATTTAGAAATCAAGCATAA   2433

ATCACTTCAACTGCTAAAAAAAAAAAAAAAAAAAAAAAAAAAAAAAA   2479
```

FIG. 2A

```
                                                                                        79
GAATTCGGCACGAGAGACGACGTGCTGAGCTGCCAGCTTAGTGGAAGCTCTGCTCTGGGTGGAGAGCAGCCTCGCTTTG
                  M   V   A   A   V   L   L   G                                          8
GTGACGCCACAGTGCTGGGACCCCTCCAGAGAGCCCCGGATTGAAGG ATG GTG GCG GCC GTC CTG CTG GGG        148
 L   S   W   L   C   S   P   L   G   A   L   V   L   D   F   N   N   I   R   S          28
CTG AGC TGG CTC TGC TCT CCC CTG GGA GCT CTG GTC CTG GAC TTC AAC AAC ATC AGG AGC        208
 S   A   D   L   H   G   A   R   K   G   S   Q   C   L   S   D   T   D   C   N          48
TCT GCT GAC CTG CAT GGG GCC CGG AAG GGC TCA CAG TGC CTG TCT GAC ACG GAC TGC AAT        268
 T   R   K   F   C   L   Q   P   R   D   E   K   P   F   C   A   T   C   R   G          68
ACC AGA AAG TTC TGC CTC CAG CCC CGC GAT GAG AAG CCG TTC TGT GCT ACA TGT CGT GGG        328
 L   R   R   C   Q   R   D   A   M   C   P   C   T   L   C   V   N   D              88
TTG CGG AGG TGC CAG CGA GAT GCC ATG TGC CCT TGC ACA CTC TGT GTG AAC GAT                388
 V   C   T   T   M   E   D   A   T   P   I   L   E   R   Q   L   D   E   Q   D        108
GTT TGT ACT ACG ATG GAA GAT GCA ACC CCA ATA TTA GAA AGG CAG CTT GAT GAG CAA GAT        448
 G   T   H   A   E   G   T   T   G   H   P   V   Q   E   N   Q   P   K   R   K        128
GGC ACA CAT GCA GAA GGA ACA ACT GGG CAC CCA GTC CAG GAA AAC CAA CCC AAA AGG AAG        508
 P   S   I   K   K   S   Q   G   R   K   G   Q   E   G   E   S   C   L   R   T        148
CCA AGT ATT AAG AAA TCA CAA GGC AGG AAG GGA CAA GAG GGA GAA AGT TGT CTG AGA ACT        568
```

FIG. 2B

```
     F    D    C    G    P    G    L    C    C    A    R    H    F    W    T    K    I    C    K    P   168
     TTT  GAC  TGT  GGC  CCT  GGA  CTT  TGC  TGT  GCT  CGT  CAT  TTT  TGG  ACG  AAA  ATT  TGT  AAG  CCA  628

V    L    F    G    Q    Q    V    C    S    R    R    G    H    K    D    T    A    Q    A    P   188
     GTC  CTT  TTG  GAG  GGA  CAG  GTC  TGC  TCC  AGA  AGA  GGG  CAT  AAA  GAC  ACT  GCT  CAA  GCT  CCA  688

E    I    F    Q    R    C    D    C    G    P    G    L    C    R    S    Q    L    T    S       208
     GAA  ATC  TTC  CAG  CGT  TGC  GAC  TGC  GGC  CCT  GGA  CTA  CTG  TGT  CGA  AGC  CAA  TTG  ACC  AGC 748

N    R    Q    H    A    R    L    R    V    C    Q    K    I    E    K    L    *               225
     AAT  CGG  CAG  CAT  GCT  CGA  TTA  AGA  GTA  TGC  CAA  AAA  ATA  GAA  AAG  CTA  TAA              799

ATATTCAAAATAAAGAAGAATCCACATTGCAAAAAAAAAAAAAAA                                                     848
```

FIG. 3A

```
GTCGACCCACGCGTCCGCGGACGCGTGGGCGGCACGGTTTCGTGGGACCCAGGCTTGCAAAGTGACGGTCATTTCTC  79
                                                                M  M  A  L  G  A  A  G  A  T  R  V   12
TTTCTTTCTCCCCTCTTGAGTCCTTCTCTGAG ATG ATG GCT CTG GGC GCA GCG GGA GCT ACC CGG GTC  144
 F  V  A  M  V  A  A  A  A  L  G  G  H  P  L  L  G  V  S  A  T                   32
TTT GTC GCG ATG GTA GCG GCG GCT CTC GGC GGC CAC CCT CTG CTG GGA GTG AGC GCC ACC  204
 L  N  S  V  L  N  S  N  A  I  K  N  L  P  P  P  L  G  G  A                      52
TTG AAC TCG GTT CTC AAT TCC AAC GCT ATC AAG AAC CTG CCC CCA CCG CTG GGC GGC GCT  264
 A  G  H  P  G  S  A  V  S  A  A  P  G  I  L  Y  P  G  G  N                      72
GCG GGG CAC CCA GGC TCT GCA GTC AGC GCC GCG CCG GGA ATC CTG TAC CCG GGG AAT      324
 K  Y  Q  T  I  D  N  Y  Q  P  Y  P  C  A  E  D  E  E  C  G                      92
AAG TAC CAG ACC ATT GAC AAC TAC CAG CCG TAC CCG TGC GCA GAG GAC GAG GAG TGC GGC  384
 T  D  E  Y  C  A  S  P  R  G  D  A  G  V  M  C  P  G  N  Y                     112
ACT GAT GAG TAC TGC GCT AGT CCC CGC GGA GAC GCA GGC GTG TGC CCC GGG AAT TAC      444
 A  C  R  K  R  K  R  M  R  C  M  R  H  A  M  F  R  G  E  I  E  E               132
GCC TGC AGG AAG CGC CGA AAA CGC ATG CGT TGC ATG CGT CAC GCT ATG TTC CGA GGA ATT GAG GAA  504
 C  K  N  G  I  C  V  S  D  Q  N  H  S  T  L  D  G  Y  S  R  R  T               152
TGC AAA AAT GGA ATA TGT GTG TCT GAT CAA AAT CAT AGC ACC TTG GAT GGG TAT TCC AGA AGA     564
 T  I  T  E  S  F  G  N  H  S  T  L  D  G  Y  S  R  R  T                        172
ACC ATC ACT GAA AGC TTT GGT AAT GAT CAT AGC ACC TTG GAT GGG TAT TCC AGA AGA ACC  624
```

FIG. 3B

```
  T   L   S   S   K   M   Y   H   T   K   G   Q   E   G   S   V   C   L   R   S    192
ACC TTG TCT TCA AAA ATG TAT CAC ACC AAA GGA CAA GAA GGT TCT GTT TGT CTC CGG TCA     684

S   D   C   A   S   G   L   C   C   A   R   H   F   W   S   K   I   C   K   P    212
TCA GAC TGT GCC TCA GGA TTG TGT TGT GCT AGA CAC TTC TGG TCC AAG ATC TGT AAA CCT     744

V   L   K   E   G   Q   V   C   T   K   H   R   R   K   G   S   H   G   L   E    232
GTC CTG AAA GAA GGT CAA GTG TGT ACC AAG CAT AGG AGA AAA GGC TCT CAT GGA CTA GAA     804

I   F   Q   R   C   Y   C   G   E   G   L   S   C   R   I   Q   K   D   H   H    252
ATA TTC CAG CGT TGT TAC TGT GGA GAA GGT CTG TCT TGC CGG ATA CAG AAA GAT CAC CAT     864

Q   A   S   N   S   S   R   L   H   T   C   Q   R   H   *    267
CAA GCC AGT AAT TCT TCT AGG CTT CAC ACT TGT CAG AGA CAC TAA                          909

ACCAGCTATCCAAATGCAGTGAACTCCTTTTATATAATAGATGCTATGAAAACCTTTTATGACCTTCATCAACTCAATC     988
CTAAGGATATACAAGTTCTGTGGTTTCAGTTAAGCATTCCAATAACACCTTCCAAAAACCTGGAGTGTAAGAGCTTTGT    1067
TTCTTTATGGAACTCCCCCTGTGATTGCAGTAAATTACTGTATTGTAAATTCTCAGTGTGGCACTTACCTGTAAATGCAA  1146
TGAAACTTTTAATTATTTTCTAAAGGTGCTGCACTGCCTATTTTCCCTCTTGTTATGTAAATTTTTGTACACATTGAT    1225
TGTTATCTTGACTGACAAATATTCTATATTGAACTGAAGTAAATCATTCAGCTTATAGTTCTTAAAAGCATAACCCTT    1304
TACCCCATTTAATTCTAGAGTCTAGAACGCAAGGATCTCTTGGAATGACAAATGATATAGGTACCTAAAATGTAACATGAA 1383
AATACTAGCTTATTTCTGAAATGTACTATCTTAATGCTTAAATTATATTCCCTTTAGGCTGTGATAGTTTTTGAAAT     1462
AAAATTTAACATTAATATCATGAAATGTTATAAGTAGACATAAAAAAAAAAAAAAAAAAGGGGCCGC               1536
```

FIG. 4A

```
GTCGACCCACGCGGTCCGGCGGGAGCCCGCGGGAGCGTAGCGCGCAAGTCCGCGCTCCCTAGGCATCGCTGCGCTGGCAGCGA  79
TTCGCTGTCTCTTGTGAGTCAGGGGACAACGCTTCGGGGCAACTGTGAGTGCGCGTGTGGGGACCTCGATTCTCTTCA  158
GATCTCGAGGATTCGGTCCGGGGACGTCTCCTGATCCCCTACTAAAGCGCCTGCTAACTTTGAAAAGGAGCACTGTGTC  237
CTGCAAAGTTTGACACATAAAGGATAGGAGAGAAAAGCAACTGAGTTGAAGGAGAAGCTGATGCGG  316
GCCTCCTGATCAATTAAGAGAGGAGAGTTAAACCGCCGAGATCCCGGCGGGACCCAAGGAGGTGCGGGGCAAGAAGGAACGG  395
AAGCGGTGCGATCCACAGGGCTGGGTTTCTTGCACCTTGGGTCACGCCTCCTTGGCGAGAAAGCGCCTCGCATTTGAT  474
TGCTTCCAGTTATTGCAGAACTTCCTGTCCTGGTGGAGAAGCGGGTCTCTCGCTTGGGTTCCGCTAATTTCTGTCCTGAGG  553
CGTGAGACTGAGTTCATAGGGTCCTGGGTCCCCGAACCAGGAAGGGTTGAGGGAACACAATCTGCAAGCCCCCGCGACC  632
CAAGTGAGGGCCCCGTGTTGGGCCCCGTGTTGGGGGTCCTCCTCCCCCTTGCATTCCCACCCCCTCCGGGCTTTGCGTCTTCCTGGGGACCC  711
               M   A   A   L   M   R   S   K   D   S   C   C   L   L   L   17
CCTCGCCGGGAG ATG GCC GCG ATG CGG AGC AAG GAT TCG TCC TGC TGC CTG CTC CTA CTG  774
    A   V   L   M   V   E   S   Q   I   G   S   S   R   A   K   L   N   S   37
GCC GCG GTG CTG ATG GTG GAG AGC TCA CAG ATC GGC AGT TCG CGG GCC AAA CTC AAC TCC  834
    I   K   S   L   S   G   G   E   T   P   G   Q   A   A   N   R   S   A   G   M   57
ATC AAG TCC TCT CTG GGC GGG GAG ACG CCT GGT CAG GCC GCC AAT CGA TCT GCG GGC ATG  894
```

FIG. 4B

| | | | | | | | | | | | | | | | | | | | | |
|---|---|---|---|---|---|---|---|---|---|---|---|---|---|---|---|---|---|---|---|---|
| Y | Q | L | A | F | G | G | S | K | K | N | L | G | Q | A | Y | P | | | 77 | |
| TAC | CAA | CTG | GCA | TTC | GGC | GGC | AGT | AAG | AAG | AAC | CTG | GGG | CAG | GCC | TAC | CCT | | | 954 | |
| C | S | D | K | E | C | V | G | R | Y | C | H | S | P | H | Q | S | | | 97 | |
| TGT | AGC | GAT | AAG | GAG | TGT | GTT | GAA | AGG | TAT | TGC | CAC | AGT | CCC | CAC | CAA | TCA | | | 1014 | |
| S | A | C | M | C | N | K | K | R | C | H | R | D | G | M | C | C | | | 117 | |
| TCG | GCC | TGC | ATG | TGT | AAT | AAA | AAG | CGC | TGC | CAC | CGA | GAT | GGC | ATG | TGC | TGC | | | 1074 | |
| P | S | T | R | C | N | G | I | C | I | P | V | T | E | S | H | L | T | P | | 137 | |
| CCC | AGT | ACC | CGC | TGC | AAT | GGC | ATC | TGT | ATC | CCA | GTT | ACT | GAA | AGC | CAT | TTA | ACC | CCT | | 1134 | |
| H | I | P | A | L | D | G | T | R | H | R | D | R | N | H | Y | Q | N | | 157 | |
| CAC | ATC | CCG | GCT | CTG | GAT | GGT | ACT | CGG | CAC | AGA | GAT | CGA | AAC | CAT | TAC | TCA | AAC | | 1194 | |
| H | D | L | G | N | Q | L | R | S | P | H | T | K | M | E | G | H | G | | 177 | |
| CAT | GAC | TTG | GGA | AAT | CAG | CTA | CGA | AGT | CCA | CAC | ACT | AAG | ATG | GAG | GGT | CAT | GGG | | 1254 | |
| H | E | G | D | P | C | L | R | S | D | C | I | Q | H | C | F | C | A | R | | 197 | |
| CAT | GAA | GGA | GAC | CCC | TGC | CTA | CGA | TCA | GAC | TGC | ATT | CAG | CAT | TGC | TTT | TGC | GCT | CGT | | 1314 | |
| H | F | W | T | K | I | C | H | G | E | P | V | L | E | Q | D | C | T | K | Q | | 217 | |
| CAT | TTC | TGG | ACC | AAA | ATC | TGC | CAT | GGG | GAA | CCA | GTG | CTC | GAA | CAG | GAC | TGT | ACC | AAA | CAA | | 1374 | |
| R | K | G | S | H | Q | L | E | R | Q | R | C | A | K | G | L | | 237 | |
| CGC | AAG | AAG | GGT | TCT | CAT | CAG | CTG | GAG | CGG | CAG | CGT | TGC | GCG | AAG | GGC | CTG | | 1434 | |
| S | C | K | V | W | K | D | A | T | Y | S | K | A | R | L | H | V | C | Q | | 257 | |
| TCT | TGC | AAA | GTA | TGG | AAA | GAT | GCC | ACC | TAC | TCC | AAA | GCC | AGA | CTC | CAT | GTG | TGT | CAG | | 1494 | |

FIG. 4C

```
K    I   *     260
AAA  ATT TGA  1503

TCACCATTGAGGAACATCATTCAATTGCAGACTGTGAAGTTGTGTATTTAATGCATTATAGCATGGTTGGAAAATAAGGTT 1582

CAGATGCAAGAATGGCTAAAATAAGAATATAGATGATCACAAAAAGGGAGAAAGAAAACATGAAC 1661

TGAATAGATTAGAATGGGTGACAAATGCAGTGCAGCCAGTGTTTCCATTATGCAACTTGTCTATGTAAATAATGTACAC 1740
```

FIG. 4D

```
ATTTGTGGAAAATGCTATTATTAAGAGAACAAGCACACAGTGGAAATTACTGATGAGTAGCATGTGACTTTCCAAGAGT  1819
TTAGGTTGTGCTGGAGGAGAGGTTTCCTTCAGATTGCTGATTGCTTATACAAATAACCTACATGCCAGATTTCTATTCA  1898
ACGTTAGAGTTTAACAAAATACTCCTAGAATAACTTGTTATACAATAGTTTCTAAAAATAAAATTGCTAAACAAGAAAT  1977
GAAAACATGGAGCATTGTTAATTTACACAGAAAATTACCTTTTGATTGTAACACTACTTCTGCTGTTCAATCAAGAG   2056
TCTTGGTAGATAAGAAAAAAATCAGTCAATATTCCAAATAATTGCAAAATAATGCCAGTTGTTTAGGAAGGCCTTTA    2135
GGAAGACAAATAAATAACAAACAAACAGCCACAAATACTTTTTTTCAAAATTTAGTTTTACCTGTAATTAATAAGAA    2214
CTGATACAAGACAAAAACAGTTCCTTCAGATTCTACGGAATGACAGTATATCTCTCTTTATCCTATGTGATTCCTGCTC  2293
TGAATGCATTATATTTTCCAAAGTATACCCATAAATTGTGACTAGTAAAATACTTACACAGAGCAGAATTTTCACAGAT  2372
GGCAAAAAATTAAAGATGTCCAATATGTGGGAAAAGAGCTAACATGTATTCATACATACTCTGTGGTAATAGACTTGAGCTGAT  2451
AACCTGTATTTTGATAGAATTAGATTGGTAAAATACATGTATTCATACATACTCTGTGGTAATAGACTTGAGCTGAT   2530
CTGTACTGCACTGGAGTAAGCAAGAAAATTGGGAAAACTTTTCGTTTGTTCAGGTTTTGGCAACACATAGATCATATG   2609
TCTGAGGCACAAGTTGGCTGTGTTCATCTTTGAAACCAGGGATGCACAGTCTAAATGAATATCTGCATGGATTTGCTAT  2688
CATAATNTTCCTATGCNGNTGAATTCNGTGTGTGAGGTCCCTGTGTCCGTCCTATCCTCAAATTATTATTTATAGTGCT  2767
GAGATCCTCAAATAATCTCAATTTCGGAGGTTTCACAAAATGGACTCCTGAAGTAGACAGAGTAGTGAGGTTTCATTGC  2846
```

FIG. 4E

CCTCTATAAGCTTCTGACTAGCCAATGGCATCATCCAATTTTCTTCCCAAACCCTCTGCAGCATCTGCTTTATTGCCAAA 2925

GGGCTAGTTTCGGTTTTCTGCCAGCCATTGCGGTTAAAAATATAAGTAGGATAACTTGTAAAACCTGCATATTGCTAA 3004

TCTATAGACACCACAGTTTCTAAATTCTTTGAAACCACTTTACTACTTTTTTTAAACTTAACTCAGTTCTAAATACTTT 3083

GTCTGGAGCACAAAACAATAAAAGGTTATCTTATAGTTGTGACTTTAAACTTTTGTAGACCACAATTCACTTTTTAGTT 3162

TTCTTTTACTTAAATCCCATCTGCAGTCTCCAGTTCTCAAATTTAAGTTCTCCCAGTAGAGATTGAGTTTGAGCCTGTATATCTATT 3241

AAAAATTTCAACTTCCCACATATATTTACTAAGATGATTAAGACTTACATTTCTGCACAGGTCTCTGCAAAAACAAAAAT 3320

TATAAACTAGTCCATCCAAGAACCAAAGTTTGTATAAACAGTTGCTATAAGCTTGGTGAAATGAAAATGGAACATTTC 3399

AATCAAACATTTCCTATATAACAATTATATTTACAATTTGGTTTCTGCAATATTTTCTTATGTCCACCCTTTTAA 3478

AAATTATTATTTGAAGTAATTTATTTACAGGAAAATGTTAATGAGATGTATTTCTTATAGAGATATTTCTTACAGAAAG 3557

CTTTGTAGCAGAATATATTTGCAGCTATTGACTTTGTAATTTAGGAAAAATGTATATATAAGATAAAAATCTATTAAATTT 3636

TTCTCCTCTAAAAACTGAAAAAAAAAAAAAAAAAAAAAAAAAAGGGGCCGC 3687

FIG. 5A

```
FGTCGACCCACGCGTCCGCTGTGGCAGCCCAGCTACGGTCGTGACCAGATCCAGCTTGCAGCTCAGCTTTGTTCATTC    79

M   Q   R   L   G   G   I   L   L   C   T   L                  12
GAATTGGGCGGCGGCCAGCGCGGAACAAAC ATG CAG CGG CTC GGG GGT ATT TTG CTG TGT ACA CTG    145

L   A   A   A   V   P   T   A   P   S   P   T   V   T   W   T   P   A             32
CTG GCG GCG GCG GTC CCC ACT GCT CCT GCT TCC CCG ACG GTC ACT TGG ACT CCG GCG        205

E   P   G   P   A   L   N   Y   P   Q   E   E   A   T   L   N   E   M   F   R     52
GAG CCG GGC GGC CCA GCT CTC AAC TAC CCT CAG GAG GAA GCT ACG CTC AAT GAG ATG TTT CGA 265

E   V   E   E   L   M   E   D   T   Q   H   K   L   R   S   A   V   E   E   M     72
GAG GTG GAG GAG CTG ATG GAA GAC ACT CAG CAC AAA CTG CGC AGT GCC GTG GAG GAG ATG    325

E   A   E   E   A   A   A   K   T   S   S   E   V   N   L   A   S   L   P   P     92
GAG GCG GAA GAA GCA GCA GCT AAA ACG TCC TCT GAG GTG AAC CTG GCA AGC TTA CCT CCC    385

N   Y   H   E   N   E   T   I   T   N   N   Q   G   N   V   F   S   T   V   H   V  112
AAC TAT CAC GAG AAT GAG ACC AGC ACG ATA ACC AAC AAC CAG GGA AAT GTG GTC TTT TCT GAG ACA GTC CAT GTG 445

Q   E   V   H   K   S   R   S   H   E   C   I   D   E   T   V   132
CAG GAA GTT CAC AAG AGC AGG AGC CAT GAA TGT ATC GAT GAA GAC                        505

I   T   V   G   D   E   Q   K   Y   F   S   S   Q   C   R   D   152
ATT ACA TCT GTA GGG GAT GAA CAG AAG TAC TTC TCC AGC CAG TGC CGG                    565

C   G   P   T   R   Y   C   Q   Y   T   K   Y   T   S   F   P   172
TGT GGG CCC ACC AGG TAC TGC CAG TAC ACC AAG TAC ACC TCC TTC CCC                    625
```

FIG. 5B

```
    D   Q   Q   M   L   C   T   R   D   S   E   C   C   G   D   Q   L   C   A   W
    GAC CAG CAG ATG CTA TGC ACC CGA GAC AGT GAG TGC TGT GGA GAC CAG CTG TGT GCC TGG   192
                                                                                      685

G   H   C   T   Q   K   A   T   K   G   G   N   G   T   I   C   D   N   Q   R
    GGT CAC TGC ACC CAA AAG GCC ACC AAA GGT GGC AAT GGG ACC ATC TGT GAC AAC CAG AGG   212
                                                                                      745

D   C   Q   P   G   L   C   C   A   F   Q   R   G   L   F   P   V   C   T
    GAT TGC CAG CCT GGC CTG TGT TGT GCC TTC CAA AGA GGC CTG TTC CCC GTG TGC ACA       232
                                                                                      805

P   L   P   V   E   G   E   L   C   H   D   P   T   S   Q   L   D   L   I
    CCC CTG CCC GTG GAG GGA GAG CTC TGC CAT GAC CCC ACC AGC CAG CTG CTG GAT CTC ATC   252
                                                                                      865

T   W   E   L   E   P   G   A   L   D   R   C   P   C   A   S   G   L   L
    ACC TGG GAA CTG GAG CCT GAA GGA GCT TTG GAC CGA TGC CCC TGC GCC AGT GGC CTC CTA   272
                                                                                      925

C   Q   P   H   S   H   S   L   V   Y   M   C   K   P   A   F   V   G   S   H
    TGC CAG CCA CAC AGC CAC AGC CTG GTG TAC ATG TGC AAG CCA GCC TTC GTG GGC AGC CAT   292
                                                                                      985

D   H   S   E   E   E   S   E   E   A   P   R   E   A   P   D   E   Y   E   D   V   G
    GAC CAC AGT GAG GAG GAG AGC GAG GAG GCC CCC AGG GAG GCC CCG GAT GAG TAC GAA GAT GTT GGC   312
                                                                                              1045

F   I   G   E   V   R   Q   R   Q   E   L   E   D   L   E   R   S   L   A   Q   M
    TTC ATA GGG GAA GTG CGC CGC CAG GAG CTG GAA GAC CTG GAG CGG AGC CTA GCC CAG ATG   332
                                                                                      1105
```

FIG. 5C

```
  A   F   E   G   P   A   P   V   E   S   L   G   G   E   E   E   E   I   *                              350
GCA TTT GAG GGG CCT GCC CCT GTG GAG TCA CTA GGC GGA GAG GAG GAG GAG ATT TAG                             1159

GCCCAGAGACCCAGTGAGTCACTGGTAGATGTGCAATAGAAATGGCTAATTTATTTCCCAGGAGTGTCCCCAAGTGTGG                         1238

AATGGCCGCAGCTCCTTCCCAGTAGCTTTTCCTCTGGCTTGACAAGTGCAGTACATTCTTCCAGCCGCCCTG                               1317

CTTCTCTGACTTGGGAAAGACAGGCATGGCGGGTAAGGGCAGCGGTGAGTCGTCCCTGCTGTTGCTAGAAACGCTGTC                          1396

TTGTTCTTCATGGATGGAAGATTTGTTTGAAGGGAGAGGATGGAAGTCTGCTCATGATGGATTTGGGGGA                                 1475

TACAGGGAGGAGGATGCCTGCCTTGCAGACGTGGACTTGGCAAAATGTAACCTTTGCTTTTGTCTTGCCGCTCCCAT                           1554

GGGCTGAGGCAGTGGCTACACAGAGCTATGCTGCTCTGTGGCCTCCCACATATTCATCCCTGTGTTTCAGCTCCTACC                          1633

TCACTGTCAGCACAGCCCTTCATAGCCACGCCCCCCTCTGCTCACCACAGCCCTCTGTGCCAGGAGGGACCAGAGGGGACTTCTCT                  1712

CAGAGCCCCATGCTCTCTCTCTCAACCCCATACCCAGCCTGCCAGCAGCAGTCCTTCCAAATGGAGGAGTGAAAT                             1791

CCTTTGGTTTAATTATTTCTCCCTTCAAGGCACGCCTGCCACTAAGGTCAGGCTGACTTGCATGTCCCTCTAACGTTCG                         1870

TAGCAGTGTGGTGGACACTGTCTTCCACCGACTGCTTCAATACCCTCTGAAAGCCAGTCGGAGTGCAGTTCGTGTAA                           1949

ATTAATTTGCAGGAAGTATACTTGGCTAATTGTAGGCTAGGATTGTGAATGAAATTTGCAAAGTGCTTAGCAACAAT                           2028

GGAAAGCCTTTCTCAGTCACACCGAGAAGTCACAACCAAGCCAGTTGTGTAGAGTACACAGCTGTGACATACAGACAGAA                         2107
```

FIG. 5D

GAAGGCTGGGCTGGATGTCAGGCCTCAGATGACGGTTTCAGGTGCCAGGAACTATTACCATTCTGTATCTATCCAGAGT 2186

TATTAAAATTGAAAGTTGCACACATTTGTATAAGCATGCCTTTCTCCTGAGTTTTAAATTATATGTATACACAAACATG 2265

TGGCCCCTCAAAGATCATGCACAAACCACTACTCTTTGCTAATTCTTGGACTTTTCTCTCTTTGATTTTCAATAAATACAAA 2344

TCCCCTTCATGCAAAAAAAAAAAAAAGGGGCCGC 2381

FIG. 6A

```
                                                                              60
hdkk-1   ~~~~~~~~~~ ~~~~~~~~~~ ~~~~~~~~~~ ~~~~~~~~~~ ~~~~~~~~~~ ~~~~~~MMAL
mdkk-1   ~~~~~~~~~~ ~~~~~~~~~~ ~~~~~~~~~~ ~~~~~~~~~~ ~~~~~~~~~~ ~~~~~~MMVV
xdkk-1   ~~~~~~~~~~ ~~~~~~~~~~ ~~~~~~~~~~ ~~~~~~~~~~ ~~~~~~~~~~ ~~~~~~~~~~
hdkk-2   MQRLGATLLC LLLAAAVPTA PAPAP..... .TATSAPV KPGPALSYPQ EEATLNEMFR
hdkk-3   MQRLGGILLC TLLAAAVPTA PAPSP..... .TVTWTPA EPGPALNYPQ EEATLNEMFR
mdkk-3   ~~~~~~~~MRRG EGPAPRRRWL LLLAVLAALC CAAAGSGGRR RAASLGEMLR
cdkk-3   ~~~~~~~~~~ ~~~~~~~~~~ ~~~~~~~~~~ ~~~~~~~~~~ ~~~~~~~~~~ ~~~~~~~~~~
hdkk-4   ~~~~~~~~~~ ~~~~~~~~~~ ~~~~~~~~~~ ~~~~~~~~~~ ~~~~~~~~~~ ~~~~~~~~~~

61                                                                   120
hdkk-1   GAAGATRVFV AMVAAALGGH PLL...G..V SATLNSVL.. NSNAIKNLP. PPLGGAAGHP
mdkk-1   CAPAAVRFLA VFTMALCSL  PLL...G..A SATLNSVLI. NSNAIKNLP. PPLGGAGGQP
xdkk-1   ~~MGSNMFPV PLIVFWGFIL DGALGFVMMT NSNSIKNVPA APAGQPIGY.
hdkk-2   ~~MA ALMRSKDSSC CLLLAAVLM ..VESSQIG SSRAKLNSIK SSLGGET..P
hdkk-3   EVEELMEDTQ HKLRSAVEEM E.AEEAAAKA SSEVNLANLP PSYHNETNTD TKVGNNTIHV
mdkk-3   EVEELMEDTQ HKLRSAVEEM E.AEEAAAKT SSEVNLASLP PNYHNETSTE TRVGNNTVHV
cdkk-3   EVEALMEDTQ HKLRNAVQEM E.AEEEGAKK LSEVNFENLP PTYHNESNTE TRIGNKTVQT
hdkk-4   ~~~~~~~~~~ ~~~~~~~~~~ ~~~~~~~~~~ ~~~~~~~~~~ ~~~~~~~~~~ ~MVAAVLLGL 121                                                                  180
hdkk-1   GSAV.....SA APGILYPG.. .GNKYQTIDN YQPYPCAEDE ECGTDEYCAS PTRG..GDAG
mdkk-1   GSAV.....SV APGVLYEG.. GNKYQTLDN  YQPYPCAEDE ECGSDEYCSS PSRGAAGVGG
xdkk-1   .YPV.....SV SPDSLYDI.. .ANKYQPLDA YPLYSCTEDD DCALDEFCHS SRNGNS....
hdkk-2   .GQAA....NR SAG.MYQGLA FGGSKKGKNL GQAYPCSSDK ECEVGRYCHS PHQGSSA...
hdkk-3   HREIHKITNN QTGQMVFSET VITSVGDEEG RRSHECIIDE DCGPSMYC.. ......QFASF
mdkk-3   HQEVHKITNN QSGQVVFSET VITSVGDEEG KRSHECIIDE DCGPTRYC.. ......QFSSF
cdkk-3   HQEIDKVTDN RTGSTIFSET IITSIKGGEN KRNHECIIDE DCETGKYC.. ......QFSTF
hdkk-4   SWLC.....SP LGALVLDFNN IRSSADLHGA RKGSQCLSDT DCNTRKFCLQ PRDEKP....
```

FIG. 6B

```
         181                                                              240
hdkk-1   VQICLACRKR RKRCMRHAMC CPGNYCKNGI CVS..SDQNH F..RGEIEET ITESFGN.DH
mdkk-1   VQICLACRKR RKRCMTHAMC CPGNYCKNGI CMP..SDHSH FP.RGEIEES IIENLGN.DH
xdkk-1   .LVCLACRKR RKRCLRDAMC CTGNYCSNGI CVPVEQDQER FQHQGYLEET ILENYNNADH
hdkk-2   ..CMVCRRK KKRCHRDGMC CPSTRCNNGI CIPV.TESIL TPHIPALDGT RHRD.RNHGH
hdkk-3   QYTCQPCRGQ RMLCTRDSEC CGDQLCVWGH CTKMAT.... .......... ..........
mdkk-3   KYTCQPCRDQ QMLCTRDSEC CGDQLCAWGH CTQKAT.... .......... ..........
cdkk-3   EYKCQPCKTQ HTHCSRDVEC CGDQLCVWGE CRKATS.... .......... ..........
hdkk-4   ..FCATCRGL RRRCQRDAMC CPGTLCVNDV CTTME.DATP ILERQLDEQD GTHAEGTTGH 241                                                              300
hdkk-1   STL..DGYSR RTTLSSKMYH TKGQEGSVCL RSSDCASGLC CA..RHFWSK ICKPVLKEGQ
mdkk-1   NAAAGDGYPR RTTLTSKIYH TKGQEGSVCL RSSDCAAGLC CA..RHFWSK ICKPVLKEGQ
xdkk-1   ATM..DTHSK LTTSPSGMQP FKGRDGDVCL RSTDCAPGLC CA..RHFWSK ICKPVLDEGQ
hdkk-2   YSNHDLGWQN LGRPHTKMSH IKGHEGDPCL RSSDCIEGFC CA..RHFWTK ICKPVLHQGE
hdkk-3   .......... .......... .RGSNGTTCD NQRDCQPGLC CAFQRGLLFP VCTPLPVEGE
mdkk-3   .......... .......... .KGGNGTTCD NQRDCQPGLC CAFQRGLLFP VCTPLPVEGE
cdkk-3   .......... .......... .RGENGTICE NQHDCNPGTC CAFQKELLFP VCTPLPEEGE
hdkk-4   PV..QENQPK RKPSIKKSQG RKGQEGESCL RTFDCGPGLC CA..RHFWTK ICKPVLLEGQ 301                                                              360
hdkk-1   VC...TKHRR KG.SHGLE.. .IFQRCYCGE GLSCRIQK.D HHQASNSSRL HTCQRH~~~
mdkk-1   VC...TKHKR KG.SHGLE.. .IFQRCYCGE GLACRIQK.D HHQASNSSRL HTCQRH~~~
xdkk-1   VC...TKHRR KG.SHGLE.. .IFQRCHCGA GLSCRLQKGE FTTVPKTSRL HTCQRH~~~
hdkk-2   VC...TKQRK KG.SHGLE.. .IFQRCDCAK GLSCKVWKD. .ATYSSKARL HVCQKI~~~
hdkk-3   LCHDPASRLL DLITWELEPD GALDRCPCAS GLLCQPH.SH SLVYVCKPTF VGSRDQDGE.
mdkk-3   LCHDPTSQLL DLITWELEPE GALDRCPCAS GLLCQPH.SH SLVYMCKPAF VGSHDESEE.
cdkk-3   PCHDPSNRLL NLITWELEPD GVLERCPCAS GLICQPQSSH STTSVCELSS NETRKNEKED
hdkk-4   VC...SRRGH KDTAQAPE.. .IFQRCDCGP GLLCRSQLTS NRQH...ARL RVCQKIEKL~
```

FIG. 6C

```
        361                                                              424
hdkk-1  ~~~~~~~~~~ ~~~~~~~~~~ ~~~~~~~~~~ ~~~~~~~~~~ ~~~~~~~~~~ ~~~~~~~~~~ ~~~~
mdkk-1  ~~~~~~~~~~ ~~~~~~~~~~ ~~~~~~~~~~ ~~~~~~~~~~ ~~~~~~~~~~ ~~~~~~~~~~ ~~~~
xdkk-1  ~~~~~~~~~~ ~~~~~~~~~~ ~~~~~~~~~~ ~~~~~~~~~~ ~~~~~~~~~~ ~~~~~~~~~~ ~~~~
hdkk-2  ~~~~~~~~~~ ~~~~~~~~~~ ~~~~~~~~~~ ~~~~~~~~~~ ~~~~~~~~~~ ~~~~~~~~~~ ~~~~
hdkk-3  .......... ILLPREVPDE YEVGSFMEEV RQELEDLERS LTEEMALGEP AAAAAALLGGEEI~
mdkk-3  .......... SQLPREAPDE YEDVGFIGEV RQELEDLERS LAQEMAFEGP APVES..LGGEEI~
cdkk-3  PLNMDEMPFI SLIPRDILSD YEESSVIQEV RKELESLE.. .DQAGVKSEH DPAHDLFLGDEI~
hdkk-4  ~~~~~~~~~~ ~~~~~~~~~~ ~~~~~~~~~~ ~~~~~~~~~~ ~~~~~~~~~~ ~~~~~~~~~~ ~~~~
```

FIG. 7A

```
CTCGAGGCCAAAATTCGGCACGAGGCCGGGCTGTGTCTAGCATAAAGGCGGAGCCCAGAAGAAGGGGCGGGGT                                                 1
                                                                                                                            77
     G   E   A   S   P   P   A   P   A   R   H   L   V   L   L   L   L   L                                                21
     GGA GAA GCC TCC CCA CCT GCC CCC GCA AGG CAT CTG GTC CTG CTG CTG CTG CTC                                              137
     S   T   L   V   P   I   S   A   A   P   I   H   D   A   D   A   Q   E   S                                            41
     TCT ACC CTG GTG CCC ATC TCC GCT GCA CCT ATC CAT GAT GCT GAC GCC CAA GAG AGC                                          197
     S   L   G   L   T   G   L   L   Q   S   L   L   Q   G   F   S   R   L   F   L   K                                    61
     TCC TTG GGT CTC ACA GGC CTC CTA CAG AGC CTC CAA GGC TTC AGC CGA CTT TTC CTG AAA                                      257
     G   N   L   L   R   G   I   D   S   L   F   S   A   P   M   D   F   R   G   L                                        81
     GGT AAC CTG CTT CGG GGC ATA GAC AGC TTA TTC TCT GCC CCC ATG GAC TTC CGG GGC CTC                                      317
     P   G   N   Y   H   K   E   E   N   Q   E   H   Q   L   G   N   T   L   S                                           101
     CCT GGG AAC TAC CAC AAA GAG GAG AAC CAG CAG CAC CAG CTG GGG AAC ACC CTC TCC                                          377
     S   H   L   Q   I   D   K   M   T   D   N   K   T   G   E   V   L   I   S   E                                       121
     AGC CAC CTC CAG ATC GAC AAG ATG ACC GAC AAC AAG ACA GGA GAG GTG CTG ATC TCC GAG                                      437
     N   V   A   E   K   E   A   I   Q   P   A   E   G   S   F   A   K   D   L   K   V   P                               141
     AAT GTG GCA GAG AAG GAG GCG CAA CCA GCG GAG GGG AGC TTC GAG AAG GAT TTG AAG GTA CCC                                  497
     R   M   E   E   K   E   A   L   V   P   K   A   T   D   S   F   H   T                                               161
     AGG ATG GAG GAG AAG GAG GCC CTG GTA CCC ATC CAG AAG GCC ACG GAC AGC TTC CAC ACA                                      557
     E   L   H   P   R   V   A   F   W   A   I   K   L   P   R   R   S   H   Q                                           181
     GAA CTC CAT CCC CGG GTG GCC TTC TGG GCC ATT AAG CTG CCA CGG AGG TCC CAC CAG                                          617
```

FIG. 7B

```
 D   A   L   E   G   G   H   W   L   S   E   K   R   H   R   L   Q   A   I   R    201
GAT GCC CTG GAG GGC GGC CAC TGG CTC AGC GAG AAG CGA CAC CGC CTG CAG GCC ATC CGG    677

D   G   L   R   K   G   T   H   K   D   V   L   E   E   G   T   E   S   S   S    221
GAT GGA CTC CGC AAG GGG ACC CAC AAG GAC GTC CTA GAA GAG GGG ACC GAG AGC TCC TCC    737

H   S   R   L   S   P   R   K   T   H   L   L   Y   I   L   R   P   S   R   Q    241
CAC TCC AGG CTG TCC CCC CGA AAG ACC CAC TTA CTG TAC ATC CTC AGG CCC TCT CGG CAG    797

L   *                                                                              243
CTG TAG                                                                             803

GGGTGGGGACCGGGGAGCACCTGCCTGTAGCCCCCATCAGACCCTGCCCCAAGCACCATATGGAAATAAAGTTCTTTCT    882

TACATCTAAAAAAAAAAAAAAAAAAAAAAAAAAATTGGCGGCCGC                                       928
```

FIG. 8A

```
                                                                                    M   C   R   L   R     5
GAATTCGGCACGAGGCAGAAGGCGCGAATGAAGGCAAAGCCTCCCACCCTGCA ATG TGT CGA CTG AGG          71

V   L   L   L   L   P   L   A   F   V   S   S   A   L   P   I   H   D            25
GTC TTG CTG CTG CTG CCC TTG GCC TTC GTG TCC TCT GCT CTC CCC ATC CAT GAT           131

V   D   S   Q   Q   N   T   S   G   F   L   G   L   Q   R   L   Q   S   F        45
GTG GAC TCT CAG CAG AAC ACC TCC GGG TTC CTG GGC CTT CAG AGG CTC CAA AGC TTT       161

S   R   L   F   L   K   N   D   L   R   D   L   D   N   F   S   S   P            65
AGT CGA CTG TTC CTA AAA AAT GAC CTA CGA GAC CTG GAC AAC TTC TCC TCC CCC           251

M   D   F   R   D   L   P   R   N   F   H   Q   E   N   E   H   R   M            85
ATG GAC TTC CGA GAC CTT CCT AGG AAC TTC CAT CAG GAG AAC GAG CAC AGA ATG           311

G   N   H   T   L   S   S   A   H   I   Q   D   K   V   T   D   N   Q   T       105
GGC AAC CAT ACC CTC TCC AGC CAC CTA CAG ATA GAC AAG GTG ACT GAC AAC CAG ACA GGG   371

E   V   H   I   S   E   K   V   E   A   S   I   E   P   E   R   N   P   E   G   125
GAG GTG CAC ATC TCG GAG AAA GTC GAG GCC TCC ATT GAG CCA GAA CGG AAC CCG GAA GGG   431

D   W   K   V   P   Q   K   V   E   A   K   E   P   V   P   Q   K   V   T       145
GAC TGG AAG GTT CCC CAA AAA GTA GAA GCA AAA GAG CCC GTG CCT GTG CAG AAG GTC ACC   491

D   S   L   H   P   E   P   R   Q   V   A   F   W   I   M   K   M   P   R   R   165
GAC AGC TTG CAC CCA GAG CCC CGG CAG GTG GCT TTC TGG ATC ATG AAG ATG CCA AGG CGG   551
```

FIG. 8B

```
      R   T   Q   P   D   V   Q   D   G   G   R   W   L   I   E   K   R   H   R   M      185
      AGG ACC CAG CCC GAT GTC CAG GAT GGA GGC CGC TGG CTC ATA GAA AAG CGA CAT CGC ATG      611

Q   A   I   R   D   G   L   R   G   G   A   R   E   D   S   L   E   D   G   V      205
      CAG GCC ATC CGG GAT GGG CTC CGT GGA GGC GCC CGT GAG GAC AGC CTG GAG GAT GGG GTC      671

H   I   P   Q   H   A   K   L   P   V   R   K   T   H   F   L   Y   I   L   R      225
      CAT ATC CCC CAA CAC GCC AAG CTG CCT GTC AGA AAG ACA CAC TTT CTC TAC ATC CTC AGG      731

P   S   Q   Q   L   *                                                                231
      CCA TCC CAA CAG CTG TAA GTGGGGACCAGATGTCCCACACCCTACCCCAACACCATATGGAAATAAAGGTTTTC      805

TTACATCTAAAAAAAAAAAAAAAAAA                                                             835
```

FIG. 10A

```
        1
hsoggy  MGEASPPAPA RRHL.LVLLL LLSTLVIPSA AAPIHDADAQ ESSLG...... ...LTGLQSL
msoggy  ~~~~~~~~~~ MCRL.RVLLL LLPLAFVSSS ALPIHDVDSQ QNTSG...... ...FLGLQRL
hdkk-3  ~~~~~~~~~~ MQRLGATLLC LLLAAAVPTA PAPAPTATSA PVKPGPALSY PQEEATLNEM
mdkk-3  ~~~~~~~~~~ MQRLGILLC  TLLAAAVPTA PAPSPTVTWT PAEPGPALNY PQEEATLNEM
                                                                *

61                                                             120
hsoggy  LQGFSRLF.. LKGNLLRGID SL.......... FSAPMDFRGL PGNYHKEENQ EHQLGNNTLS
msoggy  LQSFSRLF.. LKNDLLRDLD NF.......... FSSPMDFRDL PRNFHQEENQ EHRMGNHTLS
hdkk-3  FREVEELMED TQHKLRSAVE EMEAEEAAAK   ASSEVNLANL PPSYHNETNT DTKVGNNTIH
mdkk-3  FREVEELMED TQHKLRSAVE EMEAEEAAAK   TSSEVNLASL PPNYHNETST ETRVGNNTVH
                        *                                   *

121                                                            180
hsoggy  SHLQIDKMTD NKTGEVLISE NVVASIQPAE GSFEGDLKVP RMEEKEALVP IQKATDSFHT
msoggy  SHLQIDKVTD NQTGEVHISE KVEASIEP.E RNPEGDWKVP KVEAKEPPVP VQKVTDSLHP
hdkk-3  VHREIHKITN NQTGQMVFSE TVITSVGDEE GR........ ..RSHECII. .....DEDCGP
mdkk-3  VHQEVHKITN NQSGQVVFSE TVITSVGDEE GK........ ..RSHECII. .....DEDCGP
                      *                                   *

181                                                            240
hsoggy  ELHPR.VAFW IIKLPRRRSH .....QDALEG GHWLSEKRHR LQAIRDGLRK ..:GTHKD..
msoggy  E..PRQVAFW IMRMPRRRTQ .......PDVQDG GRWLIEKRHR MQAIRDGLRG ..:GARED..
hdkk-3  SMYCQFASFQ YTCQPCRGQR MLCTRDSECC GDQLCVWGHC TKMATRGSNG TTCDNQRDCQ:
mdkk-3  TRYCQFSSFK YTCQPCRDQQ MLCTRDSECC GDQLCAWGHC TQKATKGGNG TDCDNQRDCQ:
                                           *
```

FIG. 10B

```
         241
hsoggy   .....VLEEG TESSSHSRLS PRKTHLLYIL RPSRQL
msoggy   .....SLEDG VHIPQHAKLP VRKTHFLYIL RPSQQL
hdkk-3   PGLCCAFQRG LLFPVCTPLP V.EGELCH... DPASRLLDLI TWELEPDGAL DRCPCASGLL
mdkk-3   PGLCCAFQRG LLFPVCTPLP V.EGELCH... DPTSQLLDLI TWELEPEGAL DRCPCASGLL
                *                           *     *                        300

301
hdkk-3   CQPHSHSLVY VCKPTFVGSR DQDGEILLPR EVPDEYEVGS FMEEVRQELE DLERSLTEEM
mdkk-3   CQPHSHSLVY MCKPAFVGSH DHSEESQLPR EAPDEYEDVG FIGEVRQELE DLERSLAQEM
                                                                            360

361      379
hdkk-3   ALGEPAAAAA ALLGGEEI~
mdkk-3   AFEGPAPVES ..LGGEEEI
```

FIG. 11

```
                1                                                                                              100
hDkk-1    TKGQEGSVCL RSSDCASGLC CA..RHFWSK ICKPVLKEGQ VCTKHRRK.. ......GSHGL EIFQRCYCGE GLSCRIQKDH HQASNSSRLH TCQRH~~~~
hDkk-2    IKGHEGDPCL RSSDCIEGFC CA..RHFWTK ICKPVLHQGE VCTKQRKK.. ......GSHGL EIFQRCDCAK GLSCKVWKD. ATYSSKARLH VCQKI~~~~
hDkk-3    TRGSNGTICD NQRDCQPGLC CAFQRGLLFP VCTPLPVEGE LCHDPASRLL DLITWELEPD GALDRCPCAS GLLC...... .QPHSHSLVY VCKPTFVGSR
hDkk-4    RKGQEGESCL RTFDCGPGLC CA..RHFWTK ICKPVLLEGQ VCSRRGHK.. ....DTAQAP EIFQRCDCGP GLLCRSQLTS NR..QHARLR VCQKIEKL~~
colipase  INLENGELCM NSAQCKSN.C CQHSSALGLA RCTSMASENS ECSVKTL... ......Y GIYYKCPCER GLTCEGDKTI VGSITNTNFG ICHDAGRSKQ
```

SEQUENCE LISTING

```
<160> NUMBER OF SEQ ID NOS: 38

<210> SEQ ID NO 1
<211> LENGTH: 2479
<212> TYPE: DNA
<213> ORGANISM: Homo sapiens
<220> FEATURE:
<221> NAME/KEY: CDS
<222> LOCATION: (38)..(1087)
<223> OTHER INFORMATION: 'n' at position 1146 may be any nucleotide

<400> SEQUENCE: 1
ggcacgaggg ggcggcggct gcgggcgcag agcggag atg cag cgg ctt ggg gcc      55
                                         Met Gln Arg Leu Gly Ala
                                          1               5 acc ctg ctg tgc ctg ctg ctg gcg gcg gcg gtc ccc acg gcc ccc gcg     103
Thr Leu Leu Cys Leu Leu Leu Ala Ala Ala Val Pro Thr Ala Pro Ala
             10                  15                  20 ccc gct ccg acg gcg acc tcg gct cca gtc aag ccc ggc ccg gct ctc     151
Pro Ala Pro Thr Ala Thr Ser Ala Pro Val Lys Pro Gly Pro Ala Leu
         25                  30                  35 agc tac ccg cag gag gag gcc acc ctc aat gag atg ttc cgc gag gtt     199
Ser Tyr Pro Gln Glu Glu Ala Thr Leu Asn Glu Met Phe Arg Glu Val
     40                  45                  50 gag gaa ctg atg gag gac acg cag cac aaa ttg cgc agc gcg gtg gaa     247
Glu Glu Leu Met Glu Asp Thr Gln His Lys Leu Arg Ser Ala Val Glu
 55                  60                  65                  70 gag atg gag gca gaa gaa gct gct gct aaa gca tca tca gaa gtg aac     295
Glu Met Glu Ala Glu Glu Ala Ala Ala Lys Ala Ser Ser Glu Val Asn
                 75                  80                  85
```

```
ctg gca aac tta cct ccc agc tat cac aat gag acc aac aca gac acg      343
Leu Ala Asn Leu Pro Pro Ser Tyr His Asn Glu Thr Asn Thr Asp Thr
            90                  95                 100 aac gtt gga aat aat acc atc cat gtg cac cga gaa att cac aag ata      391
Asn Val Gly Asn Asn Thr Ile His Val His Arg Glu Ile His Lys Ile
           105                 110                 115 acc aac aac cag act gga caa atg gtc ttt tca gag aca gtt atc aca      439
Thr Asn Asn Gln Thr Gly Gln Met Val Phe Ser Glu Thr Val Ile Thr
           120                 125                 130 tct gtg gga gac gaa gaa ggc aga agg agc cac gag tgc atc atc gac      487
Ser Val Gly Asp Glu Glu Gly Arg Arg Ser His Glu Cys Ile Ile Asp
135                 140                 145                 150 gag gac tgt ggg ccc agc atg tac tgc cag ttt gcc agc ttc cag tac      535
Glu Asp Cys Gly Pro Ser Met Tyr Cys Gln Phe Ala Ser Phe Gln Tyr
                155                 160                 165 acc tgc cag cca tgc cgg ggc cag agg atg ctc tgc acc cgg gac agt      583
Thr Cys Gln Pro Cys Arg Gly Gln Arg Met Leu Cys Thr Arg Asp Ser
                170                 175                 180 gag tgc tgt gga gac cag ctg tgt gtc tgg ggt cac tgc acc aaa atg      631
Glu Cys Cys Gly Asp Gln Leu Cys Val Trp Gly His Cys Thr Lys Met
                185                 190                 195 gcc acc agg ggc agc aat ggg acc atc tgt gac aac cag agg gac tgc      679
Ala Thr Arg Gly Ser Asn Gly Thr Ile Cys Asp Asn Gln Arg Asp Cys
200                 205                 210 cag ccg ggg ctg tgc tgt gcc ttc cag aga ggc ctg ctg ttc cct gtg      727
Gln Pro Gly Leu Cys Cys Ala Phe Gln Arg Gly Leu Leu Phe Pro Val
215                 220                 225                 230 tgc aca ccc ctg ccc gtg gag ggc gag ctt tgc cat gac ccc gcc agc      775
Cys Thr Pro Leu Pro Val Glu Gly Glu Leu Cys His Asp Pro Ala Ser
                235                 240                 245 cgg ctt ctg gac ctc atc acc tgg gag cta gag cct gat gga gcc ttg      823
Arg Leu Leu Asp Leu Ile Thr Trp Glu Leu Glu Pro Asp Gly Ala Leu
                250                 255                 260 gac cga tgc cct tgt gcc agt ggc ctc ctc tgc cag ccc cac agc cac      871
Asp Arg Cys Pro Cys Ala Ser Gly Leu Leu Cys Gln Pro His Ser His
                265                 270                 275 agc ctg gtg tat gtg tgc aag ccg acc ttc gtg ggg agc cgt gac caa      919
Ser Leu Val Tyr Val Cys Lys Pro Thr Phe Val Gly Ser Arg Asp Gln
280                 285                 290 gat ggg gag atc ctg ctg ccc aga gag gtc ccc gat gag tat gaa gtt      967
Asp Gly Glu Ile Leu Leu Pro Arg Glu Val Pro Asp Glu Tyr Glu Val
295                 300                 305                 310 ggc agc ttc atg gag gag gtg cgc cag gag ctg gag gac ctg gag agg     1015
Gly Ser Phe Met Glu Glu Val Arg Gln Glu Leu Glu Asp Leu Glu Arg
                315                 320                 325 agc ctg act gaa gag atg gcg ctg agg gag cct gcg gct gcc gcc gct     1063
Ser Leu Thr Glu Glu Met Ala Leu Arg Glu Pro Ala Ala Ala Ala Ala
                330                 335                 340 gca ctg ctg gga agg gaa gag att tagatctgga ccaggctgtg gtagatgtg     1117
Ala Leu Leu Gly Arg Glu Glu Ile
            345                 350 caatagaaat agctaattta tttccccang tgtgtgcttt aagcgtgggc tgaccaggct    1177
tcttcctaca tcttcttccc agtaagtttc ccctctggct tgacagcatg aggtgttgtg   1237
catttgttca gctcccccag gctgttctcc aggcttcaca gtctggtgct tgggagagtc   1297
aggcagggtt aaactgcagg agcagtttgc cacccctgtc cagattattg gctgctttgc   1357
ctctaccagt tggcagacag ccgtttgttc tacatggctt tgataattgt ttgaggggag   1417
```

-continued

```
gagatggaaa caatgtggag tctccctctg attggttttg gggaaatgtg gagaagagtg    1477
ccctgctttg caaacatcaa cctggcaaaa atgcaacaaa tgaattttcc acgcagttct    1537
ttccatgggc ataggtaagc tgtgccttca gctgttgcag atgaaatgtt ctgttcaccc    1597
tgcattacat gtgtttattc atccagcagt gttgctcagc tcctacctct gtgccagggc    1657
agcattttca tatccaagat caattccctc tctcagcaca gcctggggag ggggtcattg    1717
ttctcctcgt ccatcaggga tttcagaggc tcagagactg caagctgctt gcccaagtca    1777
cacagctagt gaagaccaga gcagtttcat ctggttgtga ctctaagctc agtgctctct    1837
ccactacccc acaccagcct tggtgccacc aaaagtgctc cccaaaagga aggagaatgg    1897
gatttttctt ttgaggcatg cacatctgga attaaggtca aactaattct cacatccctc    1957
taaaagtaaa ctactgttag gaacagcagt gttctcacag tgtggggcag ccgtccttct    2017
aatgaagaca atgatattga cactgtccct ctttggcagt tgcattagta actttgaaag    2077
gtatatgact gagcgtagca tacaggttaa cctgcagaaa cagtacttag gtaattgtag    2137
ggcgaggatt ataaatgaaa tttgcaaaat cacttagcag caactgaaga caattatcaa    2197
ccacgtggag aaaatcaaac cgagcagggc tgtgtgaaac atggttgtaa tatgcgactg    2257
cgaacactga actctacgcc actccacaaa tgatgttttc aggtgtcatg gactgttgcc    2317
accatgtatt catccagagt tcttaaagtt taaagttgca catgattgta taagcatgct    2377
ttctttgagt tttaaattat gtataaacat aagttgcatt tagaaatcaa gcataaatca    2437
cttcaactgc taaaaaaaaa aaaaaaaaaa aaaaaaaaaa aa                       2479

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala Ala
 1               5                  10                  15

Val Pro Thr Ala Pro Ala Pro Ala Pro Thr Ala Thr Ser Ala Pro Val
                20                  25                  30

Lys Pro Gly Pro Ala Leu Ser Tyr Pro Gln Glu Glu Ala Thr Leu Asn
            35                  40                  45

Glu Met Phe Arg Glu Val Glu Glu Leu Met Glu Asp Thr Gln His Lys
        50                  55                  60

Leu Arg Ser Ala Val Glu Glu Met Glu Ala Glu Ala Ala Ala Ala Lys
    65                  70                  75                  80

Ala Ser Ser Glu Val Asn Leu Ala Asn Leu Pro Pro Ser Tyr His Asn
                85                  90                  95

Glu Thr Asn Thr Asp Thr Asn Val Gly Asn Asn Thr Ile His Val His
            100                 105                 110

Arg Glu Ile His Lys Ile Thr Asn Asn Gln Thr Gly Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190
```

```
Gly His Cys Thr Lys Met Ala Thr Arg Gly Ser Asn Gly Thr Ile Cys
            195                 200                 205

Asp Asn Gln Arg Asp Cys Gln Pro Gly Leu Cys Cys Ala Phe Gln Arg
        210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
290                 295                 300

Pro Asp Glu Tyr Glu Val Gly Ser Phe Met Glu Val Arg Gln Glu
305                 310                 315                 320

Leu Glu Asp Leu Glu Arg Ser Leu Thr Glu Glu Met Ala Leu Arg Glu
                325                 330                 335

Pro Ala Ala Ala Ala Ala Leu Leu Gly Arg Glu Glu Ile
            340                 345                 350

<210> SEQ ID NO 3
<211> LENGTH: 1050
<212> TYPE: DNA
<213> ORGANISM: Homo sapiens
<220> FEATURE:
<221> NAME/KEY: CDS
<222> LOCATION: (1)..(1050)

<400> SEQUENCE: 3 atg cag cgg ctt ggg gcc acc ctg ctg tgc ctg ctg ctg gcg gcg gcg      48
Met Gln Arg Leu Gly Ala Thr Leu Leu Cys Leu Leu Leu Ala Ala Ala
 1               5                  10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
             20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
         35                  40                  45 gag atg ttc cgc gag gtt gag gaa ctg atg gag gac acg cag cac aaa     192
Glu Met Phe Arg Glu Val Glu Glu Leu Met Glu Asp Thr Gln His Lys
     50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
 65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
                 85                  90                  95 gag acc aac aca gac acg aac gtt gga aat aat acc atc cat gtg cac     336
Glu Thr Asn Thr Asp Thr Asn Val Gly Asn Asn Thr Ile His Val His
            100                 105                 110 cga gaa att cac aag ata acc aac aac cag act gga caa atg gtc ttt     384
Arg Glu Ile His Lys Ile Thr Asn Asn Gln Thr Gly Gln Met Val Phe
        115                 120                 125 tca gag aca gtt atc aca tct gtg gga gac gaa gaa ggc aga agg agc     432
Ser Glu Thr Val Ile Thr Ser Val Gly Asp Glu Glu Gly Arg Arg Ser
    130                 135                 140 cac gag tgc atc atc gac gag gac tgt ggg ccc agc atg tac tgc cag     480
```

| | | |
|---|---|---|
| His Glu Cys Ile Ile Asp Glu Asp Cys Gly Pro Ser Met Tyr Cys Gln<br>145 150 155 160 | | |
| ttt gcc agc ttc cag tac acc tgc cag cca tgc cgg ggc cag agg atg<br>Phe Ala Ser Phe Gln Tyr Thr Cys Gln Pro Cys Arg Gly Gln Arg Met<br>165 170 175 | | 528 |
| ctc tgc acc cgg gac agt gag tgc tgt gga gac cag ctg tgt gtc tgg<br>Leu Cys Thr Arg Asp Ser Glu Cys Cys Gly Asp Gln Leu Cys Val Trp<br>180 185 190 | | 576 |
| ggt cac tgc acc aaa atg gcc acc agg ggc agc aat ggg acc atc tgt<br>Gly His Cys Thr Lys Met Ala Thr Arg Gly Ser Asn Gly Thr Ile Cys<br>195 200 205 | | 624 |
| gac aac cag agg gac tgc cag ccg ggg ctg tgc tgt gcc ttc cag aga<br>Asp Asn Gln Arg Asp Cys Gln Pro Gly Leu Cys Cys Ala Phe Gln Arg<br>210 215 220 | | 672 |
| ggc ctg ctg ttc cct gtg tgc aca ccc ctg ccc gtg gag ggc gag ctt<br>Gly Leu Leu Phe Pro Val Cys Thr Pro Leu Pro Val Glu Gly Glu Leu<br>225 230 235 240 | | 720 |
| tgc cat gac ccc gcc agc cgg ctt ctg gac ctc atc acc tgg gag cta<br>Cys His Asp Pro Ala Ser Arg Leu Leu Asp Leu Ile Thr Trp Glu Leu<br>245 250 255 | | 768 |
| gag cct gat gga gcc ttg gac cga tgc cct tgt gcc agt ggc ctc ctc<br>Glu Pro Asp Gly Ala Leu Asp Arg Cys Pro Cys Ala Ser Gly Leu Leu<br>260 265 270 | | 816 |
| tgc cag ccc cac agc cac agc ctg gtg tat gtg tgc aag ccg acc ttc<br>Cys Gln Pro His Ser His Ser Leu Val Tyr Val Cys Lys Pro Thr Phe<br>275 280 285 | | 864 |
| gtg ggg agc cgt gac caa gat ggg gag atc ctg ctg ccc aga gag gtc<br>Val Gly Ser Arg Asp Gln Asp Gly Glu Ile Leu Leu Pro Arg Glu Val<br>290 295 300 | | 912 |
| ccc gat gag tat gaa gtt ggc agc ttc atg gag gag gtg cgc cag gag<br>Pro Asp Glu Tyr Glu Val Gly Ser Phe Met Glu Glu Val Arg Gln Glu<br>305 310 315 320 | | 960 |
| ctg gag gac ctg gag agg agc ctg act gaa gag atg gcg ctg agg gag<br>Leu Glu Asp Leu Glu Arg Ser Leu Thr Glu Glu Met Ala Leu Arg Glu<br>325 330 335 | | 1008 |
| cct gcg gct gcc gcc gct gca ctg ctg gga agg gaa gag att<br>Pro Ala Ala Ala Ala Ala Leu Leu Gly Arg Glu Glu Ile<br>340 345 350 | | 1050 |

```
<210> SEQ ID NO 4
<211> LENGTH: 848
<212> TYPE: DNA
<213> ORGANISM: Homo sapiens
<220> FEATURE:
<221> NAME/KEY: CDS
<222> LOCATION: (125)..(796)

<400> SEQUENCE: 4
```

| | |
|---|---|
| gaattcggca cgagagacga cgtgctgagc tgccagctta gtggaagctc tgctctgggt | 60 |
| ggagagcagc ctcgctttgg tgacgcacag tgctgggacc ctccaggagc ccgggattg | 120 |

| | | |
|---|---|---|
| aagg atg gtg gcg gcc gtc ctg ctg ggg ctg agc tgg ctc tgc tct ccc<br>Met Val Ala Ala Val Leu Leu Gly Leu Ser Trp Leu Cys Ser Pro<br>1 5 10 15 | | 169 |
| ctg gga gct ctg gtc ctg gac ttc aac aac atc agg agc tct gct gac<br>Leu Gly Ala Leu Val Leu Asp Phe Asn Asn Ile Arg Ser Ser Ala Asp<br>20 25 30 | | 217 |
| ctg cat ggg gcc cgg aag ggc tca cag tgc ctg tct gac acg gac tgc<br>Leu His Gly Ala Arg Lys Gly Ser Gln Cys Leu Ser Asp Thr Asp Cys<br>35 40 45 | | 265 |
| aat acc aga aag ttc tgc ctc cag ccc cgc gat gag aag ccg ttc tgt<br>| | 313 |

```
                                                                                      -continued Asn Thr Arg Lys Phe Cys Leu Gln Pro Arg Asp Glu Lys Pro Phe Cys
         50                  55                  60 gct aca tgt cgt ggg ttg cgg agg agg tgc cag cga gat gcc atg tgc        361
Ala Thr Cys Arg Gly Leu Arg Arg Arg Cys Gln Arg Asp Ala Met Cys
 65                  70                  75 tgc cct ggg aca ctc tgt gtg aac gat gtt tgt act acg atg gaa gat        409
Cys Pro Gly Thr Leu Cys Val Asn Asp Val Cys Thr Thr Met Glu Asp
 80                  85                  90                  95 gca acc cca ata tta gaa agg cag ctt gat gag caa gat ggc aca cat        457
Ala Thr Pro Ile Leu Glu Arg Gln Leu Asp Glu Gln Asp Gly Thr His
                100                 105                 110 gca gaa gga aca act ggg cac cca gtc cag gaa aac caa ccc aaa agg        505
Ala Glu Gly Thr Thr Gly His Pro Val Gln Glu Asn Gln Pro Lys Arg
            115                 120                 125 aag cca agt att aag aaa tca caa ggc agg aag gga caa gag gga gaa        553
Lys Pro Ser Ile Lys Lys Ser Gln Gly Arg Lys Gly Gln Glu Gly Glu
        130                 135                 140 agt tgt ctg aga act ttt gac tgt ggc cct gga ctt tgc tgt gct cgt        601
Ser Cys Leu Arg Thr Phe Asp Cys Gly Pro Gly Leu Cys Cys Ala Arg
    145                 150                 155 cat ttt tgg acg aaa att tgt aag cca gtc ctt tgg gag gga cag gtc        649
His Phe Trp Thr Lys Ile Cys Lys Pro Val Leu Glu Gly Gln Val
160                 165                 170                 175 tgc tcc aga aga ggg cat aaa gac act gct caa gct cca gaa atc ttc        697
Cys Ser Arg Arg Gly His Lys Asp Thr Ala Gln Ala Pro Glu Ile Phe
                180                 185                 190 cag cgt tgc gac tgt ggc cct gga cta ctg tgt cga agc caa ttg acc        745
Gln Arg Cys Asp Cys Gly Pro Gly Leu Leu Cys Arg Ser Gln Leu Thr
            195                 200                 205 agc aat cgg cag cat gct cga tta aga gta tgc caa aaa ata gaa aag        793
Ser Asn Arg Gln His Ala Arg Leu Arg Val Cys Gln Lys Ile Glu Lys
        210                 215                 220 cta taaatatttc aaaataaga agaatccaca ttgcaaaaaa aaaaaaaaa aa            848
Leu

<210> SEQ ID NO 5
<211> LENGTH: 224
<212> TYPE: PRT
<213> ORGANISM: Homo sapiens

<400> SEQUENCE: 5

Met Val Ala Ala Val Leu Leu Gly Leu Ser Trp Leu Cys Ser Pro Leu
 1               5                  10                  15

Gly Ala Leu Val Leu Asp Phe Asn Asn Ile Arg Ser Ser Ala Asp Leu
            20                  25                  30

His Gly Ala Arg Lys Gly Ser Gln Cys Leu Ser Asp Thr Asp Cys Asn
         35                 40                  45

Thr Arg Lys Phe Cys Leu Gln Pro Arg Asp Glu Lys Pro Phe Cys Ala
     50                  55                  60

Thr Cys Arg Gly Leu Arg Arg Arg Cys Gln Arg Asp Ala Met Cys Cys
 65                  70                  75                  80

Pro Gly Thr Leu Cys Val Asn Asp Val Cys Thr Thr Met Glu Asp Ala
                 85                  90                  95

Thr Pro Ile Leu Glu Arg Gln Leu Asp Glu Gln Asp Gly Thr His Ala
            100                 105                 110

Glu Gly Thr Thr Gly His Pro Val Gln Glu Asn Gln Pro Lys Arg Lys
        115                 120                 125

Pro Ser Ile Lys Lys Ser Gln Gly Arg Lys Gly Gln Glu Gly Glu Ser
```

```
                130                 135                 140
Cys Leu Arg Thr Phe Asp Cys Gly Pro Gly Leu Cys Cys Ala Arg His
145                 150                 155                 160

Phe Trp Thr Lys Ile Cys Lys Pro Val Leu Leu Glu Gly Gln Val Cys
                165                 170                 175

Ser Arg Arg Gly His Lys Asp Thr Ala Gln Ala Pro Glu Ile Phe Gln
                180                 185                 190

Arg Cys Asp Cys Gly Pro Gly Leu Leu Cys Arg Ser Gln Leu Thr Ser
                195                 200                 205

Asn Arg Gln His Ala Arg Leu Arg Val Cys Gln Lys Ile Glu Lys Leu
                210                 215                 220

<210> SEQ ID NO 6
<211> LENGTH: 672
<212> TYPE: DNA
<213> ORGANISM: Homo sapiens
<220> FEATURE:
<221> NAME/KEY: CDS
<222> LOCATION: (1)..(672)

<400> SEQUENCE: 6 atg gtg gcg gcc gtc ctg ctg ggg ctg agc tgg ctc tgc tct ccc ctg    48
Met Val Ala Ala Val Leu Leu Gly Leu Ser Trp Leu Cys Ser Pro Leu
  1               5                  10                  15 gga gct ctg gtc ctg gac ttc aac aac atc agg agc tct gct gac ctg    96
Gly Ala Leu Val Leu Asp Phe Asn Asn Ile Arg Ser Ser Ala Asp Leu
                 20                  25                  30 cat ggg gcc cgg aag ggc tca cag tgc ctg tct gac acg gac tgc aat   144
His Gly Ala Arg Lys Gly Ser Gln Cys Leu Ser Asp Thr Asp Cys Asn
             35                  40                  45 acc aga aag ttc tgc ctc cag ccc cgc gat gag aag ccg ttc tgt gct   192
Thr Arg Lys Phe Cys Leu Gln Pro Arg Asp Glu Lys Pro Phe Cys Ala
         50                  55                  60 aca tgt cgt ggg ttg cgg agg agg tgc cag cga gat gcc atg tgc tgc   240
Thr Cys Arg Gly Leu Arg Arg Arg Cys Gln Arg Asp Ala Met Cys Cys
 65                  70                  75                  80 cct ggg aca ctc tgt gtg aac gat gtt tgt act acg atg gaa gat gca   288
Pro Gly Thr Leu Cys Val Asn Asp Val Cys Thr Thr Met Glu Asp Ala
                 85                  90                  95 acc cca ata tta gaa agg cag ctt gat gag caa gat ggc aca cat gca   336
Thr Pro Ile Leu Glu Arg Gln Leu Asp Glu Gln Asp Gly Thr His Ala
            100                 105                 110 gaa gga aca act ggg cac cca gtc cag gaa aac caa ccc aaa agg aag   384
Glu Gly Thr Thr Gly His Pro Val Gln Glu Asn Gln Pro Lys Arg Lys
        115                 120                 125 cca agt att aag aaa tca caa ggc agg aag gga caa gag gga gaa agt   432
Pro Ser Ile Lys Lys Ser Gln Gly Arg Lys Gly Gln Glu Gly Glu Ser
130                 135                 140 tgt ctg aga act ttt gac tgt ggc cct gga ctt tgc tgt gct cgt cat   480
Cys Leu Arg Thr Phe Asp Cys Gly Pro Gly Leu Cys Cys Ala Arg His
145                 150                 155                 160 ttt tgg acg aaa att tgt aag cca gtc ctt ttg gag gga cag gtc tgc   528
Phe Trp Thr Lys Ile Cys Lys Pro Val Leu Leu Glu Gly Gln Val Cys
                165                 170                 175 tcc aga aga ggg cat aaa gac act gct caa gct cca gaa atc ttc cag   576
Ser Arg Arg Gly His Lys Asp Thr Ala Gln Ala Pro Glu Ile Phe Gln
                180                 185                 190 cgt tgc gac tgt ggc cct gga cta ctg tgt cga agc caa ttg acc agc   624
Arg Cys Asp Cys Gly Pro Gly Leu Leu Cys Arg Ser Gln Leu Thr Ser
                195                 200                 205
```

```
aat cgg cag cat gct cga tta aga gta tgc caa aaa ata gaa aag cta      672
Asn Arg Gln His Ala Arg Leu Arg Val Cys Gln Lys Ile Glu Lys Leu
    210                 215                 220

<210> SEQ ID NO 7
<211> LENGTH: 1536
<212> TYPE: DNA
<213> ORGANISM: Homo sapiens
<220> FEATURE:
<221> NAME/KEY: CDS
<222> LOCATION: (109)..(906)

<400> SEQUENCE: 7
gtcgacccac gcgtccgcgg acgcgtgggc ggcacggttt cgtggggacc caggcttgca      60
aagtgacggt cattttctct ttctttctcc ctcttgagtc cttctgag atg atg gct     117
                                                     Met Met Ala
                                                       1 ctg ggc gca gcg gga gct acc cgg gtc ttt gtc gcg atg gta gcg gcg      165
Leu Gly Ala Ala Gly Ala Thr Arg Val Phe Val Ala Met Val Ala Ala
        5                  10                  15 gct ctc ggc ggc cac cct ctg ctg gga gtg agc gcc acc ttg aac tcg      213
Ala Leu Gly Gly His Pro Leu Leu Gly Val Ser Ala Thr Leu Asn Ser
 20                  25                  30                  35 gtt ctc aat tcc aac gct atc aag aac ctg ccc cca ccg ctg ggc ggc      261
Val Leu Asn Ser Asn Ala Ile Lys Asn Leu Pro Pro Pro Leu Gly Gly
                 40                  45                  50 gct gcg ggg cac cca ggc tct gca gtc agc gcc gcg ccg gga atc ctg      309
Ala Ala Gly His Pro Gly Ser Ala Val Ser Ala Ala Pro Gly Ile Leu
             55                  60                  65 tac ccg ggc ggg aat aag tac cag acc att gac aac tac cag ccg tac      357
Tyr Pro Gly Gly Asn Lys Tyr Gln Thr Ile Asp Asn Tyr Gln Pro Tyr
         70                  75                  80 ccg tgc gca gag gac gag gag tgc ggc act gat gag tac tgc gct agt      405
Pro Cys Ala Glu Asp Glu Glu Cys Gly Thr Asp Glu Tyr Cys Ala Ser
     85                  90                  95 ccc acc cgc gga ggg gac gca ggc gtg caa atc tgt ctc gcc tgc agg      453
Pro Thr Arg Gly Gly Asp Ala Gly Val Gln Ile Cys Leu Ala Cys Arg
100                 105                 110                 115 aag cgc cga aaa cgc tgc atg cgt cac gct atg tgc tgc ccc ggg aat      501
Lys Arg Arg Lys Arg Cys Met Arg His Ala Met Cys Cys Pro Gly Asn
                 120                 125                 130 tac tgc aaa aat gga ata tgt gtg tct tct gat caa aat cat ttc cga      549
Tyr Cys Lys Asn Gly Ile Cys Val Ser Ser Asp Gln Asn His Phe Arg
             135                 140                 145 gga gaa att gag gaa acc atc act gaa agc ttt ggt aat gat cat agc      597
Gly Glu Ile Glu Glu Thr Ile Thr Glu Ser Phe Gly Asn Asp His Ser
         150                 155                 160 acc ttg gat ggg tat tcc aga aga acc acc ttg tct tca aaa atg tat      645
Thr Leu Asp Gly Tyr Ser Arg Arg Thr Thr Leu Ser Ser Lys Met Tyr
     165                 170                 175 cac acc aaa gga caa gaa ggt tct gtt tgt ctc cgg tca tca gac tgt      693
His Thr Lys Gly Gln Glu Gly Ser Val Cys Leu Arg Ser Ser Asp Cys
180                 185                 190                 195 gcc tca gga ttg tgt tgt gct aga cac ttc tgg tcc aag atc tgt aaa      741
Ala Ser Gly Leu Cys Cys Ala Arg His Phe Trp Ser Lys Ile Cys Lys
                 200                 205                 210 cct gtc ctg aaa gaa ggt caa gtg tgt acc aag cat agg aga aaa ggc      789
Pro Val Leu Lys Glu Gly Gln Val Cys Thr Lys His Arg Arg Lys Gly
             215                 220                 225 tct cat gga cta gaa ata ttc cag cgt tgt tac tgt gga gaa ggt ctg      837
Ser His Gly Leu Glu Ile Phe Gln Arg Cys Tyr Cys Gly Glu Gly Leu
```

-continued

```
Ser His Gly Leu Glu Ile Phe Gln Arg Cys Tyr Cys Gly Glu Gly Leu
        230                 235                 240 tct tgc cgg ata cag aaa gat cac cat caa gcc agt aat tct tct agg      885
Ser Cys Arg Ile Gln Lys Asp His His Gln Ala Ser Asn Ser Ser Arg
245                 250                 255 ctt cac act tgt cag aga cac taaaccagct atccaaatgc agtgaactcc         936
Leu His Thr Cys Gln Arg His
260             265 ttttatataa tagatgctat gaaaaccttt tatgaccttc atcaactcaa tcctaaggat    996
atacaagttc tgtggtttca gttaagcatt ccaataacac cttccaaaaa cctggagtgt   1056
aagagctttg tttctttatg gaactcccct gtgattgcag taaattactg tattgtaaat   1116
tctcagtgtg gcacttacct gtaaatgcaa tgaaactttt aattattttt ctaaaggtgc   1176
tgcactgcct atttttcctc ttgttatgta aattttgta cacattgatt gttatcttga    1236
ctgacaaata ttctatattg aactgaagta aatcatttca gcttatagtt cttaaaagca   1296
taacccttta ccccatttaa ttctagagtc tagaacgcaa ggatctcttg gaatgacaaa   1356
tgataggtac ctaaaatgta acatgaaaat actagcttat tttctgaaat gtactatctt   1416
aatgcttaaa ttatatttcc ctttaggctg tgatagtttt tgaaataaaa tttaacattt   1476
aatatcatga aatgttataa gtagacataa aaaaaaaaa aaaaaaaaa gggcggccgc     1536

<210> SEQ ID NO 8
<211> LENGTH: 266
<212> TYPE: PRT
<213> ORGANISM: Homo sapiens

<400> SEQUENCE: 8

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
```

|  |  |  |  |  |  |  |  |  |  |
|---|---|---|---|---|---|---|---|---|---|
| Arg | Lys | Gly | Ser | His | Gly | Leu | Glu | Ile | Phe | Gln | Arg | Cys | Tyr | Cys | Gly |
| 225 |  |  |  | 230 |  |  |  | 235 |  |  |  | 240 |

Glu Gly Leu Ser Cys Arg Ile Gln Lys Asp His His Gln Ala Ser Asn
            245                 250                 255

Ser Ser Arg Leu His Thr Cys Gln Arg His
            260             265

<210> SEQ ID NO 9
<211> LENGTH: 798
<212> TYPE: DNA
<213> ORGANISM: Homo sapiens
<220> FEATURE:
<221> NAME/KEY: CDS
<222> LOCATION: (1)..(798)

<400> SEQUENCE: 9

```
atg atg gct ctg ggc gca gcg gga gct acc cgg gtc ttt gtc gcg atg    48
Met Met Ala Leu Gly Ala Ala Gly Ala Thr Arg Val Phe Val Ala Met
  1               5                  10                  15 gta gcg gcg gct ctc ggc ggc cac cct ctg ctg gga gtg agc gcc acc    96
Val Ala Ala Ala Leu Gly Gly His Pro Leu Leu Gly Val Ser Ala Thr
                 20                  25                  30 ttg aac tcg gtt ctc aat tcc aac gct atc aag aac ctg ccc cca ccg   144
Leu Asn Ser Val Leu Asn Ser Asn Ala Ile Lys Asn Leu Pro Pro Pro
             35                  40                  45 ctg ggc ggc gct gcg ggg cac cca ggc tct gca gtc agc gcc gcg ccg   192
Leu Gly Gly Ala Ala Gly His Pro Gly Ser Ala Val Ser Ala Ala Pro
         50                  55                  60 gga atc ctg tac ccg ggc ggg aat aag tac cag acc att gac aac tac   240
Gly Ile Leu Tyr Pro Gly Gly Asn Lys Tyr Gln Thr Ile Asp Asn Tyr
 65                  70                  75                  80 cag ccg tac ccg tgc gca gag gac gag gag tgc ggc act gat gag tac   288
Gln Pro Tyr Pro Cys Ala Glu Asp Glu Glu Cys Gly Thr Asp Glu Tyr
                 85                  90                  95 tgc gct agt ccc acc cgc gga ggg gac gca ggc gtg caa atc tgt ctc   336
Cys Ala Ser Pro Thr Arg Gly Gly Asp Ala Gly Val Gln Ile Cys Leu
                100                 105                 110 gcc tgc agg aag cgc cga aaa cgc tgc atg cgt cac gct atg tgc tgc   384
Ala Cys Arg Lys Arg Arg Lys Arg Cys Met Arg His Ala Met Cys Cys
            115                 120                 125 ccc ggg aat tac tgc aaa aat gga ata tgt gtg tct tct gat caa aat   432
Pro Gly Asn Tyr Cys Lys Asn Gly Ile Cys Val Ser Ser Asp Gln Asn
        130                 135                 140 cat ttc cga gga gaa att gag gaa acc atc act gaa agc ttt ggt aat   480
His Phe Arg Gly Glu Ile Glu Glu Thr Ile Thr Glu Ser Phe Gly Asn
145                 150                 155                 160 gat cat agc acc ttg gat ggg tat tcc aga aga acc acc ttg tct tca   528
Asp His Ser Thr Leu Asp Gly Tyr Ser Arg Arg Thr Thr Leu Ser Ser
                165                 170                 175 aaa atg tat cac acc aaa gga caa gaa ggt tct gtt tgt ctc cgg tca   576
Lys Met Tyr His Thr Lys Gly Gln Glu Gly Ser Val Cys Leu Arg Ser
            180                 185                 190 tca gac tgt gcc tca gga ttg tgt tgt gct aga cac ttc tgg tcc aag   624
Ser Asp Cys Ala Ser Gly Leu Cys Cys Ala Arg His Phe Trp Ser Lys
        195                 200                 205 atc tgt aaa cct gtc ctg aaa gaa ggt caa gtg tgt acc aag cat agg   672
Ile Cys Lys Pro Val Leu Lys Glu Gly Gln Val Cys Thr Lys His Arg
    210                 215                 220 aga aaa ggc tct cat gga cta gaa ata ttc cag cgt tgt tac tgt gga   720
```

```
Arg Lys Gly Ser His Gly Leu Glu Ile Phe Gln Arg Cys Tyr Cys Gly
225                 230                 235                 240 gaa ggt ctg tct tgc cgg ata cag aaa gat cac cat caa gcc agt aat      768
Glu Gly Leu Ser Cys Arg Ile Gln Lys Asp His His Gln Ala Ser Asn
                245                 250                 255 tct tct agg ctt cac act tgt cag aga cac                              798
Ser Ser Arg Leu His Thr Cys Gln Arg His
            260                 265

<210> SEQ ID NO 10
<211> LENGTH: 702
<212> TYPE: DNA
<213> ORGANISM: Homo sapiens
<220> FEATURE:
<221> NAME/KEY: CDS
<222> LOCATION: (1)..(537)

<400> SEQUENCE: 10 gaa ttc ggc acg agg gtt ggg agg tat tgc cac agt ccc cac caa gga       48
Glu Phe Gly Thr Arg Val Gly Arg Tyr Cys His Ser Pro His Gln Gly
 1               5                  10                  15 tca tcg gcc tgc atg gtg tgt cgg aga aaa aag aag cgc tgc cac cga       96
Ser Ser Ala Cys Met Val Cys Arg Arg Lys Lys Lys Arg Cys His Arg
                20                  25                  30 gat ggc atg tgc tgc ccc agt acc cgc tgc aat aat ggc atc tgt atc      144
Asp Gly Met Cys Cys Pro Ser Thr Arg Cys Asn Asn Gly Ile Cys Ile
            35                  40                  45 cca gtt act gaa agc atc tta acc cct cac atc ccg gct ctg gat ggt      192
Pro Val Thr Glu Ser Ile Leu Thr Pro His Ile Pro Ala Leu Asp Gly
        50                  55                  60 act cgg cac aga gat cga aac cac ggt cat tac tca aac cat gac ttg      240
Thr Arg His Arg Asp Arg Asn His Gly His Tyr Ser Asn His Asp Leu
 65                  70                  75                  80 gga tgg cag aat cta gga aga cca cac act aag atg tca cat ata aaa      288
Gly Trp Gln Asn Leu Gly Arg Pro His Thr Lys Met Ser His Ile Lys
                 85                  90                  95 ggg cat gaa gga gac ccc tgc cta cga tca tca gac tgc att gaa ggg      336
Gly His Glu Gly Asp Pro Cys Leu Arg Ser Ser Asp Cys Ile Glu Gly
            100                 105                 110 ttt tgc tgt gct cgt cat ttc tgg acc aaa atc tgc aaa cca gtg ctc      384
Phe Cys Cys Ala Arg His Phe Trp Thr Lys Ile Cys Lys Pro Val Leu
        115                 120                 125 cat cag ggg gaa gtc tgt acc aaa caa cgc aag aag ggt tct cat ggg      432
His Gln Gly Glu Val Cys Thr Lys Gln Arg Lys Lys Gly Ser His Gly
    130                 135                 140 ctg gaa att ttc cag cgt tgc gac tgt gcg aag ggc ctg tct tgc aaa      480
Leu Glu Ile Phe Gln Arg Cys Asp Cys Ala Lys Gly Leu Ser Cys Lys
145                 150                 155                 160 gta tgg aaa gat gcc acc tac tcc tcc aaa gcc aga ctc cat gtg tgt      528
Val Trp Lys Asp Ala Thr Tyr Ser Ser Lys Ala Arg Leu His Val Cys
                165                 170                 175 cag aaa att tgatcaccat tgaggaacat catcaattgc agactgtgaa              577
Gln Lys Ile gttgtgtatt taatgcatta tagcatggtg gaaaataagg ttcagatgca gaagaatggc    637
taaaataaga aacgtgataa gaatatagat gatcacaaaa aaaaaaaaaa aaaagatgcg    697
gccgc                                                                702

<210> SEQ ID NO 11
<211> LENGTH: 179
<212> TYPE: PRT
```

<213> ORGANISM: Homo sapiens

<400> SEQUENCE: 11

```
Glu Phe Gly Thr Arg Val Gly Arg Tyr Cys His Ser Pro His Gln Gly
  1               5                  10                  15

Ser Ser Ala Cys Met Val Cys Arg Arg Lys Lys Lys Arg Cys His Arg
             20                  25                  30

Asp Gly Met Cys Cys Pro Ser Thr Arg Cys Asn Asn Gly Ile Cys Ile
         35                  40                  45

Pro Val Thr Glu Ser Ile Leu Thr Pro His Ile Pro Ala Leu Asp Gly
     50                  55                  60

Thr Arg His Arg Asp Arg Asn His Gly His Tyr Ser Asn His Asp Leu
 65                  70                  75                  80

Gly Trp Gln Asn Leu Gly Arg Pro His Thr Lys Met Ser His Ile Lys
                 85                  90                  95

Gly His Glu Gly Asp Pro Cys Leu Arg Ser Ser Asp Cys Ile Glu Gly
            100                 105                 110

Phe Cys Cys Ala Arg His Phe Trp Thr Lys Ile Cys Lys Pro Val Leu
        115                 120                 125

His Gln Gly Glu Val Cys Thr Lys Gln Arg Lys Lys Gly Ser His Gly
    130                 135                 140

Leu Glu Ile Phe Gln Arg Cys Asp Cys Ala Lys Gly Leu Ser Cys Lys
145                 150                 155                 160

Val Trp Lys Asp Ala Thr Tyr Ser Ser Lys Ala Arg Leu His Val Cys
                165                 170                 175

Gln Lys Ile
```

<210> SEQ ID NO 12
<211> LENGTH: 537
<212> TYPE: DNA
<213> ORGANISM: Homo sapiens
<220> FEATURE:
<221> NAME/KEY: CDS
<222> LOCATION: (1)..(537)

<400> SEQUENCE: 12

```
gaa ttc ggc acg agg gtt ggg agg tat tgc cac agt ccc cac caa gga    48
Glu Phe Gly Thr Arg Val Gly Arg Tyr Cys His Ser Pro His Gln Gly
  1               5                  10                  15 tca tcg gcc tgc atg gtg tgt cgg aga aaa aag aag cgc tgc cac cga    96
Ser Ser Ala Cys Met Val Cys Arg Arg Lys Lys Lys Arg Cys His Arg
             20                  25                  30 gat ggc atg tgc tgc ccc agt acc cgc tgc aat aat ggc atc tgt atc   144
Asp Gly Met Cys Cys Pro Ser Thr Arg Cys Asn Asn Gly Ile Cys Ile
         35                  40                  45 cca gtt act gaa agc atc tta acc cct cac atc ccg gct ctg gat ggt   192
Pro Val Thr Glu Ser Ile Leu Thr Pro His Ile Pro Ala Leu Asp Gly
     50                  55                  60 act cgg cac aga gat cga aac cac ggt cat tac tca aac cat gac ttg   240
Thr Arg His Arg Asp Arg Asn His Gly His Tyr Ser Asn His Asp Leu
 65                  70                  75                  80 gga tgg cag aat cta gga aga cca cac act aag atg tca cat ata aaa   288
Gly Trp Gln Asn Leu Gly Arg Pro His Thr Lys Met Ser His Ile Lys
                 85                  90                  95 ggg cat gaa gga gac ccc tgc cta cga tca tca gac tgc att gaa ggg   336
Gly His Glu Gly Asp Pro Cys Leu Arg Ser Ser Asp Cys Ile Glu Gly
            100                 105                 110 ttt tgc tgt gct cgt cat ttc tgg acc aaa atc tgc aaa cca gtg ctc   384
```

```
Phe Cys Cys Ala Arg His Phe Trp Thr Lys Ile Cys Lys Pro Val Leu
        115                 120                 125 cat cag ggg gaa gtc tgt acc aaa caa cgc aag aag ggt tct cat ggg      432
His Gln Gly Glu Val Cys Thr Lys Gln Arg Lys Lys Gly Ser His Gly
    130                 135                 140 ctg gaa att ttc cag cgt tgc gac tgt gcg aag ggc ctg tct tgc aaa      480
Leu Glu Ile Phe Gln Arg Cys Asp Cys Ala Lys Gly Leu Ser Cys Lys
145                 150                 155                 160 gta tgg aaa gat gcc acc tac tcc tcc aaa gcc aga ctc cat gtg tgt      528
Val Trp Lys Asp Ala Thr Tyr Ser Ser Lys Ala Arg Leu His Val Cys
                165                 170                 175 cag aaa att                                                          537
Gln Lys Ile <210> SEQ ID NO 13
<211> LENGTH: 928
<212> TYPE: DNA
<213> ORGANISM: Homo sapiens
<220> FEATURE:
<221> NAME/KEY: CDS
<222> LOCATION: (75)..(800)

<400> SEQUENCE: 13
ctcgaggcca aaattcggca cgaggccggg ctgtggtcta gcataaaggc ggagcccaga     60
agaaggggcg gggt atg gga gaa gcc tcc cca cct gcc ccc gca agg cgg      110
              Met Gly Glu Ala Ser Pro Pro Ala Pro Ala Arg Arg
                1               5                   10 cat ctg ctg gtc ctg ctg ctg ctc ctc tct acc ctg gtg atc ccc tcc      158
His Leu Leu Val Leu Leu Leu Leu Leu Ser Thr Leu Val Ile Pro Ser
            15                  20                  25 gct gca gct cct atc cat gat gct gac gcc caa gag agc tcc ttg ggt      206
Ala Ala Ala Pro Ile His Asp Ala Asp Ala Gln Glu Ser Ser Leu Gly
        30                  35                  40 ctc aca ggc ctc cag agc cta ctc caa ggc ttc agc cga ctt ttc ctg      254
Leu Thr Gly Leu Gln Ser Leu Leu Gln Gly Phe Ser Arg Leu Phe Leu
45                  50                  55                  60 aaa ggt aac ctg ctt cgg ggc ata gac agc tta ttc tct gcc ccc atg      302
Lys Gly Asn Leu Leu Arg Gly Ile Asp Ser Leu Phe Ser Ala Pro Met
                65                  70                  75 gac ttc cgg ggc ctc cct ggg aac tac cac aaa gag gag aac cag gag      350
Asp Phe Arg Gly Leu Pro Gly Asn Tyr His Lys Glu Glu Asn Gln Glu
            80                  85                  90 cac cag ctg ggg aac aac acc ctc tcc agc cac ctc cag atc gac aag      398
His Gln Leu Gly Asn Asn Thr Leu Ser Ser His Leu Gln Ile Asp Lys
        95                  100                 105 atg acc gac aac aag aca gga gag gtg ctg atc tcc gag aat gtg gtg      446
Met Thr Asp Asn Lys Thr Gly Glu Val Leu Ile Ser Glu Asn Val Val
    110                 115                 120 gca tcc att caa cca gcg gag ggg agc ttc gag ggt gat ttg aag gta      494
Ala Ser Ile Gln Pro Ala Glu Gly Ser Phe Glu Gly Asp Leu Lys Val
125                 130                 135                 140 ccc agg atg gag gag aag gag gcc ctg gta ccc atc cag aag gcc acg      542
Pro Arg Met Glu Glu Lys Glu Ala Leu Val Pro Ile Gln Lys Ala Thr
                145                 150                 155 gac agc ttc cac aca gaa ctc cat ccc cgg gtg gcc ttc tgg atc att      590
Asp Ser Phe His Thr Glu Leu His Pro Arg Val Ala Phe Trp Ile Ile
            160                 165                 170 aag ctg cca cgg cgg agg tcc cac cag gat gcc ctg gag ggc ggc cac      638
Lys Leu Pro Arg Arg Arg Ser His Gln Asp Ala Leu Glu Gly Gly His
        175                 180                 185
```

```
tgg ctc agc gag aag cga cac cgc ctg cag gcc atc cgg gat gga ctc       686
Trp Leu Ser Glu Lys Arg His Arg Leu Gln Ala Ile Arg Asp Gly Leu
    190                 195                 200 cgc aag ggg acc cac aag gac gtc cta gaa gag ggg acc gag agc tcc       734
Arg Lys Gly Thr His Lys Asp Val Leu Glu Glu Gly Thr Glu Ser Ser
205                 210                 215                 220 tcc cac tcc agg ctg tcc ccc cga aag acc cac tta ctg tac atc ctc       782
Ser His Ser Arg Leu Ser Pro Arg Lys Thr His Leu Leu Tyr Ile Leu
                225                 230                 235 agg ccc tct cgg cag ctg tagggtggg gaccggggag cacctgcctg               830
Arg Pro Ser Arg Gln Leu
                240 tagcccccat cagaccctgc cccaagcacc atatggaaat aaagttcttt cttacatcta     890 aaaaaaaaaa aaaaaaaaaa aaaaaaattg gcggccgc                             928

<210> SEQ ID NO 14
<211> LENGTH: 242
<212> TYPE: PRT
<213> ORGANISM: Homo sapiens

<400> SEQUENCE: 14

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
            20                  25                  30

Ile His Asp Ala Asp Ala Gln Glu Ser Ser Leu Gly Leu Thr Gly Leu
        35                  40                  45

Gln Ser Leu Leu Gln Gly Phe Ser Arg Leu Phe Leu Lys Gly Asn Leu
    50                  55                  60

Leu Arg Gly Ile Asp Ser Leu Phe Ser Ala Pro Met Asp Phe Arg Gly
65                  70                  75                  80

Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Met Thr Asp Asn
            100                 105                 110

Lys Thr Gly Glu Val Leu Ile Ser Glu Asn Val Val Ala Ser Ile Gln
        115                 120                 125

Pro Ala Glu Gly Ser Phe Glu Gly Asp Leu Lys Val Pro Arg Met Glu
    130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly His Trp Leu Ser Glu
            180                 185                 190

Lys Arg His Arg Leu Gln Ala Ile Arg Asp Gly Leu Arg Lys Gly Thr
        195                 200                 205

His Lys Asp Val Leu Glu Glu Gly Thr Glu Ser Ser Ser His Ser Arg
    210                 215                 220

Leu Ser Pro Arg Lys Thr His Leu Leu Tyr Ile Leu Arg Pro Ser Arg
225                 230                 235                 240

Gln Leu

<210> SEQ ID NO 15
<211> LENGTH: 726
<212> TYPE: DNA
```

<213> ORGANISM: Homo sapiens
<220> FEATURE:
<221> NAME/KEY: CDS
<222> LOCATION: (1)..(726)

<400> SEQUENCE: 15

```
atg gga gaa gcc tcc cca cct gcc ccc gca agg cgg cat ctg ctg gtc     48
Met Gly Glu Ala Ser Pro Pro Ala Pro Ala Arg Arg His Leu Leu Val
 1               5                  10                  15 ctg ctg ctg ctc ctc tct acc ctg gtg atc ccc tcc gct gca gct cct     96
Leu Leu Leu Leu Leu Ser Thr Leu Val Ile Pro Ser Ala Ala Ala Pro
                20                  25                  30 atc cat gat gct gac gcc caa gag agc tcc ttg ggt ctc aca ggc ctc    144
Ile His Asp Ala Asp Ala Gln Glu Ser Ser Leu Gly Leu Thr Gly Leu
         35                  40                  45 cag agc cta ctc caa ggc ttc agc cga ctt ttc ctg aaa ggt aac ctg    192
Gln Ser Leu Leu Gln Gly Phe Ser Arg Leu Phe Leu Lys Gly Asn Leu
     50                  55                  60 ctt cgg ggc ata gac agc tta ttc tct gcc ccc atg gac ttc cgg ggc    240
Leu Arg Gly Ile Asp Ser Leu Phe Ser Ala Pro Met Asp Phe Arg Gly
 65                  70                  75                  80 ctc cct ggg aac tac cac aaa gag gag aac cag gag cac cag ctg ggg    288
Leu Pro Gly Asn Tyr His Lys Glu Glu Asn Gln Glu His Gln Leu Gly
                 85                  90                  95 aac aac acc ctc tcc agc cac ctc cag atc gac aag atg acc gac aac    336
Asn Asn Thr Leu Ser Ser His Leu Gln Ile Asp Lys Met Thr Asp Asn
            100                 105                 110 aag aca gga gag gtg ctg atc tcc gag aat gtg gtg gca tcc att caa    384
Lys Thr Gly Glu Val Leu Ile Ser Glu Asn Val Val Ala Ser Ile Gln
        115                 120                 125 cca gcg gag ggg agc ttc gag ggt gat ttg aag gta ccc agg atg gag    432
Pro Ala Glu Gly Ser Phe Glu Gly Asp Leu Lys Val Pro Arg Met Glu
    130                 135                 140 gag aag gag gcc ctg gta ccc atc cag aag gcc acg gac agc ttc cac    480
Glu Lys Glu Ala Leu Val Pro Ile Gln Lys Ala Thr Asp Ser Phe His
145                 150                 155                 160 aca gaa ctc cat ccc cgg gtg gcc ttc tgg atc att aag ctg cca cgg    528
Thr Glu Leu His Pro Arg Val Ala Phe Trp Ile Ile Lys Leu Pro Arg
                165                 170                 175 cgg agg tcc cac cag gat gcc ctg gag ggc ggc cac tgg ctc agc gag    576
Arg Arg Ser His Gln Asp Ala Leu Glu Gly Gly His Trp Leu Ser Glu
            180                 185                 190 aag cga cac cgc ctg cag gcc atc cgg gat gga ctc cgc aag ggg acc    624
Lys Arg His Arg Leu Gln Ala Ile Arg Asp Gly Leu Arg Lys Gly Thr
        195                 200                 205 cac aag gac gtc cta gaa gag ggg acc gag agc tcc tcc cac tcc agg    672
His Lys Asp Val Leu Glu Glu Gly Thr Glu Ser Ser Ser His Ser Arg
    210                 215                 220 ctg tcc ccc cga aag acc cac tta ctg tac atc ctc agg ccc tct cgg    720
Leu Ser Pro Arg Lys Thr His Leu Leu Tyr Ile Leu Arg Pro Ser Arg
225                 230                 235                 240 cag ctg                                                             726
Gln Leu
```

<210> SEQ ID NO 16
<211> LENGTH: 2380
<212> TYPE: DNA
<213> ORGANISM: Homo sapiens
<220> FEATURE:
<221> NAME/KEY: CDS
<222> LOCATION: (109)..(1155)

-continued

```
<400> SEQUENCE: 16
gtcgacccac gcgtccgctg tggcagccca gctaccggtc gtgaccagat ccagcttgca      60
gctcagcttt gttcattcga attgggcggc ggccagcgcg aacaaac atg cag cgg       117
                                                    Met Gln Arg
                                                      1 ctc ggg ggt att ttg ctg tgt aca ctg ctg gcg gcg gcg gtc ccc act       165
Leu Gly Gly Ile Leu Leu Cys Thr Leu Leu Ala Ala Ala Val Pro Thr
      5              10                  15 gct cct gct cct tcc ccg acg gtc act tgg act ccg gcg gag ccg ggc       213
Ala Pro Ala Pro Ser Pro Thr Val Thr Trp Thr Pro Ala Glu Pro Gly
 20              25                  30                  35 cca gct ctc aac tac cct cag gag gaa gct acg ctc aat gag atg ttt       261
Pro Ala Leu Asn Tyr Pro Gln Glu Glu Ala Thr Leu Asn Glu Met Phe
             40                  45                  50 cga gag gtg gag gag ctg atg gaa gac act cag cac aaa ctg cgc agt       309
Arg Glu Val Glu Glu Leu Met Glu Asp Thr Gln His Lys Leu Arg Ser
         55                  60                  65 gcc gtg gag gag atg gag gcg gaa gaa gca gct gct aaa acg tcc tct       357
Ala Val Glu Glu Met Glu Ala Glu Glu Ala Ala Ala Lys Thr Ser Ser
     70                  75                  80 gag gtg aac ctg gca agc tta cct ccc aac tat cac aat gag acc agc       405
Glu Val Asn Leu Ala Ser Leu Pro Pro Asn Tyr His Asn Glu Thr Ser
 85                  90                  95 acg gag acc agg gtg gga aat aac aca gtc cat gtg cac cag gaa gtt       453
Thr Glu Thr Arg Val Gly Asn Asn Thr Val His Val His Gln Glu Val
100                 105                 110                 115 cac aag ata acc aac aac cag agt gga cag gtg gtc ttt tct gag aca       501
His Lys Ile Thr Asn Asn Gln Ser Gly Gln Val Val Phe Ser Glu Thr
                 120                 125                 130 gtc att aca tct gta ggg gat gaa gaa ggc aag agg agc cat gaa tgt       549
Val Ile Thr Ser Val Gly Asp Glu Glu Gly Lys Arg Ser His Glu Cys
             135                 140                 145 atc att gat gaa gac tgt ggg ccc acc agg tac tgc cag ttc tcc agc       597
Ile Ile Asp Glu Asp Cys Gly Pro Thr Arg Tyr Cys Gln Phe Ser Ser
         150                 155                 160 ttc aag tac acc tgc cag cca tgc cgg gac cag cag atg cta tgc acc       645
Phe Lys Tyr Thr Cys Gln Pro Cys Arg Asp Gln Gln Met Leu Cys Thr
     165                 170                 175 cga gac agt gag tgc tgt gga gac cag ctg tgt gcc tgg ggt cac tgc       693
Arg Asp Ser Glu Cys Cys Gly Asp Gln Leu Cys Ala Trp Gly His Cys
180                 185                 190                 195 acc caa aag gcc acc aaa ggt ggc aat ggg acc atc tgt gac aac cag       741
Thr Gln Lys Ala Thr Lys Gly Gly Asn Gly Thr Ile Cys Asp Asn Gln
                 200                 205                 210 agg gat tgc cag cct ggc ctg tgt tgt gcc ttc caa aga ggc ctg ctg       789
Arg Asp Cys Gln Pro Gly Leu Cys Cys Ala Phe Gln Arg Gly Leu Leu
             215                 220                 225 ttc ccc gtg tgc aca ccc ctg ccc gtg gag gga gag ctc tgc cat gac       837
Phe Pro Val Cys Thr Pro Leu Pro Val Glu Gly Glu Leu Cys His Asp
         230                 235                 240 ccc acc agc cag ctg ctg gat ctc atc acc tgg gaa ctg gag cct gaa       885
Pro Thr Ser Gln Leu Leu Asp Leu Ile Thr Trp Glu Leu Glu Pro Glu
     245                 250                 255 gga gct ttg gac cga tgc ccc tgc gcc agt ggc ctc cta tgc cag cca       933
Gly Ala Leu Asp Arg Cys Pro Cys Ala Ser Gly Leu Leu Cys Gln Pro
260                 265                 270                 275 cac agc cac agt ctg gtg tac atg tgc aag cca gcc ttc gtg ggc agc       981
His Ser His Ser Leu Val Tyr Met Cys Lys Pro Ala Phe Val Gly Ser
                 280                 285                 290
```

```
cat gac cac agt gag gag agc cag ctg ccc agg gag gcc ccg gat gag      1029
His Asp His Ser Glu Glu Ser Gln Leu Pro Arg Glu Ala Pro Asp Glu
            295                 300                 305 tac gaa gat gtt ggc ttc ata ggg gaa gtg cgc cag gag ctg gaa gac      1077
Tyr Glu Asp Val Gly Phe Ile Gly Glu Val Arg Gln Glu Leu Glu Asp
        310                 315                 320 ctg gag cgg agc cta gcc cag gag atg gca ttt gag ggg cct gcc cct      1125
Leu Glu Arg Ser Leu Ala Gln Glu Met Ala Phe Glu Gly Pro Ala Pro
    325                 330                 335 gtg gag tca cta ggc gga gag gag gag att taggcccaga cccagctgag        1175
Val Glu Ser Leu Gly Gly Glu Glu Glu Ile
340                 345 tcactggtag atgtgcaata gaaatggcta atttattttc ccaggagtgt ccccaagtgt    1235
ggaatggccg cagctccttc ccagtagctt ttcctctggc ttgacaaggt acagtgcagt    1295
acatttcttc cagccgccct gcttctctga cttgggaaag acaggcatgg cgggtaaggg    1355
cagcggtgag tcgtccctcg ctgttgctag aaacgctgtc ttgttcttca tggatggaag    1415
atttgtttga agggagagga tgggaagggg tgaagtctgc tcatgatgga tttgggggat    1475
acagggagga ggatgcctgc cttgcagacg tggacttggc aaaatgtaac ctttgctttt    1535
gtcttgcgcc gctcccatgg gctgaggcag tggctacaca agagctatgc tgctctgtgg    1595
cctcccacat attcatccct gtgtttcagc tcctacctca ctgtcagcac agcccttcat    1655
agccacgccc cctcttgctc accacagcct aggagggac cagagggac ttctctcaga     1715 gccccatgct ctctctctca accccatacc agcctctgtg ccagcgacag tccttccaaa    1775
tggagggagt gaaatccttt ggtttaatta ttttctcctt caaggcacgc ctgccactaa    1835
ggtcaggctg acttgcatgt ccctctaacg ttcgtagcag tgtggtggac actgtcttcc    1895
accgactgct tcaataccte tgaaagccag tgctcggagt gcagttcgtg taaattaatt    1955
tgcaggaagt atacttggct aattgtaggg ctaggattgt gaatgaaatt tgcaaagtcg    2015
cttagcaaca atggaaagcc tttctcagtc acaccgagaa gtcacaacca agccaggttg    2075
tgtagagtac agctgtgaca tacagacaga agaaggctgg gctggatgtc aggcctcaga    2135
tgacggtttc aggtgccagg aactattacc attctgtatc tatccagagt tattaaaatt    2195
gaaagttgca cacatttgta taagcatgcc tttctcctga gttttaaatt atatgtatac    2255
acaaacatgt ggccctcaaa gatcatgcac aaaccactac tctttgctaa ttcttggact    2315
tttctctttg attttcaata aatacaaatc cccttcatgc aaaaaaaaaa aaaagggcg     2375 gccgc                                                                2380
```

<210> SEQ ID NO 17
<211> LENGTH: 349
<212> TYPE: PRT
<213> ORGANISM: Homo sapiens

<400> SEQUENCE: 17

```
Met Gln Arg Leu Gly Gly Ile Leu Leu Cys Thr Leu Leu Ala Ala Ala
1               5                   10                  15

Val Pro Thr Ala Pro Ala Pro Ser Pro Thr Val Thr Trp Thr Pro Ala
            20                  25                  30

Glu Pro Gly Pro Ala Leu Asn Tyr Pro Gln Glu Ala Thr Leu Asn
        35                  40                  45

Glu Met Phe Arg Glu Val Glu Glu Leu Met Glu Asp Thr Gln His Lys
    50                  55                  60
```

```
Leu Arg Ser Ala Val Glu Glu Met Glu Ala Glu Ala Ala Ala Lys
 65                  70                  75                  80

Thr Ser Ser Glu Val Asn Leu Ala Ser Leu Pro Pro Asn Tyr His Asn
                 85                  90                  95

Glu Thr Ser Thr Glu Thr Arg Val Gly Asn Asn Thr Val His Val His
            100                 105                 110

Gln Glu Val His Lys Ile Thr Asn Asn Gln Ser Gly Gln Val Val Phe
        115                 120                 125

Ser Glu Thr Val Ile Thr Ser Val Gly Asp Glu Glu Gly Lys Arg Ser
    130                 135                 140

His Glu Cys Ile Ile Asp Glu Asp Cys Gly Pro Thr Arg Tyr Cys Gln
145                 150                 155                 160

Phe Ser Ser Phe Lys Tyr Thr Cys Gln Pro Cys Arg Asp Gln Gln Met
                165                 170                 175

Leu Cys Thr Arg Asp Ser Glu Cys Cys Gly Asp Gln Leu Cys Ala Trp
            180                 185                 190

Gly His Cys Thr Gln Lys Ala Thr Lys Gly Gly Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Thr Ser Gln Leu Leu Asp Leu Ile Thr Trp Glu Leu
                245                 250                 255

Glu Pro Glu Gly Ala Leu Asp Arg Cys Pro Cys Ala Ser Gly Leu Leu
            260                 265                 270

Cys Gln Pro His Ser His Ser Leu Val Tyr Met Cys Lys Pro Ala Phe
        275                 280                 285

Val Gly Ser His Asp His Ser Glu Glu Ser Gln Leu Pro Arg Glu Ala
    290                 295                 300

Pro Asp Glu Tyr Glu Asp Val Gly Phe Ile Gly Glu Val Arg Gln Glu
305                 310                 315                 320

Leu Glu Asp Leu Glu Arg Ser Leu Ala Gln Glu Met Ala Phe Glu Gly
                325                 330                 335

Pro Ala Pro Val Glu Ser Leu Gly Gly Glu Glu Glu Ile
            340                 345

<210> SEQ ID NO 18
<211> LENGTH: 1047
<212> TYPE: DNA
<213> ORGANISM: Homo sapiens
<220> FEATURE:
<221> NAME/KEY: CDS
<222> LOCATION: (1)..(1047)

<400> SEQUENCE: 18 atg cag cgg ctc ggg ggt att ttg ctg tgt aca ctg ctg gcg gcg gcg    48
Met Gln Arg Leu Gly Gly Ile Leu Leu Cys Thr Leu Leu Ala Ala Ala
 1               5                  10                  15 gtc ccc act gct cct gct cct tcc ccg acg gtc act tgg act ccg gcg    96
Val Pro Thr Ala Pro Ala Pro Ser Pro Thr Val Thr Trp Thr Pro Ala
                20                  25                  30 gag ccg ggc cca gct ctc aac tac cct cag gag gaa gct acg ctc aat   144
Glu Pro Gly Pro Ala Leu Asn Tyr Pro Gln Glu Glu Ala Thr Leu Asn
            35                  40                  45 gag atg ttt cga gag gtg gag gag ctg atg gaa gac act cag cac aaa   192
Glu Met Phe Arg Glu Val Glu Glu Leu Met Glu Asp Thr Gln His Lys
```

|  |  | 50 |  |  |  |  | 55 |  |  |  |  | 60 |  |  |  |  |
|---|---|---|---|---|---|---|---|---|---|---|---|---|---|---|---|---|
| ctg | cgc | agt | gcc | gtg | gag | gag | atg | gag | gcg | gaa | gaa | gca | gct | gct | aaa | 240 |
| Leu | Arg | Ser | Ala | Val | Glu | Glu | Met | Glu | Ala | Glu | Glu | Ala | Ala | Ala | Lys |  |
| 65 |  |  |  | 70 |  |  |  |  | 75 |  |  |  |  |  | 80 |  |
| acg | tcc | tct | gag | gtg | aac | ctg | gca | agc | tta | cct | ccc | aac | tat | cac | aat | 288 |
| Thr | Ser | Ser | Glu | Val | Asn | Leu | Ala | Ser | Leu | Pro | Pro | Asn | Tyr | His | Asn |  |
|  |  |  |  | 85 |  |  |  |  | 90 |  |  |  |  | 95 |  |  |
| gag | acc | agc | acg | gag | acc | agg | gtg | gga | aat | aac | aca | gtc | cat | gtg | cac | 336 |
| Glu | Thr | Ser | Thr | Glu | Thr | Arg | Val | Gly | Asn | Asn | Thr | Val | His | Val | His |  |
|  |  |  | 100 |  |  |  |  | 105 |  |  |  |  | 110 |  |  |  |
| cag | gaa | gtt | cac | aag | ata | acc | aac | aac | cag | agt | gga | cag | gtg | gtc | ttt | 384 |
| Gln | Glu | Val | His | Lys | Ile | Thr | Asn | Asn | Gln | Ser | Gly | Gln | Val | Val | Phe |  |
|  |  | 115 |  |  |  |  | 120 |  |  |  |  | 125 |  |  |  |  |
| tct | gag | aca | gtc | att | aca | tct | gta | ggg | gat | gaa | gaa | ggc | aag | agg | agc | 432 |
| Ser | Glu | Thr | Val | Ile | Thr | Ser | Val | Gly | Asp | Glu | Glu | Gly | Lys | Arg | Ser |  |
| 130 |  |  |  |  | 135 |  |  |  |  | 140 |  |  |  |  |  |  |
| cat | gaa | tgt | atc | att | gat | gaa | gac | tgt | ggg | ccc | acc | agg | tac | tgc | cag | 480 |
| His | Glu | Cys | Ile | Ile | Asp | Glu | Asp | Cys | Gly | Pro | Thr | Arg | Tyr | Cys | Gln |  |
| 145 |  |  |  |  | 150 |  |  |  |  | 155 |  |  |  |  | 160 |  |
| ttc | tcc | agc | ttc | aag | tac | acc | tgc | cag | cca | tgc | cgg | gac | cag | cag | atg | 528 |
| Phe | Ser | Ser | Phe | Lys | Tyr | Thr | Cys | Gln | Pro | Cys | Arg | Asp | Gln | Gln | Met |  |
|  |  |  |  | 165 |  |  |  |  | 170 |  |  |  |  | 175 |  |  |
| cta | tgc | acc | cga | gac | agt | gag | tgc | tgt | gga | gac | cag | ctg | tgt | gcc | tgg | 576 |
| Leu | Cys | Thr | Arg | Asp | Ser | Glu | Cys | Cys | Gly | Asp | Gln | Leu | Cys | Ala | Trp |  |
|  |  |  | 180 |  |  |  |  | 185 |  |  |  |  | 190 |  |  |  |
| ggt | cac | tgc | acc | caa | aag | gcc | acc | aaa | ggt | ggc | aat | ggg | acc | atc | tgt | 624 |
| Gly | His | Cys | Thr | Gln | Lys | Ala | Thr | Lys | Gly | Gly | Asn | Gly | Thr | Ile | Cys |  |
|  |  | 195 |  |  |  |  | 200 |  |  |  |  | 205 |  |  |  |  |
| gac | aac | cag | agg | gat | tgc | cag | cct | ggc | ctg | tgt | tgt | gcc | ttc | caa | aga | 672 |
| Asp | Asn | Gln | Arg | Asp | Cys | Gln | Pro | Gly | Leu | Cys | Cys | Ala | Phe | Gln | Arg |  |
| 210 |  |  |  |  | 215 |  |  |  |  | 220 |  |  |  |  |  |  |
| ggc | ctg | ctg | ttc | ccc | gtg | tgc | aca | ccc | ctg | ccc | gtg | gag | gga | gag | ctc | 720 |
| Gly | Leu | Leu | Phe | Pro | Val | Cys | Thr | Pro | Leu | Pro | Val | Glu | Gly | Glu | Leu |  |
| 225 |  |  |  | 230 |  |  |  |  | 235 |  |  |  |  | 240 |  |  |
| tgc | cat | gac | ccc | acc | agc | cag | ctg | ctg | gat | ctc | atc | acc | tgg | gaa | ctg | 768 |
| Cys | His | Asp | Pro | Thr | Ser | Gln | Leu | Leu | Asp | Leu | Ile | Thr | Trp | Glu | Leu |  |
|  |  |  |  | 245 |  |  |  |  | 250 |  |  |  |  | 255 |  |  |
| gag | cct | gaa | gga | gct | ttg | gac | cga | tgc | ccc | tgc | gcc | agt | ggc | ctc | cta | 816 |
| Glu | Pro | Glu | Gly | Ala | Leu | Asp | Arg | Cys | Pro | Cys | Ala | Ser | Gly | Leu | Leu |  |
|  |  |  | 260 |  |  |  |  | 265 |  |  |  |  | 270 |  |  |  |
| tgc | cag | cca | cac | agc | cac | agt | ctg | gtg | tac | atg | tgc | aag | cca | gcc | ttc | 864 |
| Cys | Gln | Pro | His | Ser | His | Ser | Leu | Val | Tyr | Met | Cys | Lys | Pro | Ala | Phe |  |
|  |  | 275 |  |  |  |  | 280 |  |  |  |  | 285 |  |  |  |  |
| gtg | ggc | agc | cat | gac | cac | agt | gag | gag | agc | cag | ctg | ccc | agg | gag | gcc | 912 |
| Val | Gly | Ser | His | Asp | His | Ser | Glu | Glu | Ser | Gln | Leu | Pro | Arg | Glu | Ala |  |
| 290 |  |  |  |  | 295 |  |  |  |  | 300 |  |  |  |  |  |  |
| ccg | gat | gag | tac | gaa | gat | gtt | ggc | ttc | ata | ggg | gaa | gtg | cgc | cag | gag | 960 |
| Pro | Asp | Glu | Tyr | Glu | Asp | Val | Gly | Phe | Ile | Gly | Glu | Val | Arg | Gln | Glu |  |
| 305 |  |  |  |  | 310 |  |  |  |  | 315 |  |  |  |  | 320 |  |
| ctg | gaa | gac | ctg | gag | cgg | agc | cta | gcc | cag | gag | atg | gca | ttt | gag | ggg | 1008 |
| Leu | Glu | Asp | Leu | Glu | Arg | Ser | Leu | Ala | Gln | Glu | Met | Ala | Phe | Glu | Gly |  |
|  |  |  |  | 325 |  |  |  |  | 330 |  |  |  |  | 335 |  |  |
| cct | gcc | cct | gtg | gag | tca | cta | ggc | gga | gag | gag | att |  |  |  |  | 1047 |
| Pro | Ala | Pro | Val | Glu | Ser | Leu | Gly | Gly | Glu | Glu | Ile |  |  |  |  |  |
|  |  |  | 340 |  |  |  |  | 345 |  |  |  |  |  |  |  |  |

<210> SEQ ID NO 19
<211> LENGTH: 8
<212> TYPE: PRT
<213> ORGANISM: synthtic construct -continued

<400> SEQUENCE: 19

Asp Tyr Lys Asp Asp Asp Asp Lys
1               5

<210> SEQ ID NO 20
<211> LENGTH: 3696
<212> TYPE: DNA
<213> ORGANISM: Homo sapiens
<220> FEATURE:
<221> NAME/KEY: CDS
<222> LOCATION: (712)..(1500)

<400> SEQUENCE: 20

| | | |
|---|---|---|
| gtcgacccac gcgtccggcg ggagcccgcg gcgagcgtag cgcaagtccg ctccctaggc | 60 |
| atcgctgcgc tggcagcgat tcgctgtctc ttgtgagtca ggggacaacg cttcggggca | 120 |
| actgtgagtg cgcgtgtggg ggacctcgat tctcttcaga tctcgaggat tcggtccggg | 180 |
| gacgtctcct gatcccctac taaagcgcct gctaactttg aaaaggagca ctgtgtcctg | 240 |
| caaagtttga cacataaagg ataggaaaag agaggagaga aaagcaactg agttgaagga | 300 |
| gaaggagctg atgcgggcct cctgatcaat taagaggaga gttaaaccgc cgagatcccg | 360 |
| gcgggaccaa ggaggtgcgg ggcaagaagg aacggaagcg gtgcgatcca cagggctggg | 420 |
| ttttcttgca ccttgggtca cgcctccttg gcgagaaagc gcctcgcatt tgattgcttc | 480 |
| cagttattgc agaacttcct gtcctggtgg agaagcgggt ctcgcttggg ttccgctaat | 540 |
| ttctgtcctg aggcgtgaga ctgagttcat agggtcctgg gtccccgaac caggaagggt | 600 |
| tgagggaaca caatctgcaa gccccgcga cccaagtgag gggccccgtg ttggggtcct | 660 |
| ccctcccttt gcattcccac ccctccgggc tttgcgtctt cctggggacc c cct cgc | 717 |
| | Pro Arg |
| | 1 |

| cgg gag atg gcc gcg ttg atg cgg agc aag gat tcg tcc tgc tgc ctg | 765 |
|---|---|
| Arg Glu Met Ala Ala Leu Met Arg Ser Lys Asp Ser Ser Cys Cys Leu | |
| 5                   10                  15 | |

| ctc cta ctg gcc gcg gtg ctg atg gtg gag agc tca cag atc ggc agt | 813 |
|---|---|
| Leu Leu Leu Ala Ala Val Leu Met Val Glu Ser Ser Gln Ile Gly Ser | |
| 20                  25                  30 | |

| tcg cgg gcc aaa ctc aac tcc atc aag tcc tct ctg ggc ggg gag acg | 861 |
|---|---|
| Ser Arg Ala Lys Leu Asn Ser Ile Lys Ser Ser Leu Gly Gly Glu Thr | |
| 35                  40                  45                  50 | |

| cct ggt cag gcc gcc aat cga tct gcg ggc atg tac caa gga ctg gca | 909 |
|---|---|
| Pro Gly Gln Ala Ala Asn Arg Ser Ala Gly Met Tyr Gln Gly Leu Ala | |
| 55                  60                  65 | |

| ttc ggc ggc agt aag aag ggc aaa aac ctg ggg cag gcc tac cct tgt | 957 |
|---|---|
| Phe Gly Gly Ser Lys Lys Gly Lys Asn Leu Gly Gln Ala Tyr Pro Cys | |
| 70                  75                  80 | |

| agc agt gat aag gag tgt gaa gtt ggg agg tat tgc cac agt ccc cac | 1005 |
|---|---|
| Ser Ser Asp Lys Glu Cys Glu Val Gly Arg Tyr Cys His Ser Pro His | |
| 85                  90                  95 | |

| caa gga tca tcg gcc tgc atg gtg tgt cgg aga aaa aag aag cgc tgc | 1053 |
|---|---|
| Gln Gly Ser Ser Ala Cys Met Val Cys Arg Arg Lys Lys Lys Arg Cys | |
| 100                 105                 110 | |

| cac cga gat ggc atg tgc tgc ccc agt acc cgc tgc aat aat ggc atc | 1101 |
|---|---|
| His Arg Asp Gly Met Cys Cys Pro Ser Thr Arg Cys Asn Asn Gly Ile | |
| 115                 120                 125                 130 | |

| tgt atc cca gtt act gaa agc atc tta acc cct cac atc ccg gct ctg | 1149 |
|---|---|
| Cys Ile Pro Val Thr Glu Ser Ile Leu Thr Pro His Ile Pro Ala Leu | |
| 135                 140                 145 | |

-continued

| | | | | | | | | | | | | | | | | |
|---|---|---|---|---|---|---|---|---|---|---|---|---|---|---|---|---|
| gat | ggt | act | cgg | cac | aga | gat | cga | aac | cac | ggt | cat | tac | tca | aac | cat | 1197 |
| Asp | Gly | Thr | Arg | His | Arg | Asp | Arg | Asn | His | Gly | His | Tyr | Ser | Asn | His | |
| | | 150 | | | | | 155 | | | | | 160 | | | | |
| gac | ttg | gga | tgg | cag | aat | cta | gga | aga | cca | cac | act | aag | atg | tca | cat | 1245 |
| Asp | Leu | Gly | Trp | Gln | Asn | Leu | Gly | Arg | Pro | His | Thr | Lys | Met | Ser | His | |
| | | 165 | | | | | 170 | | | | | 175 | | | | |
| ata | aaa | ggg | cat | gaa | gga | gac | ccc | tgc | cta | cga | tca | tca | gac | tgc | att | 1293 |
| Ile | Lys | Gly | His | Glu | Gly | Asp | Pro | Cys | Leu | Arg | Ser | Ser | Asp | Cys | Ile | |
| | 180 | | | | | 185 | | | | | 190 | | | | | |
| gaa | ggg | ttt | tgc | tgt | gct | cgt | cat | ttc | tgg | acc | aaa | atc | tgc | aaa | cca | 1341 |
| Glu | Gly | Phe | Cys | Cys | Ala | Arg | His | Phe | Trp | Thr | Lys | Ile | Cys | Lys | Pro | |
| 195 | | | | | 200 | | | | | 205 | | | | | 210 | |
| gtg | ctc | cat | cag | ggg | gaa | gtc | tgt | acc | aaa | caa | cgc | aag | aag | ggt | tct | 1389 |
| Val | Leu | His | Gln | Gly | Glu | Val | Cys | Thr | Lys | Gln | Arg | Lys | Lys | Gly | Ser | |
| | | | | 215 | | | | | 220 | | | | | 225 | | |
| cat | ggg | ctg | gaa | att | ttc | cag | cgt | tgc | gac | tgt | gcg | aag | ggc | ctg | tct | 1437 |
| His | Gly | Leu | Glu | Ile | Phe | Gln | Arg | Cys | Asp | Cys | Ala | Lys | Gly | Leu | Ser | |
| | | | 230 | | | | | 235 | | | | | 240 | | | |
| tgc | aaa | gta | tgg | aaa | gat | gcc | acc | tac | tcc | tcc | aaa | gcc | aga | ctc | cat | 1485 |
| Cys | Lys | Val | Trp | Lys | Asp | Ala | Thr | Tyr | Ser | Ser | Lys | Ala | Arg | Leu | His | |
| | | 245 | | | | | 250 | | | | | 255 | | | | |
| gtg | tgt | cag | aaa | att | tgatcaccat tgaggaacat catcaattgc agactgtgaa | | | | | | | | | | | 1540 |
| Val | Cys | Gln | Lys | Ile | | | | | | | | | | | | |
| | 260 | | | | | | | | | | | | | | | |

| | | |
|---|---|---|
| gttgtgtatt taatgcatta tagcatggtg gaaaataagg ttcagatgca gaagaatggc | | 1600 |
| taaaataaga aacgtgataa gaatatagat gatcacaaaa agggagaaag aaaacatgaa | | 1660 |
| ctgaatagat tagaatgggt gacaaatgca gtgcagccag tgtttccatt atgcaacttg | | 1720 |
| tctatgtaaa aatgtacac atttgtggaa aatgctatta ttaagagaac aagcacacag | | 1780 |
| tggaaattac tgatgagtag catgtgactt tccaagagtt taggttgtgc tggaggagag | | 1840 |
| gtttccttca gattgctgat tgcttataca aataacctac atgccagatt tctattcaac | | 1900 |
| gttagagttt aacaaaatac tcctagaata acttgttata caataggttc taaaaataaa | | 1960 |
| attgctaaac aagaaatgaa aacatggagc attgttaatt tacaacagaa aattacccttt | | 2020 |
| tgatttgtaa cactacttct gctgttcaat caagagtctt ggtagataag aaaaaaatca | | 2080 |
| gtcaatattt ccaaataatt gcaaaataat ggccagttgt ttaggaaggc ctttaggaag | | 2140 |
| acaaataaat aacaaacaaa cagccacaaa tactttttt tcaaaatttt agttttacct | | 2200 |
| gtaattaata agaactgata caagacaaaa acagttcctt cagattctac ggaatgacag | | 2260 |
| tatatctctc tttatcctat gtgattcctg ctctgaatgc attatatttt ccaaagtata | | 2320 |
| cccataaatt gtgactagta aaatacttac acagagcaga attttcacag atggcaaaaa | | 2380 |
| aatttaaaga tgtccaatat atgtgggaaa agagctaaca gagagatcat tatttcttaa | | 2440 |
| agattggcca taacctgtat tttgatagaa ttagattggt aaatacatgt attcatacat | | 2500 |
| actctgtggt aatagagact tgagctggat ctgtactgca ctggagtaag caagaaaatt | | 2560 |
| gggaaaactt tttcgtttgt tcaggttttg gcaacacata gatcatatgt ctgaggcaca | | 2620 |
| agttggctgt tcatctttga aaccagggga tgcacagtct aaatgaatat ctgcatggga | | 2680 |
| tttgtatcat aatatttact atgcagatga attcagtgtg aggtcctgtg tccgtactat | | 2740 |
| cctcaaatta tttatttat agtgctgaga tcctcaaata atctcaattt caggaggttt | | 2800 |
| cacaaaatgg actcctgaag tagacagagt agtgaggttt cattgccctc tataagcttc | | 2860 |
| tgactagcca atggcatcat ccaatttttct tcccaaacct ctgcagcatc tgctttattg | | 2920 |
| ccaaagggct agtttcggtt ttctgcagcc attgcggtta aaaaatataa gtaggataac | | 2980 |

-continued

| | |
|---|---|
| ttgtaaaacc tgcatattgc taatctatag acaccacagt ttctaaattc tttgaaacca | 3040 |
| ctttactact ttttttaaac ttaactcagt tctaaatact ttgtctggag cacaaaacaa | 3100 |
| taaaaggtta tcttatagtt gtgactttaa acttttgtag accacaattc acttttagt | 3160 |
| tttcttttac ttaaatccca tctgcagtct caaatttaag ttctcccagt agagattgag | 3220 |
| tttgagcctg tatatctatt aaaaatttca acttcccaca tatatttact aagatgatta | 3280 |
| agacttacat tttctgcaca ggtctgcaaa acaaaaatt ataaactagt ccatccaaga | 3340 |
| accaaagttt gtataaacag gttgctataa gcttggtgaa atgaaaatgg aacatttcaa | 3400 |
| tcaaacattt cctatataac aattattata tttacaattt ggtttctgca atatttttct | 3460 |
| tatgtccacc cttttaaaaa ttattatttg aagtaattta tttacaggaa atgttaatga | 3520 |
| gatgtatttt cttatagaga tatttcttac agaaagcttt gtagcagaat atatttgcag | 3580 |
| ctattgactt tgtaatttag gaaaaatgta taataagata aaatctatta aattttctc | 3640 |
| ctctaaaaac tgaaaaaaaa aaaaaaaaaa aaaaaaaaaa aaaaagggc ggccgc | 3696 |

<210> SEQ ID NO 21
<211> LENGTH: 263
<212> TYPE: PRT
<213> ORGANISM: Homo sapiens

<400> SEQUENCE: 21

Pro Arg Arg Glu Met Ala Ala Leu Met Arg Ser Lys Asp Ser Ser Cys
1               5                   10                  15

Cys Leu Leu Leu Leu Ala Ala Val Leu Met Val Glu Ser Ser Gln Ile
            20                  25                  30

Gly Ser Ser Arg Ala Lys Leu Asn Ser Ile Lys Ser Ser Leu Gly Gly
        35                  40                  45

Glu Thr Pro Gly Gln Ala Ala Asn Arg Ser Ala Gly Met Tyr Gln Gly
    50                  55                  60

Leu Ala Phe Gly Gly Ser Lys Lys Gly Lys Asn Leu Gly Gln Ala Tyr
65                  70                  75                  80

Pro Cys Ser Ser Asp Lys Glu Cys Glu Val Gly Arg Tyr Cys His Ser
                85                  90                  95

Pro His Gln Gly Ser Ser Ala Cys Met Val Cys Arg Arg Lys Lys Lys
            100                 105                 110

Arg Cys His Arg Asp Gly Met Cys Cys Pro Ser Thr Arg Cys Asn Asn
        115                 120                 125

Gly Ile Cys Ile Pro Val Thr Glu Ser Ile Leu Thr Pro His Ile Pro
    130                 135                 140

Ala Leu Asp Gly Thr Arg His Arg Asp Arg Asn His Gly His Tyr Ser
145                 150                 155                 160

Asn His Asp Leu Gly Trp Gln Asn Leu Gly Arg Pro His Thr Lys Met
                165                 170                 175

Ser His Ile Lys Gly His Glu Gly Asp Pro Cys Leu Arg Ser Ser Asp
            180                 185                 190

Cys Ile Glu Gly Phe Cys Cys Ala Arg His Phe Trp Thr Lys Ile Cys
        195                 200                 205

Lys Pro Val Leu His Gln Gly Glu Val Cys Thr Lys Gln Arg Lys Lys
    210                 215                 220

Gly Ser His Gly Leu Glu Ile Phe Gln Arg Cys Asp Cys Ala Lys Gly
225                 230                 235                 240

Leu Ser Cys Lys Val Trp Lys Asp Ala Thr Tyr Ser Ser Lys Ala Arg

```
                    245                 250                 255
Leu His Val Cys Gln Lys Ile
                260

<210> SEQ ID NO 22
<211> LENGTH: 789
<212> TYPE: DNA
<213> ORGANISM: Homo sapiens
<220> FEATURE:
<221> NAME/KEY: CDS
<222> LOCATION: (1)..(789)

<400> SEQUENCE: 22 cct cgc cgg gag atg gcc gcg ttg atg cgg agc aag gat tcg tcc tgc        48
Pro Arg Arg Glu Met Ala Ala Leu Met Arg Ser Lys Asp Ser Ser Cys
 1               5                  10                  15 tgc ctg ctc cta ctg gcc gcg gtg ctg atg gtg gag agc tca cag atc        96
Cys Leu Leu Leu Leu Ala Ala Val Leu Met Val Glu Ser Ser Gln Ile
            20                  25                  30 ggc agt tcg cgg gcc aaa ctc aac tcc atc aag tcc tct ctg ggc ggg       144
Gly Ser Ser Arg Ala Lys Leu Asn Ser Ile Lys Ser Ser Leu Gly Gly
        35                  40                  45 gag acg cct ggt cag gcc gcc aat cga tct gcg ggc atg tac caa gga       192
Glu Thr Pro Gly Gln Ala Ala Asn Arg Ser Ala Gly Met Tyr Gln Gly
    50                  55                  60 ctg gca ttc ggc ggc agt aag aag ggc aaa aac ctg ggg cag gcc tac       240
Leu Ala Phe Gly Gly Ser Lys Lys Gly Lys Asn Leu Gly Gln Ala Tyr
65                  70                  75                  80 cct tgt agc agt gat aag gag tgt gaa gtt ggg agg tat tgc cac agt       288
Pro Cys Ser Ser Asp Lys Glu Cys Glu Val Gly Arg Tyr Cys His Ser
                85                  90                  95 ccc cac caa gga tca tcg gcc tgc atg gtg tgt cgg aga aaa aag aag       336
Pro His Gln Gly Ser Ser Ala Cys Met Val Cys Arg Arg Lys Lys Lys
            100                 105                 110 cgc tgc cac cga gat ggc atg tgc tgc ccc agt acc cgc tgc aat aat       384
Arg Cys His Arg Asp Gly Met Cys Cys Pro Ser Thr Arg Cys Asn Asn
        115                 120                 125 ggc atc tgt atc cca gtt act gaa agc atc tta acc cct cac atc ccg       432
Gly Ile Cys Ile Pro Val Thr Glu Ser Ile Leu Thr Pro His Ile Pro
    130                 135                 140 gct ctg gat ggt act cgg cac aga gat cga aac cac ggt cat tac tca       480
Ala Leu Asp Gly Thr Arg His Arg Asp Arg Asn His Gly His Tyr Ser
145                 150                 155                 160 aac cat gac ttg gga tgg cag aat cta gga aga cca cac act aag atg       528
Asn His Asp Leu Gly Trp Gln Asn Leu Gly Arg Pro His Thr Lys Met
                165                 170                 175 tca cat ata aaa ggg cat gaa gga gac ccc tgc cta cga tca tca gac       576
Ser His Ile Lys Gly His Glu Gly Asp Pro Cys Leu Arg Ser Ser Asp
            180                 185                 190 tgc att gaa ggg ttt tgc tgt gct cgt cat ttc tgg acc aaa atc tgc       624
Cys Ile Glu Gly Phe Cys Cys Ala Arg His Phe Trp Thr Lys Ile Cys
        195                 200                 205 aaa cca gtg ctc cat cag ggg gaa gtc tgt acc aaa caa cgc aag aag       672
Lys Pro Val Leu His Gln Gly Glu Val Cys Thr Lys Gln Arg Lys Lys
    210                 215                 220 ggt tct cat ggg ctg gaa att ttc cag cgt tgc gac tgt gcg aag ggc       720
Gly Ser His Gly Leu Glu Ile Phe Gln Arg Cys Asp Cys Ala Lys Gly
225                 230                 235                 240 ctg tct tgc aaa gta tgg aaa gat gcc acc tac tcc tcc aaa gcc aga       768
Leu Ser Cys Lys Val Trp Lys Asp Ala Thr Tyr Ser Ser Lys Ala Arg
                245                 250                 255
```

```
ctc cat gtg tgt cag aaa att                                          789
Leu His Val Cys Gln Lys Ile
                260
```

```
<210> SEQ ID NO 23
<211> LENGTH: 54
<212> TYPE: PRT
<213> ORGANISM: Artificial Sequence
<220> FEATURE:
<223> OTHER INFORMATION: Description of Artificial Sequence: consensus
      sequence
<223> OTHER INFORMATION: Xaa's at positions
      2,3,5,6,8-12,14-26,28,29,31-36,38-42,45-48, and
      50-53 may be any amino acid
<223> OTHER INFORMATION: Xaa's at postions 22-26 may be absent

<400> SEQUENCE: 23

Cys Xaa Xaa Asp Xaa Xaa Cys Xaa Xaa Xaa Xaa Xaa Cys Xaa Xaa Xaa
  1               5                   10                  15

Xaa Xaa Xaa Xaa Xaa Xaa Xaa Xaa Xaa Cys Xaa Xaa Cys Xaa Xaa
             20                  25                  30

Xaa Xaa Xaa Xaa Cys Xaa Xaa Xaa Xaa Cys Cys Xaa Xaa Xaa Xaa
         35                  40                  45

Cys Xaa Xaa Xaa Xaa Cys
         50
```

```
<210> SEQ ID NO 24
<211> LENGTH: 123
<212> TYPE: PRT
<213> ORGANISM: Artificial Sequence
<220> FEATURE:
<223> OTHER INFORMATION: Description of Artificial Sequence: consensus
      sequence
<223> OTHER INFORMATION: Xaa's at positions
      2,5,8,9,11,14-23,25,27-30,32,33,35-53,60,62,63,65,
      68,70,71,73-96,98,100,101,104, and 106-122 may be
      any amino acid
<223> OTHER INFORMATION: Xaa's at positions 22,23,51-58,89-96 and 116-
      122 may be absent

<400> SEQUENCE: 24

Cys Xaa Xaa Xaa Xaa Asp Cys Xaa Xaa Gly Xaa Cys Cys Xaa Xaa Xaa
  1               5                  10                  15

Xaa Xaa Xaa Xaa Xaa Xaa Xaa Cys Xaa Pro Xaa Xaa Xaa Gly Xaa
             20                  25                  30

Xaa Cys Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Cys Xaa Cys Xaa Xaa Pro
         50                  55                  60

Xaa Xaa Xaa Xaa Gly Xaa Xaa Cys Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Cys Xaa Cys Xaa Xaa Gly Leu Xaa Cys Xaa Xaa Xaa Xaa Xaa Xaa
             100                 105                 110

Xaa Xaa Xaa Xaa Xaa Xaa Xaa Xaa Xaa Xaa Cys
         115                 120
```

```
<210> SEQ ID NO 25
<211> LENGTH: 87
<212> TYPE: PRT
<213> ORGANISM: Homo sapiens
```

<400> SEQUENCE: 25

```
Ile Asn Leu Glu Asn Gly Glu Leu Cys Met Asn Ser Ala Gln Cys Lys
 1               5                  10                  15

Ser Asn Cys Cys Gln His Ser Ser Ala Leu Gly Leu Ala Arg Cys Thr
                20                  25                  30

Ser Met Ala Ser Glu Asn Ser Glu Cys Ser Val Lys Thr Leu Tyr Gly
            35                  40                  45

Ile Tyr Tyr Lys Cys Pro Cys Glu Arg Gly Leu Thr Cys Glu Gly Asp
     50                  55                  60

Lys Thr Ile Val Gly Ser Ile Thr Asn Thr Asn Phe Gly Ile Cys His
 65                  70                  75                  80

Asp Ala Gly Arg Ser Lys Gln
                85
```

<210> SEQ ID NO 26
<211> LENGTH: 835
<212> TYPE: DNA
<213> ORGANISM: Mus musculus
<220> FEATURE:
<221> NAME/KEY: CDS
<222> LOCATION: (57)..(746)

<400> SEQUENCE: 26

```
gaattcggca cgaggcagaa ggcgcgaatg aaggcaaagc ctcccaccca cctgca atg      59
                                                                Met
                                                                  1 tgt cga ctg agg gtc ttg ctg ctg ctc ccc ttg gcc ttc gtg tcc            107
Cys Arg Leu Arg Val Leu Leu Leu Leu Pro Leu Ala Phe Val Ser
              5                  10                  15 tcc tct gct ctc ccc atc cat gat gtc gac tct cag cag aac acc tcc       155
Ser Ser Ala Leu Pro Ile His Asp Val Asp Ser Gln Gln Asn Thr Ser
             20                  25                  30 ggg ttc ctg ggc ctt cag agg ctt ctc caa agc ttt agt cga ctg ttc       203
Gly Phe Leu Gly Leu Gln Arg Leu Leu Gln Ser Phe Ser Arg Leu Phe
         35                  40                  45 cta aaa aat gac ctg cta cga gac ctg gac aac ttc ttc tcc tcc ccc       251
Leu Lys Asn Asp Leu Leu Arg Asp Leu Asp Asn Phe Phe Ser Ser Pro
 50                  55                  60                  65 atg gac ttc cga gac ctt cct agg aac ttc cat cag gaa gag aac cag       299
Met Asp Phe Arg Asp Leu Pro Arg Asn Phe His Gln Glu Glu Asn Gln
                 70                  75                  80 gag cac aga atg ggc aac cat acc ctc tcc agc cac cta cag ata gac       347
Glu His Arg Met Gly Asn His Thr Leu Ser Ser His Leu Gln Ile Asp
             85                  90                  95 aag gtg act gac aac cag aca ggg gag gtg cac atc tcg gag aaa gtc       395
Lys Val Thr Asp Asn Gln Thr Gly Glu Val His Ile Ser Glu Lys Val
         100                 105                 110 gag gcc tcc att gag cca gaa cgg aac ccg gaa ggg gac tgg aag gtt       443
Glu Ala Ser Ile Glu Pro Glu Arg Asn Pro Glu Gly Asp Trp Lys Val
     115                 120                 125 ccc aaa gta gaa gca aaa gag ccc ccg gtg cct gtg cag aag gtc acc       491
Pro Lys Val Glu Ala Lys Glu Pro Pro Val Pro Val Gln Lys Val Thr
130                 135                 140                 145 gac agc ttg cac cca gag ccc cgg cag gtg gct ttc tgg atc atg aag       539
Asp Ser Leu His Pro Glu Pro Arg Gln Val Ala Phe Trp Ile Met Lys
                150                 155                 160 atg cca agg cgg agg acc cag ccc gat gtc cag gat gga ggc cgc tgg       587
Met Pro Arg Arg Arg Thr Gln Pro Asp Val Gln Asp Gly Gly Arg Trp
            165                 170                 175
```

```
ctc ata gaa aag cga cat cgc atg cag gcc atc cgg gat ggg ctc cgt      635
Leu Ile Glu Lys Arg His Arg Met Gln Ala Ile Arg Asp Gly Leu Arg
        180                 185                 190 gga ggc gcc cgt gag gac agc ctg gag gat ggg gtc cat atc ccc caa      683
Gly Gly Ala Arg Glu Asp Ser Leu Glu Asp Gly Val His Ile Pro Gln
    195                 200                 205 cac gcc aag ctg cct gtc aga aag aca cac ttt ctc tac atc ctc agg      731
His Ala Lys Leu Pro Val Arg Lys Thr His Phe Leu Tyr Ile Leu Arg
210                 215                 220                 225 cca tcc caa cag ctg taagtggga ccagatgtcc cacaccctac cccaacacca       786
Pro Ser Gln Gln Leu
                230 tatggaaata aaggttttct tacatctaaa aaaaaaaaaa aaaaaaaa                 835
```

<210> SEQ ID NO 27
<211> LENGTH: 230
<212> TYPE: PRT
<213> ORGANISM: Mus musculus

<400> SEQUENCE: 27

```
Met Cys Arg Leu Arg Val Leu Leu Leu Leu Pro Leu Ala Phe Val
1               5                   10                  15

Ser Ser Ser Ala Leu Pro Ile His Asp Val Asp Ser Gln Gln Asn Thr
            20                  25                  30

Ser Gly Phe Leu Gly Leu Gln Arg Leu Leu Gln Ser Phe Ser Arg Leu
        35                  40                  45

Phe Leu Lys Asn Asp Leu Leu Arg Asp Leu Asp Asn Phe Phe Ser Ser
    50                  55                  60

Pro Met Asp Phe Arg Asp Leu Pro Arg Asn Phe His Gln Glu Glu Asn
65                  70                  75                  80

Gln Glu His Arg Met Gly Asn His Thr Leu Ser Ser His Leu Gln Ile
                85                  90                  95

Asp Lys Val Thr Asp Asn Gln Thr Gly Glu Val His Ile Ser Glu Lys
            100                 105                 110

Val Glu Ala Ser Ile Glu Pro Glu Arg Asn Pro Glu Gly Asp Trp Lys
        115                 120                 125

Val Pro Lys Val Glu Ala Lys Glu Pro Pro Val Pro Val Gln Lys Val
    130                 135                 140

Thr Asp Ser Leu His Pro Glu Pro Arg Gln Val Ala Phe Trp Ile Met
145                 150                 155                 160

Lys Met Pro Arg Arg Thr Gln Pro Asp Val Gln Asp Gly Gly Arg
                165                 170                 175

Trp Leu Ile Glu Lys Arg His Arg Met Gln Ala Ile Arg Asp Gly Leu
            180                 185                 190

Arg Gly Gly Ala Arg Glu Asp Ser Leu Glu Asp Gly Val His Ile Pro
        195                 200                 205

Gln His Ala Lys Leu Pro Val Arg Lys Thr His Phe Leu Tyr Ile Leu
    210                 215                 220

Arg Pro Ser Gln Gln Leu
225                 230
```

<210> SEQ ID NO 28
<211> LENGTH: 690
<212> TYPE: DNA
<213> ORGANISM: Mus musculus
<220> FEATURE:
<221> NAME/KEY: CDS
<222> LOCATION: (1)..(690)

<400> SEQUENCE: 28

```
atg tgt cga ctg agg gtc ttg ctg ctg ctc ccc ttg gcc ttc gtg      48
Met Cys Arg Leu Arg Val Leu Leu Leu Leu Pro Leu Ala Phe Val
 1               5                  10                  15 tcc tcc tct gct ctc ccc atc cat gat gtc gac tct cag cag aac acc  96
Ser Ser Ser Ala Leu Pro Ile His Asp Val Asp Ser Gln Gln Asn Thr
            20                  25                  30 tcc ggg ttc ctg ggc ctt cag agg ctt ctc caa agc ttt agt cga ctg  144
Ser Gly Phe Leu Gly Leu Gln Arg Leu Leu Gln Ser Phe Ser Arg Leu
        35                  40                  45 ttc cta aaa aat gac ctg cta cga gac ctg gac aac ttc ttc tcc tcc  192
Phe Leu Lys Asn Asp Leu Leu Arg Asp Leu Asp Asn Phe Phe Ser Ser
50                  55                  60 ccc atg gac ttc cga gac ctt cct agg aac ttc cat cag gaa gag aac  240
Pro Met Asp Phe Arg Asp Leu Pro Arg Asn Phe His Gln Glu Glu Asn
65                  70                  75                  80 cag gag cac aga atg ggc aac cat acc ctc tcc agc cac cta cag ata  288
Gln Glu His Arg Met Gly Asn His Thr Leu Ser Ser His Leu Gln Ile
                85                  90                  95 gac aag gtg act gac aac cag aca ggg gag gtg cac atc tcg gag aaa  336
Asp Lys Val Thr Asp Asn Gln Thr Gly Glu Val His Ile Ser Glu Lys
            100                 105                 110 gtc gag gcc tcc att gag cca gaa cgg aac ccg gaa ggg gac tgg aag  384
Val Glu Ala Ser Ile Glu Pro Glu Arg Asn Pro Glu Gly Asp Trp Lys
        115                 120                 125 gtt ccc aaa gta gaa gca aaa gag ccc ccg gtg cct gtg cag aag gtc  432
Val Pro Lys Val Glu Ala Lys Glu Pro Pro Val Pro Val Gln Lys Val
130                 135                 140 acc gac agc ttg cac cca gag ccc cgg cag gtg gct ttc tgg atc atg  480
Thr Asp Ser Leu His Pro Glu Pro Arg Gln Val Ala Phe Trp Ile Met
145                 150                 155                 160 aag atg cca agg cgg agg acc cag ccc gat gtc cag gat gga ggc cgc  528
Lys Met Pro Arg Arg Arg Thr Gln Pro Asp Val Gln Asp Gly Gly Arg
                165                 170                 175 tgg ctc ata gaa aag cga cat cgc atg cag gcc atc cgg gat ggg ctc  576
Trp Leu Ile Glu Lys Arg His Arg Met Gln Ala Ile Arg Asp Gly Leu
            180                 185                 190 cgt gga ggc gcc cgt gag gac agc ctg gag gat ggg gtc cat atc ccc  624
Arg Gly Gly Ala Arg Glu Asp Ser Leu Glu Asp Gly Val His Ile Pro
        195                 200                 205 caa cac gcc aag ctg cct gtc aga aag aca cac ttt ctc tac atc ctc  672
Gln His Ala Lys Leu Pro Val Arg Lys Thr His Phe Leu Tyr Ile Leu
    210                 215                 220 agg cca tcc caa cag ctg                                          690
Arg Pro Ser Gln Gln Leu
225                 230
```

<210> SEQ ID NO 29
<211> LENGTH: 51
<212> TYPE: PRT
<213> ORGANISM: Artificial Sequence
<220> FEATURE:
<223> OTHER INFORMATION: Xaa at positions
    3-5,7,9-15,18,20-22,24-27,29,31,33,34,36-39,42,44,
    45, and 47-50 may be any amino acid
<223> OTHER INFORMATION: Description of Artificial Sequence: consensus
    sequence

<400> SEQUENCE: 29

```
Leu Pro Xaa Xaa Xaa His Xaa Glu Xaa Xaa Xaa Xaa Xaa Xaa Gly
 1               5                  10                  15
```

```
Asn Xaa Thr Xaa Xaa Xaa His Xaa Xaa Xaa Xaa Lys Xaa Thr Xaa Asn
            20                  25                  30

Xaa Xaa Gly Xaa Xaa Xaa Xaa Ser Glu Xaa Val Xaa Xaa Ser Xaa Xaa
        35                  40                  45

Xaa Xaa Glu
    50
```

```
<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 30
cagtgagtgc tgtggagacc                                            20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 31
tcttcagtca ggctcctctc                                            20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 32
acctgcaatg tgtcgactga g                                          21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 33
cacttacagc tgttgggatg                                            20

<210> SEQ ID NO 34
<211> LENGTH: 10
<212> TYPE: PRT
<213> ORGANISM: Homo sapiens
<220> FEATURE:
<223> OTHER INFORMATION: Xaa at position 1 may be any amino acid

<400> SEQUENCE: 34

Xaa Val Leu Asp Phe Asn Asn Ile Arg Ser
 1               5                  10

<210> SEQ ID NO 35
<211> LENGTH: 10
<212> TYPE: PRT
<213> ORGANISM: Homo sapiens

<400> SEQUENCE: 35
```

Ser Gln Gly Arg Lys Gly Gln Glu Gly Ser
1               5                   10

<210> SEQ ID NO 36
<211> LENGTH: 272
<212> TYPE: PRT
<213> ORGANISM: Mus musculus

<400> SEQUENCE: 36

Met Met Val Val Cys Ala Pro Ala Ala Val Arg Phe Leu Ala Val Phe
1               5                   10                  15

Thr Met Met Ala Leu Cys Ser Leu Pro Leu Leu Gly Ala Ser Ala Thr
            20                  25                  30

Leu Asn Ser Val Leu Ile Asn Ser Asn Ala Ile Lys Asn Leu Pro Pro
        35                  40                  45

Pro Leu Gly Gly Ala Gly Gly Gln Pro Gly Ser Ala Val Ser Val Ala
    50                  55                  60

Pro Gly Val Leu Tyr Glu Gly Gly Asn Lys Tyr Gln Thr Leu Asp Asn
65                  70                  75                  80

Tyr Gln Pro Tyr Pro Cys Ala Glu Asp Glu Glu Cys Gly Ser Asp Glu
                85                  90                  95

Tyr Cys Ser Ser Pro Ser Arg Gly Ala Ala Gly Val Gly Val Gln
            100                 105                 110

Ile Cys Leu Ala Cys Arg Lys Arg Arg Lys Arg Cys Met Thr His Ala
        115                 120                 125

Met Cys Cys Pro Gly Asn Tyr Cys Lys Asn Gly Ile Cys Met Pro Ser
    130                 135                 140

Asp His Ser His Phe Pro Arg Gly Glu Ile Glu Glu Ser Ile Ile Glu
145                 150                 155                 160

Asn Leu Gly Asn Asp His Asn Ala Ala Ala Gly Asp Gly Tyr Pro Arg
                165                 170                 175

Arg Thr Thr Leu Thr Ser Lys Ile Tyr His Thr Lys Gly Gln Glu Gly
            180                 185                 190

Ser Val Cys Leu Arg Ser Ser Asp Cys Ala Ala Gly Leu Cys Cys Ala
        195                 200                 205

Arg His Phe Trp Ser Lys Ile Cys Lys Pro Val Leu Lys Glu Gly Gln
    210                 215                 220

Val Cys Thr Lys His Lys Arg Lys Gly Ser His Gly Leu Glu Ile Phe
225                 230                 235                 240

Gln Arg Cys Tyr Cys Gly Glu Gly Leu Ala Cys Arg Ile Gln Lys Asp
                245                 250                 255

His His Gln Ala Ser Asn Ser Ser Arg Leu His Thr Cys Gln Arg His
            260                 265                 270

<210> SEQ ID NO 37
<211> LENGTH: 259
<212> TYPE: PRT
<213> ORGANISM: Xenopus laevis

<400> SEQUENCE: 37

Met Gly Ser Asn Met Phe Pro Val Pro Leu Ile Val Phe Trp Gly Phe
1               5                   10                  15

Ile Leu Asp Gly Ala Leu Gly Phe Val Met Met Thr Asn Ser Asn Ser
            20                  25                  30

Ile Lys Asn Val Pro Ala Ala Pro Ala Gly Gln Pro Ile Gly Tyr Tyr
        35                  40                  45

-continued

```
Pro Val Ser Val Ser Pro Asp Ser Leu Tyr Asp Ile Ala Asn Lys Tyr
 50                  55                  60

Gln Pro Leu Asp Ala Tyr Pro Leu Tyr Ser Cys Thr Glu Asp Asp
 65                  70                  75                  80

Cys Ala Leu Asp Glu Phe Cys His Ser Ser Arg Asn Gly Asn Ser Leu
                 85                  90                  95

Val Cys Leu Ala Cys Arg Lys Arg Lys Arg Cys Leu Arg Asp Ala
            100                 105                 110

Met Cys Cys Thr Gly Asn Tyr Cys Ser Asn Gly Ile Cys Val Pro Val
            115                 120                 125

Glu Gln Asp Gln Glu Arg Phe Gln His Gln Gly Tyr Leu Glu Glu Thr
    130                 135                 140

Ile Leu Glu Asn Tyr Asn Asn Ala Asp His Ala Thr Met Asp Thr His
145                 150                 155                 160

Ser Lys Leu Thr Thr Ser Pro Ser Gly Met Gln Pro Phe Lys Gly Arg
                165                 170                 175

Asp Gly Asp Val Cys Leu Arg Ser Thr Asp Cys Ala Pro Gly Leu Cys
            180                 185                 190

Cys Ala Arg His Phe Trp Ser Lys Ile Cys Lys Pro Val Leu Asp Glu
    195                 200                 205

Gly Gln Val Cys Thr Lys His Arg Arg Lys Gly Ser His Gly Leu Glu
    210                 215                 220

Ile Phe Gln Arg Cys His Cys Gly Ala Gly Leu Ser Cys Arg Leu Gln
225                 230                 235                 240

Lys Gly Glu Phe Thr Thr Val Pro Lys Thr Ser Arg Leu His Thr Cys
                245                 250                 255

Gln Arg His

<210> SEQ ID NO 38
<211> LENGTH: 350
<212> TYPE: PRT
<213> ORGANISM: Gallus gallus

<400> SEQUENCE: 38

Met Arg Arg Gly Glu Gly Pro Ala Pro Arg Arg Trp Leu Leu Leu
 1               5                  10                  15

Leu Ala Val Leu Ala Ala Leu Cys Cys Ala Ala Ala Gly Ser Gly Gly
                 20                  25                  30

Arg Arg Arg Ala Ala Ser Leu Gly Glu Met Leu Arg Glu Val Glu Ala
             35                  40                  45

Leu Met Glu Asp Thr Gln His Lys Leu Arg Asn Ala Val Gln Glu Met
 50                  55                  60

Glu Ala Glu Glu Glu Gly Ala Lys Lys Leu Ser Glu Val Asn Phe Glu
 65                  70                  75                  80

Asn Leu Pro Pro Thr Tyr His Asn Glu Ser Asn Thr Glu Thr Arg Ile
                 85                  90                  95

Gly Asn Lys Thr Val Gln Thr His Gln Glu Ile Asp Lys Val Thr Asp
            100                 105                 110

Asn Arg Thr Gly Ser Thr Ile Phe Ser Glu Thr Ile Ile Thr Ser Ile
            115                 120                 125

Lys Gly Gly Glu Asn Lys Arg Asn His Glu Cys Ile Ile Asp Glu Asp
    130                 135                 140

Cys Glu Thr Gly Lys Tyr Cys Gln Phe Ser Thr Phe Glu Tyr Lys Cys
145                 150                 155                 160
```

-continued

| | | | | | | | | | | | | | | |
|---|---|---|---|---|---|---|---|---|---|---|---|---|---|---|
|Gln|Pro|Cys|Lys 165|Thr|Gln|His|Thr|His 170|Cys|Ser|Arg|Asp|Val 175|Glu|Cys|
|Cys|Gly|Asp|Gln 180|Leu|Cys|Val|Trp|Gly 185|Glu|Cys|Arg|Lys|Ala 190|Thr|Ser|
|Arg|Gly|Glu 195|Asn|Gly|Thr|Ile|Cys 200|Glu|Asn|Gln|His|Asp 205|Cys|Asn|Pro|
|Gly|Thr 210|Cys|Cys|Ala|Phe|Gln 215|Lys|Glu|Leu|Leu|Phe 220|Pro|Val|Cys|Thr|
|Pro 225|Leu|Pro|Glu|Glu|Gly 230|Glu|Pro|Cys|His|Asp 235|Pro|Ser|Asn|Arg|Leu 240|
|Leu|Asn|Leu|Ile|Thr 245|Trp|Glu|Leu|Glu|Pro 250|Asp|Gly|Val|Leu|Glu 255|Arg|
|Cys|Pro|Cys|Ala|Ser 260|Gly|Leu|Ile|Cys 265|Gln|Pro|Gln|Ser|Ser 270|His|Ser|
|Thr|Thr|Ser 275|Val|Cys|Glu|Leu|Ser 280|Ser|Asn|Glu|Thr|Arg 285|Lys|Asn|Glu|
|Lys|Glu 290|Asp|Pro|Leu|Asn|Met 295|Asp|Glu|Met|Pro|Phe 300|Ile|Ser|Leu|Ile|
|Pro 305|Arg|Asp|Ile|Leu|Ser 310|Asp|Tyr|Glu|Glu|Ser 315|Ser|Val|Ile|Gln|Glu 320|
|Val|Arg|Lys|Glu|Leu 325|Glu|Ser|Leu|Glu|Asp 330|Gln|Ala|Gly|Val|Lys 335|Ser|
|Glu|His|Asp|Pro 340|Ala|His|Asp|Leu|Phe 345|Leu|Gly|Asp|Glu|Ile 350| | |

US 7,057,017 B2

HUMAN DICKKOPF-RELATED PROTEIN AND NUCLEIC ACID MOLECULES AND USES THEREFOR

CROSS-REFERENCE TO RELATED APPLICATIONS

This application is a continuation of U.S. patent application Ser. No. 09/263,022, filed Mar. 5, 1999 now abandoned, which is a continuation-in-part of International Application No. PCT/US98/07894, filed Apr. 16, 1998, designating the United States, which is a continuation-in-part of U.S. patent application Ser. No. 09/009,802, filed Jan. 20, 1998, which claims the benefit of U.S. patent application Ser. No. 60/071,589, filed Jan. 15, 1998. The contents of each of the above-referenced patent applications are incorporated herein by reference in their entirety.

BACKGROUND OF THE INVENTION

Secreted proteins play an integral role in the formation, differentiation, and maintenance of cells in multicellular organisms. For instance, secretory proteins are known in the art to be involved in signaling between cells which are not in direct contact. Such secreted signaling molecules are particularly important in the development of vertebrate tissue during embryogenesis as well as in the maintenance of the differentiated state of adult tissues. For example, inductive interactions that occur between neighboring cell layers and tissues in the developing embryo are largely dependent on the existence and regulation of secreted signaling molecules. In inductive interactions, biochemical signals secreted by one cell population influence the developmental fate of a second cell population, typically by altering the fate of the second cell population. For example, the Wnt proteins are now recognized as one of the major families of developmentally important signaling molecules in organisms ranging from *Drosophila* to mice.

The Wnt gene family encode a large class of secreted proteins related to the Int1/Wnt1 proto-oncogene and *Drosophila* wingless ("Wg"), a *Drosophila* Wnt1 homologue, (Cadigan et al. (1997) *Genes & Development* 11:3286–3305). Wnts are expressed in a variety of tissues and organs and are required for many developmental processes, including segmentation in *Drosophila*, endoderm development in *Caenorhabditis elegans*, establishment of limb polarity, neural crest differentiation, kidney morphogenesis, sex determination, and brain development in mammals (reviewed in Parr and McMahon (1994) *Curr. Opinion Genetics & Devel.* 4:523–528; Cadigan and Nusse, supra).

Recent studies in diverse organisms have led to identification of several components of the Wnt signal transduction pathway in responding cells (Cadigan and Nusse, supra). Wnt signals are transduced by the Frizzled ("Fz") family of seven transmembrane domain receptors (Bhanot et al. (1996) *Nature* 382:225–230). The resulting signal leads to the activation of the cytoplasmic protein Dishevelled (Dsh) and stabilization of Armadillo/β-catenin (Perrimon (1994) *Cell* 76:781–784). Negative regulators of the Wnt pathway include glycogen synthase kinase 3 (GSK3)/shaggy (Perrimon, supra), the tumor suppressor gene product adenomatous polyposis coli (APC) (Gumbiner (1997) *Curr. Biol.* 7:R443–436) and a novel protein, called Axin (Zeng et al. (1997) *Cell* 90:181–192). In the absence of a Wnt ligand, these proteins promote phosphorylation and then degradation of β-catenin, whereas Wnt signaling inactivates GSK3, thus preventing β-catenin degradation. As a result, β-catenin is translocated to the nucleus, where it forms a complex with TCF transcription factors and activates target gene expression (Cadigan and Nusse, supra). Deregulation of this pathway can lead to carcinogenesis (reviewed by Gumbiner, supra), emphasizing the long-recognized connection between Wnts, normal development and cancer. This connection has been further established recently with the identification the c-Myc protooncogene as a target of Wnt signaling (He et al. (1998) *Science* 281:1509–3512).

While the outcome of Wnt signaling may be influenced by multiple intracellular regulatory mechanisms, recent studies have identified several classes of secreted factors which can modulate Wnt action outside of the cell. These include Cerberus, a secreted Wnt inhibitor implicated in head development (Bouwmeester et al (1996) *Nature* 382:595–601), and a family of proteins related to the extracellular domain of Frizzled. These Frizzled-related proteins ("FRPs") (Rattner et al. (1997) *Proc. Natl. Acad. Sci. USA* 94:2859–2863), also known as secreted apoptosis-related proteins ("SARPs"), are encoded by several independently discovered genes including FrzA/FRP1, SDF5/FRP2, FrzB/FRP3, FRP4 and Sizzled (Melkonyan et al. (1997) *Proc. Natl. Acad. Sci. USA* 94:13636–13641; Finch et al. (1997) *Proc. Natl. Acad. Sci. USA* 94:6770–6775; Wang et al. (1997) *Cell* 88:747–766; Leyns et al. (1997) *Cell* 88:747–756; Mayr et al. (1997) *Mech. Dev.* 63:109–325; and Salic et al. (1997) *Development* 124:4739–4748). These proteins inhibit the ability of Xwnt8 to induce a secondary axis in frog embryos (for review see Zorn (1997) *Curr. Biol.* 7:R501–504), and are thought to compete for binding of Wnt ligands to the Frizzled receptors. Data on binding of certain FRPs to Xwnt8 (Wang et al., (1997) *Biochem. Biophys. Res. Comm.* 236:502–504; and Leyns et al., supra) and Wg corroborate this notion (Rattner et al., supra).

It is now recognized that many of these families of signaling molecules have a dual role to play in both the development of an organism as well as in promoting or maintaining the differentiated state of tissues in the adult animal. Furthermore, major families of signaling molecules have been implicated in controlling proliferation of cells in mature adult tissue, for example, during normal cell turnover in the adult organism as well as in tissue regeneration activated as a result of damage to the adult tissue. Given the important role of these signalling molecules such as the Wnts and FRPs in both developing and adult tissues, there exists a need for identifying novel modulators of such molecules for use in regulating a variety of cellular processes.

SUMMARY OF THE INVENTION

The present invention is based, at least in part, on the discovery of nucleic acid molecules which encode a novel family of secreted human proteins, referred to herein as the human Dickkopf proteins or "hDkks" (formerly referred to as the "Cysteine-Rich Secreted Proteins", "CRSPs", "CRISPYs", or "CRSP proteins"). The Dkk molecules of the present invention are useful as modulating agents in regulating a variety of cellular processes. Accordingly, in one aspect, this invention provides isolated nucleic acid molecules encoding Dkk proteins or biologically active portions thereof, as well as nucleic acid fragments suitable as primers or hybridization probes for the detection of Dkk-encoding nucleic acids. In another aspect, this invention provides isolated nucleic acid molecules encoding Dkk-related proteins (e.g., Soggy proteins) or biologically active portions thereof, as well as nucleic acid fragments suitable as primers or hybridization probes for the detection of Dkk- or Soggy-encoding nucleic acids.

In one embodiment, a Dkk nucleic acid molecule is 60% homologous to the nucleotide sequence shown in SEQ ID NO:1, SEQ ID NO:3, the nucleotide sequence of the DNA insert of the plasmid deposited with ATCC as Accession Number 98452 or complement thereof. In yet another embodiment, a Dkk nucleic acid molecule is 80% homologous to the nucleotide sequence shown in SEQ ID NO:4, SEQ ID NO:6, or a complement thereof. In yet another embodiment, a Dkk nucleic acid molecule is 60% homologous to the nucleotide sequence shown in SEQ ID NO:7, SEQ ID NO:9, or the nucleotide sequence of the DNA insert of the plasmid deposited with ATCC as Accession Number 98633, or a complement thereof. In yet another embodiment, a Dkk nucleic acid molecule is 85% homologous to the nucleotide sequence shown in SEQ ID NO:7, SEQ ID NO:9, or the nucleotide sequence of the DNA insert of the plasmid deposited with ATCC as Accession Number 98633, or a complement thereof. In yet another embodiment, a Dkk nucleic acid molecule is 70% homologous to the nucleotide sequence shown in SEQ ID NO:20, SEQ ID NO:22, or the nucleotide sequence of the DNA insert of the plasmid deposited with ATCC as Accession Number 201740, or a complement thereof. In yet another embodiment, a nucleic acid molecule of the present invention (e.g., a Dkk-related nucleic acid molecule) is 90% homologous to the nucleotide sequence shown in SEQ ID NO:13, SEQ ID NO:15, or a complement thereof.

In a preferred embodiment, an isolated Dkk nucleic acid molecule has the nucleotide sequence shown SEQ ID NO:3, or a complement thereof. In another embodiment, a Dkk nucleic acid molecule further comprises nucleotides 1–37 of SEQ ID NO:1. In yet another preferred embodiment, a Dkk nucleic acid molecule further comprises nucleotides 1088–2479 of SEQ ID NO:1. In another preferred embodiment, an isolated Dkk nucleic acid molecule has the nucleotide sequence shown in SEQ ID NO:1.

In another preferred embodiment, an isolated Dkk nucleic acid molecule has the nucleotide sequence shown SEQ ID NO:6, or a complement thereof. In another embodiment, a Dkk nucleic acid molecule further comprises nucleotides 1–124 of SEQ ID NO:4. In yet another preferred embodiment, a Dkk nucleic acid molecule further comprises nucleotides 797–848 of SEQ ID NO:4. In another preferred embodiment, an isolated Dkk nucleic acid molecule has the nucleotide sequence shown in SEQ ID NO:4.

In another preferred embodiment, an isolated Dkk nucleic acid molecule has the nucleotide sequence shown SEQ ID NO:9, or a complement thereof. In another embodiment, a Dkk nucleic acid molecule further comprises nucleotides 1–108 of SEQ ID NO:7. In yet another preferred embodiment, a Dkk nucleic acid molecule further comprises nucleotides 907–1536 of SEQ ID NO:7. In another preferred embodiment, an isolated Dkk nucleic acid molecule has the nucleotide sequence shown in SEQ ID NO:7.

In another preferred embodiment, an isolated Dkk nucleic acid molecule has the nucleotide sequence shown SEQ ID NO:22, or a complement thereof. In another embodiment, a Dkk nucleic acid molecule further comprises nucleotides 1–723 of SEQ ID NO:20. In yet another preferred embodiment, a Dkk nucleic acid molecule further comprises nucleotides 1501–3687 of SEQ ID NO:20. In yet another preferred embodiment, an isolated Dkk nucleic acid molecule has the nucleotide sequence shown in SEQ ID NO:20.

In another preferred embodiment, an isolated nucleic acid molecule of the present invention (e.g., a Dkk-related nucleic acid molecule) has the nucleotide sequence shown SEQ ID NO:15, or a complement thereof. In another embodiment, a nucleic acid molecule further comprises nucleotides 1–74 of SEQ ID NO:13. In yet another preferred embodiment, a nucleic acid molecule further comprises nucleotides 801–928 of SEQ ID NO:13. In yet another preferred embodiment, an isolated nucleic acid molecule has the nucleotide sequence shown in SEQ ID NO:13.

In another embodiment, a Dkk nucleic acid molecule includes a nucleotide sequence encoding a protein having an amino acid sequence sufficiently homologous to the amino acid sequence of SEQ ID NO:2, SEQ ID NO:5, SEQ ID NO:8, or SEQ ID NO:21. In another preferred embodiment, a Dkk nucleic acid molecule includes a nucleotide sequence encoding a protein having an amino acid sequence at least 60% homologous to the amino acid sequence of SEQ ID NO:2. In yet another preferred embodiment, a Dkk nucleic acid molecule includes a nucleotide sequence encoding a protein having an amino acid sequence at least 60% homologous to the amino acid sequence of SEQ ID NO:5. In yet another preferred embodiment, a Dkk nucleic acid molecule includes a nucleotide sequence encoding a protein having an amino acid sequence at least 60% homologous to the amino acid sequence of SEQ ID NO:8. In yet another preferred embodiment, a Dkk nucleic acid molecule includes a nucleotide sequence encoding a protein having an amino acid sequence at least 75% homologous to the amino acid sequence of SEQ ID NO:8. In yet another preferred embodiment, a Dkk nucleic acid molecule includes a nucleotide sequence encoding a protein having an amino acid sequence at least 65% homologous to the amino acid sequence of SEQ ID NO:21. In another embodiment, a nucleic acid molecule of the present invention (e.g., a Dkk-related nucleic acid molecule) includes a nucleotide sequence encoding a protein having an amino acid sequence sufficiently homologous to the amino acid sequence of SEQ ID NO:14 (e.g., encodes a protein having an amino acid sequence which is 60% homologous to the amino acid sequence of SEQ ID NO:14).

In another embodiment, an isolated nucleic acid molecule of the present invention encodes a Dkk protein which includes a signal sequence and at least one cysteine-rich region, and is secreted. In another embodiment, an isolated nucleic acid molecule of the present invention encodes a Dkk protein which includes a signal sequence and a cysteine-rich region, wherein the cysteine-rich region comprises at least one cysteine-rich domain, and is secreted. In yet another embodiment, a Dkk nucleic acid molecule encodes a Dkk protein and is a naturally occurring nucleotide sequence.

In another embodiment, an isolated nucleic acid molecule of the present invention encodes a Dkk-related protein (e.g., a Soggy protein) which includes a signal sequence, lacks cysteine-rich domains, and is secreted. In another embodiment, an isolated nucleic acid molecule of the present invention encodes a Dkk-related protein (e.g., a Soggy protein) which includes a signal sequence and a Soggy domain, and is secreted. In yet another embodiment, a nucleic acid molecule of the present invention encodes a Dkk-related protein and is a naturally occurring nucleotide sequence.

Another embodiment of the invention features nucleic acid molecules which specifically detect Dkk nucleic acid molecules relative to nucleic acid molecules encoding non-Dkk proteins (or specifically detect Dkk-related nucleic acid molecules). For example, in one embodiment, a nucleic acid molecule hybridizes under stringent conditions to a nucleic acid molecule consisting of nucleotides 470–2479 of nucleotide sequence shown in SEQ ID NO:1, to nucleotides 1–475 of nucleotide sequence shown in SEQ ID NO:4, or to nucleotides 1–600 of nucleotide sequence shown in SEQ ID NO:7, or hybridizes under stringent conditions to the nucleotide sequence of the DNA insert of the plasmid deposited with ATCC as Accession Number 98452, to the nucleotide sequence of the DNA insert of the plasmid deposited with ATCC as Accession Number 98633, or to the nucleotide sequence of the DNA insert of the plasmid deposited with ATCC as Accession Number 201740. In another embodiment, the nucleic acid molecule is at least 500 nucleotides in length and hybridizes under stringent conditions to a nucleic acid molecule comprising the nucleotide sequence shown in SEQ ID NO:1, SEQ ID NO:4, SEQ ID NO:7, SEQ ID NO:13, or SEQ ID NO:20 or a complement thereof.

Another embodiment of the invention provides an isolated nucleic acid molecule which is antisense to the coding strand of a Dkk nucleic acid or Dkk-related nucleic acid. Another embodiment of the invention provides an isolated nucleic acid molecules in a form suitable for expression of mRNA. In another embodiment, the isolated nucleic acid molecules are in a form suitable for expression of protein. In yet another embodiment, the isolated nucleic acid molecules are free from vector seqeunces.

Another aspect of the invention provides a vector comprising a Dkk nucleic acid molecule or Dkk-related nucleic acid molecule. In certain embodiments, the vector is a recombinant expression vector. In another embodiment, the invention provides a host cell containing a vector of the invention. The invention also provides a method for producing a Dkk protein or Dkk-related protein by culturing in a suitable medium, a host cell of the invention containing a recombinant expression vector such that a Dkk protein or Dkk-related protein is produced.

Another aspect of this invention features isolated or recombinant Dkk proteins and polypeptides or Dkk-related proteins and polypeptides. In one embodiment, an isolated Dkk protein has a signal sequence and a cysteine-rich region which comprises two cysteine-rich domains, and is secreted. In another embodiment, an isolated Dkk protein has an amino acid sequence sufficiently homologous to the amino acid sequence of SEQ ID NO:2, SEQ ID NO:5, SEQ ID NO:8, or SEQ ID NO:21. In a preferred embodiment, a Dkk protein has an amino acid sequence at least about 60% homologous to the amino acid sequence of SEQ ID NO:2. In another preferred embodiment, a Dkk protein has an amino acid sequence at least about 60% homologous to the amino acid sequence of SEQ ID NO:5. In another preferred embodiment, a Dkk protein has an amino acid sequence at least about 60% homologous to the amino acid sequence of SEQ ID NO:8. In another preferred embodiment, a Dkk protein has an amino acid sequence at least about 75% homologous to the amino acid sequence of SEQ ID NO:8. In another preferred embodiment, a Dkk protein has an amino acid sequence at least about 65% homologous to the amino acid sequence of SEQ ID NO:21. In another embodiment, a Dkk protein has the amino acid sequence of SEQ ID NO:2, SEQ ID NO:5, SEQ ID NO:8, or SEQ ID NO:21. In another preferred embodiment, a protein of the present invention has an amino acid sequence at least about 60% homologous to the amino acid sequence of SEQ ID NO:14. In another embodiment, a protein has the amino acid sequence of SEQ ID NO:14.

Another embodiment of the invention features an isolated Dkk protein which is encoded by a nucleic acid molecule having a nucleotide sequence at least about 60% homologous to a nucleotide sequence of SEQ ID NO:1, or a complement thereof. Another embodiment of the invention features an isolated Dkk protein which is encoded by a nucleic acid molecule having a nucleotide sequence at least about 80% homologous to a nucleotide sequence of SEQ ID NO:4, or a complement thereof. Another embodiment of the invention features an isolated Dkk protein which is encoded by a nucleic acid molecule having a nucleotide sequence at least about 60% homologous to a nucleotide sequence of SEQ ID NO:7, or a complement thereof. Another embodiment of the invention features an isolated Dkk protein which is encoded by a nucleic acid molecule having a nucleotide sequence at least about 85% homologous to a nucleotide sequence of SEQ ID NO:7, or a complement thereof. Another embodiment of the invention features an isolated Dkk protein which is encoded by a nucleic acid molecule having a nucleotide sequence at least about 70% homologous to a nucleotide sequence of SEQ ID NO:20, or a complement thereof. Another embodiment of the invention features an isolated protein which is encoded by a nucleic acid molecule having a nucleotide sequence at least about 90% homologous to a nucleotide sequence of SEQ ID NO:13, or a complement thereof. This invention further features an isolated protein which is encoded by a nucleic acid molecule having a nucleotide sequence which hybridizes under stringent hybridization conditions to a nucleic acid molecule comprising the nucleotide sequence of SEQ ID NO:1, SEQ ID NO:4, SEQ ID NO:7, SEQ ID NO:13, SEQ ID NO:20, or a complement thereof.

The proteins of the present invention, or biologically active portions thereof, can be operatively linked to a non-Dkk polypeptide or non-Dkk-related polypeptide to form fusion proteins. The invention further features antibodies that specifically bind Dkk or Dkk-related proteins, such as monoclonal or polyclonal antibodies. In addition, the proteins or biologically active portions thereof can be incorporated into pharmaceutical compositions, which optionally include pharmaceutically acceptable carriers.

In another aspect, the present invention provides a method for detecting Dkk expression (or the expression of a Dkk-related molecule) in a biological sample by contacting the biological sample with an agent capable of detecting a nucleic acid molecule, protein or polypeptide of the present invention such that the presence of a Dkk (of Dkk-related) nucleic acid molecule, protein or polypeptide is detected in the biological sample.

In another aspect, the present invention provides a method for detecting the presence of a Dkk activity (or Dkk-related activity) in a biological sample by contacting the biological sample with an agent capable of detecting an indicator of Dkk activity (or Dkk-related activity) such that the presence of the activity is detected in the biological sample.

In another aspect, the invention provides a method for modulating Dkk activity (or Dkk-related activity) comprising contacting the cell with an agent that modulates the activity such that the activity in the cell is modulated. In one embodiment, the agent inhibits Dkk activity (or Dkk-related activity). In another embodiment, the agent stimulates Dkk activity (or Dkk-related activity). In one embodiment, the agent is an antibody that specifically binds to a Dkk (or Dkk-related) protein. In another embodiment, the agent modulates expression of a protein (e.g., a Dkk or a Dkk-related protein) by modulating transcription of a gene or translation of a mRNA of the present invention. In yet another embodiment, the agent is a nucleic acid molecule having a nucleotide sequence that is antisense to the coding strand of a mRNA or gene of the present invention.

In one embodiment, the methods of the present invention are used to treat a subject having a disorder characterized by aberrant expression or activity of a protein or nucleic acid of the invention by administering to the subject an agent which is a modulator of Dkk or a Dkk-related molecule. In one embodiment, the modulator is a Dkk or Dkk-related protein. In another embodiment the modulator is a Dkk or Dkk-related nucleic acid molecule. In yet another embodiment, the modulator is an antibody peptide, peptidomimetic, or other small molecule. In a preferred embodiment, the disorder characterized by aberrant protein or nucleic acid expression is a developmental, differentiative, or proliferative disorder.

The present invention also provides a diagnostic assay for identifying the presence or absence of a genetic alteration characterized by at least one of (i) aberrant modification or mutation of a gene encoding a Dkk or Dkk-related protein; (ii) mis-regulation of said gene; and (iii) aberrant post-translational modification of a Dkk or Dkk-related protein, wherein a wild-type form of said gene encodes an protein with a Dkk or Dkk-related activity.

In another aspect the invention provides a method for identifying a compound that binds to or modulates the activity of a Dkk or Dkk-related protein, by providing a indicator composition comprising a Dkk or Dkk-related protein having a biological activity, contacting the indicator composition with a test compound, and determining the effect of the test compound on the activity in the indicator composition to identify a compound that modulates the activity of a Dkk or Dkk-related protein.

Other features and advantages of the invention will be apparent from the following detailed description and claims.

BRIEF DESCRIPTION OF THE DRAWINGS

FIGS. 1A–1D depict the cDNA sequence and predicted amino acid sequence of human Dkk-3. The nucleotide sequence corresponds to nucleic acids 1 to 2479 of SEQ ID NO:1. The amino acid sequence corresponds to amino acids 1 to 350 of SEQ ID NO:2.

FIGS. 2A and 2B depict the cDNA sequence and predicted amino acid sequence of human Dkk-4. The nucleotide sequence corresponds to nucleic acids 1 to 848 of SEQ ID NO:4. The amino acid sequence corresponds to amino acids 1 to 224 of SEQ ID NO:5.

FIGS. 3A and 3B depict the cDNA sequence and predicted amino acid sequence of human Dkk-1. The nucleotide sequence corresponds to nucleic acids 1 to 1536 of SEQ ID NO:7. The amino acid sequence corresponds to amino acids 1 to 266 of SEQ ID NO:8.

FIGS. 4A–4E depict the cDNA sequence and predicted amino acid sequence of full-length human Dkk-2. The nucleotide sequence corresponds to nucleic acids 1 to 3687 of SEQ ID NO:20. The amino acid sequence corresponds to amino acids 1 to 259 of SEQ ID NO:21.

FIGS. 5A–5D depict the cDNA sequence and predicted amino acid sequence of murine Dkk-3. The nucleotide sequence corresponds to nucleic acids 1 to 2381 of SEQ ID NO:16. The amino acid sequence corresponds to amino acids 1 to 349 of SEQ ID NO:17.

FIGS. 6A–6C depict a multiple sequence alignment of the amino acid sequences of hDkk-1 (corresponding the SEQ ID NO:8), mDkk-1 (having Accession No. AF030434 and corresponding to SEQ ID NO:36), Xenopus Dkk-1 ("xDkk-1") (having Accession No. AF030433 and corresponding to SEQ ID NO:37), hDkk-2 (corresponding to SEQ ID NO:21), hDkk-3 (corresponding to SEQ ID NO:2), mDkk-3 (corresponding to SEQ ID NO:17), chicken Dkk-3 ("cDkk-3") (having Accession No. D26311 and corresponding to SEQ ID NO:38), and hDkk-4 (corresponding to SEQ ID NO:5). The alignment was performed using the ClustalW algorithm as implemented in the GCG program PILEUP. The alignment provides information regarding the relationship between the Dkk proteins of the instant invention. Predicted signal peptides are underlined, N-glycosylation sites are indicated by a thick bar, CRD-1 by an open box, CRD-2 by a shaded box. The proteolytic cleavage site within hDkk4 is indicated by an arrow.

FIGS. 7A and 7B depict the cDNA sequence and predicted amino acid sequence of human Soggy. The nucleotide sequence corresponds to nucleic acids 1 to 928 of SEQ ID NO:13. The amino acid sequence corresponds to amino acids 1 to 242 of SEQ ID NO:14.

FIGS. 8A and 8B depict the cDNA sequence and predicted amino acid sequence of murine Soggy-1. The nucleotide sequence corresponds to nucleic acids 1 to 835 of SEQ ID NO:26. The amino acid sequence corresponds to amino acids 1 to 230 of SEQ ID NO:27.

FIGS. 10A and 10B depict a multiple sequence alignment of hSoggy-1 (corresponding to SEQ ID NO:14), murine Soggy-1 (corresponding to SEQ ID NO:27), hDkk-3 (corresponding to SEQ ID NO:2), and mDkk-3 (corresponding to SEQ ID NO:17). The alignment was generated as described in the legend for FIGS. 6A–6C. The alignment provides details regarding the relationship between the Dkk-3 and Soggy-1 proteins of the instant invention. Predicted signal peptides are underlined, N-glycosylation sites are indicated by a thick bar. CRD-1 and CRD-2 within Dkk-3 are indicated for reference by open and shaded boxes.

FIG. 11 depicts a multiple sequence alignment of the carboxy-terminal cysteine-rich domains of hDkk-1, hDkk-2, hDkk-3, hDkk-4 with human colipase (having accession No. J02883). The carboxy-terminal cysteine-rich domains of the Dkk proteins are indicated by an open box. The alignment was generated using PILEUP (gap penalties of 12 for opening and 12 for extending). A minor adjustment was necessary since PILEUP inserts a single gap in hDkk-1 and hDkk-2 between Gly56 and Ser57, even with a gap opening penalty of 15. The conserved residues are indicated. The disulfide-bonding pattern typical for the colipase family and predicted for the Dkk family is indicated below the alignment.

DETAILED DESCRIPTION OF THE INVENTION

Figure 9:
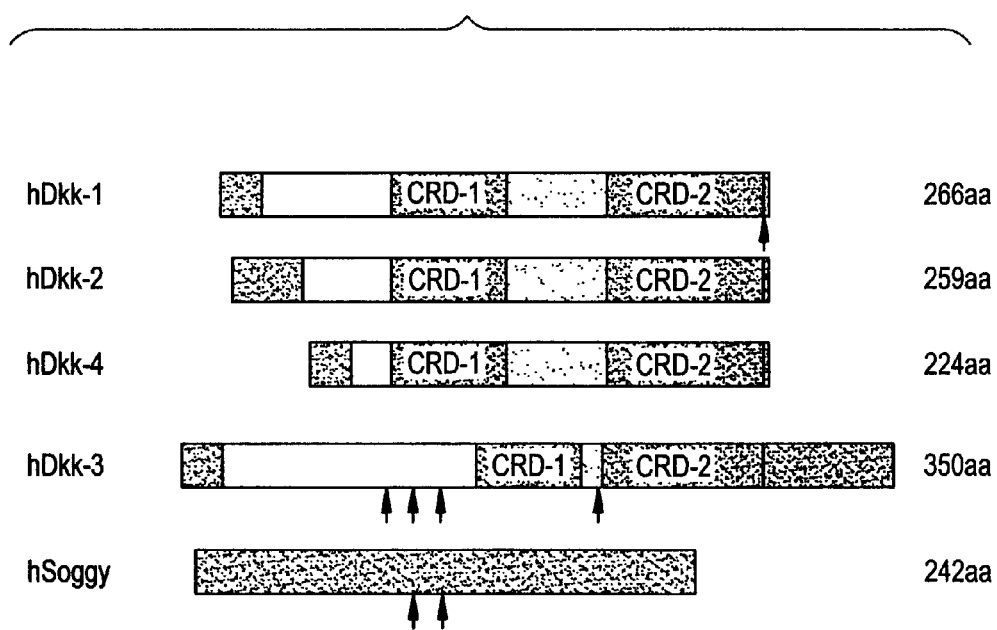
FIG. 9 is a schematic diagram illustrating the Dkk and Dkk-related proteins of the instant invention. The figure depicts the structural domains of the human Dkks and Soggy. Signal peptides are indicated by darkened boxes. The cysteine-rich domains of a Dkk cysteine-rich region are depicted as CRD-1 and CRD-2. Branches indicate sites of N-glycosylation.

The present invention is based on the discovery of novel molecules, referred to herein as Dkk protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain and having sufficient amino acid or nucleotide sequence homology as defined herein. Such family members can be naturally-occurring and can be from either the same or different species. For example, a family can contain a first protein of human origin, as well as other, distinct proteins of human origin or alternatively, can contain homologues of non-human origin. Members of a family may also have common functional characteristics.

In one embodiment, a Dkk family member is identified based on the presence of at least one "cysteine-rich domain" in the protein molecule or corresponding amino acid sequence. As defined herein, a "cysteine-rich domain" refers to a portion of a Dkk protein (e.g., hDkk-3) which is rich in cysteine residues. In a preferred embodiment, a "cysteine-rich domain" is a protein domain having an amino acid sequence of about 45–85 amino acids of which preferably 10 amino acids are cysteine residues located at the same relative amino acid position as the cysteine residues in human Dkk-3 having SEQ ID NO:2 (e.g., amino acid residues 147–195 of SEQ ID NO:2). In another embodiment, a "cysteine-rich domain" has 30–100 amino acids, preferably about 35–95 amino acids, more preferably about 40–90 amino acids, more preferably about 50–80 amino acids, even more preferably about 55–75, 60–70, or 65 amino acids, of which at least about 3–20, preferably about 5–15, or more preferably about 6, 7, 8, 9, 10, 11, 12, 13, 14, 15, 16, 17, 18, 19, or 20 amino acids are cysteine residues.

A preferred Dkk protein of the present invention has a first cysteine-rich domain ("CRD-1") referred to herein as an "amino-terminal cysteine-rich domain" or "N-terminal cysteine-rich domain" and a second cysteine-rich domain ("CRD-2"), referred to herein as a "carboxy-terminal cysteine-rich domain" or "C-terminal cysteine-rich domain". As defined herein, an "amino-terminal cysteine-rich domain" is a protein domain having an amino acid sequence of about 45–55 amino acids of which preferably 10 amino acids are cysteine residues located at the same relative position as the cysteine residues in an amino-terminal cysteine-rich domain of human Dkk-3 having SEQ ID NO:2 (e.g., amino acid residues 147–195 of SEQ ID NO:2). In another embodiment, an "amino-terminal cysteine-rich domain" has 30–70, preferably 35–65, more preferably about 40–60, and even more preferably about 46, 47, 48, 49, 50, 51, 52, 53, or 54 amino acids, of which at least about 3–20, preferably about 5–15, or more preferably about 6, 7, 8, 9, 10, 11, 12, 13, 14, 15, 16, 17, 18, 19, or 20 amino acids are cysteine residues. In a preferred embodiment, an amino-terminal cysteine-rich domain has the following consensus sequence: C-X(2)-D-X(2)-C-X(5)-C-X(8–13)-C-X(2)-C-X(6)-C-X(5)-C-C-X(4)-C-X(4)-C (SEQ ID NO:23). The consensus sequences described herein are described according to standard Prosite Signature designation (e.g., all amino acids are indicated according to their universal single letter designation; X designates any amino acid; X(n) designates any n amino acids, e.g., X (2) designates any 2 amino acids; and [LIVM] indicates any one of the amino acids appearing within the brackets, e.g., any one of L, I, V, or M, in the alternative, any one of Leu, Ile, Val, or Met.)

As defined herein, a "carboxy-terminal cysteine-rich domain" is a protein domain having an amino acid sequence of about 80–85 amino acids of which preferably 10 amino acids are cysteine residues located at the same relative position as the cysteine residues in a carboxy-terminal cysteine-rich domain of human Dkk-3 having SEQ ID NO:2 (e.g., amino acid residues 201–284 of SEQ ID NO:2). In another embodiment, a "carboxy-terminal cysteine-rich domain" has 65–100, preferably 70–95, more preferably about 75–90, and even more preferably about 81, 82, 83, or 84 amino acids, of which at least about 3–20, preferably about 5–15, or more preferably about 6, 7, 8, 9, 10, 11, 12, 13, 14, 15, 16, 17, 18, 19, or 20 amino acids are cysteine residues. In a preferred embodiment, a carboxy-terminal cysteine-rich domain has the following consensus sequence: C-X(4)-D-C-X(2)-G-X-C-C-X(8–10)-C-X-P-X(4)-G-X(2)-C-X(16–24)-C-X-C-X(2)-P-X(4)-G-X(2)-C-X(16–24)-C-X-C-X(2)-G-L-X-C-X(10–17)-C (SEQ ID NO:24).

A preferred protein of the present invention is a hDkk-3 protein (human Dkk-3) containing an amino-terminal cysteine-rich domain including about amino acids 147–195 of SEQ ID NO:2, having 10 cysteine residues, and a carboxy-terminal cysteine-rich domain including about amino acids 201–284 of SEQ ID NO:2, having 10 cysteine residues (the positions of the cysteine residues are depicted in FIG. 6). In another embodiment, a hDkk-4 (human Dkk-4) protein contains an amino-terminal cysteine-rich domain including about amino acids 41–90 of SEQ ID NO:5, having 10 cysteine residues, and a carboxy-terminal cysteine-rich domain including about amino acids 138–218 of SEQ ID NO:5, having 10 cysteine residues (the positions of the cysteine residues are depicted in FIG. 6). In another embodiment, a hDkk-1 protein (human Dkk-1) contains an amino-terminal cysteine-rich domain including about amino acids 85–138 of SEQ ID NO:8, having 10 cysteine residues, and a carboxy-terminal cysteine-rich domain including about amino acids 182–263 of SEQ ID NO:8, having 10 cysteine residues (the positions of the cysteine residues are depicted in FIG. 6). In another embodiment, a hDkk-2 protein (human Dkk-2) contains an amino-terminal cysteine-rich domain including about amino acids 78–127 of SEQ ID NO:21, having 10 cysteine residues, and a carboxy-terminal cysteine-rich domain including about amino acids 176–256 of SEQ ID NO:21, having 10 cysteine residues (the positions of the cysteine residues are depicted in FIG. 6).

Alignment of the human Dkk proteins with human colipase (having Accession No. J02883) indicates that the carboxy-terminal cysteine-rich domains of the human Dkk proteins have a pattern of cysteines typical of colipase (FIG. 11 and Avarind and Koonin, supra). Within colipase, these cysteine residues are involved in disulfide bonding which gives rise to a structure termed the "colipase fold". The "colipase fold" is typical of a range of small proteins which are involved in protein-protein interactions including, but not limited to the colipases, snake and scorpion toxins and protease inhibitors (Hubbard et al. (1997) *Nucleic Acids Res.* 25:236–239. These proteins have a series of short β strands with large connecting loops, which are held together by disulfide bonds. The disulfide-bonding pattern typical for colipase and predicted for the Dkk family is indicated below the alignment of FIG. 11. Conserved hydrophobic residues between the Dkks and human colipase suggest that the Dkks, like the colipases, interact with lipids (e.g., Leu51 of human colipase, SEQ ID NO:25 which corresponds to Leu271 of hDkk-3 (SEQ ID NO:2); Leu200 of hDkk-4 (SEQ ID NO:5); Leu243 of hDkk-1 (SEQ ID NO:8); and Leu237 of hDkk-2 (SEQ ID NO:21). The carboxy-terminal cysteine-rich domain of the Dkk family, may function in the membrane association of Dkk, which in turn may be required for the inhibition of Wnt secretion or Wnt:7 transmembrane receptor interaction. In addition, inhibition of Wnt function by the Dkk family may be closely associated with the cell membrane and the carboxy-terminal cysteine-rich domain of the Dkk family may mediate this association. Furthermore, the amino-terminal cysteine-rich domain of the Dkk family may directly interact with Wnt or its receptor. Accordingly, a preferred Dkk protein of the present invention comprises a carboxy-terminal cysteine-rich domain. In one embodiment, a Dkk protein comprising a carboxy-terminal cysteine-rich domain lacks the amino-terminal cysteine-rich domain.

In a preferred embodiment, the cysteine residues of a cysteine-rich domain are located at the same relative amino acid position as the cysteine residues in human Dkk-3 having SEQ ID NO:2. In another preferred embodiment, the cysteine residues of a cysteine-rich domain are located at the same relative position as the cysteine residues in a cysteine-rich domain of human Dkk-3 having SEQ ID NO:2. For example, as shown in FIG. 6, human Dkk-4 has at least about 10 cysteine residues located at the same relative amino acid position as the cysteine residues in human Dkk-3 having SEQ ID NO:2 (e.g., cys151 in Dkk-4, SEQ ID NO:5, is located at the same relative amino acid position as cys214 in Dkk-3, SEQ ID NO:2; cys156 in Dkk-4, SEQ ID NO:5, is located at the same relative amino acid position as cys219 in Dkk-3, SEQ ID NO:2; and cys157 in Dkk-4, SEQ ID NO:5, is located at the same relative amino acid position as cys220 in Dkk-3, SEQ ID NO:2). Similarly, as shown in FIG. 6, Dkk-1 has at least about 10 cysteine residues located at the same relative amino acid position as the cysteine residues in human Dkk-3 having SEQ ID NO:2. As also shown in FIG. 6, Dkk-2 has at least about 10 cysteine residues located at the same relative amino acid position as the cysteine residues in human Dkk-3 having SEQ ID NO:2. Table I sets forth at least 20 cysteine residues in each of hDkk-4, hDkk-1, and hDkk-2 which are located in the same relative position as 20 cysteine residues in hDkk-3.

TABLE I

| cysteine | aa position in hDkk-3 | aa position in hDkk-4 | aa position in hDkk-1 | aa position in hDkk-2 |
| --- | --- | --- | --- | --- |
| 1 | 147 | 41 | 85 | 78 |
| 2 | 153 | 47 | 91 | 84 |
| 3 | 159 | 53 | 97 | 90 |
| 4 | 168 | 63 | 111 | 100 |
| 5 | 171 | 66 | 114 | 103 |
| 6 | 178 | 73 | 121 | 110 |
| 7 | 184 | 79 | 127 | 116 |
| 8 | 185 | 80 | 128 | 117 |
| 9 | 190 | 85 | 133 | 122 |
| 10 | 195 | 90 | 138 | 127 |
| 11 | 208 | 145 | 189 | 183 |
| 12 | 214 | 151 | 195 | 189 |
| 13 | 219 | 156 | 200 | 194 |
| 14 | 220 | 157 | 201 | 195 |
| 15 | 231 | 166 | 210 | 204 |
| 16 | 241 | 176 | 220 | 214 |
| 17 | 265 | 194 | 237 | 231 |
| 18 | 267 | 196 | 239 | 233 |
| 19 | 273 | 202 | 245 | 239 |
| 20 | 284 | 218 | 263 | 256 |

The first 10 rows of Table I contain 10 cysteine residues that are included within the first, or amino-terminal, cysteine-rich domain of each of hDkks-3, -4, -1, and -2. The last 10 rows of Table I contain 10 cysteine residues that are included within the second, or carboxy-terminal, cysteine-rich domain of each of hDkks-3, -4, -1, and -2.

Preferred Dkk proteins have more than one cysteine-rich domain, more preferably have at least two cysteine-rich domains and, thus, have a cysteine-rich region. As used herein, the term "cysteine-rich region" refers to a protein domain which includes at least two cysteine-rich domains and has an amino acid sequence of about 120–200 amino acid residues of which at least about 20 of the amino acids are cysteine residues. In another embodiment, a "cysteine-rich region" has preferably about 140–180 amino acid residues, and even more preferably at least about 135–175 amino acids of which at least about 10–30, preferably about 15–20, and more preferably about 16, 17, 18, or 19 of the amino acids are cysteine residues. In a preferred embodiment, a cysteine-rich region is located in the C-terminal region of a Dkk protein. For example, in one embodiment, a hDkk-3 protein contains a cysteine rich region containing about amino acids 147–284 of SEQ ID NO:2, having 20 cysteine residues at the positions indicated in FIG. 6. In another embodiment, a hDkk-4 protein contains a cysteine rich region containing about amino acids 41–218 of SEQ ID NO:5, having 20 cysteine residues at the positions indicated in FIG. 6. In another embodiment, a hDkk-1 protein contains a cysteine rich region containing about amino acids 85–263 of SEQ ID NO:8, having 20 cysteine residues at the positions indicated in FIG. 6. In another embodiment, a hDkk-2 protein contains a cysteine rich region containing about amino acids 78–256 of SEQ ID NO:21, having 20 cysteine residues at the positions indicated in FIG. 6.

In another embodiment, in addition to cysteine-rich domains, the cysteine-rich region contains a spacer region which separates the first and second cysteine-rich domains. As used herein, the "spacer region" refers to amino acid residues which are located between the first and second cysteine-rich domains of a cysteine-rich region and includes amino acid residues located C-terminal to the first cysteine-rich domain and N-terminal to the second cysteine-rich domain. As defined herein, a "spacer region" refers to a protein domain of about 5–70 amino acids, preferably about 10–65 amino acids, more preferably about 15–60 amino acids, even more preferably about 20–55 amino acids, and even more preferably about 25–50, 30–45 or 35–40 amino acids. For example, hDkk-3 protein contains a spacer region of about amino acids 196–200 of SEQ ID NO:2; hDkk-4 protein contains a spacer region of about amino acids 91–137 of SEQ ID NO:5; hDkk-1 protein contains a spacer region of about amino acids 139–181 of SEQ ID NO:8; and hDkk-2 protein contains a spacer region of about amino acids 128–175 of SEQ ID NO:21. The spacer regions of hDkk-1, hDkk-2 and hDkk-4 are remarkably conserved in length (e.g., the spacer region of hDkk-1 consists of 43 amino acid residues, the spacer region of hDkk-2 consists of 48 amino acid residues and the spacer region of hDkk-4 consists of 47 amino acid residues, suggesting that the close proximity of CRD-1 and CRD-2 is important in Dkk function. Accordingly, in one embodiment, the spacer region functions to spacially restrict the separation of CRD-1 from CRD-2.

In another embodiment of the invention, the Dkk protein has at least one cysteine-rich domain, preferably a cysteine-rich region, and a signal sequence. As used herein, a "signal sequence" refers to a peptide containing about 18–24 amino acids which occurs at the N-terminus of secretory and integral membrane proteins and which contains at least about 40–70% hydrophobic amino acid residues (e.g., alanine, valine, leucine, isoleucine, phenylalanine, tyrosine, tryptophan, or proline). In another embodiment, a signal sequence contains at least about 8–34, 9–33, 10–32, 11–31, 12–30, 13–29, 14–28 amino acid residues, preferably about 15–27 amino acid residues, more preferably about 16–26 amino acid residues, more preferably about 17–25 amino acid residues, and more preferably about 18–24, 19–23, 20–22, or 21 amino acid residues, and has at least about about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a hDkk-3 protein contains a signal sequence of about amino acids 1–23 of SEQ ID NO:2. In another embodiment, a hDkk-4 protein contains a signal sequence of about amino acids 1–19 of SEQ ID NO:5. In another embodiment, a hDkk-1 protein contains a signal sequence of about amino acids 1–20 of SEQ ID NO:8. In another embodiment, a hDkk-2 protein contains a signal sequence of about amino acids 1–33 of SEQ ID NO:21. A preferred Dkk protein of the present invention is a human protein (e.g., encoded by a nucleotide sequence correpsonding to a naturally-occurring human gene).

Accordingly, one embodiment of the invention features a Dkk protein having at least one cysteine-rich domain, preferably at least one cysteine-rich region. Another embodiment features a Dkk protein having at least one cysteine-rich region, wherein the cysteine-rich region includes at least one cysteine-rich domain. Another embodiment features a Dkk protein having at least one cysteine-rich region, wherein the cysteine-rich region includes at least two cysteine-rich domains. Another embodiment features a protein or domain within a protein having 20, 30, 40, 50, 60, 70, 80, 90, 95, or 99% homology to a cysteine-rich domain of a Dkk protein of the invention (e.g., hDkk-3, hDkk-4, hDkk-1, or hDkk-2).

Yet another embodiment of the invention features a Dkk protein having at least one cysteine-rich domain, preferably at least one cysteine-rich region and a signal peptide. Another embodiment features a Dkk protein having at least one cysteine-rich domain, preferably at least one cysteine-rich region and a signal peptide, wherein the cysteine-rich region includes at least two cysteine-rich domains. Another embodiment features a Dkk protein having at least one cysteine-rich domain, preferably at least one cysteine-rich region and a signal peptide, wherein the cysteine-rich region includes at least two cysteine-rich domains and a spacer.

Yet another aspect of the invention features Dkk proteins having domains and/or regions which are conserved among a subset of Dkk proteins but are not necessarily conserved among all Dkk family members. In one embodiment, a Dkk protein (e.g., Dkk-3) has an "extended N-terminal region" which is extended in length as compared to, for example, the "N-terminal regions" of other Dkk family members (e.g., Dkk-4, Dkk-1, and Dkk-2). As defined herein, an "N-terminal region" of a Dkk proteins consists of amino acid residues found between the signal peptide and CRD-1 of a Dkk protein. Preferably, the first amino acid residue of an N-terminal region of Dkk is the first residue of a mature Dkk protein and the last residue of an N-terminal region of Dkk is the residue preceeding the first cysteine residue of CRD-1. In a preferred embodiment, an N-terminal region is about 1–20 amino acid residues in length, preferably about 21–30, 31–40, 41–50, 51–60, 61–70, 71–80, 81–90, 91–100, 101–110, 111–120, 121–130, 131–140, 141–150, 151–160 or more amino acid residues in length In contrast, an "extended N-terminal region" is at least about 71–80, 81–90, 91–100, 101–110, 111–120, 121–130, 131–140, 141–150, 151–160 or more amino acid residues in length. For example, in one embodiment, a hDkk-4 protein includes an "N-terminal region" of about amino acids 20–40 of SEQ ID NO:5 (21 amino acid residues in length). In another embodiment, a hDkk-1 protein includes an N-terminal region of about amino acids 21–84 of SEQ ID NO:8 (64 amino acid residues in length). In another embodiment, a hDkk-2 protein includes an "N-terminal region" of about amino acids 34–77 of SEQ ID NO:21 (44 amino acid residues in length). In another embodiment, a hDkk-3 protein has an "extended N-terminal region" of about amino acids 23–146 of SEQ ID NO:2 (124 amino acid residues in length).

In another embodiment, a Dkk protein (e.g., Dkk-3) has an "acidic C-terminal region" which incudes amino acid residues found C-terminal to CRD-2 of a Dkk protein. Preferably, the first amino acid residue of an acidic C-terminal region is the residue following the last cysteine of CRD-2 and the last residue of an acidic C-terminal region is the last residue of a Dkk protein. In a preferred embodiment, an acidic C-terminal region is about 65–66 amino acid residues in length and has about 27–25% acidic amino acid residues (e.g., glutamic acid or aspartic acid). In another preferred embodiment, an acidic C-terminal region is about 55–80 amino acid residues in length, preferably about 60–75 amino acid residues in length, and more preferably about 64–70 amino acid residues in length and has about 21–35% acidic amino acid residues, preferably about 23–33% acidic amino acid residues, and more preferably about 25–31% acidic amino acid residues. Preferably, an acidic C-terminal region is involved in protein-protein interactions. For example, in one embodiment, a hDkk-3 protein has an acidic C-terminal region from about amino acids 285–350 of SEQ ID NO:2.

Preferred Dkk molecules of the present invention have an amino acid sequence sufficiently homologous to the amino acid sequence of SEQ ID NO:2, SEQ ID NO:5, SEQ ID NO:8, or SEQ ID NO:21. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains and/or a common functional activity. For example, amino acid or nucleotide sequences which share common structural domains have at least about 40% homology, preferably 50% homology, more preferably 60%–70% homology across the amino acid sequences of the domains and contain at least one, preferably two, more preferably three, and even more preferably four, five or six structural domains, are defined herein as sufficiently homologous. Furthermore, amino acid or nucleotide sequences which share at least 40%, preferably 50%, more preferably 60, 70, or 80% homology and share a common functional activity are defined herein as sufficiently homologous.

As used interchangeably herein, a "Dkk activity", "biological activity of Dkk" or "functional activity of Dkk", refers to an activity exerted by a Dkk protein, polypeptide or nucleic acid molecule (e.g., an activity on a Dkk responsive cell) as determined in vivo, or in vitro, according to standard techniques. In one embodiment, a Dkk activity is a direct activity, such as an association with a Dkk-target molecule. As used herein, a "target molecule" is a molecule with which a Dkk protein binds or interacts in nature, such that Dkk-mediated function is acheived. A Dkk target molecule can be a non-Dkk molecule or a Dkk protein or polypeptide of the present invention. In an exemplary embodiment, a Dkk target molecule is a membrane-bound protein (e.g., a cell-surface receptor or "Dkk receptor") or a modified form of such a protein which has been altered such that the protein is soluble (e.g., recombinantly produced such that the protein does not express a membrane-binding domain). In another embodiment, a Dkk target is a second soluble protein molecule (e.g., a "Dkk binding partner" or "Dkk substrate"). In such an exemplary embodiment, a Dkk binding partner can be a second soluble non-Dkk protein or a second Dkk protein molecule of the present invention. Alternatively, a Dkk activity is an indirect activity, such as a cellular signaling activity mediated by interaction of the Dkk protein with a second protein (e.g., a Dkk receptor). As used herein, the term "Dkk receptor" refers to a protein or protein complex, to which a Dkk protein, e.g., human Dkk, can bind. A receptor can be a cell surface receptor, e.g., a peptide, growth factor, or nuclear hormone receptor. Dkk receptors can be isolated by methods known in the art and further described herein. Interaction of a Dkk protein with a Dkk receptor can result in transduction of a signal from the cell surface to the nucleus. The signal transduced can be, an increase in intracellular calcium, an increase in phosphatidylinositol or other molecule, and can result in, e.g., in phosphorylation of specific proteins, a modulation of gene transcription and any of the other biological activities set forth herein.

In a preferred embodiment, a Dkk activity is at least one or more of the following activities: (i) interaction of a Dkk protein with and/or binding to a second molecule, (e.g., a protein, such as a Dkk receptor, a soluble form of a Dkk receptor, a receptor for a member of the wnt family of signaling proteins, or a non-Dkk signaling molecule, for example, a lipid included in a cell membrane); (ii) interaction of a Dkk protein with an intracellular protein via a membrane-bound Dkk receptor; (iii) complex formation between a soluble Dkk protein and a second soluble Dkk binding partner (e.g., a non-Dkk protein molecule or a second Dkk protein molecule); (iv) interaction with other extracellular proteins (e.g., regulation of wnt-dependent cellular adhesion to extracellular matrix components); (v) binding to and eliminating an undesirable molecule (e.g., a detoxifying activity or defense function); and/or (vi) an enzymatic activity. In yet another preferred embodiment, a Dkk activity is at least one or more of the following activities: (1) modulation of cellular signal transduction, either in vitro or in vivo (e.g., modulation, e.g., antagonism, of the activity of members of the wnt family of secreted proteins or supression of wnt-dependent signal transduction, for example suppression of Wnt 2b, Wnt3 and/or Wnt8-dependent signal transduction by hDkk-1 and/or hDkk-4); (2) regulation of communication between cells (e.g., regulation of wnt-dependent cell-cell interactions); (3) regulation of expression of genes whose expression is modulated by binding of Dkk (e.g., hDkk-3) to a receptor; (4) regulation of gene transcription in a cell involved in development or differentiation, either in vitro or in vivo (e.g., induction of cellular differentiation); (5) regulation of gene transcription in a cell involved in development or differentiation, wherein at least one gene encodes a differentiation-specific protein; (6) regulation of gene transcription in a cell involved in development or differentaition, wherein at least one gene encodes a second secreted protein; (7) regulation of gene transcription in a cell involved in development or differentiation, wherein at least one gene encodes a signal transduction molecule; (8) regulation of cellular proliferation, either in vitro or in vivo (e.g., induction of cellular proliferation or inhibition of proliferation as in the case of supression of tumorigenesis (e.g., suppression of glial cell tumor growth, for example, glioblastoma growth)); (9) formation and maintenance of ordered spatial arrangements of differentiated tissues in vertebrates, both adult and embryonic (e.g., induction of head formation during vertebrate development or maintenance of hematopoietic progenitor cells); (10) modulation of cell death, such as stimulation of cell survival; (11) regulating cell migration; and/or (12) immune modulation.

As referred to herein, "differentiation-specific proteins" include proteins involved in the transition of a cell from the undifferentiated to the differentiated phenotype. For example, such proteins can be differentiation specific structural proteins or differentiation-specific transcription factors. Such differentiation-specific proteins are generally expressed at higher levels in cells which are making the transition from the undifferentiated to the differentiated phenotype (e.g., during embryonic development or during regeneration of mature tissue in the adult animal), or are expresed at higher levels in fully-differentiated or terminally-differentiated cells as compared to their undifferentiated counterparts. Also, as referred to herein, "differentiation-specific genes" include nucleic acid molecules which encode differentiation-specific proteins.

Accordingly, another embodiment of the invention features isolated Dkk proteins and polypeptides having a Dkk activity. Preferred Dkk proteins have at least one cysteine-rich region and a Dkk activity. In another preferred embodiment, the Dkk protein has at least one cysteine-rich region, wherein the cysteine-rich region comprises at least one cysteine-rich domain, and a Dkk activity. In another preferred embodiment, the Dkk protein has at least one cysteine-rich region, wherein the cysteine-rich region comprises at least two cysteine-rich domains, and a Dkk activity. In yet another preferred embodiment, a Dkk protein further comprises a signal sequence. In still another preferred embodiment, a Dkk protein has a cysteine-rich region, a Dkk activity, and an amino acid sequence sufficiently homologous to an amino acid sequence of SEQ ID NO:2, SEQ ID NO:5, SEQ ID NO:8, or SEQ ID NO:21.

A preferred Dkk fragment comprises a carboxy-terminal cysteine-rich domain. In one embodiment, a Dkk fragment comprises a carboxy-terminal cysteine-rich domain and retains a biological activity of a Dkk protein. In yet another embodiment, a Dkk fragment lacks an amino-terminal cysteine-rich domain.

The human Dkk-3 cDNA, which is approximately 2479 nucleotides in length, encodes a protein which is approximately 350 amino acid residues in length. The human Dkk-3 protein contains an N-terminal signal sequence and a cysteine-rich region comprising two cysteine-rich domains. A Dkk cysteine-rich region can be found at least, for example, from about amino acids 147–284 of SEQ ID NO:2. The hDkk-3 cysteine-rich region comprises an amino-terminal cysteine-rich domain from about amino acids 147–195 of SEQ ID NO:2 and a carboxy-terminal cysteine-rich domain from about amino acids 201–284 of SEQ ID NO:2. The human Dkk-3 protein is a secreted protein which further contains a signal sequence at about amino acids 1–21, 1–22, 1–23, or 1–24 of SEQ ID NO:2. Accordingly, a mature human Dkk-3 protein begins at about amino acid residue 22, 23, 24, or 25 of SEQ ID NO:2 and is about 329, 328, 327, or 326 amino acids in length. The prediction of such a signal peptide can be made, for example, utilizing the computer algorithm SIGNALP (Nielsen, et al., (1997) *Protein Engineering* 10:1–6).

The human Dkk-4 cDNA, which is approximately 848 nucleotides in length, encodes a protein which is approximately 224 amino acid residues in length. The human Dkk-4 protein contains an N-terminal signal sequence and a cysteine-rich region comprising two cysteine-rich domains. A Dkk cysteine-rich region can be found at least, for example, from about amino acids 41–218 of SEQ ID NO:5. The hDkk-4 cysteine-rich region comprises an amino-terminal cysteine-rich domain from about amino acids 41–90 of SEQ ID NO:5 and a carboxy-terminal cysteine-rich domain from about amino acids 138–218 of SEQ ID NO:5. The human Dkk-4 protein is a secreted protein which further contains a signal sequence at about amino acids 1–17, 1–18, 1–19, or 1–20 of SEQ ID NO:5. Accordingly, a mature human Dkk-4 protein begins at about amino acid residue 18, 19, 20, or 21 of SEQ ID NO:5 and is about 207, 206, 205, or 204 amino acids in length. A preferred fragment of hDkk-4 comprises amino acid residues 134–224 of SEQ ID NO:5. In another embodiment, a preferred fragment of hDkk-4 consists of amino acid residues 134–224 of SEQ ID NO:5.

The human Dkk-1 cDNA, which is approximately 1536 nucleotides in length, encodes a protein which is approximately 266 amino acid residues in length. The human Dkk-1 protein contains an N-terminal signal sequence and a cysteine-rich region comprising two cysteine-rich domains. A Dkk cysteine-rich region can be found at least, for example, from about amino acids 85–263 of SEQ ID NO:8. The hDkk-1 cysteine-rich region comprises an amino-terminal cysteine-rich domain from about amino acids 85–138 of SEQ ID NO:8 and a carboxy-terminal cysteine-rich domain from about amino acids 182–263 of SEQ ID NO:8. The human Dkk-1 protein is a secreted protein which further contains a signal sequence at about amino acids 1–18, 1–19, 1–20, or 1–21 of SEQ ID NO:8. Accordingly, a mature human Dkk-1 protein begins at about amino acid residue 19, 20, 21, or 22 of SEQ ID NO:8 and is about 248, 247, 246, or 245 amino acids in length.

The human Dkk-2 cDNA, which is approximately 3687 nucleotides in length, encodes a protein which is approximately 259 amino acid residues in length. The human Dkk-2 protein contains a cysteine-rich region comprising two cysteine-rich domains. A Dkk cysteine-rich region can be found at least, for example, from about amino acids 78–256 of SEQ ID NO:21. The hDkk-2 cysteine-rich region comprises an amino-terminal cysteine-rich domain from about amino acids 78–127 of SEQ ID NO:21 and a carboxy-terminal cysteine-rich domain from about amino acids 176–256 of SEQ ID NO:21. The human Dkk-2 protein is a secreted protein which further contains a signal sequence at about amino acids 1–31, 1–32, 1–33, or 1–34 of SEQ ID NO:21. Accordingly, a mature human Dkk-2 protein begins at about amino acid residue 32, 33, 34, or 35 of SEQ ID NO:21 and is about 228, 227, 226, or 225 amino acids in length.

Dkk proteins of the present invention can be used to identify additional Dkk-related proteins or family members. For example, a protein having homology to hDkk-3 was identified using the nucleotide sequence encoding the N-terminal unique region of hDkk-3 to search a nucleotide sequence database. A human cDNA clone (Accession No.: AA397836) was identified from the dBEST database as having homology to hDkk-3 and was fully sequenced. The encoded protein is referred to herein as human "Soggy-1" or "Dkk-like-N". The nucleotide and predicted amino acid sequence of human Soggy-1 are depicted in FIG. 7. The nucleotide sequence of human Soggy-1 (SEQ ID NO:13) encodes a protein having 242 amino acids (SEQ ID NO:14). The nucleotide sequence of human Soggy-1 includes a 5' untranslated region containing nucleotides 1–74 of SEQ ID NO:13, a coding region containing nucleotides 75–800 of SEQ ID NO:13 (corresponding to nucleotides 1–726 of SEQ ID NO:15), and a 3' untranslated region containing nucleotides 801–928 of SEQ ID NO:13. The Soggy-1 protein (amino acid residues 32–132) has 25% identity to an N-terminal domain of human Dkk-3 (consisting of amino acid residues 22–140) as determined by ALIGN, Myers and Miller, (1989) *CABIOS*, utilizing a PAM120 weight residue table, a gap length penalty of 12, and a gap penalty of 4.

Two murine cDNA clones were further identified from the database and fully sequenced. Combining the sequence information from these two clones resulted in a full-length sequence for murine Soggy-1. The nucleotide sequence and predicted amino acid sequence of murine Soggy-1 are depicted in FIG. 8. The nucleotide sequence of murine Soggy-1 (SEQ ID NO:26) encodes a protein having 230 amino acids (SEQ ID NO:27). The nucleotide sequence of murine Soggy-1 includes a 5' untranslated region containing nucleotides 1–56 of SEQ ID NO:26, a coding region containing nucleotides 57–746 of SEQ ID NO:26 (corresponding to SEQ ID NO:26), and a 3' untranslated region containing nucleotides 747–835 of SEQ ID NO:26. Human and murine Soggy-1 proteins display 59% overall identity. An alignment of human and murine Soggy proteins to human and murine Dkk-3 proteins is depicted in FIG. 10.

In one embodiment, a Soggy protein is identified based on the presence of at least one soggy domain or "SGY" domain in the protein or corresponding nucleic acid molecule. As defined herein, a "SGY domain" includes a protein domain of a Soggy protein (e.g., hSoggy-1) having an amino acid sequence of about 45–56 amino acids and having at least about 25–40% identity with amino acid residues 90–140 of hDkk-3 (leu90-glu140 of SEQ ID NO:2). In another embodiment, a "SGY domain" has 46–55, preferably 47–54, more preferably about 48–53, and even more preferably about 49–52 or 50–51 amino acids, and has at least about 27–38%, preferably about 28–37%, more preferably about 29–36%, even more preferably about 30–35%, and even more preferably about 31–34%, or 32–33% identity with amino acid residues 90–140 of hDkk-3 (Leu90-Glu140 of SEQ ID NO:2). In yet another embodiment, a "SGY domain" has the following consensus sequence: L-P-X(3)-H-X-E-X(7)-G-N-X-T-X(3)-H-X(4)-K-X-T-X-N-X(2)-G-X(4)-S-E-X-V-X(2)-S-X(4)-E (SEQ ID NO:29). For example, human Soggy-I has a SGY domain from about amino acid residues 81–131 (Leu 81-Glu131 of SEQ ID NO:14) having 33% identity with amino acid residues 90–140 of hDkk-3 (leu90-glu140 of SEQ ID NO:2). Likewise, murine Soggy-1 has a SGY domain from about amino acid residues 71–120 (Leu 71-Glu120 of SEQ ID NO:27) having 33% identity with amino acid residues 90–140 of hDkk-3 (leu90-glu140 of SEQ ID NO:2). The SGY domains of human and murine Soggy-1 are depicted by shaded boxes in FIG. 10.

In another embodiment of the invention, a Soggy protein has at least one SGY domain and a signal sequence. For example, in one embodiment, a hSoggy-1 protein contains a signal sequence of about amino acids 1–29, 1–30, 1–31, or 1–32 of SEQ ID NO:14. Accordingly, a mature hSoggy-1 protein begins at about amino acid residue 30, 31, 32, or 33 of SEQ ID NO:14 and is about 213, 212, 211, or 210 amino acids in length. In another embodiment, a mSoggy-1 protein contains a signal sequence of about amino acids 1–19, 1–20, 1–21, or 1–22 of SEQ ID NO:27. Accordingly, a mature mSoggy-1 protein begins at about amino acid residue 211, 210, 209, or 208 of SEQ ID NO:28 and is about 213, 212, 211, or 210 amino acids in length.

Various aspects of the invention are described in further detail in the following subsections:

I. Isolated Nucleic Acid Molecules

One aspect of the invention pertains to isolated nucleic acid molecules that encode Dkk proteins or biologically active portions thereof, as well as nucleic acid fragments sufficient for use as hybridization probes to identify Dkk-encoding nucleic acids (e.g., Dkk mRNA) and fragments for use as PCR primers for the amplification or mutation of Dkk nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Dkk nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. An isolated chromosome is not an isolated nucleic acid molecule as defined herein. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:4, SEQ ID NO:7, SEQ ID NO:13, or SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, the nucleotide sequence of the DNA insert of the plasmid deposited with ATCC as Accession Number 201740, or a portion thereof, can be isolated using standard molecular biology techniques and the sequence information provided herein. Using all or portion of the nucleic acid sequence of SEQ ID NO:1, SEQ ID NO:4, SEQ ID NO:7, SEQ ID NO:13, or SEQ ID NO:20, or the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, as a hybridization probe, Dkk nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, SEQ ID NO:4, SEQ ID NO:7, SEQ ID NO:13, or SEQ ID NO:20, or the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, can be isolated by the polymerase chain reaction (PCR) using synthetic oligonucleotide primers designed based upon the sequence of SEQ ID NO:1, SEQ ID NO:4, SEQ ID NO:7, SEQ ID NO:13, or SEQ ID NO:20, or the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Dkk nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human Dkk-3 cDNA. This cDNA comprises sequences encoding the human Dkk-3 protein (i.e., "the coding region", from nucleotides 38-1087), as well as 5' untranslated sequences (nucleotides 1 to 37) and 3' untranslated sequences (nucleotides 1088 to 2479). Alternatively, the nucleic acid molecule can comprise only the coding region of SEQ ID NO:1 (e.g., nucleotides 38 to 1087, corresponding to SEQ ID NO:3). A plasmid containing the full-length nucleotide sequence encoding hDkk-3 was deposited with the American Type Culture Collection (ATCC), presently at 10801 University Boulevard, Manassas, Va. 20110-2209, on Jun. 11, 1997 and assigned Accession Number 98452.

In another preferred embodiment, an isolated nucleic acid molecule of the invention comprises the nucleotide sequence shown in SEQ ID NO:4. The sequence of SEQ ID NO:4 corresponds to the human Dkk-4 cDNA. This cDNA comprises sequences encoding the human Dkk-4 protein (i.e., "the coding region", from nucleotides 125–796), as well as 5' untranslated sequences (nucleotides 1 to 124) and 3' untranslated sequences (nucleotides 797 to 848). Alternatively, the nucleic acid molecule can comprise only the coding region of SEQ ID NO:4 (e.g., nucleotides 125 to 796, corresponding to SEQ ID NO:6).

In another preferred embodiment, an isolated nucleic acid molecule of the invention comprises the nucleotide sequence shown in SEQ ID NO:7. The sequence of SEQ ID NO:7 corresponds to the human Dkk-1 cDNA. This cDNA comprises sequences encoding the human Dkk-1 protein (i.e., "the coding region", from nucleotides 109–906), as well as 5' untranslated sequences (nucleotides 1 to 108) and 3' untranslated sequences (nucleotides 907–1536). Alternatively, the nucleic acid molecule can comprise only the coding region of SEQ ID NO:7 (e.g., nucleotides 109–906, corresponding to SEQ ID NO:9). A plasmid containing the full-length nucleotide sequence encoding hDkk-1 was deposited with the American Type Culture Collection (ATCC), presently at 10801 University Boulevard. Manassas, Va. 20110-9209, on Jan. 16, 1998 and assigned Accession Number 98633.

In another preferred embodiment, an isolated nucleic acid molecule of the invention comprises the nucleotide sequence shown in SEQ ID NO:20. The sequence of SEQ ID NO:20 corresponds to the human Dkk-2 cDNA. This cDNA comprises sequences encoding the human Dkk-2 protein (i.e., "the coding region", from nucleotides 724–1500), 5' untranslated sequences (nucleotides 1–723), as well as 3' untranslated sequences (nucleotides 1501–3687). Alternatively, the nucleic acid molecule can comprise only the coding region of SEQ ID NO:20 (e.g., nucleotides 724 to 1500, corresponding to SEQ ID NO:22). A plasmid, clone fthul33, containing the full-length nucleotide sequence encoding hDkk-2 was deposited with the American Type Culture Collection (ATCC), presently at 10801 University Boulevard. Manassas, Va. 20110-2209, on Mar. 2, 1999 and assigned Accession Number 201740.

In another preferred embodiment, an isolated nucleic acid molecule of the invention comprises the nucleotide sequence shown in SEQ ID NO:13. The sequence of SEQ ID NO:13 corresponds to the human Soggy cDNA. This cDNA comprises sequences encoding the human Soggy protein (i.e., "the coding region", from nucleotides 75 to 800), as well as 5' untranslated sequences (nucleotides 1 to 74) and 3' untranslated sequences (nucleotides 801 to 928). Alternatively, the nucleic acid molecule can comprise only the coding region of SEQ ID NO:13 (e.g., nucleotides 75 to 800, corresponding to SEQ ID NO:15).

In another preferred embodiment, an isolated nucleic acid molecule of the invention comprises a nucleic acid molecule which is a complement of the nucleotide sequence shown in SEQ ID NO:1, SEQ ID NO:4, SEQ ID NO:7, SEQ ID NO:13, or SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, or a portion of any of these nucleotide sequences. A nucleic acid molecule which is complementary to the nucleotide sequence shown in SEQ ID NO:1, SEQ ID NO:4, SEQ ID NO:7, SEQ ID NO:13, or SEQ ID NO:20, or the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, is one which is sufficiently complementary to the nucleotide sequence shown in SEQ ID NO:1, SEQ ID NO:4, SEQ ID NO:7, SEQ ID NO:13, or SEQ ID NO:20, or the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, such that it can hybridize to the nucleotide sequence shown in SEQ ID NO:1, SEQ ID NO:4, SEQ ID NO:7, SEQ ID NO:13, or SEQ ID NO:20, or the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, thereby forming a stable duplex.

In still another preferred embodiment, an isolated nucleic acid molecule of the present invention comprises a nucleotide sequence which is at least about 30–35%, preferably about 40–45%, more preferably about 50–55%, even more preferably about 60–65%, and even more preferably at least about 70–75%, 80–85%, 90–95% or more homologous to the nucleotide sequences shown in SEQ ID NO:1, SEQ ID NO:3, SEQ ID NO:4, SEQ ID NO:6, SEQ ID NO:7, SEQ ID NO:9, SEQ ID NO:13, SEQ ID NO:15, SEQ ID NO:20, or SEQ ID NO:22, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, or a portion of any of these nucleotide sequences.

In one aspect, the present invention features isolated nucleic acid molecules which are linear (e.g., linear fragments of double-stranded DNA, linear strands of single-stranded DNA, single-stranded RNA molecules, and oligonucleotides). Another aspect of the present invention features circular nucleic acid molecules (e.g., double-standed DNA molecules, for example, plasmid molecules including the nucleotide sequences shown in SEQ ID NO:1, SEQ ID NO:3, SEQ ID NO:4, SEQ ID NO:6, SEQ ID NO:7, SEQ ID NO:9, SEQ ID NO:13, SEQ ID NO:15, SEQ ID NO:20, or SEQ ID NO:22, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, or a portion of any of these nucleotide sequences).

In one embodiment, the isolated nucleic acid molecules of the present invention are DNA molecules which are in a form suitable for expression (e.g., suitable for expression of corresponding messenger RNA or mRNA). In another embodiment, the isolated nucleic acid molecules are DNA molecules which are in a form suitable for expression of corresponding protein (e.g., in a form, for example, in a vector, which is capable of expressing protein, e.g., in the appropriate orientation for expression from regulatory elements and/or in-frame with appropriate regulatory elements). In another embodiment, the isolated nucleic acids are in a form suitable for determination of nucleic acid sequence (e.g., in a form suitable for sequencing, for example, is a sequencing vector including a M13, T7, T3 and SP6 promoter. Examples of sequencing vectors include, but are not limited to pBluescript (Stratagene™), pT7T3D (Pharmcia™) and pCR2.1 (InVitrogen). In yet another embodiment, the isolated nucelic acid molecules are free from vector sequences. In a preferred embodiment, an isolated nucleic acid molecule is free from sequencing vector sequences.

Moreover, the nucleic acid molecule of the invention can comprise only a portion of the nucleic acid sequence of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, for example a fragment which can be used as a probe or primer or a fragment encoding a biologically active portion of a Dkk protein or Dkk-related protein. The nucleotide sequence determined from the cloning of the human Dkk genes allows for the generation of probes and primers designed for use in identifying and/or cloning Dkk homologues in other cell types, e.g., from other tissues, as well as Dkk homologues from other mammals and Dkk-related proteins. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense sequence of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, of an anti-sense sequence of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, or of a naturally occurring mutant of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740. In an exemplary embodiment, a nucleic acid molecule of the present invention comprises a nucleotide sequence which hybridizes under stringent hybridization conditions to a nucleic acid molecule consisting of nucleotides 470–2479 of SEQ ID NO:1 or to a nucleic acid molecule consisting of nucleotides 1–475 of SEQ ID NO:4.

Probes based on human nucleotide sequences (e.g. the human Dkk nucleotide sequence) can be used to detect transcripts or genomic sequences encoding the same or homologous proteins. For instance, primers based on the nucleic acid represented in SEQ ID NOs:1 or 3 can be used in PCR reactions to clone Dkk homologs (e.g., hDkk-3 homologues). In a preferred embodiment of the invention, Dkk homologs are cloned by PCR amplification (e.g., RT-PCR) using primers hybridizing to a portion of the nucleotide sequence encoding the Dkk cysteine rich domain. Likewise, probes based on the subject Dkk sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a Dkk protein, such as by measuring a level of a Dkk-encoding nucleic acid in a sample of cells from a subject e.g., detecting Dkk mRNA levels or determining whether a genomic Dkk gene has been mutated or deleted.

A nucleic acid fragment encoding a "biologically active portion of a Dkk or Dkk-related protein" can be prepared by isolating a portion of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, which encodes a polypeptide having a biological activity (the biological activities of the Dkk and Dkk-related proteins have previously been described), expressing the encoded portion of the protein (e.g., by recombinant expression in vitro) and assessing the activity of the encoded portion of the protein.

The invention further encompasses nucleic acid molecules that differ from the nucleotide sequence shown in SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, due to degeneracy of the genetic code and thus encode the same proteins as those encoded by the nucleotide sequence shown in SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740. In another embodiment, an isolated nucleic acid molecule of the invention has a nucleotide sequence encoding a protein having an amino acid sequence shown in SEQ ID NO:2, SEQ ID NO: 5, SEQ ID NO:8, SEQ ID NO:14, or SEQ ID NO:21.

In addition to the human nucleotide sequences shown in SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, it will be appreciated by those skilled in the art that DNA sequence polymorphisms that lead to changes in the amino acid sequences of the Dkk or Dkk-related proteins may exist within a population (e.g., the human population). Such genetic polymorphism in the Dkk or Dkk-related genes may exist among individuals within a population due to natural allelic variation. As used herein, the terms "gene" and "recombinant gene" refer to nucleic acid molecules comprising an open reading frame encoding a protein, preferably a mammalian Dkk or Dkk-related protein. Such natural allelic variations can typically result in 1–5% variance in the nucleotide sequence of a Dkk or Dkk-related gene. Any and all such nucleotide variations and resulting amino acid polymorphisms in genes that are the result of natural allelic variation and that do not alter the functional activity of a Dkk or Dkk-related protein are intended to be within the scope of the invention.

Moreover, nucleic acid molecules encoding Dkk or Dkk-related proteins from other species, and thus which have a nucleotide sequence which differs from the human sequence of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, are intended to be within the scope of the invention. For example, a murine Dkk-3 cDNA has been identified based of the nucleotide sequence of human Dkk-3. The nucleotide sequence of murine Dkk-3 (SEQ ID NO:16) encodes a hDkk-3 protein having 349 amino acids. The nucleotide and amino acid sequences of murine Dkk-3 are depicted in FIG. 5. The coding region of murine Dkk-3 is represented by SEQ ID NO:18. A plasmid containing the full-length nucleotide sequence encoding mDkk-3 was deposited with the American Type Culture Collection (ATCC), presently at 10801 University Boulevard, Manassas, Va. 20110-2209, on Jan. 16, 1998 and assigned Accession Number 98634. Likewise, a murine Dkk-related protein (Soggy-1) has been identified based of the nucleotide sequence of human Dkk-3. The nucleotide sequence of murine Soggy-1 (SEQ ID NO:26) encodes a protein having 230 amino acids (SEQ ID NO:27). The nucleotide and amino acid sequences of murine Soggy-1 are depicted in FIG. 8. The coding region of murine Soggy-1 is represented by SEQ ID NO:28.

Nucleic acid molecules corresponding to natural allelic variants and homologues of the Dkk or Dkk-related cDNAs of the invention can be isolated based on their homology to the human nucleic acids disclosed herein using the human cDNA, or a portion thereof, as a hybridization probe according to standard hybridization techniques under stringent hybridization conditions. Examples of tissues and/or libraries suitable for isolation of the subject nucleic acids include brain, spinal chord and heart tissue. cDNA encoding a Dkk protein (e.g., a hDkk-3 protein) can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a hDkk-3 protein can also be cloned using established polymerase chain reaction techniques in accordance with the nucleotide sequence information provided by the invention. The nucleic acid of the invention can be DNA or RNA or analogs thereof.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740. In another embodiment, the nucleic acid is at least 30, 50, 100, 250, 300, 400 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the Dkk or Dkk-related sequences that may exist in the population, the skilled artisan will further appreciate that changes can be introduced by mutation into the nucleotide sequences of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, thereby leading to changes in the amino acid sequence of the encoded Dkk proteins, without altering the functional ability of the Dkk proteins. For example, nucleotide substitutions leading to amino acid substitutions (particularly conservative amino acid substitutions) at "non-essential" amino acid residues can be made in the sequence of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740. A "non-essential" amino acid residue is a residue that can be altered from the wild-type sequence of Dkk (or wild-type Dkk-related sequence) (e.g., the sequence of SEQ ID NO:2, SEQ ID NO:5, SEQ ID NO:8, SEQ ID NO:14, or SEQ ID NO:21) without altering the biological activity, whereas an "essential" amino acid residue is required for biological activity. For example, amino acid residues that are conserved among the Dkk or Dkk-related proteins of the present invention (e.g., cysteine residues within cysteine-rich domains), are predicted to be particularly unamenable to alteration. Furthermore, amino acid residues that are conserved between Dkk protein and other proteins having cysteine-rich domains are not likely to be amenable to alteration.

Accordingly, another aspect of the invention pertains to nucleic acid molecules encoding Dkk or Dkk-related proteins that contain changes in amino acid residues that are not essential for activity. Such proteins differ in amino acid sequence from SEQ ID NO:2, SEQ ID NO:5, SEQ ID NO:8, SEQ ID NO:14, or SEQ ID NO:21 yet retain biological activity. In one embodiment, the isolated nucleic acid molecule comprises a nucleotide sequence encoding a protein, wherein the protein comprises an amino acid sequence at least about 60% homologous to the amino acid sequence of SEQ ID NO:2, SEQ ID NO:5, SEQ ID NO:8, SEQ ID NO:14, or SEQ ID NO:21. Preferably, the protein encoded by the nucleic acid molecule is at least about 65–70% homologous to SEQ ID NO:2, SEQ ID NO:5, SEQ ID NO:8, SEQ ID NO:14, or SEQ ID NO:21, more preferably at least about 75–80% homologous to SEQ ID NO:2, SEQ ID NO:5, SEQ ID NO:8, SEQ ID NO:14, or SEQ ID NO:21, even more preferably at least about 85–90% homologous to SEQ ID NO:2, SEQ ID NO:5, SEQ ID NO:8, SEQ ID NO:14, or SEQ ID NO:21, and most preferably at least about 95% homologous to SEQ ID NO:2, SEQ ID NO:5, SEQ ID NO:8, SEQ ID NO:14, or SEQ ID NO:21.

An isolated nucleic acid molecule encoding a Dkk protein homologous to the protein of SEQ ID NO:2, SEQ ID NO:5, SEQ ID NO:8, SEQ ID NO:14, or SEQ ID NO:21 can be created by introducing one or more nucleotide substitutions, additions or deletions into the nucleotide sequence of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, such that one or more amino acid substitutions, additions or deletions are introduced into the encoded protein. Mutations can be introduced into SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, by standard techniques, such as site-directed mutagenesis and PCR-mediated mutagenesis.

Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, for example, a predicted nonessential amino acid residue in a Dkk protein (e.g., one not located in a cysteine-rich domain) is preferably replaced with another amino acid residue from the same side chain family. Alternatively, in another embodiment, mutations can be introduced randomly along all or part of a Dkk or Dkk-related coding sequence, such as by saturation mutagenesis, and the resultant mutants can be screened for biological activity to identify mutants that retain activity. Following mutagenesis of SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633, or the nucleotide sequence of the DNA insert of the plasmid deposited with ATCC as Accession Number 201740, the encoded protein can be expressed recombinantly and the activity of the protein can be determined.

In a preferred embodiment, a mutant Dkk or Dkk-related protein can be assayed for intracellular calcium, an increase in phosphatidylinositol or other molecule, and can result, e.g., in phosphorylation of specific proteins, a modulation of gene transcription and any of the other biological activities set forth herein.

In a preferred embodiment, a mutant Dkk or Dkk-related protein can also be assayed for the ability to (1) modulate cellular signal transduction, either in vitro or in vivo; (2) regulate communication between cells; (3) regulate expression of genes whose expression is modulated by binding of Dkk (e.g., hDkk-3) to a receptor; (4) regulate gene transcription in a cell involved in development or differentiation, either in vitro or in vivo; (5) regulate cellular proliferation, either in vitro or in vivo; (6) form and/or maintain ordered spatial arrangements of differentiated tissues in vertebrates; (7) modulate cell death (e.g. cell survival); (8) regulate cell migration; and/or (9) modulate immune system function.

In addition to the nucleic acid molecules encoding Dkk or Dkk-related proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Dkk coding strand, or to only a portion thereof. In one embodiment, an antisense nucleic acid molecule is antisense to a "coding region" of the coding strand of a nucleotide sequence encoding Dkk. The term "coding region" refers to the region of the nucleotide sequence comprising codons which are translated into amino acid residues (e.g., the coding region of human Dkk-3 corresponds to SEQ ID NO:3, the coding region of human Dkk-4 corresponds to SEQ ID NO:6, the coding region of human Dkk-1 corresponds to SEQ ID NO:9, the coding region of human Dkk-2 corresponds to SEQ ID NO:22, and the coding region of human Soggy corresponds to SEQ ID NO:15). In another embodiment, the antisense nucleic acid molecule is antisense to a "noncoding region" of the coding strand of a nucleotide sequence encoding a Dkk or Dkk-related protein. The term "noncoding region" refers to 5' and 3' sequences which flank the coding region that are not translated into amino acids (i.e., also referred to as 5' and 3' untranslated regions).

Given the coding strand sequences disclosed herein (e.g., SEQ ID NO:3, SEQ ID NO:6, SEQ ID NO:9, SEQ ID NO:15, or SEQ ID NO:22), antisense nucleic acids of the invention can be designed according to the rules of Watson and Crick base pairing. The antisense nucleic acid molecule can be complementary to the entire coding region of a Dkk or Dkk-related mRNA, but more preferably is an oligonucleotide which is antisense to only a portion of the coding or noncoding region of the mRNA. For example, the antisense oligonucleotide can be complementary to the region surrounding the translation start site of Dkk mRNA. An antisense oligonucleotide can be, for example, about 5, 10, 15, 20, 25, 30, 35, 40, 45, 50, 55, 60, 65, 70, 75, 80, 85, or 90 nucleotides in length. In a preferred embodiment, an oligonucleotide is about 30–90, preferably about 40–80, more preferably about 50–70 nucleotides in length and is antisense to a portion of SEQ ID NO:1 from about nucleotides 1–150. In another embodiment, an oligonucleotide is antisense to a portion of SEQ ID NO:4 from about nucleotides 25–225. In another embodiment, an oligonucleotide is antisense to a portion of SEQ ID NO:7 from about nucleotides 1–200. In another embodiment, an oligonucleotide is antisense to a portion of SEQ ID NO:20 from about nucleotides 625–825. In yet another embodiment, an oligonucleotide is antisense to a portion of SEQ ID NO:13 from about nucleotides 1–175.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives, acridine substituted nucleotides, can be used. Alternatively, the antisense nucleic acid molecule can by synthesized to increase transport across cellular membranes, e.g., methylphosphonate derivatives. The antisense molecules can include a 3'-terminal cap (e.g., a 3'-aminopropyl modification), a biotin moiety, or even a 3'-3' terminal linkage.

Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i. e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a Dkk or Dkk-related protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., (1987) *Nucleic Acids. Res.* 15:6625–6641). The antisense nucleic acid molecule can also comprise a 2'-o-methylribonucleotide (Inoue et al., (1987) *Nucleic Acids Res.* 15:6131–6148) or a chimeric RNA-DNA analogue (Inoue et al., (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave Dkk or Dkk-related mRNA transcripts to thereby inhibit translation of Dkk or Dkk-related mRNA. A ribozyme having specificity for a Dkk- or Dkk-related-encoding nucleic acid can be designed based upon the nucleotide sequence of a Dkk or Dkk-related cDNA disclosed herein (i.e., SEQ ID NO:1, SEQ ID NO:4, SEQ ID NO:7, SEQ ID NO:13, SEQ ID NO:20, the nucleotide sequence of the DNA insert of the plasmid deposited with ATCC as Accession Number 98452, the nucleotide sequence of the DNA insert of the plasmid deposited with ATCC as Accession Number 98633). For example, a derivative of a Tetrahymena L-19 IVS RNA can be constructed in which the nucleotide sequence of the active site is complementary to the nucleotide sequence to be cleaved in a Dkk-encoding mRNA. See, e.g., Cech et al., U.S. Pat. No. 4,987,071; and Cech et al., U.S. Pat. No. 5,116,742. Alternatively, Dkk (or Dkk-related) mRNA can be used to select a catalytic RNA having a specific ribonuclease activity from a pool of RNA molecules. See, e.g., Bartel, D. and Szostak, J. W. (1993) *Science* 261:1411–1418.

Alternatively, gene expression can be inhibited by targeting nucleotide sequences complementary to the regulatory region of the Dkk or Dkk-related gene (e.g., the promoter and/or enhancers) to form triple helical structures that prevent transcription of the gene in target cells. See generally, Helene, C. (1991) *Anticancer Drug Des.* 6(6):569–84; Helene, C. et al., (1992) *Ann. N. Y Acad. Sci.* 660:27–36; and Maher, L. J. (1992) *Bioassays* 14(12):807–15.

In yet another embodiment, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. PNAS 93: 14670–675.

PNAs of Dkk or Dkk-related nucleic acid molecules can be used therapeutic and diagnostic applications. For example, PNAs can be used as antisense or antigene agents for sequence-specific modulation of gene expression by, for example, inducing transcription or translation arrest or inhibiting replication. PNAs of Dkk or Dkk-related nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of Dkk can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of Dkk nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric moleclues can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810, published Dec. 15, 1988) or the blood-brain barrier (see, e.g., PCT Publication No. WO89/10134, published Apr. 25, 1988). In addition, oligonucleotides can be modified with hybridization-triggered cleavage agents (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated Dkk Proteins and Anti-Dkk Antibodies

One aspect of the invention pertains to isolated Dkk proteins, Dkk-related proteins and biologically active portions thereof, as well as polypeptide fragments suitable for use as immunogens to raise antibodies. In one embodiment, native Dkk or Dkk-related proteins can be isolated from cells or tissue sources by an appropriate purification scheme using standard protein purification techniques. In another embodiment, proteins are produced by recombinant DNA techniques. Alternative to recombinant expression, a Dkk or Dkk-related protein or polypeptide can be synthesized chemically using standard peptide synthesis techniques.

An "isolated" or "purified" protein or biologically active portion thereof is substantially free of cellular material or other contaminating proteins from the cell or tissue source from which the Dkk or Dkk-related protein is derived, or substantially free from chemical precursors or other chemicals when chemically synthesized. The language "substantially free of cellular material" includes preparations of protein in which the protein is separated from cellular components of the cells from which it is isolated or recombinantly produced. In one embodiment, the language "substantially free of cellular material" includes preparations of Dkk or Dkk-related protein having less than about 30% (by dry weight) of non-Dkk protein or non-Dkk-related protein (also referred to herein as a "contaminating protein"), more preferably less than about 20% of non-Dkk protein or non-Dkk-related protein, still more preferably less than about 10% of non-Dkk protein or non-Dkk-related protein, and most preferably less than about 5% non-Dkk protein or non-Dkk-related protein. When the Dkk or Dkk-related protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Dkk or Dkk-related protein in which the protein is separated from chemical precursors or other chemicals which are involved in the synthesis of the protein. In one embodiment, the language "substantially free of chemical precursors or other chemicals" includes preparations of Dkk protein having less than about 30% (by dry weight) of chemical precursors, non-Dkk chemicals, or non-Dkk-related chemicals, more preferably less than about 20% chemical precursors, non-Dkk chemicals, or non-Dkk-related chemicals, still more preferably less than about 10% chemical precursors, non-Dkk chemicals, or non-Dkk-related chemicals, and most preferably less than about 5% chemical precursors, non-Dkk chemicals, or non-Dkk-related chemicals.

Biologically active portions of a Dkk or Dkk-related protein include peptides comprising amino acid sequences sufficiently homologous to or derived from the amino acid sequence of the Dkk or Dkk-related protein, e.g., the amino acid sequence shown in SEQ ID NO:2, SEQ ID NO:5, SEQ ID NO:8, SEQ ID NO:14, or SEQ ID NO:21, which include less amino acids than the full length proteins, and exhibit at least one activity of a Dkk or Dkk-related protein. Typically, biologically active portions comprise a domain or motif with at least one activity of the Dkk or Dkk-related protein. A biologically active portion of a protein can be a polypeptide which is, for example, 10, 25, 50, 100 or more amino acids in length.

In one embodiment, a biologically active portion of a Dkk protein comprises at least a cysteine-rich region. In another embodiment, a biologically active portion of a Dkk protein comprises at least a cysteine-rich region, wherein the cysteine-rich region includes at least one cysteine-rich domain. In yet another embodiment, a biologically active portion of a Dkk protein comprises at least a signal sequence.

In another embodiment, a biologically active portion of a Dkk-related protein (e.g., a Soggy protein) comprises at least a Soggy domain. In yet another embodiment, a biologically active portion of a Dkk-related protein comprises at least a signal sequence.

In an alternative embodiment, a biologically active portion of a Dkk or Dkk-related protein comprises an amino acid sequence lacking a signal sequence.

It is to be understood that a preferred biologically active portion of a Dkk or Dkk-related protein of the present invention may contain at least one of the above-identified structural domains. A more preferred biologically active portion of a Dkk or Dkk-related protein may contain at least two of the above-identified structural domains. An even more preferred biologically active portion of a protein may contain at least three of the above-identified structural domains. A particularly preferred biologically active portion of a protein of the present invention may contain at least four of the above-identified structural domains.

Moreover, other biologically active portions, in which other regions of the protein are deleted, can be prepared by recombinant techniques and evaluated for one or more of the functional activities of a native Dkk or Dkk-related protein.

In a preferred embodiment, the Dkk protein has an amino acid sequence shown in SEQ ID NO:2 or an amino acid sequence at least about 55% homologous to SEQ ID NO:2. In another preferred embodiment, the Dkk protein has an amino acid sequence shown in SEQ ID NO:5 or an amino acid sequence at least about 35% homologous to SEQ ID NO:5. In another preferred embodiment, the Dkk protein has an amino acid sequence shown in SEQ ID NO:8 or an amino acid sequence at least about 85% homologous to SEQ ID NO:8. In another preferred embodiment, the Dkk protein has an amino acid sequence shown in SEQ ID NO:21 or an amino acid sequence at least about 35% homologous to SEQ ID NO:21. In another preferred embodiment, the protein has an amino acid sequence shown in SEQ ID NO:14 or an amino acid sequence at least about 60% homologous to SEQ ID NO:14. In still another preferred embodiment, a protein of the present invention comprises an amino acid sequence which is at least about 30–35%, preferably about 40–45%, more preferably about 50–55%, even more preferably about 60–65%, and even more preferably at least about 70–75%, 80–85%, 90–95% or more homologous to the amino acid sequences shown in SEQ ID NO:2, SEQ ID NO:5, SEQ ID NO:8, SEQ ID NO:14, or SEQ ID NO:21.

In other embodiments, the protein is substantially homologous to SEQ ID NO:2, SEQ ID NO:5, SEQ ID NO:8, SEQ ID NO:14, or SEQ ID NO:21, and, preferably, retains the functional activity of the protein of SEQ ID NO:2, SEQ ID NO:5, SEQ ID NO:8, SEQ ID NO:14, or SEQ ID NO:21, yet differs in amino acid sequence due to natural allelic variation or mutagenesis, as described in detail in subsection I above. Accordingly, in another embodiment, the protein is a protein which comprises an amino acid sequence at least about 60% homologous to the amino acid sequence of SEQ ID NO:2, SEQ ID NO:5, SEQ ID NO:8, SEQ ID NO:14, or SEQ ID NO:21 and, preferably, retains the functional activity of the proteins of SEQ ID NO:2, SEQ ID NO:5, SEQ ID NO:8, SEQ ID NO:14, or SEQ ID NO:11, respectively. Preferably, the protein is at least about 70% homologous to SEQ ID NO:2, SEQ ID NO:5, SEQ ID NO:8, SEQ ID NO:14, or SEQ ID NO:21, more preferably at least about 80% homologous to SEQ ID NO:2, SEQ ID NO:5, SEQ ID NO:8, SEQ ID NO:14, or SEQ ID NO:21, even more preferably at least about 90% homologous to SEQ ID NO:2, SEQ ID NO:5, SEQ ID NO:8, SEQ ID NO:14, or SEQ ID NO:21, and most preferably at least about 95% or more homologous to SEQ ID NO:2, SEQ ID NO:5, SEQ ID NO:8, SEQ ID NO:14, or SEQ ID NO:21.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In one embodiment, an alignment is a global alignment, e.g., an overall sequence alignment. In another embodiment, an alignment is a local alignment. In a preferred embodiment, the length of a sequence aligned for comparison purposes is at least 30%, preferably at least 40%, more preferably at least 50%, even more preferably at least 60%, and even more preferably at least 70%, 80%, or 90% of the length of the reference sequence to which it is aligned (e.g., when aligning a second sequence to the Dkk amino acid sequence of SEQ ID NO:2, at least 105, preferably at least 145, more preferably at least 175, even more preferably at least 210, and even more preferably at least 245, 280 or 315 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, 5, or 4 and a length weight of 1, 2, 3, 4, 5, or 6. In yet another embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J Mol. Biol.* 215:403–10. BLAST nucleotide searches can be performed with the NBLAST program, score=100, wordlength=12 to obtain nucleotide sequences homologous to Dkk nucleic acid molecules of the invention. BLAST protein searches can be performed with the XBLAST program, score=50, wordlength=3 to obtain amino acid sequences homologous to Dkk protein molecules of the invention. To obtain gapped alignments for comparison purposes, Gapped BLAST can be utilized as described in Altschul et al., (1997) *Nucleic Acids Res.*

25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides Dkk or Dkk-related chimeric or fusion proteins. As used herein, a "chimeric protein" or "fusion protein" comprises a Dkk or Dkk-related polypeptide operatively linked to a non-Dkk polypeptide or non-Dkk-related polypeptide. A "Dkk polypeptide" or "Dkk-related polypeptide" refers to a polypeptide having an amino acid sequence corresponding to Dkk or a Dkk-related protein, whereas a "non-Dkk polypeptide" or "non-Dkk-related polypeptide" refers to a polypeptide having an amino acid sequence corresponding to a protein which is not substantially homologous to the Dkk or Dkk-related protein, e.g., a protein which is different from the Dkk or Dkk-related protein and which is derived from the same or a different organism. Within a Dkk or Dkk-related fusion protein the Dkk or Dkk-related polypeptide can correspond to all or a portion of a Dkk or Dkk-related protein. In a preferred embodiment, a Dkk or Dkk-related fusion protein comprises at least one biologically active portion of a Dkk protein. In another preferred embodiment, a Dkk or Dkk-related fusion protein comprises at least two biologically active portions of a Dkk or Dkk-related protein. In another preferred embodiment, a Dkk or Dkk-related fusion protein comprises at least three biologically active portions of a Dkk or Dkk-related protein. Within the fusion protein, the term "operatively linked" is intended to indicate that the Dkk or Dkk-related polypeptide and the non-Dkk or non-Dkk-related polypeptide are fused in-frame to each other. The non-Dkk or non-Dkk-related polypeptide can be fused to the N-terminus or C-terminus of the Dkk or Dkk-related polypeptide.

For example, in one embodiment, the fusion protein is a GST-Dkk fusion protein in which the Dkk sequences are fused to the C-terminus of the GST sequences. Such fusion proteins can facilitate the purification of recombinant Dkk.

In another embodiment, the fusion protein is a Dkk or Dkk-related protein containing a heterologous signal sequence at its N-terminus. For example, the native Dkk signal sequence (i.e., about amino acids 1 to 23 of SEQ ID NO:2) can be removed and replaced with a signal sequence from another protein. In certain host cells (e.g., mammalian host cells), expression and/or secretion of Dkk or Dkk-related proteins can be increased through use of a heterologous signal sequence.

In yet another embodiment, the fusion protein is a Dkk-immunoglobulin fusion protein in which the Dkk sequences comprising primarily the Dkk cysteine-rich regions are fused to sequences derived from a member of the immunoglobulin protein family. Soluble derivatives have also been made of cell surface glycoproteins in the immunoglobulin gene superfamily consisting of an extracellular domain of the cell surface glycoprotein fused to an immunoglobulin constant (Fc) region (see e.g., Capon, et al. (1989) *Nature* 337:525–531 and Capon U.S. Pat. Nos. 5,116,964 and 5,428,130 [CD4-IgG1 constructs]; Linsley, P. S. et al. (1991) *J. Exp. Med.* 173:721–730 [a CD28-IgG1 construct and a B7-1-IgG1 construct]; and Linsley, P. S. et al. (1991) *J Exp. Med.* 174:561–569 and U.S. Pat. No. 5,434,131[a CTLA4-IgG1]). Such fusion proteins have proven useful for modulating receptor-ligand interactions. Soluble derivatives of cell surface proteins of the tumor necrosis factor receptor (TNFR) superfamily proteins have been made consisting of an extracellular domain of the cell surface receptor fused to an immunoglobulin constant (Fc) region (See for example Moreland et al. (1997) *N. Engl. J. Med.* 337(3):141–147; van der Poll et al. (1997) *Blood* 89(10):3727–3734; and Ammann et al. (1997) *J. Clin. Invest.* 99(7):1699–1703.)

The Dkk-immunoglobulin fusion proteins of the invention can be incorporated into pharmaceutical compositions and administered to a subject to inhibit an interaction between a Dkk ligand and a Dkk receptor on the surface of a cell, to thereby suppress Dkk-mediated signal transduction in vivo. The Dkk-immunoglobulin fusion proteins can be used to affect the bioavailability of a Dkk cognate receptor. Inhibition of the Dkk ligand/Dkk interaction may be useful therapeutically for both the treatment of differentiative or proliferative disorders, as well as modulating (e.g., promoting or inhibiting) developmental responses, cell adhesion, and/or cell fate. Moreover, the Dkk-immunoglobulin fusion proteins of the invention can be used as immunogens to produce anti-Dkk antibodies in a subject, to purify Dkk ligands and in screening assays to identify molecules which inhibit the interaction of Dkk with a Dkk ligand.

Preferably, a Dkk or Dkk-related chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al., John Wiley & Sons: 1992). Moreover, many expression vectors are commercially available that already encode a fusion moiety (e.g., a GST polypeptide). A Dkk-encoding nucleic acid or nucleic acid encoding a Dkk-related protein can be cloned into such an expression vector such that the fusion moiety is linked in-frame to the protein.

The present invention also pertains to variants of the Dkk or Dkk-related proteins which function as either agonists (mimetics) or as antagonists. Variants of the Dkk or Dkk-related proteins can be generated by mutagenesis, e.g., discrete point mutation or truncation of a Dkk or Dkk-related protein. An agonist of the Dkk or Dkk-related proteins can retain substantially the same, or a subset, of the biological activities of the naturally occurring form of a Dkk or Dkk-related protein. An antagonist of a Dkk or Dkk-related protein can inhibit one or more of the activities of the naturally occurring form of the protein by, for example, competitively binding to a downstream or upstream member of cellular signaling cascade which includes the Dkk or Dkk-related protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the Dkk or Dkk-related protein.

In one embodiment, variants of a Dkk or Dkk-related protein which function as either agonists (mimetics) or as antagonists can be identified by screening combinatorial libraries of mutants, e.g., truncation mutants, of a Dkk or Dkk-related protein for protein agonist or antagonist activity. In one embodiment, a variegated library of Dkk or Dkk-related variants is generated by combinatorial mutagenesis at the nucleic acid level and is encoded by a variegated gene library. A variegated library of Dkk or Dkk-related variants can be produced by, for example, enzymatically ligating a mixture of synthetic oligonucleotides into gene sequences such that a degenerate set of potential Dkk or Dkk-related sequences is expressible as individual polypeptides, or alternatively, as a set of larger fusion proteins (e.g., for phage display) containing the set of Dkk or Dkk-related sequences therein. There are a variety of methods which can be used to produce libraries of potential Dkk or Dkk-related variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Dkk or Dkk-related sequences. Methods for synthesizing degenerate oligonucleotides are known in the art (see, e.g., Narang, S. A. (1983) *Tetrahedron* 39:3; Itakura et al., (1984) *Annu. Rev. Biochem.* 53:323; Itakura et al, (1984) *Science* 198:1056; Ike et al., (1983) *Nucleic Acid Res.* 11:477.

In addition, libraries of fragments of a Dkk or Dkk-related protein coding sequence can be used to generate a variegated population of Dkk or Dkk-related fragments for screening and subsequent selection of variants of a Dkk or Dkk-related protein. In one embodiment, a library of coding sequence fragments can be generated by treating a double stranded PCR fragment of a Dkk coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Dkk protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Dkk or Dkk-related proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify Dkk variants (Arkin and Yourvan (1992) *PNAS* 89:7811–7815; Delgrave et al., (1993) *Protein Engineering* 6(3):327–33 1).

In one embodiment, cell based assays can be exploited to analyze a variegated Dkk or Dkk-related library. For example, a library of expression vectors can be transfected into a cell line which ordinarily responds to a particular ligand in a Dkk-dependent manner. The transfected cells are then contacted with the ligand and the effect of expression of the mutant on signaling by the ligand can be detected, e.g., by measuring any of a number of immune cell responses. Plasmid DNA can then be recovered from the cells which score for inhibition, or alternatively, potentiation of ligand induction, and the individual clones further characterized.

An isolated Dkk protein, Dkk-related protein, or a portion or fragment thereof, can be used as an immunogen to generate antibodies that bind Dkk or Dkk-related proteins using standard techniques for polyclonal and monoclonal antibody preparation. A full-length Dkk or Dkk-related protein can be used or, alternatively, the invention provides antigenic peptide fragments for use as immunogens. The antigenic peptide of Dkk comprises at least 8 amino acid residues of the amino acid sequence shown in SEQ ID NO:2, SEQ ID NO:5, SEQ ID NO:8, SEQ ID NO:14, or SEQ ID NO:21 and encompasses an epitope of Dkk or Dkk-related protein such that an antibody raised against the peptide forms a specific immune complex with the protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of Dkk or Dkk-related proteins that are located on the surface of the protein, e.g., hydrophilic regions.

A Dkk or Dkk-related immunogen typically is used to prepare antibodies by immunizing a suitable subject, (e.g., rabbit, goat, mouse or other mammal) with the immunogen. An appropriate immunogenic preparation can contain, for example, recombinantly expressed Dkk or Dkk-related protein or a chemically synthesized Dkk or Dkk-related polypeptide. The preparation can further include an adjuvant, such as Freund's complete or incomplete adjuvant, or similar immunostimulatory agent. Immunization of a suitable subject with an immunogenic Dkk preparation, for example, induces a polyclonal anti-Dkk antibody response.

Accordingly, another aspect of the invention pertains to anti-Dkk antibodies as well as antobodies to Dkk-related proteins. The term "antibody" as used herein refers to immunoglobulin molecules and immunologically active portions of immunoglobulin molecules, i.e., molecules that contain an antigen binding site which specifically binds (immunoreacts with) an antigen, such as Dkk or Dkk-related antigens. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Dkk or Dkk-related polypeptides. The term "monoclonal antibody" or "monoclonal antibody composition", as used herein, refers to a population of antibody molecules that contain only one species of an antigen binding site capable of immunoreacting with a particular epitope of Dkk or a or Dkk-related protein. A monoclonal antibody composition thus typically displays a single binding affinity for a particular Dkk or Dkk-related protein with which it immunoreacts.

Polyclonal antibodies can be prepared as described above by immunizing a suitable subject with a Dkk or Dkk-related immunogen. The antibody titer in the immunized subject can be monitored over time by standard techniques, such as with an enzyme linked immunosorbent assay (ELISA) using immobilized Dkk or Dkk-related protein. If desired, the antibody molecules directed against Dkk or Dkk-related protein can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al., (1981) *J. Immunol.* 127:539–46; Brown et al., (1980) *J Biol. Chem*. 255:4980–83; Yeh et al., (1976) *PNAS* 76:2927–31; and Yeh et al, (1982) *Int. J Cancer* 29:269–75), the more recent human B cell hybridoma technique (Kozbor et al, (1983) *Immunol Today* 4:72), the EBV-hybridoma technique (Cole et al, (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J Biol. Med.*, 54:387–402; M. L. Gefter et al., (1977) *Somatic Cell Genet.* 3:231–36). Briefly, an immortal cell line (typically a myeloma) is fused to lymphocytes (typically splenocytes) from a mammal immunized with a Dkk or Dkk-related immunogen as described above, and the culture supernatants of the resulting hybridoma cells are screened to identify a hybridoma producing a monoclonal antibody that binds Dkk or Dkk-related protein.

Any of the many well known protocols used for fusing lymphocytes and immortalized cell lines can be applied for the purpose of generating a monoclonal antibody (see, e.g., G. Galfre et al., (1977) *Nature* 266:55052; Gefter et al, *Somatic Cell Genet.*, cited supra; Lerner, *Yale J. Biol. Med.*, cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Dkk or Dkk-related protein, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with Dkk or Dkk-related protein to thereby isolate immunoglobulin library members that bind Dkk or Dkk-related protein. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication WO 92/20791; Markland et al., PCT International Publication No. WO 92/15679; Breitling et al., PCT International Publication WO 93/01288; McCafferty et al., PCT International Publication No. WO 92/01047; Garrard et al., PCT International Publication No. WO 92/09690; Ladner et al., PCT International Publication No. WO 90/02809; Fuchs et al., (1991) *Bio/Technology* 9:1370–1372; Hay et al., (1992) *Hum. Antibod. Hybridomas* 3:81–85; Huse et al., (1989) *Science* 246:1275–1281; Griffiths et al., (1993) *EMBO J* 12:725–734; Hawkins et al., (1992) *J Mol. Biol.* 226:889–896; Clarkson etal., (1991) *Nature* 352:624–628; Gram etal., (1992) *PNAS* 89:3576–3580; Garrad et al., (1991) *Bio/Technology* 9:1373–1377; Hoogenboom et al., (1991) *Nuc. Acid Res.* 19:4133–4137; Barbas et al., (1991) *PNAS* 88:7978–7982; and McCafferty et al., *Nature* (1990) 348:552–554.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al., International Application No. PCT/US86/02269; Akira, et al., European Patent Application 184,187; Taniguchi, M., European Patent Application 171,496; Morrison et al., European Patent Application 173,494; Neuberger et al., PCT International Publication No. WO 86/01533; Cabilly et al, U.S. Pat. No. 4,816,567; Cabilly et al., European Patent Application 125,023; Better et al., (1988) *Science* 240:1041–1043; Liu et al., (1987) *PNAS* 84:3439–3443; Liu et al., (1987) *J. Immunol.* 139:3521–3526; Sun et al., (1987) *PNAS* 84:214–218; Nishimura et al., (1987) *Canc. Res.* 47:999–1005; Wood et al., (1985) *Nature* 314:446–449; and Shaw et al., (1988) *J. Natl. Cancer Inst.* 80:1553–1559); Morrison, S. L. (1985) *Science* 229:1202–1207; Oi et al., (1986) *BioTechniques* 4:214; Winter U.S. Pat. No. 5,225,539; Jones et al., (1986) *Nature* 321:552–525; Verhoeyan et al., (1988) *Science* 239:1534; and Beidler et al., (1988) *J. Immunol.* 141:4053–4060.

An antibody (e.g., monoclonal antibody) can be used to isolate Dkk or Dkk-related protein by standard techniques, such as affinity chromatography or immunoprecipitation. An antibody can facilitate the purification of natural Dkk or Dkk-related protein from cells and of recombinantly produced Dkk or Dkk-related protein expressed in host cells. Moreover, an antibody can be used to detect Dkk or Dkk-related protein (e.g., in a cellular lysate or cell supernatant) in order to evaluate the abundance and pattern of expression of the Dkk or Dkk-related protein. Antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding Dkk or a nucleic acid encoding a Dkk-related protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., Dkk proteins, Dkk-related proteins, mutant forms of Dkk or Dkk-related proteins, fusion proteins, etc.).

The recombinant expression vectors of the invention can be designed for expression of Dkk or Dkk-related proteins in prokaryotic or eukaryotic cells. For example, Dkk can be expressed in bacterial cells such as E. coli, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in activity assays, in ligand binding (e.g., direct assays or competitive assays described in detail below), to generate antibodies specific for Dkk or Dkk-related proteins, as examples. In a preferred embodiment, a Dkk or Dkk-related fusion expressed in a retroviral expression vector of the present invention can be utilized to infect bone marrow cells which are subsequently transplanted into irradiated recipients. The pathology of the subject recipient is then examined after sufficient time has passed (e.g six (6) weeks).

Examples of suitable inducible non-fusion *E. coli* expression vectors include pTrc (Amann et al, (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the Dkk or Dkk-related expression vector is a yeast expression vector. Examples of vectors for expression in yeast *S. cerivisae* include pYepSec1 (Baldari, et al., (1987) *Embo J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, Dkk or Dkk-related protein can be expressed in insect cells using baculovirus expression vectors. Baculovirus vectors available for expression of proteins in cultured insect cells (e.g., Sf9 cells) include the pAc series (Smith et al., (1983) *Mol. Cell Biol.* 3:2156–2165) and the pVL series (Lucklow and Summers (1989) *Virology* 170: 31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al., (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al., (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al., (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to Dkk mRNA or a Dkk-related mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Dkk protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al., (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Dkk or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a Dkk or Dkk-related protein. Accordingly, the invention further provides methods for producing Dkk or Dkk-related proteins using the host cells of the invention. In one embodiment, the method comprises culturing the host cell of invention (into which a recombinant expression vector encoding Dkk or a Dkk-related protein has been introduced) in a suitable medium such that protein is produced. In another embodiment, the method further comprises isolating Dkk or a Dkk-related protein from the medium or the host cell.

The host cells of the invention can also be used to produce nonhuman transgenic animals. For example, in one embodiment, a host cell of the invention is a fertilized oocyte or an embryonic stem cell into which Dkk-coding sequences (or Dkk-related coding sequences) have been introduced. Such host cells can then be used to create non-human transgenic animals in which exogenous Dkk sequences (or Dkk-related sequences) have been introduced into their genome or homologous recombinant animals in which endogenous Dkk sequences (or Dkk-related sequences) have been altered. Such animals are useful for studying the function and/or activity of Dkk or Dkk-related proteins and for identifying and/or evaluating modulators of Dkk or Dkk-related protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous Dkk or Dkk-related gene has been altered by homologous recombination between the endogenous gene and an exogenous DNA molecule introduced into a cell of the animal, e.g., an embryonic cell of the animal, prior to development of the animal.

A transgenic animal of the invention can be created, for example, by introducing Dkk-encoding nucleic acid into the male pronuclei of a fertilized oocyte, e.g., by microinjection, retroviral infection, and allowing the oocyte to develop in a pseudopregnant female foster animal. The human Dkk cDNA sequence of SEQ ID NO:1, SEQ ID NO:4, SEQ ID NO:7, or SEQ ID NO:20 can be introduced as a transgene into the genome of a non-human animal. Alternatively, a nonhuman homologue of a human Dkk gene, such as a mouse Dkk gene, can be isolated based on hybridization to the human Dkk CDNA (described further in subsection I above) and used as a transgene. Intronic sequences and polyadenylation signals can also be included in the transgene to increase the efficiency of expression of the transgene. A tissue-specific regulatory sequence(s) can be operably linked to the Dkk transgene to direct expression of Dkk protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al, and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the Dkk transgene in its genome and/or expression of Dkk mRNA in tissues or cells of the animals. A transgenic founder animal can then be used to breed additional animals carrying the transgene. Moreover, transgenic animals carrying a transgene encoding Dkk can further be bred to other transgenic animals carrying other transgenes.

To create a homologous recombinant animal, a vector is prepared which contains at least a portion of a Dkk gene into which a deletion, addition or substitution has been introduced to thereby alter, e.g., functionally disrupt, the Dkk gene. The Dkk gene can be a human gene (e.g., the cDNA of SEQ ID NO:3, SEQ ID NO: 6, SEQ ID NO:9 or SEQ ID NO:22), but more preferably, is a non-human homologue of a human Dkk gene. For example, a mouse Dkk gene of SEQ ID NO:16 can be used to construct a homologous recombination vector suitable for altering an endogenous Dkk gene in the mouse genome. In a preferred embodiment, the vector is designed such that, upon homologous recombination, the endogenous Dkk gene is functionally disrupted (i.e., no longer encodes a functional protein; also referred to as a "knock out" vector). Alternatively, the vector can be designed such that, upon homologous recombination, the endogenous Dkk gene is mutated or otherwise altered but still encodes functional protein (e.g., the upstream regulatory region can be altered to thereby alter the expression of the endogenous Dkk protein). In the homologous recombination vector, the altered portion of the Dkk gene is flanked at its 5' and 3' ends by additional nucleic acid of the Dkk gene to allow for homologous recombination to occur between the exogenous Dkk gene carried by the vector and an endogenous Dkk gene in an embryonic stem cell. The additional flanking Dkk nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Dkk gene has homologously recombined with the endogenous Dkk gene are selected (see e.g., Li, E. et al., (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al. It is also within the scope of the present invention to practice the above-described transgenic methodology utilizing nucleic acid molecules which encode Dkk-related proteins.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al., (1992) *PNAS* 89:6232–6236. Another example of a recombinase system is the FLP recombinase system of *Saccharomyces cerevisiae* (O'Gorman et al., (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al., (1997) Nature 385:810–813. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The Dkk and Dkk-related nucleic acid molecules, Dkk and Dkk-related proteins, and anti-Dkk or anti-Dkk-related protein antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary. active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Dkk protein, Dkk-related protein or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The molecules of the present invention (e.g., nucleic acid molecules, proteins, protein homologues, and antibodies described herein) can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a Dkk protein of the invention has one or more of the following activities: intracellular calcium, an increase in phosphatidylinositol or other molecule, and can result, e.g., in phosphorylation of specific proteins, a modulation of gene transcription and any of the other biological activities set forth herein.

In a preferred embodiment, a Dkk activity is at least one or more of the following activities: (i) interaction of a Dkk protein with and/or binding to a second molecule, (e.g., a protein, such as a Dkk (e.g., hDkk-3) receptor, a soluble form of a Dkk receptor, a receptor for a member of the wnt family of signaling proteins, or a non-Dkk signaling molecule); (ii) interaction of a Dkk protein with an intracellular protein via a membrane-bound Dkk receptor; (iii) complex formation between a soluble Dkk protein and a second soluble Dkk binding partner (e.g., a non-Dkk protein molecule or a second Dkk protein molecule); (iv) interaction with other extracellular proteins (e.g., regulation of wnt-dependent cellular adhesion to extracellular matrix components); (v) binding to and eliminating an undesirable molecule (e.g., a detoxifying activity or defense function); and/or (vi) an enzymatic activity, and can can thus be used in, for example, (1) modulation of cellular signal transduction, either in vitro or in vivo (e.g., antagonism of the activity of members of the wnt family of secreted proteins or supression of wnt-dependent signal transduction); (2) regulation of communication between cells (e.g., regulation of wnt-dependent cell-cell interactions); (3) regulation of expression of genes whose expression is modulated by binding of Dkk (e.g., hDkk-3) to a receptor; (4) regulation of gene transcription in a cell involved in development or differentiation, either in vitro or in vivo (e.g., induction of cellular differentiation); (5) regulation of gene transcription in a cell involved in development or differentiation, wherein at least one gene encodes a differentiation-specific protein; (6) regulation of gene transcription in a cell involved in development or differentaition, wherein at least one gene encodes a second secreted protein; (7) regulation of gene transcription in a cell involved in development or differentiation, wherein at least one gene encodes a signal transduction molecule; (8) regulation of cellular proliferation, either in vitro or in vivo (e.g., induction of cellular proliferation or inhibition of proliferation, for example, inhibition of tumorigenesis (e.g., inhibition of glioblastoma proliferation)); (9) formation and maintenance of ordered spatial arrangements of differentiated tissues in vertebrates, both adult and embryonic (e.g., induction of head formation during vertebrate development or maintenance of hematopoietic progenitor cells); (10) modulation of cell death, such as stimulation of cell survival; (11) regulating cell migration; and/or (12) immune modulation.

Accordingly one embodiment of the present invention involves a method of use (e.g., a diagnostic assay, prognostic assay, or a prophylactic/therapeutic method of treatment) wherein a molecule of the present invention (e.g., a Dkk protein, Dkk nucleic acid, or a Dkk modulator) is used, for example, to diagnose, prognose and/or treat a disease and/or condition in which any of the aforementioned activities (i.e., activities (i)–(vi) and (1)–(12) in the above paragraph) is indicated. In another embodiment, the present invention involves a method of use (e.g., a diagnostic assay, prognostic assay, or a prophylactic/therapeutic method of treatment) wherein a molecule of the present invention (e.g., a Dkk protein, Dkk nucleic acid, or a Dkk modulator) is used, for example, for the diagnosis, prognosis, and/or treatment of subjects, preferably a human subject, in which any of the aforementioned activities is pathologically perturbed. In a preferred embodiment, the methods of use (e.g., diagnostic assays, prognostic assays, or prophylactic/therapeutic methods of treatment) involve administering to a subject, preferably a human subject, a molecule of the present invention (e.g., a Dkk protein, Dkk nucleic acid, or a Dkk modulator) for the diagnosis, prognosis, and/or therapeutic treatment. In another embodiment, the methods of use (e.g., diagnostic assays, prognostic assays, or prophylactic/therapeutic methods of treatment) involve administering to a human subject a molecule of the present invention (e.g., a Dkk protein, Dkk nucleic acid, or a Dkk modulator).

Other embodiments of the invention pertain to the use of isolated nucleic acid molecules of the invention can be used, for example, to express Dkk or Dkk-related protein (e.g., via a recombinant expression vector in a host cell in gene therapy applications), to detect Dkk or Dkk-related mRNA (e.g., in a biological sample) or a genetic alteration in a Dkk or Dkk-related gene, and to modulate Dkk or Dkk-related activity, as described further below. In addition, the Dkk or Dkk-related proteins can be used to screen drugs or compounds which modulate the Dkk activity as well as to treat disorders characterized by insufficient or excessive production of Dkk or Dkk-related protein or production of Dkk or Dkk-related protein forms which have decreased or aberrant activity compared to Dkk or Dkk-related wild type protein (e.g., developmental disorders or proliferative diseases such as cancer as well as diseases, ocular disorders (e.g., blindness) conditions or disorders characterized by abnormal cell differentiation and/or survival, an abnormal extracellular structure, or an abnormality in a defense mechanism). Moreover, the antibodies of the invention can be used to detect and isolate Dkk or Dkk-related proteins, regulate the bioavailability of Dkk or Dkk-related proteins, and modulate Dkk or Dkk-related activity. The term "an aberrant activity", as applied to an activity of a protein such as Dkk (e.g., hDkk-3), refers to an activity which differs from the activity of the wild-type or native protein or which differs from the activity of the protein in a healthy subject. An activity of a protein can be aberrant because it is stronger than the activity of its native counterpart. Alternatively, an activity can be aberrant because it is weaker or absent related to the activity of its native counterpart. An aberrant activity can also be a change in an activity. For example an aberrant protein can interact with a different protein relative to its native counterpart. A cell can have an aberrant Dkk (e.g., hDkk-3) activity due to overexpression or underexpression of the gene encoding Dkk.

A. Screening Assays:

The invention provides a method (also referred to herein as a "screening assay") for identifying modulators, i.e., candidate or test compounds or agents (e.g., peptides, peptidomimetics, small molecules or other drugs) which bind to Dkk or Dkk-related proteins or have a stimulatory or inhibitory effect on, for example, Dkk or Dkk-related expression or activity. Modulators can include, for example, agonists and/or antagonists. The term "agonist", as used herein, is meant to refer to an agent that mimics or upregulates (e.g. potentiates or supplements) a Dkk or Dkk-related (e.g., hDkk-3) bioactivity. An agonist can be a compound which mimics a bioactivity of a Dkk or Dkk-related protein, such as transduction of a signal from a Dkk receptor, by, e.g., interacting with a hDkk-3 receptor. An agonist can also be a compound that upregulates expression of a Dkk or Dkk-related gene. An agonist can also be a compound which modulates the expression or activity of a protein which is located downstream, for example, of a Dkk receptor, thereby mimicking or enhancing the effect of binding of Dkk to a Dkk receptor.

"Antagonist" as used herein is meant to refer to an agent that inhibits, decreases or suppresses a bioactivity (e.g., hDkk-3). An antagonist can be a compound which decreases signalling from a Dkk or Dkk-related protein, e.g., a compound that is capable of binding to hDkk-3 or to a hDkk-3 receptor. A preferred antagonist inhibits the interaction between a Dkk or Dkk-related protein and another molecule, such as a Dkk receptor. Alternatively, an antagonist can be a compound that downregulates expression of a Dkk or Dkk-related gene. An antagonist can also be a compound which modulates the expression or activity of a protein which is located downstream of a Dkk receptor, thereby antagonizing the effect of binding of Dkk to a Dkk receptor.

In one embodiment, the invention provides assays for screening candidate or test compounds which bind to or modulate the activity of a Dkk or Dkk-related protein or polypeptide or biologically active portion thereof. In another embodiment, the invention provides assays for screening candidate or test compounds which bind to or modulate the activity of a Dkk receptor. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J Med. Chem.* 37:2678; Cho et al., (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner USP 5,223,409), spores (Ladner USP '409), plasmids (Cull et al (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a Dkk receptor on the cell surface is contacted with a test compound and the ability of the test compound to bind to a Dkk receptor determined. The cell, for example, can be of mammalian origin or a yeast cell. Determining the ability of the test compound to bind to a Dkk receptor can be accomplished, for example, by coupling the test compound with a radioisotope or enzymatic label such that binding of the test compound to the Dkk receptor can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a test compound to interact with a Dkk receptor without the labeling of any of the interactants. For example, a microphysiometer can be used to detect the interaction of a test compound with a Dkk receptor without the labeling of either the test compound or the receptor. McConnell, H. M. et al. (1992) *Science* 257:1906–1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and receptor.

In a preferred embodiment, the assay comprises contacting a cell which expresses a Dkk receptor on the cell surface with a Dkk protein or biologically-active portion thereof, to form an assay mixture, contacting the assay mixture with a test compound, and determining the ability of the test compound to interact with a Dkk receptor, wherein determining the ability of the test compound to interact with a Dkk receptor comprises determining the ability of the test compound to preferentially bind to the Dkk receptor as compared to the ability of Dkk, or a biologically active portion thereof, to bind to the receptor.

In another embodiment, an assay is a cell-based assay comprising contacting a cell expressing a Dkk target molecule with a test compound and determining the ability of the test compound to modulate (e.g. stimulate or inhibit) the activity of the Dkk target molecule. Determining the ability of the test compound to modulate the activity of a Dkk target molecule can be accomplished, for example, by determining the ability of the Dkk protein to bind to or interact with the Dkk target molecule.

Determining the ability of the Dkk protein to bind to or interact with a Dkk target molecule can be accomplished by one of the methods described above for determining direct binding. In a preferred embodiment, determining the ability of the Dkk protein to bind to or interact with a Dkk target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a Dkk-responsive regulatory element operatively linked to a nucleic acid encoding a detectable marker, e.g., luciferase), or detecting a cellular response, for example, development, differentiation or rate of proliferation.

In yet another embodiment, an assay of the present invention is a cell-free assay in which a Dkk or Dkk-related protein or biologically active portion thereof is contacted with a test compound and the ability of the test compound to bind to the Dkk or Dkk-related protein or biologically active portion thereof is determined. Binding of the test compound to the Dkk or Dkk-related protein can be determined either directly or indirectly as described above. In a preferred embodiment, the assay includes contacting the Dkk or Dkk-related protein or biologically active portion thereof with a known compound which binds Dkk or the Dkk-related protein to form an assay mixture, contacting the assay mixture with a test compound, and determining the ability of the test compound to interact with a Dkk or Dkk-related protein, wherein determining the ability of the test compound to interact with a Dkk or Dkk-related protein comprises determining the ability of the test compound to preferentially bind to Dkk or a Dkk-related protein or biologically active portion thereof as compared to the known compound.

In another embodiment, the assay is a cell-free assay in which a Dkk or Dkk-related protein or biologically active portion thereof is contacted with a test compound and the ability of the test compound to modulate (e.g., stimulate or inhibit) the activity of the Dkk or Dkk-related protein or biologically active portion thereof is determined. Determining the ability of the test compound to modulate the activity of a Dkk or Dkk-related protein can be accomplished, for example, by determining the ability of the Dkk or Dkk-related protein to bind to a target molecule (e.g., a Dkk-target molecule) by one of the methods described above for determining direct binding. Determining the ability of the Dkk or Dkk-related protein to bind to a target molecule can also be accomplished using a technology such as real-time Biomolocular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

In an alternative embodiment, determining the ability of the test compound to modulate the activity of a Dkk or Dkk-related protein can be accomplished by determining the ability of the Dkk or Dkk-related protein to further modulate the activity of a target molecule (e.g., a Dkk-target molecule). For example, the catalytic/enzymatic activity of the target molecule on an appropriate substrate can be determined as previously described.

In yet another embodiment, the cell-free assay involves contacting a Dkk or Dkk-related protein or biologically active portion thereof with a known compound which binds the Dkk or Dkk-related protein to form an assay mixture, contacting the assay mixture with a test compound, and determining the ability of the test compound to interact with the Dkk or Dkk-related protein, wherein determining the ability of the test compound to interact with the Dkk or Dkk-related protein comprises determining the ability of the Dkk or Dkk-related protein to preferentially bind to or modulate the activity of a target molecule (e.g., a Dkk target molecule).

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with a Dkk (e.g., hDkk-3) protein or a Dkk (e.g.; hDkk-3) binding partner, e.g., a receptor. The receptor can be soluble or the receptor can be present on a cell surface. To the mixture of the compound and the Dkk protein or Dkk binding partner is then added a composition containing a Dkk binding partner or a Dkk protein, respectively. Detection and quantification of complexes of Dkk proteins and Dkk binding partners provide a means for determining a compound's efficacy at inhibiting (or potentiating) complex formation between Dkk and a binding partner. The efficacy of the compound can be assessed by generating dose response curves from data obtained using various concentrations of the test compound. Moreover, a control assay can also be performed to provide a baseline for comparison. In the control assay, isolated and purified Dkk polypeptide or binding partner is added to a composition containing the Dkk binding partner or Dkk polypeptide, and the formation of a complex is quantitated in the absence of the test compound.

The cell-free assays of the present invention are amenable to use of both soluble and/or membrane-bound forms of isolated proteins (e.g. Dkk proteins or biologically active portions thereof or Dkk target molecules). In the case of cell-free assays in which a membrane-bound form an isolated protein is used (e.g., a Dkk target molecule or receptor) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either Dkk, a Dkk-related protein or a target molecule to facilitate separation of complexed from uncomplexed forms of one or both of the proteins, as well as to accommodate automation of the assay. Binding of a test compound to a Dkk or Dkk-related protein, or interaction of a Dkk or Dkk-related protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/Dkk fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or Dkk protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of Dkk binding or activity determined using standard techniques.

Other techniques for immobilizing proteins on matrices can also be used in the screening assays of the invention. For example, either a Dkk protein, Dkk-related protein, or a Dkk target molecule can be immobilized utilizing conjugation of biotin and streptavidin. Biotinylated protein or target molecules can be prepared from biotin-NHS (N-hydroxy-succinimide) using techniques well known in the art (e.g., biotinylation kit, Pierce Chemicals, Rockford, IL), and immobilized in the wells of streptavidin-coated 96 well plates (Pierce Chemical). Alternatively, antibodies reactive with Dkk, Dkk-related protein, or target molecules but which do not interfere with binding of the protein to its target molecule can be derivatized to the wells of the plate, and unbound target, Dkk, or Dkk-related protein trapped in the wells by antibody conjugation. Methods for detecting such complexes, in addition to those described above for the GST-immobilized complexes, include immunodetection of complexes using antibodies reactive with the Dkk or Dkk-related protein or target molecule, as well as enzyme-linked assays which rely on detecting an enzymatic activity associated with the Dkk or Dkk-related protein or target molecule.

In another embodiment, modulators of Dkk or Dkk-related expression are identified in a method wherein a cell is contacted with a candidate compound and the expression of Dkk or Dkk-related mRNA or protein in the cell is determined. The level of expression of mRNA or protein in the presence of the candidate compound is compared to the level of expression of mRNA or protein in the absence of the candidate compound. The candidate compound can then be identified as a modulator of Dkk or Dkk-related expression based on this comparison. For example, when expression of Dkk mRNA or protein is greater (statistically significantly greater) in the presence of the candidate compound than in its absence, the candidate compound is identified as a stimulator of Dkk mRNA or protein expression. Alternatively, when expression of Dkk mRNA or protein is less (statistically significantly less) in the presence of the candidate compound than in its absence, the candidate compound is identified as an inhibitor of Dkk mRNA or protein expression. The level of Dkk or Dkk-related mRNA or protein expression in the cells can be determined by methods described herein for detecting Dkk mRNA or protein.

In yet another aspect of the invention, the Dkk or Dkk-related proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al., (1993) *Biotechniques* 14:920–924; Iwabuchi et al. (1993) *Oncogene* 8:1693–1696; and Brent WO94/10300), to identify other proteins, which bind to or interact with Dkk or Dkk-related proteins ("binding proteins" or "bp") and modulate Dkk or Dkk-related activity. Such binding proteins are also likely to be involved in the propagation of signals by the Dkk or Dkk-related proteins as, for example, downstream elements of a Dkk-mediated signaling pathway. Alternatively, such binding proteins are likely to be cell-surface molecules associated with non-Dkk expressing cells, wherein such binding proteins are involved in signal transduction.

The two-hybrid system is based on the modular nature of most transcription factors, which consist of separable DNA-binding and activation domains. Briefly, the assay utilizes two different DNA constructs. In one construct, the gene that codes for a Dkk protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Dkk-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Dkk or Dkk-related protein.

This invention further pertains to novel agents identified by the above-described screening assays and to processes for producing such agents by use of these assays. Accordingly, in one embodiment, the present invention includes a compound or agent obtainable by a method comprising the steps of any one of the aforementioned screening assays (e.g., cell-based assays or cell-free assays). For example, in one embodiment, the invention includes a compound or agent obtainable by a method comprising contacting a cell which expresses a target molecule with a test compound and the determining the ability of the test compound to bind to, or modulate the activity of, the target molecule. In another embodiment, the invention includes a compound or agent obtainable by a method comprising contacting a cell which expresses a target molecule with a Dkk or Dkk-related protein or biologically-active portion thereof, to form an assay mixture, contacting the assay mixture with a test compound, and determining the ability of the, test compound to interact with, or modulate the activity of, the target molecule. In another embodiment, the invention includes a compound or agent obtainable by a method comprising contacting a Dkk or Dkk-related protein or biologically active portion thereof with a test compound and determining the ability of the test compound to bind to, or modulate (e.g., stimulate or inhibit) the activity of, the Dkk or Dkk-related protein or biologically active portion thereof. In yet another embodiment, the present invention includes a compound or agent obtainable by a method comprising contacting a Dkk or Dkk-related protein or biologically active portion thereof with a known compound which binds the Dkk or Dkk-related protein to form an assay mixture, contacting the assay mixture with a test compound, and determining the ability of the test compound to interact with, or modulate the activity of the Dkk or Dkk-related protein.

Accordingly, it is within the scope of this invention to further use an agent identified as described herein in an appropriate animal model. For example, an agent identified as described herein (e.g., a Dkk modulating agent, an antisense Dkk nucleic acid molecule, a Dkk-specific antibody, or a Dkk-binding partner) can be used in an animal model to determine the efficacy, toxicity, or side effects of treatment with such an agent. Alternatively, an agent identified as described herein can be used in an animal model to determine the mechanism of action of such an agent.

The present inventon also pertains to uses of novel agents identified by the above-described screening assays for diagnoses, prognoses, and treatments as described herein. Accordingly, it is within the scope of the present invention to use such agents in the design, formulation, synthesis, manufacture, and/or production of a drug or pharmaceutical composition for use in diagnosis, prognosis, or treatment, as described herein. For example, in one embodiment, the present invention includes a method of synthesizing or producing a drug or pharmaceutical composition by reference to the structure and/or properties of a compound obtainable by one of the above-described screening assays. For example, a drug or pharmaceutical composition can be synthesized based on the structure and/or properties of a compound obtained by a method in which a cell which expresses a target molecule (e.g., a Dkk target molecule) is contacted with a test compound and the ability of the test compound to bind to, or modulate the activity of, the target molecule is determined. In another exemplary embodiment, the present invention includes a method of synthesizing or producing a drug or pharmaceutical composition based on the structure and/or properties of a compound obtainable by a method in which a Dkk or Dkk-related protein or biologically active portion thereof is contacted with a test compound and the ability of the test compound to bind to, or modulate (e.g., stimulate or inhibit) the activity of, the Dkk or Dkk-related protein or biologically active portion thereof is determined.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the Dkk or Dkk-related nucleotide sequences, described herein, can be used to map the location of the Dkk or Dkk-related genes on a chromosome. The mapping of the Dkk or Dkk-related sequences to chromosomes is an important first step in correlating these sequences with genes associated with disease.

Briefly, Dkk or Dkk-related genes can be mapped to chromosomes by preparing PCR primers (preferably 15–25 bp in length) from the Dkk or Dkk-related nucleotide sequences. Computer analysis of the Dkk or Dkk-related sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the Dkk or Dkk-related sequences will yield an amplified fragment.

Somatic cell hybrids are prepared by fusing somatic cells from different mammals (e.g, human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al., (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the Dkk or Dkk-related nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al., (1990) *PNAS*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with a Dkk or Dkk-related gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The Dkk or Dkk-related sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the Dkk or Dkk-related nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The Dkk or Dkk-related nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:4, SEQ ID NO:7, SEQ ID NO:13, or SEQ ID NO:20, can comfortably provide positive individual identification with a panel of perhaps 10 to 1,000 primers which each yield a noncoding amplified sequence of 100 bases. If predicted coding sequences, such as those in SEQ ID NO:3, SEQ ID NO:6, SEQ ID NO:9, SEQ ID NO:15 or SEQ ID NO:22 are used, a more appropriate number of primers for positive individual identification would be 500–2,000.

If a panel of reagents from Dkk or Dkk-related nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial Dkk or Dkk-related Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NOs:1, SEQ ID NO:4, SEQ ID NO:7, SEQ ID NO:13, or SEQ ID NO:20 are particularly appropriate for this use as greater numbers of polymorphisms occur in the noncoding regions, making it easier to differentiate individuals using this technique. Examples of polynucleotide reagents include the Dkk nucleotide sequences or portions thereof, e.g., fragments derived from the noncoding regions of SEQ ID NO:1, SEQ ID NO:4, SEQ ID NO:7, SEQ ID NO:13, or SEQ ID NO:20, having a length of at least 20 bases, preferably at least 30 bases.

The Dkk or Dkk-related nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such Dkk or Dkk-related probes can be used to identify tissue by species and/or by organ type.

In a similar fashion, these reagents, e.g., Dkk or Dkk-related primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining Dkk or Dkk-related protein and/or nucleic acid expression as well as Dkk or Dkk-related activity, in the context of a biological sample (e.g., blood, serum, cells, tissue) to thereby determine whether an individual is afflicted with a disease or disorder, or is at risk of developing a disorder, associated with aberrant Dkk or Dkk-related expression or activity, such as aberrant cell proliferation, differentiation, and/or survival resulting for example in a neurodegenerative disease (e.g., Alzheimer's disease, Parkinson's disease, Huntington's chorea, amylotrophic lateral sclerosis and the like, as well as spinocerebellar degenerations) or cancer (for example, cancers of the epithelia (e.g., carcinomas of the pancreas, stomach, liver, secretory glands (e.g., adenocarcinoma) bladder, lung, breast, skin (e.g., malignant melanoma), reproductive tract including prostate gland, ovary, cervix and uterus); cancers of the hematopoietic and immune system (e.g., leukemias and lymphomas); cancers of the central nervous, brain system and eye (e.g., gliomas, glioblastoma, neuroblastoma and retinoblastoma); and cancers of connective tissues, bone, muscles and vasculature (e.g., sarcomas)). The invention also provides for prognostic (or predictive) assays for determining whether an individual is at risk of developing a disorder associated with Dkk or Dkk-related protein, nucleic acid expression or activity. For example, mutations in a Dkk or Dkk-related gene can be assayed in a biological sample. Such assays can be used for prognostic or predictive purpose to thereby phophylactically treat an individual prior to the onset of a disorder characterized by or associated with Dkk or Dkk-related protein, nucleic acid expression or activity.

Another aspect of the invention pertains to monitoring the influence of agents., (e.g., drugs, compounds) on the expression or activity of Dkk or Dkk-related in clinical trials.

These and other agents are described in further detail in the following sections.

1. Diagnostic Assays

An exemplary method for detecting the presence or absence of Dkk or Dkk-related protein or nucleic acid in a biological sample involves obtaining a biological sample from a test subject and contacting the biological sample with a compound or an agent capable of detecting Dkk or Dkk-related protein or nucleic acid (e.g., mRNA, genomic DNA) that encodes Dkk or Dkk-related protein such that the presence of Dkk or Dkk-related protein or nucleic acid is detected in the biological sample. A preferred agent for detecting Dkk or Dkk-related mRNA or genomic DNA is a labeled nucleic acid probe capable of hybridizing to Dkk or Dkk-related mRNA or genomic DNA. The nucleic acid probe can be, for example, a full-length Dkk nucleic acid, such as the nucleic acid of SEQ ID NO:1, SEQ ID NO:4, SEQ ID NO:7, SEQ ID NO:13, SEQ ID NO:20, the DNA insert of the plasmid deposited with ATCC as Accession Number 98452, the DNA insert of the plasmid deposited with ATCC as Accession Number 98633, or the nucleotide sequence of the DNA insert of the plasmid deposited with ATCC as Accession Number 201740, or a portion thereof, such as an oligonucleotide of at least 15, 30, 50, 100, 250 or 500 nucleotides in length and sufficient to specifically hybridize under stringent conditions to Dkk or Dkk-related mRNA or genomic DNA. Other suitable probes for use in the diagnostic assays of the invention are described herein.

A preferred agent for detecting Dkk or Dkk-related protein is an antibody capable of binding to the protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect Dkk or Dkk-related mRNA, protein, or genomic DNA in a biological sample in vitro as well as in vivo. For example, in vitro techniques for detection of Dkk or Dkk-related mRNA include Northern hybridizations and in situ hybridizations. In vitro techniques for detection of Dkk or Dkk-related protein include enzyme linked immunosorbent assays (ELISAs), Western blots, immunoprecipitations and immunofluorescence. In vitro techniques for detection of Dkk or Dkk-related genomic DNA include Southern hybridizations. Furthermore, in vivo techniques for detection of Dkk or Dkk-related protein include introducing into a subject a labeled antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Dkk or Dkk-related protein, mRNA, or genomic DNA, such that the presence of Dkk or Dkk-related protein, mRNA or genomic DNA is detected in the biological sample, and comparing the presence of Dkk or Dkk-related protein, mRNA or genomic DNA in the control sample with the presence of Dkk or Dkk-related protein, mRNA or genomic DNA in the test sample.

The invention also encompasses kits for detecting the presence of Dkk or a Dkk-related protein in a biological sample. For example, the kit can comprise a labeled compound or agent capable of detecting Dkk or Dkk-related protein or mRNA in a biological sample; means for determining the amount of Dkk or Dkk-related protein or mRNA in the sample; and means for comparing the amount of Dkk or Dkk-related protein or mRNA in the sample with a standard. The compound or agent can be packaged in a suitable container. The kit can further comprise instructions for using the kit to detect Dkk or Dkk-related protein or nucleic acid.

2. Prognostic Assays

The diagnostic methods described herein can furthermore be utilized to identify subjects having or at risk of developing a disease or disorder associated with aberrant Dkk expression or activity. For example, the assays described herein, such as the preceding diagnostic assays or the following assays, can be utilized to identify a subject having or at risk of developing a disorder associated with Dkk or Dkk-related protein, nucleic acid expression or activity such as a proliferative disorder, a differentiative or developmental disorder, a hematopoietic disorder as well as diseases, conditions or disorders characterized by abnormal cell survival, abnormal extracellular structure, or an abnormality in a defense mechanism. Alternatively, the prognostic assays can be utilized to identify a subject having or at risk for developing a differentiative or proliferative disease (e.g., cancer). Thus, the present invention provides a method for identifying a disease or disorder associated with aberrant Dkk or Dkk-related expression or activity in which a test sample is obtained from a subject and Dkk or Dkk-related protein or nucleic acid (e.g., mRNA, genomic DNA) is detected, wherein the presence of Dkk or Dkk-related protein or nucleic acid is diagnostic for a subject having or at risk of developing a disease or disorder associated with aberrant Dkk or Dkk-related expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Dkk or Dkk-related expression or activity. For example, such methods can be used to determine whether a subject can be effectively treated with an agent for a disorder, such as a proliferative disorder, a differentiative or developmental disorder, a hematopoietic disorder, as well disorders characterized by abnormal cell survival, an abnormal extracellular structure, or an abnormality in a defense mechanism. Alternatively, such methods can be used to determine whether a subject can be effectively treated with an agent for a differentiative or proliferative disease (e.g., cancer). Thus, the present invention provides methods for determining whether a subject can be effectively treated with an agent for a disorder associated with aberrant Dkk or Dkk-related expression or activity in which a test sample is obtained and Dkk or Dkk-related protein or nucleic acid expression or activity is detected (e.g., wherein the abundance of Dkk or Dkk-related protein or nucleic acid expression or activity is diagnostic for a subject that can be administered the agent to treat a disorder associated with aberrant Dkk or Dkk-related expression or activity.)

The methods of the invention can also be used to detect genetic alterations in a Dkk or Dkk-related gene, thereby determining if a subject with the altered gene is at risk for a disorder characterized by aberrant development, aberrant cellular differentiation, aberrant cellular proliferation or an aberrant hematopoietic response. In preferred embodiments, the methods include detecting, in a sample of cells from the subject, the presence or absence of a genetic alteration characterized by at least one of an alteration affecting the integrity of a gene encoding a Dkk or Dkk-related-protein, or the mis-expression of the Dkk or Dkk-related gene. For example, such genetic alterations can be detected by ascertaining the existence of at least one of 1) a deletion of one or more nucleotides from a Dkk or Dkk-related gene; 2) an addition of one or more nucleotides to a Dkk or Dkk-related gene; 3) a substitution of one or more nucleotides of a Dkk or Dkk-related gene, 4) a chromosomal rearrangement of a Dkk or Dkk-related gene; 5) an alteration in the level of a messenger RNA transcript of a Dkk or Dkk-related gene, 6) aberrant modification of a Dkk or Dkk-related gene, such as of the methylation pattern of the genomic DNA, 7) the presence of a non-wild type splicing pattern of a messenger RNA transcript of a Dkk or Dkk-related gene, 8) a non-wild type level of a Dkk or Dkk-related-protein, 9) allelic loss of a Dkk or Dkk-related gene, and 10) inappropriate post-translational modification of a Dkk or Dkk-related-protein. As described herein, there are a large number of assay techniques known in the art which can be used for detecting alterations in a Dkk or Dkk-related gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the Dkk or Dkk-related-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a Dkk or Dkk-related gene under conditions such that hybridization and amplification of the Dkk or Dkk-related-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Dkk or Dkk-related gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in a Dkk or Dkk-related gene can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in Dkk can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Dkk or Dkk-related gene and detect mutations by comparing the sequence of the sample Dkk or Dkk-related sequence with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the Dkk or Dkk-related gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type Dkk or Dkk-related sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Dkk cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a Dkk sequence, e.g., a wild-type Dkk sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Dkk or Dkk-related genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *MutatRes* 285:125–144; and Hayashi (1992) *GenetAnal Tech Appl* 9:73–79). Single-stranded DNA fragments of sample and control Dkk or Dkk-related nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3 end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Dkk gene.

Furthermore, any cell type or tissue in which Dkk or a Dkk-related sequence is expressed may be utilized in the prognostic assays described herein.

3. Monitoring of Effects During Clinical Trials

Monitoring the influence of agents (e.g., drugs, compounds) on the expression or activity of Dkk or Dkk-related molecule (e.g., modulation of cellular signal transduction, regulation of gene transcription in a cell involved in development or differentiation, regulation of cellular proliferation) can be applied not only in basic drug screening, but also in clinical trials. For example, the effectiveness of an agent determined by a screening assay as described herein to increase Dkk or Dkk-related gene expression, protein levels, or upregulate Dkk or Dkk-related activity, can be monitored in clinical trials of subjects exhibiting decreased Dkk or Dkk-related gene expression, protein levels, or downregulated Dkk or Dkk-related activity. Alternatively, the effectiveness of an agent determined by a screening assay to decrease Dkk or Dkk-related gene expression, protein levels, or downregulate Dkk or Dkk-related activity, can be monitored in clinical trials of subjects exhibiting increased Dkk or Dkk-related gene expression, protein levels, or upregulated Dkk or Dkk-related activity. In such clinical trials, the expression or activity of Dkk or Dkk-related and, preferably, other genes that have been implicated in, for example, a proliferative disorder can be used as a "read out" or markers of the phenotype of a particular cell.

For example, and not by way of limitation, genes, including Dkk and Dkk-related genes, that are modulated in cells by treatment with an agent (e.g., compound, drug or small molecule) which modulates Dkk or Dkk-related activity (e.g., identified in a screening assay as described herein) can be identified. Thus, to study the effect of agents on proliferative disorders, developmental or differentiative disorder, hematopoietic disorder as well disorders characterized by abnormal cell differentiation and/or survival, an abnormal extracellular structure, or an abnormality in a defense mechanism, for example, in a clinical trial, cells can be isolated and RNA prepared and analyzed for the levels of expression of Dkk, Dkk-related, and other genes implicated in the proliferative disorder, developmental or differentiative disorder, hematopoietic disorder as well as disorders characterized by abnormal cell differentiation and/or survival, an abnormal extracellular structure, or an abnormality in a defense mechanism, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Dkk, Dkk-related, or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a Dkk or Dkk-related protein, mRNA, or genomic DNA in the preadministration sample; (iii) obtaining one or more post-administration samples from the subject; (iv) detecting the level of expression or activity of the Dkk or Dkk-related protein, mRNA, or genomic DNA in the post-administration samples; (v) comparing the level of expression or activity of the Dkk or Dkk-related protein, mRNA, or genomic DNA in the pre-administration sample with the Dkk or Dkk-related protein, mRNA, or genomic DNA in the post administration sample or samples; and (vi) altering the administration of the agent to the subject accordingly. For example, increased administration of the agent may be desirable to increase the expression or activity of Dkk or Dkk-related nucleic acid or protein to higher levels than detected, i.e., to increase the effectiveness of the agent. Alternatively, decreased administration of the agent may be desirable to decrease expression or activity of Dkk or Dkk-related nucleic acid or protein to lower levels than detected, ie. to decrease the effectiveness of the agent. According to such an embodiment, Dkk or Dkk-related expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant Dkk or Dkk-related expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the Dkk or Dkk-related molecules of the present invention or Dkk or Dkk-related modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant Dkk or Dkk-related expression or activity, by administering to the subject an agent which modulates Dkk or Dkk-related expression or at least one Dkk or Dkk-related activity. Subjects at risk for a disease which is caused or contributed to by aberrant Dkk or Dkk-related expression or activity can be identified by, for example, any or a combination of diagnostic or prognostic assays as described herein. Administration of a prophylactic agent can occur prior to the manifestation of symptoms characteristic of the Dkk or Dkk-related aberrancy, such that a disease or disorder is prevented or, alternatively, delayed in its progression. Depending on the type of Dkk or Dkk-related aberrancy, for example, an agonist or antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating Dkk or Dkk-related expression or activity for therapeutic purposes. The modulatory method of the invention involves contacting a cell with an agent that modulates one or more of the activities of Dkk or Dkk-related protein activity associated with the cell. An agent that modulates Dkk or Dkk-related protein activity can be an agent as described herein, such as a nucleic acid or a protein, a naturally-occurring target molecule of a Dkk or Dkk-related protein, a peptide, a Dkk or Dkk-related peptidomimetic, or other small molecule. In one embodiment, the agent stimulates one or more Dkk or Dkk-related protein activity. Examples of such stimulatory agents include active Dkk or Dkk-related protein and a nucleic acid molecule encoding Dkk or Dkk-related that has been introduced into the cell. In another embodiment, the agent inhibits one or more Dkk or Dkk-related protein activity. Examples of such inhibitory agents include antisense Dkk or Dkk-related nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a Dkk or Dkk-related protein or nucleic acid molecule. The present invention also provides methods of modulating the function, morphology, proliferation, and/or differentiation of cells in the tissues in which a Dkk or Dkk-related protein or nucleic acid molecule is expressed. Alternatively, Dkk or Dkk-related polypeptides, nucleic acids, and modulators thereof, can be used to treat disorders associated with abnormal or aberrant metabolism or function of cells in the tissues in which the Dkk or Dkk-related protein or nucleic acid molecule is expressed.

For example, tissues in which Dkk-3 is expressed include embryonic eye, bone, and cartilage, fetal brain, lung, and kidney, and adult heart (in particular, atrioventricular valves and atrial myocytes), eye (in particular, the integrating bipolar and ganglion cells of the retina, the ciliary body, and lens epithelium), brain (in particular, neurons of the cortex and hippocampus), placenta, lung, and skeletal muscle. Accordingly, Dkk-3 polypeptides, nucleic acids, or modulators thereof, can be used to treat cardiovascular disorders, such as ischemic heart disease (e.g., angina pectoris, myocardial infarction, and chronic ischemic heart disease), hypertensive heart disease, pulmonary heart disease, valvular heart disease (e.g., rheumatic fever and rheumatic heart disease, endocarditis, mitral valve prolapse, and aortic valve stenosis), congenital heart disease (e.g., valvular and vascular obstructive lesions, atrial or ventricular septal defect, and patent ductus arteriosus), or myocardial disease (e.g., myocarditis, congestive cardiomyopathy, and hypertrophic cariomyopathy).

In another embodiment, Dkk-3 polypeptides, nucleic acids, or modulators thereof, can be used to treat optic disorders such as diseases associated with amaurosis (e.g., a. fugax and a. albuminuric) diseases associated with amblyopia, glaucoma, optic neuropathy (e.g., ischemic neuropathy, optic neuritis, and infiltrative neuropathy), opthalmia (e.g., o. catarrhal, trachoma, o. neuroparalytic, and conjunctiva), visual disorders resulting from systemic disease or disorders of other tissues (e.g., diabetes mellitus, hyperthyroidism, and vitamin A or riboflavin deficiency), or tumors, neoplasms, and metastases.

In another embodiment, Dkk-3 polypeptides, nucleic acids, or modulators thereof, can be used to treat disorders of the brain, such as cerebral edema, senile dementia of the Alzeimer type, epilepsy, amnesia, hydrocephalus, brain herniations, iatrogenic disease (due to, e.g., infection, toxins, or drugs), inflammations (e.g., bacterial and viral meningitis, encephalitis, and cerebral toxoplasmosis), cerebrovascular diseases (e.g., hypoxia, ischemia, and infarction, intracranial hemorrhage and vascular malformations, and hypertensive encephalopathy), and tumors (e.g., neuroglial tumors, neuronal tumors, tumors of pineal cells, meningeal tumors, primary and secondary lymphomas, intracranial tumors, and medulloblastoma), and to treat injury or trauma to the brain.

In another embodiment, Dkk-3 polypeptides, nucleic acids, or modulators thereof, can be used to treat placental disorders, such as toxemia of pregnancy (e.g., preeclampsia and eclampsia), placentitis, or spontaneous abortion.

In another embodiment, Dkk-3 polypeptides, nucleic acids, or modulators thereof, can be used to treat pulmonary disorders, such as atelectasis, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchioloalveolar carcinoma, bronchial carcinoid, hamartoma, and mesenchymal tumors).

In another embodiment, Dkk-3 polypeptides, nucleic acids, or modulators thereof, can be used to treat disorders of skeletal muscle, such as muscular atrophy (due to, e.g., denervation, malnutrition, loss of blood supply, or neuromuscular disease, e.g., amyotonia congenita, amyotrophic lateral sclerosis of Charcot, and progressive muscular atrophy of Aran-Duchenne), myositis (due to, e.g., bacterial, viral, fungal or parasitic infection), muscular dystrophies (e.g., Duchenne type, Becker type, facioscapulohumeral, limb-girdle, myotonic dystrophy, and ocular myopathy), myasthenia gravis, or tumors and tumor-like lesions of muscles (e.g., traumatic myositis ossificans, desmoids, musculoaponeurotic fibromatosis, Dupuytren's contracture, nodular (pseudosarcomatous) fasciitis, rhadomyoma, rhabdomyosarcoma, and granular cell myoblastomas).

Tissues in which Dkk-4 is expressed include cerebellum, activated human T-lymphocytes, lung, and esophagus. Accordingly, in one embodiment, Dkk-4 polypeptides, nucleic acids, or modulators thereof, can be used to treat disorders of the cerebellum, such as disturbances of synergy (e.g., asynergia or limb ataxia, dysmetria, decomposition of movement, hypermetria, hypometria, dysdiadochokinesia, hypotonia, tremor, dysarthria, nystagmus), disturbances of equilibrium (due to, e.g., a lesion involving the vestibulocerebellum), disturbances of gait stance, or tone (due to, e.g., a lesion or degeneration of the spinocerebellum), or tumors (e.g., astrocytoma and medulloblastoma).

In another embodiment, Dkk-4 polypeptides, nucleic acids, or modulators thereof, can be used to treat lymphocytic disorders, such as lymphopenia, lymphocytosis, acute and chronic lymphadenitis, malignant lymphomas (e.g, Non-Hodgkin's lymphomas, Hodgkin's lymphomas, leukemias, multiple myeloma, histiocytoses, and angioimmunoblastic lymphadenopathy).

In another embodiment, Dkk-4 polypeptides, nucleic acids, or modulators thereof, can be used to treat pulmonary disorders, such as atelectasis, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchiolovlveolar carcinoma, bronchial carcinoid, hamartoma, and mesenchymal tumors).

In another embodiment, Dkk-4 polypeptides, nucleic acids, or modulators thereof, can be used to treat esophageal disorders, such as neuromuscular disturbances (e.g., achalasia, annular narrowings, Schatzki's rings, hiatal hernia, Mallory-Weiss syndrome), esophagitis (due to e.g., bacteremia, viremia, fungal infections, uremia, graft-versus-host disease, chemotherapy, radiation, and prolonged gastric intubation), diverticula (e.g., Zenker's diverticulum), systemic sclerosis, varices (due to, e.g., portal hypertension, systemic amyloidosis and sarcoidosis), or tumors or neoplasms (e.g., leimyoma, fibromas, lipomas, hemangiomas, lymphangiomas, squamous papillomas, adenocarcinomas and undifferentiated carcinomas, and sarcomas).

Dkk-1 is highly expressed, for example, in placenta. Accordingly, Dkk-1 polypeptides, nucleic acids, or modulators thereof, can be used to treat placental disorders, such as toxemia of pregnancy (e.g., preeclampsia and eclampsia), placentitis, or spontaneous abortion.

Tissues in which Dkk-2 is expressed include, for example, heart, brain, placenta, lung, and skeletal muscle. Accordingly, Dkk-2 polypeptides, nucleic acids, or modulators thereof, can be used to treat cardiovascular disorders, such as ischemic heart disease (e.g., angina pectoris, myocardial infarction, and chronic ischemic heart disease), hypertensive heart disease, pulmonary heart disease, valvular heart disease (e.g., rheumatic fever and rheumatic heart disease, endocarditis, mitral valve prolapse, and aortic valve stenosis), congenital heart disease (e.g., valvular and vascular obstructive lesions, atrial or ventricular septal defect, and patent ductus arteriosus), or myocardial disease (e.g., myocarditis, congestive cardiomyopathy, and hypertrophic cariomyopathy).

In another embodiment, Dkk-2 polypeptides, nucleic acids, or modulators thereof, can be used to treat disorders of the brain, such as cerebral edema, senile dementia of the Alzeimer type, epilepsy, amnesia, hydrocephalus, brain herniations, iatrogenic disease (due to, e.g., infection, toxins, or drugs), inflammations (e.g., bacterial and viral meningitis, encephalitis, and cerebral toxoplasmosis), cerebrovascular diseases (e.g., hypoxia, ischemia, and infarction, intracranial hemorrhage and vascular malformations, and hypertensive encephalopathy), and tumors (e.g., neuroglial tumors, neuronal tumors, tumors of pineal cells, meningeal tumors, primary and secondary lymphomas, intracranial tumors, and medulloblastoma), and to treat injury or trauma to the brain.

In another embodiment, Dkk-2 polypeptides, nucleic acids, or modulators thereof, can be used to treat placental disorders, such as toxemia of pregnancy (e.g., preeclampsia and eclampsia), placentitis, or spontaneous abortion.

In another embodiment, Dkk-2 polypeptides, nucleic acids, or modulators thereof, can be used to treat pulmonary disorders, such as atelectasis, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchiolovlveolar carcinoma, bronchial carcinoid, hamartoma, and mesenchymal tumors).

In another embodiment, Dkk-2 polypeptides, nucleic acids, or modulators thereof, can be used to treat disorders of skeletal muscle, such as muscular atrophy (due to, e.g., denervation, malnutrition, loss of blood supply, or neuromuscular disease, e.g., amyotonia congenita, amyotrophic lateral sclerosis of Charcot, and progressive muscular atrophy of Aran-Duchenne), myositis (due to, e.g., bacterial, viral, fungal or parasitic infection), muscular dystrophies (e.g., Duchenne type, Becker type, facioscapulohumeral, limb-girdle, myotonic dystrophy, and ocular myopathy), myasthenia gravis, or tumors and tumor-like lesions of muscles (e.g., traumatic myositis ossificans, desmoids, musculoaponeurotic fibromatosis, Dupuytren's contracture, nodular (pseudosarcomatous) fasciitis, rhadomyoma, rhabdomyosarcoma, and granular cell myoblastomas).

Soggy-1 is expressed in, for example, testis (e.g., spermatogenic epithelium of the seminiferous tubules, spermatogonia) and in embryonic developing dorsal root ganglia, cartilage primordium of the nasal septum, and the eye. Accordingly, Soggy-1 polypeptides, nucleic acids, or modulators thereof, can be used to treat testicular disorders, such as unilateral testicular enlargment (e.g., nontuberculous, granulomatous orchitis), inflammatory diseases resulting in testicular dysfunction (e.g., gonorrhea and mumps), and tumors (e.g., germ cell tumors, interstitial cell tumors, androblastoma, testicular lymphoma and adenomatoid tumors). In another embodiment, Soggy-I polypeptides, nucleic acids, or modulators thereof, can be used to treat infertility due to, for example, spermatogenetic failure.

In one aspect, the above-described methods involve administering an agent (e.g., an agent identified by a screening assay described herein), or combination of agents that modulates (e.g., upregulates or downregulates) Dkk or Dkk-related expression or activity. In another embodiment, the method involves administering a Dkk or Dkk-related protein or nucleic acid molecule as therapy to compensate for reduced or aberrant Dkk or Dkk-related expression or activity.

A preferred embodiment of the present invention involves a method for treatment of a disease or disorder associated with a Dkk or Dkk-related protein which includes the step of administering a therapeutically effective amount of an antibody to a Dkk or Dkk-related protein to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Stimulation of Dkk or Dkk-related activity is desirable in situations in which Dkk or Dkk-related activity is abnormally downregulated and/or in which increased Dkk or Dkk-related activity is likely to have a beneficial effect. Likewise, inhibition of Dkk or Dkk-related activity is desirable in situations in which Dkk or Dkk-related activity is abnormally upregulated and/or in which decreased Dkk or Dkk-related activity is likely to have a beneficial effect. One example of such a situation is where a subject has a disorder characterized by aberrant development or cellular differentiation. Another example of such a situation is where the subject has a proliferative disease (e.g., cancer) or a neurogenerative disorder. Yet another example of such a situation is where it is desireable to acheive tissue regeneration in a subject (e.g., where a subject has undergone brain or spinal cord injury and it is desirable to regenerate neuronal tissue in a regulated manner.)

Accordingly, in one embodiment, the disease is a disease characterized by an abnormal cell proliferation, differentiation, and/or survival. For example, the disease can be a hyper-or hypoproliferative disease. The invention also provides methods for treating diseases characterized by an abnormal cell proliferation, differentiation, and/or survival in a subject, which are not characterized by an abnormal Dkk or Dkk-related activity (e.g., hDkk-3 activity). In fact, since Dkk is likely to be capable of modulating the proliferative state of a cell (i.e., state of proliferation, differentiation, and or survival of a cell), Dkk can regulate disease wherein the abnormal proliferative state of a cell results from a defect other than an abnormal Dkk activity.

Hyperproliferative diseases can be treated with Dkk or Dkk-related (e.g., hDkk-3) therapeutics include neoplastic and hyperplastic diseases, such as various forms of cancers and leukemias, and fibroproliferative disorders. Other hyperproliferative diseases that can be treated or prevented with the subject Dkk or Dkk-related therapeutics (e.g. hDkk-3 therapeutics) include malignant conditions, premalignant conditions, and benign conditions. The condition to be treated or prevented can be a solid tumor, such as a tumor arising in an epithelial tissue. Accordingly, treatment of such a cancer could comprise administration to the subject of a Dkk or Dkk-related therapeutic decreasing the interaction of Dkk with a Dkk receptor. Other cancers that can be treated or prevented with a Dkk or Dkk-related protein include cancers of the epithelia (e.g., carcinomas of the pancreas, kidney, stomach, colon, esophagus liver, secretory glands (e.g., adenocarcinoma) bladder, lung, breast, skin (e.g., malignant melanoma, seminoma squamous adenocarcinoma), reproductive tract including prostate gland, testis, ovary, cervix and uterus); cancers of the hematopoietic and immune system (e.g., leukemias and lymphomas); cancers of the central nervous, brain system and eye (e.g., malignant astrocytoma, gliomas, neuroblastoma and retinoblastoma); and cancers of connective tissues, bone, heart, muscles and vasculature (e.g., sarcomas, for example, osteosarcoma). Additional solid tumors within the scope of the invention include those that can be found in a medical textbook.

The condition to be treated or prevented can also be a soluble tumor, such as leukemia, either chronic or acute, including chronic or acute myelogenous leukemia, chronic or acute lymphocytic leukemia, promyelocytic leukemia, monocytic leukemia, myelomonocytic leukemia, and erythroleukemia. Yet other proliferative disorders that can be treated with a Dkk or Dkk-related therapeutic of the invention include heavy chain disease, multiple myeloma, lymphoma, e.g., Hodgkin's lymphoma and non-Hodgkin's lymphoma, and Waldenstroem's macroglobulemia.

Diseases or conditions characterized by a solid or soluble tumor can be treated by administrating a Dkk or Dkk-related therapeutic either locally or systemically, such that aberrant cell proliferation is inhibited or decreased. Methods for administering the compounds of the invention are further described below.

The invention also provides methods for preventing the formation and/or development of tumors. For example, the development of a tumor can be preceded by the presence of a specific lesion, such as a pre-neoplastic lesion, e.g., hyperplasia, metaplasia, and dysplasia, which can be detected, e.g., by cytologic methods. Such lesions can be found, e.g., in epithelial tissue. Thus, the invention provides a method for inhibiting progression of such a lesion into a neoplastic lesion, comprising administering to the subject having a preneoplastic lesion an amount of a Dkk or Dkk-related therapeutic sufficient to inhibit progression of the preneoplastic lesion into a neoplastic lesion.

The invention also provides for methods for treating or preventing diseases or conditions in which proliferation of cells is desired. For example, Dkk or Dkk-related therapeutics can be used to stimulate tissue repair or wound healing, such as after surgery or to stimulate tissue healing from burns. Other diseases in which proliferation of cells is desired are hypoproliferative diseases, i.e., diseases characterized by an abnormally low proliferation of certain cells.

In yet another embodiment, the invention provides a method for treating or preventing diseases or conditions characterized by aberrant cell differentiation. Accordingly, the invention provides methods for stimulating cellular differentiation in conditions characterized by an inhibition of normal cell differentiation which may or may not be accompanied by excessive proliferation. Alternatively, Dkk or Dkk-related therapeutics can be used to inhibit differentiation of specific cells.

In a preferred method, the aberrantly proliferating and/or differentiating cell is a cell present in the nervous system. A role for Dkk in the nervous system is suggested at least in part from the fact that human Dkk-3 is expressed in human fetal brain. Accordingly, the invention provides methods for treating diseases or conditions associated with a central or peripheral nervous system. For example, the invention provides methods for treating lesions of the nervous system associated with an aberrant proliferation, differentiation or survival of any of the following cells: cells of the central nervous system including neurons and glial cells (e.g., astrocytes and oligodendrocytes) and supporting cells of peripheral neurons (e.g., Schwann cells and satellite cells). Disorders of the nervous system include, but are not limited to: spinal cord injuries, brain injuries, brain tumors (e.g., astrocytic tumors, for example, astrocytomas and glioblastomas), lesions associated with surgery, ischemic lesions, malignant lesions, infectious lesions, degenerative lesions (e.g., Parkinson's disease, Alzheimer's disease, Huntington's chorea, amyotrophic lateral sclerosis), demyelinlating diseases (e.g., multiple sclerosis, human immunodeficiency associated myelopathy, transverse myelopathy, progressive multifocal leukoencephalopathy, pontine myelinolysis), motor neuron injuries, progressive spinal muscular atrophy, progressive bulbar palsy, primary lateral sclerosis, infantile and juvenile muscular atrophy, progressive bulbar paralysis of childhood (i.e., Fazio-Londe syndrome), poliomyelitis, and hereditary motorsensory neuropathy (i.e., Charcot-Marie-Tooth disease).

In another embodiment, the invention provides a method for enhancing the survival and/or stimulating proliferation and/or differentiation of cells and tissues in vitro. In a preferred embodiment, Dkk or Dkk-related therapeutics are used to promote tissue regeneration and/or repair (e.g., to treat nerve injury). For example, tissues from a subject can be obtained and grown in vitro in the presence of a Dkk or Dkk-related therapeutic, such that the tissue cells are stimulated to proliferate and/or differentiate. The tissue can then be readministered to the subject.

Among the approaches which may be used to ameliorate disease symptoms involving an aberrant Dkk or Dkk-related activity and/or an abnormal cell proliferation, differentiation, and/or survival, are, for example, antisense, ribozyme, and triple helix molecules described above. Examples of suitable compounds include the antagonists, agonists or homologues described in detail above.

Yet other Dkk or Dkk-related therapeutics consist of a first peptide comprising a Dkk or Dkk-related peptide capable of binding to a Dkk receptor, and a second peptide which is cytotoxic. Such therapeutics can be used to specifically target and lyse cells expressing or overexpressing a receptor for Dkk.

3. Pharmacogenomics

The Dkk or Dkk-related molecules of the present invention, as well as agents, or modulators which have a stimulatory or inhibitory effect on Dkk or Dkk-related activity (e.g., Dkk or Dkk-related gene expression) as identified by a screening assay described herein can be administered to individuals to treat (prophylactically or therapeutically) disorders (e.g., proliferative or developmental disorders) associated with aberrant Dkk or Dkk-related activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a Dkk or Dkk-related molecule or Dkk or Dkk-related modulator as well as tailoring the dosage and/or therapeutic regimen of treatment with a Dkk or Dkk-related molecule or Dkk or Dkk-related modulator.

Pharmacogenomics deals with clinically significant hereditary variations in the response to drugs due to altered drug disposition and abnormal action in affected persons. See e.g., Eichelbaum, M., *Clin Exp Pharmacol Physiol*, 1996, 23(10–11):983–985 and Linder, M. W., *Clin Chem*, 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a Dkk protein or Dkk receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a Dkk molecule or Dkk modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a Dkk molecule or Dkk or Dkk-related modulator, such as a modulator identified by one of the exemplary screening assays described herein.

This invention is further illustrated by the following examples which should not be construed as limiting. The contents of all references, patents and published patent applications cited throughout this application are hereby incorporated by reference.

EXAMPLES

The invention is based, at least in part, on the discovery of a family of genes encoding human cysteine-rich secreted proteins which are related to Xenopus Dickkopf (Dkk) proteins. This family includes hDkk-1, hDkk-2, hDkk-3, and hDkk-4. hDkks 1–4 contain two highly conserved cysteine-rich domains (CRDs), the most C-terminal of which demonstrates similarity to the colipase protein family. The invention is based also in part on the discovery of a family of Dkk-related proteins, referred to as Soggy proteins, as well as the genes encoding Soggy proteins. Soggy-1 is a novel secreted protein which is related to the N-terminal region of Dkk-3 but lacks CRDs. The following examples illustrate the structure and function of each of these novel human secreted proteins.

Example 1

Isolation And Characterization of Human hDkk-3 cDNA

In this example, the isolation and characterization of the gene encoding human Dkk-3 (also referred to as "hDkk-3", "Cysteine Rich Secreted Protein-1", "CRSP-1" "CRISPY-1" or "TANGO 59") is described.

Isolation of a Human Dkk-3 cDNA

The invention is based at least in part on the discovery of a human gene encoding a secreted protein, referred to herein as human Dickkopf-3 (hDkk-3). A partial cDNA was isolated using a Signal Sequence Trap method. This methodology takes advantage of the fact that molecules such as Dkk have an amino terminal signal sequence which directs certain secreted and membrane-bound proteins through the cellular secretory apparatus.

Briefly, a randomly primed cDNA library using mRNA prepared from human fetal brain tissue (Clontech, Palo Alto Calif.) was made by using the Stratagene-ZAP-cDNA Synthesis™ kit, (catalog #20041). The cDNA was ligated into the mammalian expression vector pTrap adjacent to a cDNA encoding placental alkaline phosphatase lacking a secretory signal. The plasmids were transformed into E. coli and DNA was prepared using the Wizard™ DNA purification kit (Promega). DNA was transfected into COS-7 cells with lipofectamine™ (Gibco-BRL). After 48 hours incubation the COS cell supernatants were assayed for alkaline phosphatase on a Wallac Micro-Beta scintillation counter using the Phospha-Light™ kit (Tropix Inc. Catalog #BP300). The individual plasmid DNAs scoring positive in the COS cell Alkaline Phosphatase secretion assay were further analyzed by DNA sequencing using standard procedures.

Using a partial cDNA isolated by the above-described method (clone Amhb3c2), a full length cDNA encoding human Dkk-3 was isolated from a lambda Ziplox™ human fetal brain cDNA library using conventional hybridization techniques (Sambrook et al., supra). The nucleotide sequence encoding the full length human Dkk-3 protein is shown in FIG. 1 and is set forth as SEQ ID NO: 1. The full length protein encoded by this nucleic acid is comprised of about 350 amino acids and has the amino acid sequence shown in FIG. 1 and set forth as SEQ ID NO:2. The coding portion (open reading frame) of SEQ ID NO:1 is set forth as SEQ ID NO:3. DNA for the clone Fmhb059 was deposited with the ATCC as Accession No. 98452.

Analysis of Human hDkk-3

Determination of the hydrophobicity profile of human Dkk-3 having the amino acid sequence set forth in SEQ ID NO:2 indicated the presence of a hydrophobic region from about amino acid 1 to about amino acid 22 of SEQ ID NO:2. Further analysis of the amino acid sequence SEQ ID NO:2 using a signal peptide prediction program predicted the presence of a signal peptide from about amino acid 1 to about amino acid 22 of SEQ ID NO:2. Accordingly, the mature hDkk-3 protein includes about 328 amino acids spanning from about amino acid 23 to about amino acid 350 of SEQ ID NO:2. The presence of the signal sequence, in addition to the fact that hDkk-3 has been identified using a Signal Sequence Trap system, indicates that hDkk-3 is a secreted protein. Furthermore, the prediction of such a signal peptide and signal peptide cleavage site can be made, for example, utilizing the computer algorithm SIGNALP (Nielsen, et al., (1997) *Protein Engineering* 10:1–6).

Examination of the cDNA sequence depicted in FIG. 1 shows that human Dkk-3 is particularly rich in cysteine residues. As shown in FIG. 1, hDkk-3 contains 20 cysteine residues located between amino acid 147 and amino acid 284 of SEQ ID NO: 2. This region has been termed the cysteine-rich region. These cysteine residues can form 10 disulfide bridges.

A BLAST search (Altschul et al., (1990) *J. Mol. Biol.* 215:403) of the nucleotide and the amino acid sequences of hDkk-3 has revealed that hDkk-3 is similar to a chicken cDNA encoding a protein of unknown function having GenBank Accession No. D263 11. This cDNA was isolated from a chicken lens cDNA library and was shown to be expressed in lens fibers and lens epithelium, but not in neural retina nor in liver cells. (Sawada et al., (1996) *Int. J. Dev. Biol.* 40:531). hDkk-3 and the chicken protein have 56% amino acid sequence identity and 72% amino acid sequence similarity. The amino acid sequence similarity between the chicken protein and human Dkk-3 is particularly high in the cysteine-rich domain of hDkk-3 which is located between amino acids 147 and 284 of SEQ ID NO: 2. In particular, the 20 cysteine residues of hDkk-3 located in this region are present in the chicken protein.

Figure 12:
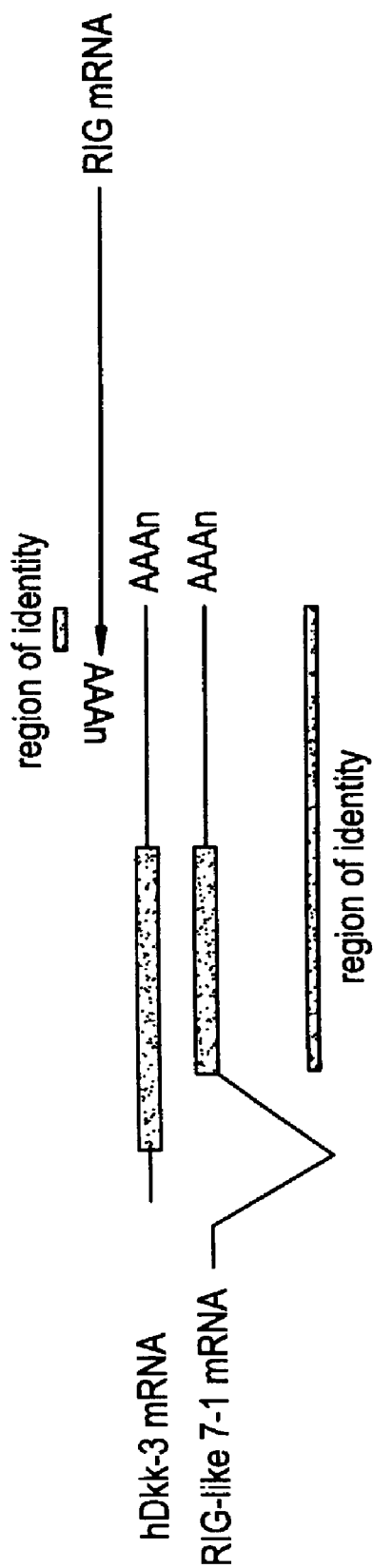
FIG. 12 is a schematic diagram depicting the relationship between the hDkk-3 nucleotide sequence (corresponding to SEQ ID NO:1) and those of RIG and RIG-like 7-1 (Accession Nos. U32331 and AF034208, respectively). Thick bars indicate regions of sequence identity between hDkk-3 and RIG or RIG-like 7-1 mRNAs. As between RIG and hDkk-3, there exists a short region of identity within the 3' untranslated regions of the mRNAs when the mRNAs are aligned in reverse orientation. As between hDkk-3 and RIG-like 7-1, there exists a longer region of identity, however, RIG-like 7-1 lacks a signal sequence and, accordingly, is not predicted to be secreted.

Two genes recently identified in a screen for suppressors of glioblastoma formation (Ligon et al. (1997) *Oncogene* 14:1075–1081) also show homology to hDkk-3. These genes, RIG ("Regulated In Glioblastoma") and RIG-like 7-1 (GenBank Accession Nos. U3233 1 and AF034208, respectively) were identified in a differential screen for mRNAs regulated by the introduction of a normal copy of chromosome 10 into a glioblastoma cell line harboring a deletion in chromosome 10 that promotes tumorigenesis. A schematic diagram summarizing the relationship between the sequences of the hDkk-3 and the RIG genes is presented as FIG. 12. The indicated region of identity between hDkk-3 and RIG comprises a short portion of the 3' UTR of the human Dkk-3 mRNA (e.g, RIG mRNA is ~100% identical to residues 2479 to 2153 of SEQ ID NO:1). RIG-like 7-1 is homologous to hDkk-3 accross a longer region (e.g., 97% identical from about nucleotides 316 to 2438 of SEQ ID NO:1) although the encoded RIG-like 7-1 protein lacks the Dkk N-terminal signal sequence and is not therefore predicted to be a secreted protein. These data associate hDkk-3 with human glioblastoma and suggest that hDkk-3 may be important in the suppression of the tumorigenic phenotype. A role in glioblastoma is also consistent with the high level of hDkk-3 mRNA expression observed in human brain tissue. In addition, the co-localization of the hDkk-3, RIG and RIG-like genes to a region of chromosome 11 (11p15.1) implicated in the development of human malignant astrocytoma (Ligon et al., supra) further indicates a role for these genes in tumorigenesis.

Human hDkk-3 protein has also some amino acid sequence similarity to metallothionein, particularly in the cyteine-rich domain.

Tissue Distribution of hDkk-3 mRNA

For Northern blots, all hybridizations were to Clontech Multiple Tissue Northern Blots and were performed in ExpressHyb solution (Clontech) for 1–20 hours. All probes were prepared by random primed radiolabelling (Prime-It, Stratagene). Blots were washed sequentially to a final stringency of 0.2×SSC/0.2% SDS and exposed to autoradiographic film. Hybridizations of a control β-actin cDNA probe consistently demonstrated even loading of the Northern blots. The results of hybridization of the probe to various mRNA samples are described below.

Hybridization of a Clontech Fetal Multiple Tissue Northern (NFTN) blot (Clontech, LaJolla, Calif.) containing RNA from fetal brain, lung, liver, and kidney indicated the presence of high levels of hDkk-3 mRNA (~2.5 kb) in fetal brain, lung, and slightly lower levels of hDkk-3 mRNA in fetal kidney. However, no significant level of hDkk-3 mRNA was found in fetal liver.

Hybridization of a Clontech human Multiple Tissue Northern (MTN) blot (Clontech, LaJolla, Calif.) containing RNA from adult heart, brain, placenta, lung, liver, skeletal muscle, kidney, and pancreas with a human Dkk-3 probe indicated the presence of high levels of hDkk-3 mRNA in heart, slightly lower levels in brain, and much lower levels in placenta and lung. Some hDkk-3 mRNA was also found in adult skeletal muscle. However, no significant levels of hDkk-3 mRNA was observed in adult liver, kidney, or pancreas. Interestingly, the chicken gene which is homologous to hDkk-3 was not expressed at detectable levels in liver either (Sawada et al., (1996) *Int. Dev. Biol.* 40:531).

Further hybridization of a Clontech human Multiple Tissue Northern (MTN) blot (Clontech, LaJolla, Calif.) including RNA from bone marrow, adrenal gland, trachea, lymph node, spinal cord, thyroid, and stomach revealed high levels of expression of hDkk-3 in mRNA isolated from adult spinal cord, and lower level expression in adrenal gland, trachea, thyroid, and stomach.

Thus, hDkk-3 is expressed in a tissue specific manner, with the strongest expression observed in brain, heart, and spinal cord.

Example 2

Isolation And Characterization of mDkk-3 cDNA

In this example, the isolation and characterization of the gene encoding murine Dkk-3 (also referred to as "mDkk-3", "murine Cysteine Rich Secreted Protein-1", "murine CRSP-1" or "murine CRISPY-1") is described.

Identification of a Murine Dkk-3 cDNA

A full length mDkk-3 cDNA was identified by comparison of the hDkk-3 sequence to a proprietary EST Database using the BLAST-X algorithm. A single clone identified in a adult mouse brain cDNA library was obtained and sequenced fully. DNA for the clone Fmmb059s was deposited with the ATCC as Accession No. 98634. mDkk-3 is predicted to have a signal peptide from residues 1 to 23 of SEQ ID NO:17, cleavage of which results in a mature protein having 326 amino acids in length corresponding to amino acids 24 to 349 of SEQ ID NO:17.

Tissue Distribution of mDkk-3 mRNA

To determine the expression pattern of mDkk-3, in situ hybridization was performed as follows. Normal mouse embryos and adult mouse tissues were collected from C57BL/6 mice, embedded in TissueTek™ O.C.T Compound (Sakura Finetek U.S.A., Inc., Torrance, Calif.), frozen on dry ice, and stored at −80° C. Cryostat serial sections (8 μm) were thaw mounted on Superfrost Plus™ slides (VWR Scientific, West Chester, Pa.) and air dried on a slide warmer at 40° C. for 20 minutes. Sections were then fixed with 4% formaldehyde in DEPC treated 0.1 M phosphate-buffered saline (PBS, pH 7.5) at room temperature for 10 minutes and rinsed twice in DEPC-PBS. Sections were rinsed in 0.1 M triethanolamine-HCl (TEA, pH 8.0), incubated in 0.25% acetic anhydride-TEA for 10 minutes and rinsed in DEPC-2×SSC (standard sodium citrate). Sections were dehydrated through a series of graded ethanols, incubated in 100% chloroform for 5 minutes, rinsed in 100% and 95% ethanol for 1 minutes and air dried.

Antisense and sense RNA transcripts were prepared by in vitro transcription (Riboprobe Gemini System™, Promega) of PCR amplified cDNA templates. Template amplification primers were as follows;

| | | |
|---|---|---|
| mDkk-3 forward | 5'-CAGTGAGTGCTGTGGAGACC-3' | (SEQ ID NO: 30), and |
| reverse | 5'-TCTTCAGTCAGGCTCCTCTC-3' | (SEQ ID NO: 31). |

Probes were labeled with $^{35}$S-UTP (NEN) and purified on G-25 spin columns (Pharmacia). The hybridization cocktail contained: 50% formamide, 10% dextran sulfate, 0.1% sodium dodecyl sulfate (SDS), 0.1% sodium thiosulfate, 1× Denhardt's solution, 0.6 M NaCl, 10 mM Tris (pH 7.5), 1 mM EDTA, 100 mM dithiothreitol (DTT), 0.1 mg/ml sheared salmon sperm, 50 μg/ml yeast tRNA, 0.5 mg/ml yeast total RNA, and $^{35}$S-UTP labeled probe at a concentration of 5×10$^7$ c.p.m./100 μl of final hybridization solution; 100 μl of hybridization solution was put on each section. The sections were then covered with a glass coverslip and incubated in a humidifed chamber at 55° C. for 18 h. After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 ug/ml RNase A for 30 minutes, and finally in TNE for 10 minutes. Slides were then rinsed with 2× SSC at room temperature, washed in 2×SSC at 50° C. for 1 h, 0.2×SSC at 55° C. for 1 h and 0.2×SSC at 60° C. for 1 h. Sections were dehydrated with a series of graded concentrations of ethanol 0.3 M ammonium acetate, air dried and exposed to Kodak Biomax MR™ scientific imaging film for 6 days at room temperature.

mDkk-3 expression in the brain was found to be highly localized to the cortex and hippocampus but was not observed in the dentate gyrus. Higher power magnification confirmed the mDkk-3 mRNA was localized to neurons within these structures. In the adult eye, mDkk-3 mRNA was found to be highly expressed in the retina, ciliary body, and lens epithelium. Expression in the retina was localized to the integrating bipolar and ganglion cells. In adult heart, mDkk-3 was detected in the atrioventricular valves and also in myocytes of the atria. Expression was highly restricted to the atria and noticeably absent from ventricular tissue. High level expression of mDkk-3 mRNA was also observed in developing eye, bone and cartilage in day 14 embryos. These findings corroborate and extend the northern analysis of hDkk-3 mRNA expression in human tissues and also suggest that Dkk-3 may play a role in bone and ocular physiology in addition to functions in neural and cardiac tissues.

Example 3

Secretion and Post-Translational Modification of Dkk-3

This example describes the secretion and post-translational modification (e.g., glycosylation and processing) of hDkk-3 as well as methods for small and large scale purification of hDkk-3.

hDkk-3 Expression Constructs

Expression constructs for two forms of hDkk-3 were prepared using the mammalian expression vector pMET-stop. Form-1 comprised a cDNA incorporating the complete 350aa hDkk-3 protein coding sequence (hDkk-3flag.long) and form-2 comprised the entire hDkk-3 protein coding sequence except for the final 18 amino acids (hDkk-3flag.short). A C-terminal sequence encoding the FLAG epitope (DYKDDDDK) (SEQ ID NO:19) was added to both hDkk-3 forms for ease of detection and purification. hDkk-3flag cDNAs were generated by PCR from a full length hDkk-3 cDNA template and ligated into pMET-stop using EcoR1 and SalI restriction sites.

Trial Transfection—Small Scale Expression

Expression constructs for hDkk-3flag.long and hDkk-3flag.short were transfected into 293T cells using 10 μl of lipofectamine (GIBCO/BRL) and 2 μg of DNA per well of a 6-well plate of cells which were 70–80% confluent. After 5 hours at 37° C., cells were fed with 1 ml of 20%FCS/DMEM. After incubation overnight at 37° C., cells were conditioned in 1 ml OptiMEM for 48 hours at 37° C. Samples of supernatant and cell pellets were solubilized in boiling SDS-PAGE gel buffer, run out on a 4–20% SDS-PAGE gel, transferred to a nylon membrane and probed with the anti-FLAG monoclonal antibody M2. Samples from both supernatant and pellet samples showed significant immunoreactivity within a molecular weight range of 40–65 kDa on autoradiographic film using a HRP conjugated secondary antibody and ECL detection reagents. Thus, both forms of hDkk-3 tested are secreted from 293T cells thereby confirming experimentally that hDkk-3 is a secreted protein. It should be noted that the molecular weights of both forms of hDkk-3 tested are greater than predicted from the amino acid sequence, suggesting that the hDkk-3 proteins secreted by 293T cells may be glycosylated. This is consistent with the presence of four potential sites for N-linked glycosylation in the hDkk-3 protein (e.g., at about amino acids 96–99, 106–109, 121–124, and 204–207 of SEQ ID NO:2).

Deglycosylation of hDkk-3

Given the heterogenous nature of secreted human Dkk-3, the effect of N-Glycanase treatment on the mobility of secreted flag-tagged hDkk-3 was studied. Briefly, 1 mL samples of 293T cell supernatants collected 72 hours after transfection with the appropriate constructs were incubated with 50 μL anti-flag M2 agarose beads (Sigma) for 16 hrs at 4° C. Beads were washed with PBS (pH7.4) containing, sequentially, 0.1%, 0.05% and 0.01% Triton X-100. The beads were resuspended in 20 μL of 20 mM sodium phosphate, pH 7.5, 50 mM EDTA, 0.02% sodium azide, (incubation buffer) together with 0.5% SDS, 5% 2-mercaptoethanol and boiled for 2 minutes. The supernatant was split into equal 10 μL aliquots which were diluted with 10 μL incubation buffer, 5μL 5% NP-40 and then with either 5μL N-Glycanase (Oxford Glycosystems) in enzyme buffer (20 mM Tris-HCl, 1 mM EDTA, 50 mM NaCl, 0.02% sodium azide pH 7.5) or with enzyme buffer alone as control. After 18 hours at 37° C., samples were boiled in equal volumes of SDS-PAGE buffer and analyzed by SDS-PAGE and Western blotting. For western analysis, samples were electroblotted onto PVDF (Novex) after SDS-PAGE on 4–20% gradient gels, probed with M2 anti-flag antibody (1:500, Sigma) followed by HRP conjugated sheep anti-mouse IgG (1:5000, Amersham), developed with chemiluminescent reagents (Renaissance, Dupont) and exposed to autoradiography film (Biomax MR2 film, Kodak).

Utilizing the above-described methodology, it was determined that hDkk-3 protein displayed a significant increase in mobility following N-Glycanase treatment. The major 45–65 kD form of soluble hDkk-3 was observed as two species of 45–55 and 40 kD following deglycosylation. This finding is consistent with the presence of multiple potential sites of N-linked glycosylation in the hDkk-3 protein. The reason for the heterogeneity of deglycosylated hDkk-3 reflects either proteolytic processing or incomplete removal of carbohydrate from one or more attachment sites. A 30 kD hDkk3 species was also observed in these experiments, the mobility of which was unaltered by N-Glycanase treatment. This form was only observed after overnight incubation of the samples and may be a non-specific degradation product.

Large Scale hDkk-3 Protein Production

For scale-up of hDkk-3flag.long protein expression, 30×150 mM plates of 293T cells at 70–80% confluence were transfected with 27 μg DNA, 100 μl lipofectamine in 18 ml OptiMEM for 5 hours at 37° C. 18 ml of 10%FCS/DMEM was added to each plate and incubated overnight at 37° C. 24 hours after the start of transfection, transfection supernatant was aspirated and 35 mls OptiMEM was added to each plate and the plates incubated at 37° C. for 72 hours. Conditioned medium was harvested, spun at 4000 rpm for 30 min. at 4° C., and filtered through a 0.45 micron filter unit. 1100 ml was passed over a 1.6×10 cm anti-FLAG M2 affinity column pre-equilibrated in PBS pH7.4 buffer at a flow rate of 2.0 ml per minute. After washing with 200 ml of PBS pH 7.4 buffer, bound material was eluted by a step of 200 mM Glycine pH 3.0 buffer and 0.5 ml fractions collected. Upon elution, a significant protein peak was detected by absorbance at 280 nm. Samples corresponding to conditioned medium, flow through and eluted fractions were analyzed by Coomassie blue and silver stained SDS-PAGE and by western blot analysis as described above. Significant immunoreactivity within a molecular weight range of 40–65 kDa was detected in conditioned medium and eluted fractions but not in the flow through sample, indicating that the secreted hDkk-3flag.long protein bound to the affinity column specifically and was eluted efficiently by the described conditions. Coomassie blue staining of SDS-PAGE gels suggested that the predominant immunoreactive protein constituted >90% of the protein present in the bound and eluted protein peak. Peak fractions of eluted protein were pooled and dialysed against Phosphate Buffered Saline resulting in a 4 ml volume of recombinant hDkk-3flag.long protein at a concentration of approximately 1 mg/ml.

Example 4

Isolation and Characterization of hDkk-4

In this example, the isolation and characterization of the gene encoding human Dkk-4 (also referred to as "hDkk-4", "Cysteine Rich Secreted Protein-2", "CRSP-2" or "CRISPY-2") is described.

Isolation and Analysis of a Human Dkk-4 cDNA

To identify novel proteins related to hDkk-3, the human Dkk-3 amino acid sequence was used to search the dbEST database using TBLASTN (WashUversion, 2.0, BLOSUM62 search matrix). A dbEST clone with accession number AA565546 was identified as having homology to a portion of the hDkk-3 cDNA. This clone was obtained from the IMAGE consortium and sequenced fully to define the entire hDkk-4 sequence depicted in FIG. 2.

Determination of the hydrophobicity profile of human Dkk-4 having the amino acid sequence set forth in SEQ ID NO:5 indicated the presence of a hydrophobic region from about amino acid 1 to about amino acid 19 of SEQ ID NO:5. Further analysis of the amino acid sequence SEQ ID NO:5 using a signal peptide prediction program predicted the presence of a signal peptide from about amino acid 1 to about amino acid 19 of SEQ ID NO:5. Accordingly, the mature hDkk-4 protein includes about 205 amino acids spanning from about amino acid 20 to about amino acid 224 of SEQ ID NO:5.

Tissue Distribution of hDkk-4 hDkk-4 mRNA was undetectable by Northern analysis in all adult and fetal human tissues examined. Accordingly, a survey was performed of a cDNA library panel by PCR with hDkk-4 specific PCR primers. Using such primers, products were identified in libraries prepared from cerebellum, activated human T-lymphocytes, lung and esophagus.

Secretion and Post-Translational Modification of human Dkk-4

Flag epitope-tagged human Dkk-4 protein was transiently overexpressed in 293T cells and analyzed as described previously for hDkk-3. Soluble hDkk-4 was consistently detected as three major immunoreactive species of approximately 40 kD [form (i)], 30–32 kD [form (ii)] and 15–17 kD [form (iii)]. Neither form (i), (ii) or (iii) was significantly affected by N-glycanase treatment, consistent with the absence of N-glycosylation sites from the protein.

To determine the possible cause of heterogeneity in the size of secreted hDkk-4, Edman N-terminal sequencing of anti-flag affinity purified material corresponding to bands (i), (ii) and (iii) was performed. Briefly, flag-tagged Dkk-4 protein was isolated by passing the conditioned media over an M2-biotin (Sigma)/streptavidin Poros column (2.1×30 mm, PE Biosystems); the column was then washed with PBS, pH 7.4 and flag-tagged protein eluted with 200 mM glycine, pH 3.0. Eluted fractions with 280 nm absorbance greater than background were analyzed by SDS-PAGE and western blot. Purified Dkk-4 protein bound to PVDF membrane after SDS-PAGE and electroblotting was sequenced for N-terminal amino acid analysis on a PE Applied Biosystems Model 494 Procise instrument using Edman-based chemistry protein sequencing. The amino acid residues were analyzed by HPLC (Spherogel micro PTH 3-micron column) and determined by separation and peak height as compared to standards.

The N-terminal sequence of band (i) was found to be XVLDFNNIRS (SEQ ID NO:34) which corresponds exactly to the predicted signal peptide cleavage site (between Ala-18 and Leu-19). Because the same band is identified by anti-flag antibodies, which recognize the C-terminal epitope tag, band (i) was thus identified as the full length, mature hDkk-4 protein. The band (iii) N-terminal sequence was found to be SQGRKGQEGS (SEQ ID NO:38) which corresponds to CRD-2 cleaved at the dibasic site Lys132/Lys133 (e.g., Lys113/Lys114 of the mature protein following cleavage of the a 19 amino acid signal sequence or Lys 114/Lys 115 following cleavage of a 18 amino acid signal sequence). These data obtained for bands (i) and (iii) indicate clearly that hDkk4 is proteolytically processed by 293T cells, resulting in the release of CRD-2 (a 91 amino acid biologically-active fragment) from the full length protein.

Moreover, the three major species migrated similarly on SDS-PAGE conducted under either reducing or non-reducing conditions. Thus, each of the major C-terminal (anti-flag immunoreactive) hDkk-4 species exist as independent proteolytic fragments that are not covalently linked via disulfide bonds to other subunits or complex components when secreted from 293T cells.

Example 5

Isolation and Characterization of hDkk-1

In this example, the isolation and characterization of the gene encoding human Dkk-1 (also referred to as "hDkk-1", "Cysteine Rich Secreted Protein-3", "CRSP-3" or "CRISPY-3") is described.

Identification of a Human Dkk-1 cDNA

Searching a proprietary database of EST information using the sequence of hDkk-3, an hdkk-1 partial sequence was found corresponding to a clone from a human fetal kidney cDNA library having the identification code jthKb075a10. This clone was sequenced further and to define the entire hDkk-1 sequence depicted in FIG. 3. DNA for the clone jthKb075a10 was deposited with the ATCC as Accession No. 98633. hDkk-1 has a predicted signal peptide from about amino acid residue 1 to 20 of SEQ ID NO:8, cleavage of which results in a mature protein having 246 amino acid resudues in length and corresponding to amino acid residues 21 to 266 of SEQ ID NO:8.

Tissue Distribution of hDkk-1

Northern blot analysis of various tissues including heart, brain, placenta, lung, liver, skeletal muscle, kidney, and pancreas was performed as previously described using a probe specific for hDkk-1. A ~1.8 kb hDkk1 mRNA was detected at high levels in human placenta, but not in other tissues tested.

Secretion and Post-Translational Modification of hDkk-1

Flag epitope-tagged human Dkk-1 protein was transiently overexpressed in 293T cells and analyzed as described previously. hDkk-1 was efficiently secreted from mammalian cells and was readily detected in conditioned medium of transfected cells. Mature secreted hDkk-1 migrated with a molecular weight of approximately 42–50 kD. Treatment with N-Glycanase had no significant effect on the mobility of soluble hDkk-1. Although hDkk-1 contains one potential site of N-linked glycosylation at its extreme C-terminus (e.g., at amino acids 256–259 of SEQ ID NO8), this site is not conserved in Xenopus Dkk-1 (Glinka et al., supra) and appears not to be a major site of carbohydrate addition in 293T cells.

Example 6

Isolation and Characterization of hDkk-2

In this example, the isolation and characterization of the gene encoding human Dkk-2 (also referred to as "hDkk-2", "Cysteine Rich Secreted Protein-4", "CRSP-4" or "CRISPY-4") is described.

Isolation of a Human Dkk-2 cDNA

Using the hDkk-3 sequence to query the dbEST database, a clone having similarity to a portion of hDkk-3 was identified having Accession No. W55979. This clone was subsequently obtained from the IMAGE consortium and sequenced to define a partial hDkk-2 sequence set forth as SEQ ID NO:10. This cDNA comprises a coding region from nucleotides 1–537, as well as 3' untranslated sequences (nucleotides 538 to 702). The coding region alone is set forth as SEQ ID NO:12. The predicted amino acid sequence corresponds to amino acids 1 to 179 of SEQ ID NO:11. A cDNA encoding full length hDkk-2 was isolated from a human fetal lung lambda Ziplox libraries by conventional plaque hybridization (Sambrook et al., 1989) and fully sequenced. The full-length nucleotide sequence is set forth as SEQ ID NO:20 and the predicted amino acid sequence is set forth as SEQ ID NO:21. The coding region alone is set forth as SEQ ID NO:22. The predicted amino acid sequence corresponds to amino acids 1 to 259 of SEQ ID NO:21. DNA for the clone fthu133 was deposited with the ATCC as Accession No. 201740. hDkk-2 has a predicted signal peptide from about amino acid residue 1 to 33 of SEQ ID NO:21, cleavage of which results in a mature protein having 226 amino acid resudues in length and corresponding to amino acid residues 34 to 259 of SEQ ID NO:21.

Tissue Distribution of hDkk-2

Northern blot analysis of various tissues (e.g., heart, brain, skeletal muscle, colon, thymus, spleen, kidney, liver, small intestine, placenta, lung, and peripheral blood leukocytes) was performed as previously described using a probe specific for hDkk-2. Of the tissues tested, hDkk-2 mRNA expression was highest in heart, brain, placenta, lung, and skeletal muscle. hDkk-2 transcripts of approximately 4.0 and 4.5 kb were observed.

Secretion and Post-translational Modification of hDkk-2

Flag epitope-tagged human Dkk-2 protein was transiently overexpressed in 293T cells and analyzed as described previously. Soluble hDkk-2 was detected as a major species of 15–17 kD, closely similar in size to form (iii) of hDkk-4. Additional minor forms of hDkk-2 were also observed in certain experiments in the range of 20–21 kD. Deglycosylation of hDkk-2 was not studied since the protein sequence lacks potential N-glycosylation sites. By comparison with the data presented in Example 4 regarding the dibasic proteolytic cleavage site in the hDkk-4 protein sequences, it is predicted that the major 15–17 kD form of hDkk-2 detected in these experiments corresponds to CRD-2, as was the case for hDkk-4.

Example 7

Isolation of Soggy Proteins

In this example, the isolation and characterization of the gene encoding human and murine Soggy-1 (also referred to as "Cysteine Rich Secreted Protein-N" or "CRISP-N") is described.

Identification of a Human and Murine Soggy-1 cDNAs

Human Soggy-1 was identified as a novel protein with similarity to the N-terminal domain of hDkk3. A human partial sequence was identified in the dbEST database for a clone having the accession number AA397836. This clone was obtained from the IMAGE collection and sequenced fully to define the entire human Soggy-1 sequence depicted in FIG. 7. Two murine partial sequences were likewise identified in the dBEST database. The clones were obtained from the IMAGE consortium and sequenced. The entire murine Soggy-1 sequence is depicted in FIG. 8. Human and murine Soggy cDNAs encode proteins of 242aa and 230aa, respectively, and are predicted to be secreted owing to the presence of N-terminal signal peptides. hsoggy-1 has a predicted signal peptide from about amino acid residue 1 to 30 of SEQ ID NO:14, cleavage of which results in a mature protein having 194 amino acid resudues in length and corresponding to amino acid residues 31 to 224 of SEQ ID NO:14. mSoggy-1 has a predicted signal peptide from about amino acid residue 1 to 20 of SEQ ID NO:27, cleavage of which results in a mature protein having 210 amino acid resudues in length and corresponding to amino acid residues 21 to 230 of SEQ ID NO:27. Human and murine Soggy proteins display 59% overall identity although significant amino acid identities are seen beyond this domain that extend into the CRDs of Dkk-3 (FIG. 10). However, cysteine residues are not conserved within these domains and the residues shared by Soggy and Dkk-3 are poorly conserved in other Dkks indicating that the sequence relationship between these proteins is unique. Homology is most obvious within a 51 amino acid region in which 33% identity is observed between hSoggy, mSoggy, hDkk-3 and mDkk-3. This 51 amino acid domain is referred to herein as an SGY domain. Human and mouse Soggy-1 proteins each possess 2 sites of potential N-linked glycosylation which are within the SGY domain and are also conserved with Dkk3. (e.g., NNTL, corresponding to amino acid residues 97–100 of SEQ ID NO:14 and NKTG corresponding to amino acid residues 112–115 of SEQ ID NO:14). In contrast to other Dkks, the C-terminal domain of Soggy-1 shows no similarity to other protein sequences in the public databases nor does it contain any cysteine residues. Soggy was so named in view of its lack of CRDs compared to hDkk-3, which had been previously designated Cysteine Rich Secreted Protein-1 ("CRISPY-1").

Tissue Distribution of Soggy-1

To investigate Soggy-1 mRNA expression, a mouse cDNA probe was used on murine Nothern blots. A 1 kb mSoggy-1 mRNA was expressed at very high levels in testis and, interestingly, demonstrated transient expression during mouse embryogenesis. Soggy-1 mRNA, which was undetectable at day 7 of gestation, was transiently expressed at day 11 and day 15, after which the expression level declined to undetectable levels. Thus, mSoggy-1 displays a developmentally regulated pattern of expression.

In situ analysis was performed as described in Example 1. For detection of murine Soggy-1, the following primers were used:

mSoggy forward 5'-ACCTGCAATGTGTCGACTGAG-3' (SEQ ID NO:32), and
reverse 5'-CACTTACAGCTGTTGGGATG-3' (SEQ ID NO:33).

Consistent with the Northern analysis, very high level expression of Soggy-1 mRNA was observed by in situ analysis in adult testis. Upon high magnification, Soggy-1 mRNA was found to be expressed at high levels in the spermatogenic epithelium of the seminiferous tubules and in the spermatogonia at various stages of development. A series of saggital sections of mouse embryos from E13.5–E17.5 and post-natal day 1.5 pups were also analyzed. In E15.5 embryos, Soggy-1 mRNA transcripts were localized to the developing dorsal root ganglia (DRGs) and also found in the cartilage primordium of the nasal septum. Soggy-1 expression was also seen in the eye from E13.5 to E16.5, as observed for mDkk-3. Expression of Soggy-1 mRNA at various stages of development is consistent with the northern analysis described above and suggests that Soggy-1 may play a role in multiple stages of development.

Secretion and Post-Translational Modification of Soggy Proteins

Flag epitope-tagged human Soggy-1 protein was transiently overexpressed in 293T cells and analysed as previously described. hSoggy was efficiently secreted from transfected 293T cells and migrated with a molecular weight of approximately 40–50 kD. Given the heterogenous nature of secreted human Soggy-1, the effect of N-Glycanase treatment on the mobility of secreted flag-tagged hSoggy-1 was studied. hSoggy displayed a 5–10 kD decrease in apparent molecular weight after N-Glycanase treatment, consistent with the presence of 2 potential sites of N-glycosylation in the protein.

Example 8

Structure of the Dkk Family Proteins and Dkk-Related Proteins

The amino acid and nucleotide homology between Dkk family members and Dkk-related proteins is set forth in the following tables. Where indicated, mDkk-1 and xDkk-1 correspond to a murine and Xenopus proteins set forth in Glinks et al., supra, and having Accession Nos: AF030433 and AF030434, respectively. Likewise cDkk-3 has Accession No. D26311

Table II sets forth overall sequence identities as determined using the ALIGN program, (version 2.0) using a PAM120 weight residue table, a gap length penalty of 12, and a gap penalty of 4:

|  | hDkk-3 | hDkk-4 | hDkk-1 | hDkk-2 | mDkk-1 | xDkk-1 | CLF-EST |
|---|---|---|---|---|---|---|---|
| hDkk-3 | 100 | 16.0 | 18.6 | 15.1 | 18.5 | 16.5 | 53.0 |
| hDkk-4 |  | 100 | 33.7 | 35.2 | 32.6 | 33.7 | 16.2 |
| hDkk-1 |  |  | 100 | 33.1 | 80.2 | 53.5 | 17.4 |
| hDkk-2 |  |  |  | 100 | 30.5 | 33.7 | 12.5 |

Table III sets forth nucleic acid identities as determined using the using the Wilbur Lipman DNA alignment program, Ktuple: 3; Gap Penalty: 3; Window: 20:

|  | hDkk-3 | hDkk-4 | hDkk-1 | hDkk-2 | mDkk-1 | xDkk-1 | CLF-EST |
|---|---|---|---|---|---|---|---|
| hDkk-3 | 100 | 30.0 | 37.2 | 34.7 | 31.5 | 45.4 | 58.8 |
| hDkk-4 |  | 100 | 43.0 | 35.9 | 38.8 | 38.4 | 36.7 |
| hDkk-1 |  |  | 100 | 59.3 | 66.4 | 53.7 | 32.1 |
| hDkk-2 |  |  |  | 100 | 38.8 | 38.4 | 36.7 |

Table IV sets forth local amino acid identities as determined using the Smith-Waterman algorithm as implemented in the program Bestfit of the GCG package, with gap penalties of 8 for opening and 1 for extending:

| hDkk-1 |  |  |  |  |  |  |  |  |
|---|---|---|---|---|---|---|---|---|
| mDkk-1 | 82 |  |  |  |  |  |  |  |
| xDkk-1 | 64 | 63 |  |  |  |  |  |  |
| hDkk-2 | 50 | 48 | 47 |  |  |  |  |  |
| hDkk-3 | 39 | 37 | 37 | 37 |  |  |  |  |
| mDkk-3 | 36 | 33 | 38 | 40 | 83 |  |  |  |
| cDkk-3 | 34 | 31 | 35 | 36 | 61 | 60 |  |  |
| hDkk-4 | 45 | 43 | 47 | 46 | 40 | 39 | 34 |  |
|  | hDkk-1 | mDkk-1 | xDkk-1 | hDkk-2 | hDkk-3 | mDkk-3 | cDkk-3 | hDkk-4 |

A multiple alignment of the amino acid sequences of hDkk-1, hDkk-2, hDkk-3, hDkk-4, mDkk-1, mDkk-3, xDkk-1, and cDkk-3 is shown in FIG. 6. Predicted signal peptides are underlined, N-glycosylation sites are indicated by a thick bar, CRD-1 by an open box and CRD-2 by a shaded box. The proteolytic cleavage site within hDkk4 is indicated by a double asterisk. The domain structure of the full length human Dkk proteins of the present invention as well as human Soggy are schematically illustrated in FIG. 9. Signal peptides (darkened boxes), Cysteine Rich Domain 1 ("CRD-1") (also referred to as the "amino-terminal cysteine-rich domain"), Cysteine Rich Domain 2 ("CRD-2") (also referred to as the "carboxy-terminal cysteine-rich domain"), the soggy domain (SGY) within hDkk-3 and hSoggy-1, and sites of N-glycosylation are indicated.

As demonstrated at least in FIGS. 6 and 9, human Dkks 1 through 4 each possess an N-terminal signal peptide and contain two conserved cysteine-rich domains (CRDs) separated by a linker or spacer region. Each CRD possesses 10 conserved cysteine residues. The second CRD has elsewhere been described as a colipase-like domain because the positions of the ten conserved cysteines in this domain have been shown to be closely similar to those in proteins of the colipase family (Aravind and Koonin, supra). Conservation of CRD-1 and CRD-2 suggests important functions for these domains. In contrast to the CRDs, the linker or spacer region that joins CRD-1 and CRD-2 is highly variable between hDkks, being notably larger in hDkk-1, -2 and -4 (50–55aa) as compared to Dkk-3 (12aa). Four potential sites of N-linked glycosylation are present in hDkk3 and are conserved in chicken and mouse Dkk-3. These sites are not conserved in other Dkk famiy members. hDkk1 possesses one potential N-glycosylation site located close to the C-terminus of the protein which is conserved in murine Dkk-1 but not in Xenopus Dkk-1 (FIG. 6). In addition, each hDkk possesses several potential dibasic proteolytic cleavage sites, suggesting the proteins may be subject to post-translational processing. hDkk3 is the most divergent of the four human Dkks and possesses an extended N-terminal unique region which precedes CRD-1 and an extended C-terminal unique region which is highly acidic.

Example 9

Effects of hDkks and Soggy on Wnt-induced Axis Duplication in Xenopus Embryos

This Example describes the functional activities of the hDkk and Soggy proteins of the present invention.

Xenopus Embryo Culture and RNA Microinjections

Eggs were obtained from Xenopus females injected with 700 units of human chorionic gonadotropin, fertilized in vitro and cultured in 0.1×MMR (Newport and Kirschner (1982) Cell 30:675–686). Embryonic stages were determned according to Nieuwkoop and Faber (1967) Normal table of Xenopus laevis (Daudin) Amsterdam: North Holland Publ. All cDNAs were subcloned into pCS2 vector (Rupp et al. (1984) Genes & Development 8:1311–1323), and capped mRNAs were synthesized in vitro as described (Krieg and Melton (1984) Nucleic Acids Res. 12:7057–7070, using the Message Machine kit (Ambion). The following plasmids were used as templates for mRNA synthesis: hDkk-1-pCS2, hDkk-2-pCS2, hDkk-3-pCS2, hDkk-4-pCS2, hSoggy-pCS2, Xwnt8 (Christian etal, (1991) Development 111: 1045–1055), Xwnt2B (Landesman and Sokol (1997) Mech. Dev. 61:1199–209), Xwnt3a (Wolda et al. (1993) Dev. Biol. 155:46–5), Xfz8-pXT7 (Itoh et al. (1998) Mech. Devel. 74:145–157), Xdsh-pXT7 (Sokol, et al. (1995) Mech. Devel. 74:145–157). Protein expression from all pCS2-Dkk constructs was confirmed by in vitro transcription and translation (TNT, Promega). For secondary axis induction, a single ventral blastomere of 4- or 8-cell embryos was injected with 10 nl of a solution containing 2–4 pg of Xwnt8 mRNA, 2.5–5 pg of Xwnt3a mRNA or 10 pg of Xwnt2B mRNA as described (Itoh et al. (1995) supra.). The effect of Dkk RNAs was tested by coinjecting Wnt mRNAs with 2.5 ng of hDkk mRNAs. For studies of Frizzled and Dhshevelled, 5 ng Fz8 and 1 ng Xdsh mRNAs were injected as indicated. After injections, embryos were cultured in 3% Ficoll 400 (Pharmacia), 0.5×MMR. Secondary axes were scored at stage 35 as complete, when they contained anterior neuroectodermal derivatives including pronounced cement gland and eyes, and as partial, when the secondary neural tube with melanocytes, but without head structures, was apparent.

Inhibition of Secondary Axis Induction by hDkk-1 and hDkk-4 in Xenopus Embryos hDkk-1 or hDkk-2 mRNAs were coinjected with Xwnt8 mRNA into single ventral blastomeres of 4- or 8-cell embryos. Injected embryos were cultured for 2 days and secondary axes were scored based on external morphology. Xwnt8 injected embryos displayed complete axis duplication, which was inhibited by co-injection with mRNAs encoding hDkk-1 and hDkk-4. To determine whether hDkks interacted with specific Wnt ligands, several different Wnts were assayed in combination with hDkk-1 or hDkk-4 for secondary axis formation. hDkk-1 and hDkk-4 inhibited axis duplication in response to Xwnt3a and Xwnt2b in addition to Xwnt8. hDkk-1 consistently demonstrated stronger inhibition of Wnt signaling than hDkk-4. Thus, hDkk-1 and hDkk -4 do not show any clear selectivity for the Wnt ligands used in this study. This compares to the FRPs, which also show little specificity with respect to their ability to inhibit Wnts (Leyns et al. (1997) supra; Wang et al. (1997) supra; Salic et al. (1997) supra; Mayr et al. (1997) supra; Finch et al. (1997) supra).

To investigate the mechanism by which hDkk-1 and hDkk-4 inhibit Wnt signaling, Dkk mRNAs were coinjected with Xdsh, a downstream component of the Wnt signaling pathway (Itoh et al. (1998) supra). hDkks-1 and -4 did not block secondary axis formation by Xdsh, indicating that Dkks function upstream of, or parallel with, Xdsh signaling. Similar findings have been reported previously for xDkk-1 (Glinka et al. (1998) supra). It was also determined whether hDkks could antagonize signaling by Xenopus Frizzled-8 (Xfz8), which can also induce a secondary axis through Wnt signaling (Itoh et al. (1998) supra). Neither hDkk-1 or hDkk-4 inhibited the axis-inducing activity of Xfz8 mRNA. This data, taken together with the fact that hDkk-1 and hDkk-4 are secreted, indicate that Dkks antagonize Wnt signaling at a point upstream of Wnt receptors.

Assay for Inhibition of Secondary Axis Induction by hDkk-2, hDkk-3 and hSoggy-1 in Xenopus Embryos hDkk-2, hDkk-3 or Soggy mRNAs were coinjected with Xwnt8 mRNA into single ventral blastomeres of 4- or 8-cell embryos and secondary axes were scored after two days as described for hDkk-1 and hDkk-4. Injection of mRNAs encoding hDkk-2, hDkk-3 or hSoggy-1 had no effect on Xwnt8-induced axis duplication. The ability of hDkk-2, hDkk-3 and hSoggy-1 to interact with specific Wnt ligands was also determined as described previously. hDkk-2, hDkk-3 and hSoggy-1 were inactive against each of the three Wnts tested. The lack of activity of hDkk-2, hDkk-3 and hSoggy-1 suggests that these proteins antagonize other members of the Wnt superfamily not tested here, or that they perform functions distinct from Wnt inhibition.

Example 10

Preparation of Antibodies Specific for hDkk and hSoggy Proteins

This example describes the making of polyclonal antibodies specific for hDkk-1, hDkk-4, hDkk-1, hDkk-2, and hSoggy-1.

Peptides were synthesized using Fmoc solid phase methodology utilizing MAP resin technology which increases the antigenic response (Tarn (1988) *Proc. Natl. Acad. Sci. USA* 85:5409–5413. For each protein, the peptides used for immunization are listed below:

| hDkk-3 | | |
|---|---|---|
| peptide #44 | FREVEELMEDTQHKL | (residues 51–65 of SEQ ID NO:2) |
| peptide #46 | GSFMEEVRQELEDLE | (residues 311–325 of SEQ ID NO:2) |
| hDkk-4 | | |
| peptide #91 | HAEGTTGHPVQENQP | (residues 111–125 of SEQ ID NO:5) |
| hDkk-1 | | |
| peptide #93 | GNKYQTIDNYQPYPC | (residues 71–85 of SEQ ID NO:8) |
| hDkk-2 | | |
| peptide #56 | GHYSNHDLGWQNLGR | (residues 73–87 of SEQ ID NO:11) |
| hSoggy-1 | | |
| peptide #58 | LQAIRDGLRKGTHKD | (residues 197–211 of SEQ ID NO:14) |

Peptides were designed to meet at least the following criteria: (1) not included within the cysteine-rich domain; (2) not including an N-glycosylation site; and (3) hydrophilic (e.g., solvent exposed).

Antibodies were generated in New Zealand white rabbits over a 10-week period. The immunogen includes KLH-peptide emulsified by mixing with an equal volume of Freund's Adjuvant, and injected into three subcutaneous dorsal sites, for a total of 0.1 mg peptide per immunization. Animals were bled from the articular artery. The blood was allowed to clot and the serum collected by centrifugation. The serum is stored at −20° C.

For purification, peptide antigens were immobilized on an activated support. Antisera was passed through the sera column and then washed. Specific antibodies were eluted via a pH gradient, collected and stored in a borate buffer (0.125 M total borate) at ~0.25 mg/ml. The anti-peptide titers were determined using ELISA methodology with free peptide bound in solid phase (1 µg/well). Detection was obtained using biotinylated anti-rabbit IgG, HRP-SA conjugate, and ABTS.

All antibodies performed well in ELISA assays. Anti-peptide #44, #46, and #58 are particularly useful for detection of hDkk-3 and hSoggy-1, respectively, as determined by western blotting of supernatants from hDkk-3- and hSoggy-1-transfected 293T cells.

The Dkk family comprises a novel family of secreted proteins which to date includes hDkk-1, hDkk-2, hDkk-3, hDkk-4, xDkk-1, mDkk-1 and cDkk-1. Structurally, Dkks 1–4 are related by several conserved features. Firstly, all four proteins are secreted proteins. Secondly, Dkks 1–4 each possess two distinct cysteine rich domains. Each domain contains 10 conserved cysteine residues, and these domains are highly conserved between family members. The C-terminal cysteine rich domain, referred to as CRD-2, bears significant similarity to proteins of the colipase family and sequence conservation among the Dkks is greatest within CRD-2 (Aravind and Koonin, supra). This may reflect a need for Dkks to interact with lipids in order to regulate Wnt function, since Wnt proteins remain tightly associated with the cell surface.

Despite the similarities between Dkks 1–4, notable differences between these family members appear with regard to their mRNA expression patterns. In adult human tissues hDkk-1 and hDkk-4 showed highly restricted mRNA expression patterns while hDkk-2 and hDkk-3 are more widely expressed. Murine Dkk-3 mRNA was found to be restricted to the myocytes of the atria in the heart, neurons of the cortex and hippocampus in the brain and also to the retinal neurons and lens epithelium in the eye. Such specific expression patterns reflect localized action of the Dkks as regulators of Wnt activity and/or that of other signaling molecules. Different Wnt family members have been shown to have divergent patterns of mRNA expression in adult and embryonic mammalian tissues. For example, murine Wnts 4, 7a and 7b are expressed in brain and lung, whereas Wnt6 is highly expressed in testis (Gavin et al., 1990). Wnts 5b and 13 are more broadly expressed (Gavin et al. (1990) supra; Katoh et al. (1996) supra). Although Wnts have been studied mostly in the context of their roles in embryonic development and tumorigensis, the expression of many family members in normal adult human and mouse tissues, together with their regulators such as the Dkks, suggests that these signaling proteins play important roles in normal tissue homeostasis.

Marked differences in the post-translational processing of different human Dkk proteins was also observed. hDkk-3 is secreted from 293T cells as a heterogeneously glycosylated protein, whereas Dkk-1, 2 and 4 proteins show no evidence of glycosylation. This is consistent with sequence analysis that identifies 4 potential sites of N-glycosylation in the hDkk-3 protein but no sites in either hDkk-2 or hDkk-4. A single putative site in hDkk-1 does not appear to be utilized in 293T cells and may well not be a significant site for N-linked carbohydrate addition in view of its C-terminal location and lack of conservation with xDkk-1. C-terminal proteolysis of hDkk4 in 293T cells was also characterized. Dkk proteins contain multiple potential sites of proteolytic processing. Secreted hDkk-4 was consistently detected as three major C-terminal fragments. N-terminal sequencing identified two of these as mature, full length hDkk4 and CRD-2, which was derived from the full length protein by a specific proteolytic event at lysines 132 and 133. Thus, the hDkk-4 CRD-2 is released from the full length protein upon expression in 293T cells. Similar processing of hDkk4 in COS cells has been observed.

Within the Dkk family, Dkks 1, 2 and 4 display closest similarity whereas Dkk-3 is more distantly related. For example, Dkk-3 contains a linker region connecting CRD-1 and CRD-2 which is shorter than in other Dkks. Dkk-3 also possesses extended N-and C-terminal regions compared to other Dkks. Within the Dkk-3 N-terminal unique region, a distinct domain has been identified that is also found in Soggy (the SGY domain). The SGY domains of human and mouse Soggy-1 and Dkk-3 proteins contain two conserved sites of N-linked glycosylation. Protein expression studies confirm that, like hDkk3, hSoggy is secreted as a glycoprotein. Murine Soggy-1 is highly expressed in adult testis and also displays a highly restricted mRNA expression in E15–E16 mouse embryos, being localized mainly to the cartilage primordia within the developing vertebrae/developing dorsal root ganglia. Soggy mRNA was also detected at high levels in the developing eye, similar to Dkk-3. This developmentally regulated pattern of Soggy expression overlaps with that of Dkk-3 suggesting that Soggy may play a role in the regulation of Dkk-3 function.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated polypeptide comprising at least 30 contiguous amino acids of the amino acid sequence of SEQ ID NO:8.

2. The isolated polypeptide of claim 1, wherein said polypeptide comprises at least 50 contiguous amino acids of the amino acid sequence of SEQ ID NO:8.

3. The isolated polypeptide of claim 2, wherein said polypeptide comprises amino acids 85–138 of SEQ ID NO:8.

4. The isolated polypeptide of claim 1, wherein said polypeptide comprises at least 100 contiguous amino acids of the amino acid sequence of SEQ ID NO:8.

5. The isolated polypeptide of claim 1, wherein said polypeptide comprises amino acids 85–138 of SEQ ID NO:8.

6. The isolated polypeptide of claim 1, wherein said polypeptide comprises amino acids 85–263 of SEQ ID NO:8.

7. The isolated polypeptide of claim 1, wherein said polypeptide comprises the amino acid sequence from about amino acid residue 21 to amino avid residue 266 of SEQ ID NO:8.

8. The isolated polypeptide of claim 7, wherein said polypeptide comprises the amino acid sequence from amino acid residue 21 to amino acid residue 266 of SEQ ID NO:8.

9. The isolated polypeptide of claim 1, wherein said polypeptide comprises the amino acid sequence of SEQ ID NO:8.

10. A fusion protein comprising a first polypeptide that is operatively linked to a second polypeptide, wherein said first polypeptide comprises at least 30 contiguous amino acids of the amino acid sequence of SEQ ID NO:8.

11. The fusion protein of claim 10, wherein said first polypeptide comprises at least 50 contiguous amino acids of the amino acid sequence of SEQ ID NO:8.

12. The isolated polypeptide of claim 10, wherein said first polypeptide comprises the amino acid sequence from amino acid residue 21 to amino acid residue 26 of SEQ ID NO:8.

13. The fusion protein of claim 10, wherein said first polypeptide comprises at least 100 contiguous amino acids of the amino acid sequence of SEQ ID NO:8.

14. The isolated polypeptide of claim 13, wherein said first polypeptide comprises amino acids 85–138 of SEQ ID NO:8.

15. The fusion protein of claim 10, wherein said first polypeptide comprises the amino acid sequence from about amino acid residue 21 to amino acid residue 266 of SEQ ID NO:8.

16. The fusion protein of claim 10, wherein said first polypeptide comprises the amino acid sequence of SEQ ID NO:8.

17. The fusion protein of claim 10, wherein said second polypeptide is glutathione-S-transferase (GST).

18. The fusion protein of claim 10, wherein said second polypeptide is a heterologous signal sequence or an immunoglobulin superfamily polypeptide.

19. The isolated polypeptide of claim 11, wherein said first polypeptide comprises amino acids 85–138 of SEQ ID NO:8.

20. The isolated polypeptide of claim 10, wherein said first polypeptide comprises amino acids amino acids 85–263 of SEQ ID NO:8.

* * * * *